(12) United States Patent
Arnold et al.

(10) Patent No.: US 9,249,401 B2
(45) Date of Patent: Feb. 2, 2016

(54) POLYPEPTIDES HAVING CELLULASE ACTIVITY

(75) Inventors: Frances H. Arnold, La Canada, CA (US); Pete Heinzelman, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 845 days.

(21) Appl. No.: 12/755,328

(22) Filed: Apr. 6, 2010

(65) Prior Publication Data

US 2010/0255542 A1 Oct. 7, 2010

Related U.S. Application Data

(60) Provisional application No. 61/166,993, filed on Apr. 6, 2009, provisional application No. 61/177,882, filed on May 13, 2009.

(51) Int. Cl.
*C12N 9/42* (2006.01)
*C12P 19/14* (2006.01)

(52) U.S. Cl.
CPC .............. *C12N 9/2437* (2013.01); *C12P 19/14* (2013.01); *C12Y 302/01091* (2013.01); *C07K 2319/00* (2013.01)

(58) Field of Classification Search
IPC ..................................................... C12N 9/2437
See application file for complete search history.

(56) References Cited

U.S. PATENT DOCUMENTS

| 7,348,168 | B2 | 3/2008 | Wu et al. | |
| 8,263,379 | B2 * | 9/2012 | Tomashek et al. | 435/200 |
| 2003/0170861 | A1 | 9/2003 | Adney et al. | |
| 2012/0135500 | A1 * | 5/2012 | Aehle et al. | 435/209 |

FOREIGN PATENT DOCUMENTS

| WO | 2004/056981 | * | 7/2004 |
| WO | 2006074005 A2 | | 7/2006 |
| WO | 2008025164 A1 | | 3/2008 |

OTHER PUBLICATIONS

P. Heinzelman et al. SCHEMA Recombination of a Fungal Cellulase Uncovers a Single Mutation That Contributes Markedly to Stability* J. Biol. Chem 284:26229-26233 (Jul. 2009).*
Alignment of SEQ ID No. 13 to SEQ ID No. 2 of WO 04/056981.*
Bingzhou Cao, First Office Action in Patent Application No. 201080015610.9, The State Intellectual Property Office of the People's Republic of China, Date of Issue: Jul. 3, 2012.
Bingzhou Cao, Third Office Action in Patent Application No. 201080015610.9, The State Intellectual Property Office of the People's Republic of China, Date of Issue: Sep. 16, 2013.
Kim Seung Beom, International Search Report and Written Opinion, PCT/US2010/030133, Korean Intellectual Property Office, Date of Mailing: Jan. 27, 2011.
Agnes Wittmann-Regis, International Preliminary Report on Patentability and Written Opinion, PCT/US2010/030133, The International Bureau of WIPO, Date of Mailing: Oct. 20, 2011.

* cited by examiner

*Primary Examiner* — Rebecca Prouty
(74) *Attorney, Agent, or Firm* — Gavrilovich, Dodd & Lindsey LLP; Joseph R. Baker, Jr.

(57) ABSTRACT

The present disclosure relates to CBH II chimera fusion polypeptides, nucleic acids encoding the polypeptides, and host cells for producing the polypeptides.

7 Claims, 11 Drawing Sheets

FIGURE 14A-D

SEQUENCE LISTING

```
<160> NUMBER OF SEQ ID NOS: 107

<210> SEQ ID NO 1
<211> LENGTH: 1083
<212> TYPE: DNA
<213> ORGANISM: Humicola insolens
<220> FEATURE:
<221> NAME/KEY: CDS
<222> LOCATION: (1)..(1083)

<400> SEQUENCE: 1 ggt aac ccc ttt gaa ggt gtt cag ctg tgg gct aat aac tat tat aga      48
Gly Asn Pro Phe Glu Gly Val Gln Leu Trp Ala Asn Asn Tyr Tyr Arg
1               5                   10                  15 tct gag gta cat aca ctg gcc att ccg caa att aca gac ccc gcg ttg      96
Ser Glu Val His Thr Leu Ala Ile Pro Gln Ile Thr Asp Pro Ala Leu
            20                  25                  30 cgt gcc gca gct agt gct gtg gct gag gtg cca agt ttt caa tgg ctg     144
Arg Ala Ala Ala Ser Ala Val Ala Glu Val Pro Ser Phe Gln Trp Leu
        35                  40                  45 gac aga aat gta aca gtg gat act ttg ttg gta cag act ttg tca gaa     192
Asp Arg Asn Val Thr Val Asp Thr Leu Leu Val Gln Thr Leu Ser Glu
    50                  55                  60 atc cgt gag gcc aat caa gca ggt gct aat ccc caa tat gca gcg caa     240
Ile Arg Glu Ala Asn Gln Ala Gly Ala Asn Pro Gln Tyr Ala Ala Gln
65                  70                  75                  80 atc gtg gtc tat gat ctg ccc gat aga gac tgt gca gct gcc gcc tcg     288
Ile Val Val Tyr Asp Leu Pro Asp Arg Asp Cys Ala Ala Ala Ala Ser
                85                  90                  95 aat ggt gaa tgg gca ata gcg aac aac ggt gta aac aat tac aaa gct     336
Asn Gly Glu Trp Ala Ile Ala Asn Asn Gly Val Asn Asn Tyr Lys Ala
            100                 105                 110 tac att aat aga att aga gag ata ttg ata agt ttt tcg gac gtt aga     384
Tyr Ile Asn Arg Ile Arg Glu Ile Leu Ile Ser Phe Ser Asp Val Arg
        115                 120                 125 acg ata tta gtc att gag cca gat agt cta gct aat atg gtc aca aat     432
Thr Ile Leu Val Ile Glu Pro Asp Ser Leu Ala Asn Met Val Thr Asn
    130                 135                 140 atg aat gtc ccg aag tgt tcc ggt gca gcc agc act tat agg gaa tta     480
Met Asn Val Pro Lys Cys Ser Gly Ala Ala Ser Thr Tyr Arg Glu Leu
145                 150                 155                 160 acc ata tat gca ctg aag caa ttg gat ctg cct cat gtc gct atg tac     528
Thr Ile Tyr Ala Leu Lys Gln Leu Asp Leu Pro His Val Ala Met Tyr
                165                 170                 175 atg gat gcc ggc cac gct gga tgg tta ggc tgg ccg gca aac att cag     576
Met Asp Ala Gly His Ala Gly Trp Leu Gly Trp Pro Ala Asn Ile Gln
            180                 185                 190 cca gcc gca gaa ttg ttt gcc aaa att tac gaa gat gct gga aag cct     624
Pro Ala Ala Glu Leu Phe Ala Lys Ile Tyr Glu Asp Ala Gly Lys Pro
        195                 200                 205 aga gca gtg aga ggt ctt gca act aat gtt gct aat tac aat gca tgg     672
Arg Ala Val Arg Gly Leu Ala Thr Asn Val Ala Asn Tyr Asn Ala Trp
    210                 215                 220 tca gtt tca tcc cct cca cca tac aca agt cca aat cca aac tac gat     720
Ser Val Ser Ser Pro Pro Pro Tyr Thr Ser Pro Asn Pro Asn Tyr Asp
225                 230                 235                 240 gaa aag cat tat atc gaa gca ttc aga ccc tta tta gaa gcc cgt ggt     768
Glu Lys His Tyr Ile Glu Ala Phe Arg Pro Leu Leu Glu Ala Arg Gly
                245                 250                 255
```

```
ttc cca gcc caa ttt ata gtg gat cag gga aga tca ggt aag caa cca    816
Phe Pro Ala Gln Phe Ile Val Asp Gln Gly Arg Ser Gly Lys Gln Pro
        260                 265                 270 act ggc caa aag gag tgg ggg cat tgg tgt aat gct att ggc aca gga    864
Thr Gly Gln Lys Glu Trp Gly His Trp Cys Asn Ala Ile Gly Thr Gly
    275                 280                 285 ttt ggt atg aga cct act gct aat acc ggt cac cag tat gtg gat gct    912
Phe Gly Met Arg Pro Thr Ala Asn Thr Gly His Gln Tyr Val Asp Ala
290                 295                 300 ttt gtt tgg gtt aaa ccg ggc ggt gaa tgc gac ggg acc agc gat act    960
Phe Val Trp Val Lys Pro Gly Gly Glu Cys Asp Gly Thr Ser Asp Thr
305                 310                 315                 320 acg gcg gcc aga tat gat tat cat tgt ggt ctg gaa gat gca tta aaa    1008
Thr Ala Ala Arg Tyr Asp Tyr His Cys Gly Leu Glu Asp Ala Leu Lys
                325                 330                 335 cca gct cct gaa gcc ggc cag tgg ttc aac gaa tac ttc att caa ttg    1056
Pro Ala Pro Glu Ala Gly Gln Trp Phe Asn Glu Tyr Phe Ile Gln Leu
            340                 345                 350 ctt agg aac gct aac ccg ccc ttt taa                                1083
Leu Arg Asn Ala Asn Pro Pro Phe
        355                 360

<210> SEQ ID NO 2
<211> LENGTH: 360
<212> TYPE: PRT
<213> ORGANISM: Humicola insolens

<400> SEQUENCE: 2

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
    130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
    210                 215                 220
```

-continued

```
Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
            245                 250                 255

Phe Pro Ala Gln Phe Ile Val Asp Gln Gly Arg Ser Gly Lys Gln Pro
        260                 265                 270

Thr Gly Gln Lys Glu Trp Gly His Trp Cys Asn Ala Ile Gly Thr Gly
    275                 280                 285

Phe Gly Met Arg Pro Thr Ala Asn Thr Gly His Gln Tyr Val Asp Ala
290                 295                 300

Phe Val Trp Val Lys Pro Gly Glu Cys Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
            340                 345                 350

Leu Arg Asn Ala Asn Pro Pro Phe
            355                 360

<210> SEQ ID NO 3
<211> LENGTH: 1077
<212> TYPE: DNA
<213> ORGANISM: Hypocrea jecorina
<220> FEATURE:
<221> NAME/KEY: CDS
<222> LOCATION: (1)..(1077)

<400> SEQUENCE: 3 ggt aat cca ttc gtt ggg gtg aca ccc tgg gcg aac gcc tat tat gct        48
Gly Asn Pro Phe Val Gly Val Thr Pro Trp Ala Asn Ala Tyr Tyr Ala
1               5                   10                  15 tct gag gtt tca tcc cta gct att ccc tct tta aca ggt gca atg gct        96
Ser Glu Val Ser Ser Leu Ala Ile Pro Ser Leu Thr Gly Ala Met Ala
            20                  25                  30 aca gcc gcc gct gcc gtt gca aag gtc cct tcc ttc atg tgg ctg gat       144
Thr Ala Ala Ala Ala Val Ala Lys Val Pro Ser Phe Met Trp Leu Asp
        35                  40                  45 act ttg gac aaa acc ccc tta atg gaa caa acg ttg gct gat ata cgt       192
Thr Leu Asp Lys Thr Pro Leu Met Glu Gln Thr Leu Ala Asp Ile Arg
    50                  55                  60 act gcg aat aaa aac ggc ggc aat tat gct gga caa ttt gtg gtt tat       240
Thr Ala Asn Lys Asn Gly Gly Asn Tyr Ala Gly Gln Phe Val Val Tyr
65                  70                  75                  80 gac ctg ccg gat aga gat tgt gct gca cta gcg agc aac ggg gag tac       288
Asp Leu Pro Asp Arg Asp Cys Ala Ala Leu Ala Ser Asn Gly Glu Tyr
                85                  90                  95 agc att gcg gat ggc ggt gtc gca aag tac aaa aac tat ata gat act       336
Ser Ile Ala Asp Gly Gly Val Ala Lys Tyr Lys Asn Tyr Ile Asp Thr
            100                 105                 110 atc agg caa ata gtt gtc gaa tac agt gat att cgt acg ctg ctt gta       384
Ile Arg Gln Ile Val Val Glu Tyr Ser Asp Ile Arg Thr Leu Leu Val
        115                 120                 125 atc gaa ccc gat tcc tta gcg aac ttg gta aca aat cta ggt act ccg       432
Ile Glu Pro Asp Ser Leu Ala Asn Leu Val Thr Asn Leu Gly Thr Pro
    130                 135                 140 aag tgt gcg aac gcg cag agt gct tat ctt gag tgc atc aat tat gca       480
Lys Cys Ala Asn Ala Gln Ser Ala Tyr Leu Glu Cys Ile Asn Tyr Ala
145                 150                 155                 160 gtc acc cag ttg aat ttg cca aac gtt gca atg tat ctt gat gct ggt       528
Val Thr Gln Leu Asn Leu Pro Asn Val Ala Met Tyr Leu Asp Ala Gly
```

```
Val Thr Gln Leu Asn Leu Pro Asn Val Ala Met Tyr Leu Asp Ala Gly
            165                 170                 175 cat gcc ggg tgg ttg ggt tgg cca gca aat cag gat ccc gct gcg cag      576
His Ala Gly Trp Leu Gly Trp Pro Ala Asn Gln Asp Pro Ala Ala Gln
        180                 185                 190 ctg ttt gca aat gtt tac aaa aat gcc tca agt cct aga gcg ctg agg      624
Leu Phe Ala Asn Val Tyr Lys Asn Ala Ser Ser Pro Arg Ala Leu Arg
            195                 200                 205 ggt ctt gca aca aat gtt gct aat tac aac gga tgg aat att acc tca      672
Gly Leu Ala Thr Asn Val Ala Asn Tyr Asn Gly Trp Asn Ile Thr Ser
    210                 215                 220 ccc cca tca tac aca caa gga aat gct gtt tac aat gaa aaa ctt tat      720
Pro Pro Ser Tyr Thr Gln Gly Asn Ala Val Tyr Asn Glu Lys Leu Tyr
225                 230                 235                 240 att cat gcc att ggt cca ctg ctg gct aat cac gga tgg agt aat gcc      768
Ile His Ala Ile Gly Pro Leu Leu Ala Asn His Gly Trp Ser Asn Ala
                245                 250                 255 ttt ttc att aca gat caa ggg aga agt ggt aaa caa cct act gga caa      816
Phe Phe Ile Thr Asp Gln Gly Arg Ser Gly Lys Gln Pro Thr Gly Gln
            260                 265                 270 caa caa tgg ggt gac tgg tgt aat gtt atc ggt act ggg ttt ggc atc      864
Gln Gln Trp Gly Asp Trp Cys Asn Val Ile Gly Thr Gly Phe Gly Ile
        275                 280                 285 aga cca tca gcg aat acg ggt gat tca ttg ttg gac tca ttt gtt tgg      912
Arg Pro Ser Ala Asn Thr Gly Asp Ser Leu Leu Asp Ser Phe Val Trp
    290                 295                 300 gtt aaa ccc ggg ggt gaa tgt gat gga acg agt gat tct tct gct cca      960
Val Lys Pro Gly Gly Glu Cys Asp Gly Thr Ser Asp Ser Ser Ala Pro
305                 310                 315                 320 agg ttc gat tct cat tgc gca tta cca gat gct ttg cag cca gca cct     1008
Arg Phe Asp Ser His Cys Ala Leu Pro Asp Ala Leu Gln Pro Ala Pro
                325                 330                 335 caa gca gga gct tgg ttc caa gct tat ttt gta caa tta ctg act aac     1056
Gln Ala Gly Ala Trp Phe Gln Ala Tyr Phe Val Gln Leu Leu Thr Asn
            340                 345                 350 gcc aat cct agt ttt cta taa                                         1077
Ala Asn Pro Ser Phe Leu
            355

<210> SEQ ID NO 4
<211> LENGTH: 358
<212> TYPE: PRT
<213> ORGANISM: Hypocrea jecorina

<400> SEQUENCE: 4

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
                20                  25                  30

Thr Ala Ala Ala Val Ala Lys Val Pro Ser Phe Met Trp Leu Asp
        35                  40                  45

Thr Leu Asp Lys Thr Pro Leu Met Glu Gln Thr Leu Ala Asp Ile Arg
    50                  55                  60

Thr Ala Asn Lys Asn Gly Gly Asn Tyr Ala Gly Gln Phe Val Val Tyr
65                  70                  75                  80

Asp Leu Pro Asp Arg Asp Cys Ala Ala Leu Ala Ser Asn Gly Glu Tyr
                85                  90                  95

Ser Ile Ala Asp Gly Gly Val Ala Lys Tyr Lys Asn Tyr Ile Asp Thr
                100                 105                 110
```

```
Ile Arg Gln Ile Val Val Glu Tyr Ser Asp Ile Arg Thr Leu Leu Val
            115                 120                 125

Ile Glu Pro Asp Ser Leu Ala Asn Leu Val Thr Asn Leu Gly Thr Pro
130                 135                 140

Lys Cys Ala Asn Ala Gln Ser Ala Tyr Leu Glu Cys Ile Asn Tyr Ala
145                 150                 155                 160

Val Thr Gln Leu Asn Leu Pro Asn Val Ala Met Tyr Leu Asp Ala Gly
            165                 170                 175

His Ala Gly Trp Leu Gly Trp Pro Ala Asn Gln Asp Pro Ala Ala Gln
            180                 185                 190

Leu Phe Ala Asn Val Tyr Lys Asn Ala Ser Ser Pro Arg Ala Leu Arg
            195                 200                 205

Gly Leu Ala Thr Asn Val Ala Asn Tyr Asn Gly Trp Asn Ile Thr Ser
210                 215                 220

Pro Pro Ser Tyr Thr Gln Gly Asn Ala Val Tyr Asn Glu Lys Leu Tyr
225                 230                 235                 240

Ile His Ala Ile Gly Pro Leu Leu Ala Asn His Gly Trp Ser Asn Ala
            245                 250                 255

Phe Phe Ile Thr Asp Gln Gly Arg Ser Gly Lys Gln Pro Thr Gly Gln
            260                 265                 270

Gln Gln Trp Gly Asp Trp Cys Asn Val Ile Gly Thr Gly Phe Gly Ile
            275                 280                 285

Arg Pro Ser Ala Asn Thr Gly Asp Ser Leu Leu Asp Ser Phe Val Trp
290                 295                 300

Val Lys Pro Gly Gly Glu Cys Asp Gly Thr Ser Asp Ser Ser Ala Pro
305                 310                 315                 320

Arg Phe Asp Ser His Cys Ala Leu Pro Asp Ala Leu Gln Pro Ala Pro
            325                 330                 335

Gln Ala Gly Ala Trp Phe Gln Ala Tyr Phe Val Gln Leu Leu Thr Asn
            340                 345                 350

Ala Asn Pro Ser Phe Leu
            355

<210> SEQ ID NO 5
<211> LENGTH: 1077
<212> TYPE: DNA
<213> ORGANISM: Chaetomium thermophilium
<220> FEATURE:
<221> NAME/KEY: CDS
<222> LOCATION: (1)..(1077)

<400> SEQUENCE: 5 ggt aac cct ttc agt ggt gtg cag tta tgg gct aat act tac tat tct     48
Gly Asn Pro Phe Ser Gly Val Gln Leu Trp Ala Asn Thr Tyr Tyr Ser
1               5                   10                  15 tca gaa gtc cac acc tta gct atc cca agc tta agt cca gaa tta gcg     96
Ser Glu Val His Thr Leu Ala Ile Pro Ser Leu Ser Pro Glu Leu Ala
                20                  25                  30 gct aag gcg gcg aaa gta gct gaa gtg cca tca ttc caa tgg tta gat    144
Ala Lys Ala Ala Lys Val Ala Glu Val Pro Ser Phe Gln Trp Leu Asp
            35                  40                  45 aga aac gtg act gtg gat act ctg ttt tct ggt aca ctt gct gag ata    192
Arg Asn Val Thr Val Asp Thr Leu Phe Ser Gly Thr Leu Ala Glu Ile
        50                  55                  60 agg gcg gct aac caa agg gga gct aat cca cca tat gct ggc atc ttt    240
Arg Ala Ala Asn Gln Arg Gly Ala Asn Pro Pro Tyr Ala Gly Ile Phe
65                  70                  75                  80
```

```
gtg gtt tat gac ctt cct gat aga gat tgt gct gcc gct gca agc aat    288
Val Val Tyr Asp Leu Pro Asp Arg Asp Cys Ala Ala Ala Ala Ser Asn
                85                  90                  95 ggt gaa tgg agt ata gct aac aac ggt gct aac aac tat aag aga tat    336
Gly Glu Trp Ser Ile Ala Asn Asn Gly Ala Asn Asn Tyr Lys Arg Tyr
                100                 105                 110 atc gat aga att aga gaa ttg ttg att cag tac tca gat atc agg aca    384
Ile Asp Arg Ile Arg Glu Leu Leu Ile Gln Tyr Ser Asp Ile Arg Thr
                115                 120                 125 att ttg gtt att gaa cca gac agt cta gca aat atg gtt act aac atg    432
Ile Leu Val Ile Glu Pro Asp Ser Leu Ala Asn Met Val Thr Asn Met
        130                 135                 140 aac gta caa aaa tgt tct aac gca gca tct acg tat aaa gaa ctg act    480
Asn Val Gln Lys Cys Ser Asn Ala Ala Ser Thr Tyr Lys Glu Leu Thr
145                 150                 155                 160 gtg tat gca ttg aaa cag ttg aac ttg cca cac gta gcc atg tat atg    528
Val Tyr Ala Leu Lys Gln Leu Asn Leu Pro His Val Ala Met Tyr Met
                165                 170                 175 gat gca ggt cac gcc ggc tgg tta ggc tgg ccc gct aat ata cag cct    576
Asp Ala Gly His Ala Gly Trp Leu Gly Trp Pro Ala Asn Ile Gln Pro
                180                 185                 190 gcc gca gaa tta ttc gcg caa ata tac aga gac gct gga cgt ccg gct    624
Ala Ala Glu Leu Phe Ala Gln Ile Tyr Arg Asp Ala Gly Arg Pro Ala
                195                 200                 205 gcg gtc agg ggt ctt gcc act aac gtt gca aat tac aac gct tgg tca    672
Ala Val Arg Gly Leu Ala Thr Asn Val Ala Asn Tyr Asn Ala Trp Ser
        210                 215                 220 ata gcg agt cct cca tcg tac aca agc cct aac cca aac tac gat gag    720
Ile Ala Ser Pro Pro Ser Tyr Thr Ser Pro Asn Pro Asn Tyr Asp Glu
225                 230                 235                 240 aag cat tac ata gaa gca ttt gct cct ttg ctt cgt aac caa ggt ttt    768
Lys His Tyr Ile Glu Ala Phe Ala Pro Leu Leu Arg Asn Gln Gly Phe
                245                 250                 255 gat gca aag ttt atc gtc gat acc gga aga aac ggc aag cag ccg aca    816
Asp Ala Lys Phe Ile Val Asp Thr Gly Arg Asn Gly Lys Gln Pro Thr
                260                 265                 270 ggg cag cta gaa tgg ggg cac tgg tgc aat gtc aag ggt acg ggt ttc    864
Gly Gln Leu Glu Trp Gly His Trp Cys Asn Val Lys Gly Thr Gly Phe
                275                 280                 285 ggt gtt aga ccc acg gct aac act ggg cat gag ttg gtt gat gca ttc    912
Gly Val Arg Pro Thr Ala Asn Thr Gly His Glu Leu Val Asp Ala Phe
        290                 295                 300 gtt tgg gta aaa ccc gga gga gag tca gac ggt act tct gat act agt    960
Val Trp Val Lys Pro Gly Gly Glu Ser Asp Gly Thr Ser Asp Thr Ser
305                 310                 315                 320 gct gcc aga tac gat tac cac tgt ggc ctt tct gat gct ttg aca cca   1008
Ala Ala Arg Tyr Asp Tyr His Cys Gly Leu Ser Asp Ala Leu Thr Pro
                325                 330                 335 gcc cct gaa gcc ggg caa tgg ttc cag gcc tac ttc gaa caa cta ttg   1056
Ala Pro Glu Ala Gly Gln Trp Phe Gln Ala Tyr Phe Glu Gln Leu Leu
                340                 345                 350 att aac gca aac cca cca tag                                       1077
Ile Asn Ala Asn Pro Pro
            355

<210> SEQ ID NO 6
<211> LENGTH: 358
<212> TYPE: PRT
<213> ORGANISM: Chaetomium thermophilium
```

<400> SEQUENCE: 6

```
Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
            20                  25                  30

Ala Lys Ala Ala Lys Val Ala Glu Val Pro Ser Phe Gln Trp Leu Asp
        35                  40                  45

Arg Asn Val Thr Val Asp Thr Leu Phe Ser Gly Thr Leu Ala Glu Ile
    50                  55                  60

Arg Ala Ala Asn Gln Arg Gly Ala Asn Pro Pro Tyr Ala Gly Ile Phe
65                  70                  75                  80

Val Val Tyr Asp Leu Pro Asp Arg Asp Cys Ala Ala Ala Ser Asn
                85                  90                  95

Gly Glu Trp Ser Ile Ala Asn Asn Gly Ala Asn Tyr Lys Arg Tyr
                100                 105                 110

Ile Asp Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Lys Glu Leu Thr
145                 150                 155                 160

Val Tyr Ala Leu Lys Gln Leu Asn Leu Pro His Val Ala Met Tyr Met
                165                 170                 175

Asp Ala Gly His Ala Gly Trp Leu Gly Trp Pro Ala Asn Ile Gln Pro
                180                 185                 190

Ala Ala Glu Leu Phe Ala Gln Ile Tyr Arg Asp Ala Gly Arg Pro Ala
            195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300

Val Trp Val Lys Pro Gly Gly Glu Ser Asp Gly Thr Ser Asp Thr Ser
305                 310                 315                 320

Ala Ala Arg Tyr Asp Tyr His Cys Gly Leu Ser Asp Ala Leu Thr Pro
                325                 330                 335

Ala Pro Glu Ala Gly Gln Trp Phe Gln Ala Tyr Phe Glu Gln Leu Leu
            340                 345                 350

Ile Asn Ala Asn Pro Pro
        355
```

<210> SEQ ID NO 7
<211> LENGTH: 267
<212> TYPE: DNA
<213> ORGANISM: Artificial Sequence
<220> FEATURE:
<223> OTHER INFORMATION: CBD Linker
<220> FEATURE:

-continued

```
<221> NAME/KEY: CDS
<222> LOCATION: (1)..(267)

<400> SEQUENCE: 7 gct agc tgc tca agc gtc tgg ggc caa tgt ggt ggc cag aat tgg tcg    48
Ala Ser Cys Ser Ser Val Trp Gly Gln Cys Gly Gly Gln Asn Trp Ser
1               5                   10                  15 ggt ccg act tgc tgt gct tcc gga agc aca tgc gtc tac tcc aac gac    96
Gly Pro Thr Cys Cys Ala Ser Gly Ser Thr Cys Val Tyr Ser Asn Asp
            20                  25                  30 tat tac tcc cag tgt ctt ccc ggc gct gca agc tca agc tcg tcc acg   144
Tyr Tyr Ser Gln Cys Leu Pro Gly Ala Ala Ser Ser Ser Ser Ser Thr
        35                  40                  45 cgc gcc gcg tcg acg act tct cga gta tcc ccc aca aca tcc cgg tcg   192
Arg Ala Ala Ser Thr Thr Ser Arg Val Ser Pro Thr Thr Ser Arg Ser
    50                  55                  60 agc tcc gcg acg cct cca cct ggt tct act act acc aga gta cct cca   240
Ser Ser Ala Thr Pro Pro Pro Gly Ser Thr Thr Thr Arg Val Pro Pro
65                  70                  75                  80 gtc gga tcg gga acc gct acg tat tca                               267
Val Gly Ser Gly Thr Ala Thr Tyr Ser
                85

<210> SEQ ID NO 8
<211> LENGTH: 89
<212> TYPE: PRT
<213> ORGANISM: Artificial Sequence
<220> FEATURE:
<223> OTHER INFORMATION: Synthetic Construct

<400> SEQUENCE: 8

Ala Ser Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser
                85

<210> SEQ ID NO 9
<211> LENGTH: 21
<212> TYPE: DNA
<213> ORGANISM: Artificial Sequence
<220> FEATURE:
<223> OTHER INFORMATION: Oligonucleotide Primer CBH2L

<400> SEQUENCE: 9
gctgaacgtg tcatcggtta c                                            21

<210> SEQ ID NO 10
<211> LENGTH: 23
<212> TYPE: DNA
<213> ORGANISM: Artificial Sequence
<220> FEATURE:
<223> OTHER INFORMATION: Oligonucleotide Primer RSQ3080

<400> SEQUENCE: 10
```

```
gcaacacctg gcaattcctt acc                                              23
```

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide Primer CBH2LPCR

<400> SEQUENCE: 11

```
gctgaacgtg tcatcgttac ttag                                             24
```

<210> SEQ ID NO 12
<211> LENGTH: 356
<212> TYPE: PRT
<213> ORGANISM: Phanerochaete chrysosporium

<400> SEQUENCE: 12

```
Asn Asn Pro Trp Thr Gly Phe Gln Ile Phe Leu Ser Pro Tyr Tyr Ala
1               5                   10                  15

Asn Glu Val Ala Ala Ala Lys Gln Ile Thr Asp Pro Thr Leu Ser
            20                  25                  30

Ser Lys Ala Ala Ser Val Ala Asn Ile Pro Thr Phe Thr Trp Leu Asp
        35                  40                  45

Ser Val Ala Lys Ile Pro Asp Leu Gly Thr Tyr Leu Ala Ser Ala Ser
    50                  55                  60

Ala Leu Gly Lys Ser Thr Gly Thr Lys Gln Leu Val Gln Ile Val Ile
65                  70                  75                  80

Tyr Asp Leu Pro Asp Arg Asp Cys Ala Ala Lys Ala Ser Asn Gly Glu
                85                  90                  95

Phe Ser Ile Ala Asn Asn Gly Gln Ala Asn Tyr Glu Asn Tyr Ile Asp
            100                 105                 110

Gln Ile Val Ala Gln Ile Gln Gln Phe Pro Asp Val Arg Val Val Ala
        115                 120                 125

Val Ile Glu Pro Asp Ser Leu Ala Asn Leu Val Thr Asn Leu Asn Val
    130                 135                 140

Gln Lys Cys Ala Asn Ala Lys Thr Thr Tyr Leu Ala Cys Val Asn Tyr
145                 150                 155                 160

Ala Leu Thr Asn Leu Ala Lys Val Gly Val Tyr Met Tyr Met Asp Ala
                165                 170                 175

Gly His Ala Gly Trp Leu Gly Trp Pro Ala Asn Leu Ser Pro Ala Ala
            180                 185                 190

Gln Leu Phe Thr Gln Val Trp Gln Asn Ala Gly Lys Ser Pro Phe Ile
        195                 200                 205

Lys Gly Leu Ala Thr Asn Val Ala Asn Tyr Asn Ala Leu Gln Ala Ala
    210                 215                 220

Ser Pro Asp Pro Ile Thr Gln Gly Asn Pro Asn Tyr Asp Glu Ile His
225                 230                 235                 240

Tyr Ile Asn Ala Leu Ala Pro Leu Leu Gln Gln Ala Gly Trp Asp Ala
                245                 250                 255

Thr Phe Ile Val Asp Gln Gly Arg Ser Gly Val Gln Asn Ile Arg Gln
            260                 265                 270

Gln Trp Gly Asp Trp Cys Asn Ile Lys Gly Ala Gly Phe Gly Thr Arg
        275                 280                 285

Pro Thr Thr Asn Thr Gly Ser Gln Phe Ile Asp Ser Ile Val Trp Val
    290                 295                 300
```

```
Lys Pro Gly Gly Glu Cys Asp Gly Thr Ser Asn Ser Ser Ser Pro Arg
305                 310                 315                 320

Tyr Asp Ser Thr Cys Ser Leu Pro Asp Ala Ala Gln Pro Ala Pro Glu
            325                 330                 335

Ala Gly Thr Trp Phe Gln Ala Tyr Phe Gln Thr Leu Val Ser Ala Ala
        340                 345                 350

Asn Pro Pro Leu
        355

<210> SEQ ID NO 13
<211> LENGTH: 358
<212> TYPE: PRT
<213> ORGANISM: Artificial Sequence
<220> FEATURE:
<223> OTHER INFORMATION: Chimeric CBH II polypeptide

<400> SEQUENCE: 13

Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
            20                  25                  30

Ala Lys Ala Ala Lys Val Ala Glu Val Pro Ser Phe Met Trp Leu Asp
        35                  40                  45

Thr Leu Asp Lys Thr Pro Leu Met Glu Gln Thr Leu Ala Asp Ile Arg
    50                  55                  60

Thr Ala Asn Lys Asn Gly Ala Asn Pro Pro Tyr Ala Gly Ile Phe Val
65                  70                  75                  80

Val Tyr Asp Leu Pro Asp Arg Asp Cys Ala Ala Ala Ser Asn Gly
                85                  90                  95

Glu Trp Ser Ile Ala Asn Asn Gly Ala Asn Asn Tyr Lys Arg Tyr Ile
            100                 105                 110

Asp Arg Ile Arg Glu Leu Leu Ile Gln Tyr Ser Asp Ile Arg Thr Ile
        115                 120                 125

Leu Val Ile Glu Pro Asp Ser Leu Ala Asn Met Val Thr Asn Met Asn
    130                 135                 140

Val Gln Lys Cys Ser Asn Ala Ala Ser Thr Tyr Lys Glu Leu Thr Val
145                 150                 155                 160

Tyr Ala Leu Lys Gln Leu Asn Leu Pro His Val Ala Met Tyr Met Asp
                165                 170                 175

Ala Gly His Ala Gly Trp Leu Gly Trp Pro Ala Asn Ile Gln Pro Ala
            180                 185                 190

Ala Glu Leu Phe Ala Gln Ile Tyr Arg Asp Ala Gly Arg Pro Ala Ala
        195                 200                 205

Val Arg Gly Leu Ala Thr Asn Val Ala Asn Tyr Asn Ala Trp Ser Val
    210                 215                 220

Ser Ser Pro Pro Pro Tyr Thr Ser Pro Asn Pro Asn Tyr Asp Glu Lys
225                 230                 235                 240

His Tyr Ile Glu Ala Phe Arg Pro Leu Leu Glu Ala Arg Gly Phe Pro
                245                 250                 255

Ala Gln Phe Ile Val Asp Gln Gly Arg Ser Gly Lys Gln Pro Thr Gly
            260                 265                 270

Gln Lys Glu Trp Gly His Trp Cys Asn Ala Ile Gly Thr Gly Phe Gly
        275                 280                 285

Met Arg Pro Thr Ala Asn Thr Gly His Gln Tyr Val Asp Ala Phe Val
    290                 295                 300
```

```
Trp Val Lys Pro Gly Gly Glu Cys Asp Gly Thr Ser Asp Thr Ser Ala
305                 310                 315                 320

Ala Arg Tyr Asp Tyr His Cys Gly Leu Ser Asp Ala Leu Thr Pro Ala
            325                 330                 335

Pro Glu Ala Gly Gln Trp Phe Gln Ala Tyr Phe Glu Gln Leu Leu Ile
            340                 345                 350

Asn Ala Asn Pro Pro Phe
            355

<210> SEQ ID NO 14
<211> LENGTH: 360
<212> TYPE: PRT
<213> ORGANISM: Artificial Sequence
<220> FEATURE:
<223> OTHER INFORMATION: Chimeric CBH II polypeptide

<400> SEQUENCE: 14

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Gln Phe Ile Val Asp Gln Gly Arg Ser Gly Lys Gln Pro
            260                 265                 270

Thr Gly Gln Lys Glu Trp Gly His Trp Cys Asn Ala Ile Gly Thr Gly
        275                 280                 285

Phe Gly Met Arg Pro Thr Ala Asn Thr Gly His Gln Tyr Val Asp Ala
290                 295                 300
```

```
Phe Val Trp Val Lys Pro Gly Gly Glu Cys Asp Gly Thr Ser Asp Thr
305                 310                 315                 320

Ser Ala Ala Arg Tyr Asp Tyr His Cys Gly Leu Ser Asp Ala Leu Thr
                325                 330                 335

Pro Ala Pro Glu Ala Gly Gln Trp Phe Gln Ala Tyr Phe Glu Gln Leu
                340                 345                 350

Leu Ile Asn Ala Asn Pro Pro Phe
                355                 360
```

<210> SEQ ID NO 15
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 15

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ala Ser Ala Val Ala Glu Val Pro Ser Phe Gln Trp Leu
            35                  40                  45

Asp Arg Asn Val Thr Val Asp Thr Leu Leu Val Gln Thr Leu Ser Glu
        50                  55                  60

Ile Arg Glu Ala Asn Gln Ala Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Lys Glu Leu
145                 150                 155                 160

Thr Val Tyr Ala Leu Lys Gln Leu Asn Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Gln Ile Tyr Arg Asp Ala Gly Arg Pro
        195                 200                 205

Ala Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Asn Ala Phe Phe Ile Thr Asp Gln Gly Arg Ser Gly Lys Gln
            260                 265                 270

Pro Thr Gly Gln Gln Gln Trp Gly Asp Trp Cys Asn Val Ile Gly Thr
        275                 280                 285

Gly Phe Gly Ile Arg Pro Ser Ala Asn Thr Gly Asp Ser Leu Leu Asp
290                 295                 300
```

```
Ser Phe Val Trp Val Lys Pro Gly Gly Glu Cys Asp Gly Thr Ser Asp
305                 310                 315                 320

Thr Thr Ala Ala Arg Tyr Asp Tyr His Cys Gly Leu Glu Asp Ala Leu
            325                 330                 335

Lys Pro Ala Pro Glu Ala Gly Gln Trp Phe Asn Glu Tyr Phe Ile Gln
            340                 345                 350

Leu Leu Arg Asn Ala Asn Pro Phe
            355                 360

<210> SEQ ID NO 16
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 16

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Gln Trp Leu Asp
            35                  40                  45

Arg Asn Val Thr Val Asp Thr Leu Leu Val Gln Thr Leu Ser Glu Ile
50                  55                  60

Arg Glu Ala Asn Gln Ala Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
            115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Arg Glu Leu Thr
145                 150                 155                 160

Ile Tyr Ala Leu Lys Gln Leu Asp Leu Pro His Val Ala Met Tyr Met
            165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
            195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
            245                 250                 255

Asp Ala Gln Phe Ile Val Asp Gln Gly Arg Ser Gly Lys Gln Pro Thr
            260                 265                 270

Gly Gln Lys Glu Trp Gly His Trp Cys Asn Ala Ile Gly Thr Gly Phe
            275                 280                 285

Gly Met Arg Pro Thr Ala Asn Thr Gly His Gln Tyr Val Asp Ala Phe
290                 295                 300
```

```
Val Trp Val Lys Pro Gly Gly Glu Cys Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355

<210> SEQ ID NO 17
<211> LENGTH: 357
<212> TYPE: PRT
<213> ORGANISM: Artificial Sequence
<220> FEATURE:
<223> OTHER INFORMATION: Chimeric CBH II Polypeptide

<400> SEQUENCE: 17

Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
            20                  25                  30

Ala Lys Ala Lys Val Ala Glu Val Pro Ser Phe Gln Trp Leu Asp
        35                  40                  45

Arg Asn Val Thr Val Asp Thr Leu Leu Val Gln Thr Leu Ser Glu Ile
50                  55                  60

Arg Glu Ala Asn Gln Ala Gly Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
            100                 105                 110

Arg Ile Arg Glu Ile Leu Ile Ser Phe Ser Asp Val Arg Thr Ile Leu
        115                 120                 125

Val Ile Glu Pro Asp Ser Leu Ala Asn Met Val Thr Asn Met Asn Val
130                 135                 140

Pro Lys Cys Ser Gly Ala Ala Ser Ala Tyr Leu Glu Cys Ile Asn Tyr
145                 150                 155                 160

Ala Val Thr Gln Leu Asn Leu Pro Asn Val Ala Met Tyr Leu Asp Ala
                165                 170                 175

Gly His Ala Gly Trp Leu Gly Trp Pro Ala Asn Gln Asp Pro Ala Ala
            180                 185                 190

Gln Leu Phe Ala Asn Val Tyr Lys Asn Ala Ser Ser Pro Arg Ala Leu
        195                 200                 205

Arg Gly Leu Ala Thr Asn Val Ala Asn Tyr Asn Ala Trp Ser Val Ser
210                 215                 220

Ser Pro Pro Pro Tyr Thr Ser Pro Asn Pro Asn Tyr Asp Glu Lys His
225                 230                 235                 240

Tyr Ile Glu Ala Phe Arg Pro Leu Leu Glu Ala Arg Gly Phe Pro Ala
                245                 250                 255

Gln Phe Ile Val Asp Gln Gly Arg Ser Gly Lys Gln Pro Thr Gly Gln
            260                 265                 270

Lys Glu Trp Gly His Trp Cys Asn Ala Ile Gly Thr Gly Phe Gly Met
        275                 280                 285

Arg Pro Thr Ala Asn Thr Gly His Gln Tyr Val Asp Ala Phe Val Trp
290                 295                 300
```

```
Val Lys Pro Gly Gly Glu Cys Asp Gly Thr Ser Asp Thr Thr Ala Ala
305                 310                 315                 320

Arg Tyr Asp Tyr His Cys Gly Leu Glu Asp Ala Leu Lys Pro Ala Pro
                325                 330                 335

Glu Ala Gly Gln Trp Phe Asn Glu Tyr Phe Ile Gln Leu Leu Arg Asn
            340                 345                 350

Ala Asn Pro Pro Phe
        355

<210> SEQ ID NO 18
<211> LENGTH: 357
<212> TYPE: PRT
<213> ORGANISM: Artificial Sequence
<220> FEATURE:
<223> OTHER INFORMATION: Chimeric CBH II Polypeptide

<400> SEQUENCE: 18

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Gln Trp Leu Asp
        35                  40                  45

Arg Asn Val Thr Val Asp Thr Leu Phe Ser Gly Thr Leu Ala Glu Ile
    50                  55                  60

Arg Ala Ala Asn Gln Arg Gly Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
            100                 105                 110

Arg Ile Arg Glu Leu Leu Ile Gln Tyr Ser Asp Ile Arg Thr Ile Leu
        115                 120                 125

Val Ile Glu Pro Asp Ser Leu Ala Asn Met Val Thr Asn Met Asn Val
130                 135                 140

Gln Lys Cys Ser Asn Ala Ala Ser Thr Tyr Lys Glu Leu Thr Val Tyr
145                 150                 155                 160

Ala Leu Lys Gln Leu Asn Leu Pro His Val Ala Met Tyr Met Asp Ala
                165                 170                 175

Gly His Ala Gly Trp Leu Gly Trp Pro Ala Asn Ile Gln Pro Ala Ala
            180                 185                 190

Glu Leu Phe Ala Gln Ile Tyr Arg Asp Ala Gly Arg Pro Ala Ala Val
        195                 200                 205

Arg Gly Leu Ala Thr Asn Val Ala Asn Tyr Asn Ala Trp Ser Val Ser
210                 215                 220

Ser Pro Pro Pro Tyr Thr Ser Pro Asn Pro Asn Tyr Asp Glu Lys His
225                 230                 235                 240

Tyr Ile Glu Ala Phe Arg Pro Leu Leu Glu Ala Arg Gly Phe Pro Ala
                245                 250                 255

Lys Phe Ile Val Asp Thr Gly Arg Asn Gly Lys Gln Pro Thr Gly Gln
            260                 265                 270

Leu Glu Trp Gly His Trp Cys Asn Val Lys Gly Thr Gly Phe Gly Val
        275                 280                 285

Arg Pro Thr Ala Asn Thr Gly His Glu Leu Val Asp Ala Phe Val Trp
290                 295                 300
```

```
Val Lys Pro Gly Gly Glu Ser Asp Gly Thr Ser Asp Thr Ser Ala Ala
305                 310                 315                 320

Arg Tyr Asp Tyr His Cys Gly Leu Ser Asp Ala Leu Thr Pro Ala Pro
                325                 330                 335

Glu Ala Gly Gln Trp Phe Gln Ala Tyr Phe Glu Gln Leu Leu Ile Asn
            340                 345                 350

Ala Asn Pro Pro Phe
            355

<210> SEQ ID NO 19
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 19

Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
                20                  25                  30

Ala Lys Ala Ala Lys Val Ala Glu Val Pro Ser Phe Gln Trp Leu Asp
            35                  40                  45

Arg Asn Val Thr Val Asp Thr Leu Leu Val Gln Thr Leu Ser Glu Ile
50                  55                  60

Arg Glu Ala Asn Gln Ala Gly Ala Asn Pro Pro Tyr Ala Gly Ile Phe
65                  70                  75                  80

Val Val Tyr Asp Leu Pro Asp Arg Asp Cys Ala Ala Ala Ala Ser Asn
                85                  90                  95

Gly Glu Trp Ser Ile Ala Asn Asn Gly Ala Asn Asn Tyr Lys Arg Tyr
            100                 105                 110

Ile Asp Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Val Ser Ser Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
                245                 250                 255

Pro Ala Gln Phe Ile Val Asp Gln Gly Arg Ser Gly Lys Gln Pro Thr
            260                 265                 270

Gly Gln Lys Glu Trp Gly His Trp Cys Asn Ala Ile Gly Thr Gly Phe
        275                 280                 285

Gly Met Arg Pro Thr Ala Asn Thr Gly His Gln Tyr Val Asp Ala Phe
290                 295                 300
```

```
Val Trp Val Lys Pro Gly Gly Glu Cys Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 20
<211> LENGTH: 356
<212> TYPE: PRT
<213> ORGANISM: Artificial Sequence
<220> FEATURE:
<223> OTHER INFORMATION: Chimeric CBH II Polypeptide

<400> SEQUENCE: 20

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
                20                  25                  30

Thr Ala Ala Ala Val Ala Lys Val Pro Ser Phe Met Trp Leu Asp
            35                  40                  45

Thr Leu Asp Lys Thr Pro Leu Met Glu Gln Thr Leu Ala Asp Ile Arg
50                  55                  60

Thr Ala Asn Lys Asn Gly Gly Asn Tyr Ala Gly Gln Phe Val Val Tyr
65                  70                  75                  80

Asp Leu Pro Asp Arg Asp Cys Ala Ala Leu Ala Ser Asn Gly Glu Tyr
                85                  90                  95

Ser Ile Ala Asp Gly Gly Val Ala Lys Tyr Lys Asn Tyr Ile Asp Arg
            100                 105                 110

Ile Arg Glu Ile Leu Ile Ser Phe Ser Asp Val Arg Thr Ile Leu Val
            115                 120                 125

Ile Glu Pro Asp Ser Leu Ala Asn Met Val Thr Asn Met Asn Val Pro
130                 135                 140

Lys Cys Ser Gly Ala Ala Ser Ala Tyr Leu Glu Cys Ile Asn Tyr Ala
145                 150                 155                 160

Val Thr Gln Leu Asn Leu Pro Asn Val Ala Met Tyr Leu Asp Ala Gly
                165                 170                 175

His Ala Gly Trp Leu Gly Trp Pro Ala Asn Gln Asp Pro Ala Ala Gln
            180                 185                 190

Leu Phe Ala Asn Val Tyr Lys Asn Ala Ser Ser Pro Arg Ala Leu Arg
            195                 200                 205

Gly Leu Ala Thr Asn Val Ala Asn Tyr Asn Gly Trp Asn Ile Thr Ser
210                 215                 220

Pro Pro Ser Tyr Thr Gln Gly Asn Ala Val Tyr Asn Glu Lys Leu Tyr
225                 230                 235                 240

Ile His Ala Ile Gly Pro Leu Leu Ala Asn His Gly Trp Ser Ala Lys
                245                 250                 255

Phe Ile Val Asp Thr Gly Arg Asn Gly Lys Gln Pro Thr Gly Gln Leu
            260                 265                 270

Glu Trp Gly His Trp Cys Asn Val Lys Gly Thr Gly Phe Gly Val Arg
            275                 280                 285

Pro Thr Ala Asn Thr Gly His Glu Leu Val Asp Ala Phe Val Trp Val
290                 295                 300
```

```
Lys Pro Gly Gly Glu Ser Asp Gly Thr Ser Asp Thr Thr Ala Ala Arg
305                 310                 315                 320

Tyr Asp Tyr His Cys Gly Leu Asp Ala Leu Lys Pro Ala Pro Glu
            325                 330                 335

Ala Gly Gln Trp Phe Asn Glu Tyr Phe Ile Gln Leu Leu Arg Asn Ala
        340                 345                 350

Asn Pro Pro Phe
        355

<210> SEQ ID NO 21
<211> LENGTH: 358
<212> TYPE: PRT
<213> ORGANISM: Artificial Sequence
<220> FEATURE:
<223> OTHER INFORMATION: Chimeric CBH II Polypeptide

<400> SEQUENCE: 21

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
50                  55                  60

Ile Arg Ala Ala Asn Gln Arg Gly Gly Asn Tyr Ala Gly Gln Phe Val
65                  70                  75                  80

Val Tyr Asp Leu Pro Asp Arg Asp Cys Ala Ala Leu Ala Ser Asn Gly
            85                  90                  95

Glu Tyr Ser Ile Ala Asp Gly Gly Val Ala Lys Tyr Lys Asn Tyr Ile
            100                 105                 110

Asp Arg Ile Arg Glu Leu Leu Ile Gln Tyr Ser Asp Ile Arg Thr Ile
        115                 120                 125

Leu Val Ile Glu Pro Asp Ser Leu Ala Asn Met Val Thr Asn Met Asn
130                 135                 140

Val Gln Lys Cys Ser Asn Ala Ala Ser Thr Tyr Arg Glu Leu Thr Ile
145                 150                 155                 160

Tyr Ala Leu Lys Gln Leu Asp Leu Pro His Val Ala Met Tyr Met Asp
            165                 170                 175

Ala Gly His Ala Gly Trp Leu Gly Trp Pro Ala Asn Ile Gln Pro Ala
        180                 185                 190

Ala Glu Leu Phe Ala Lys Ile Tyr Glu Asp Ala Gly Lys Pro Arg Ala
    195                 200                 205

Val Arg Gly Leu Ala Thr Asn Val Ala Asn Tyr Asn Ala Trp Ser Val
210                 215                 220

Ser Ser Pro Pro Tyr Thr Ser Pro Asn Pro Asn Tyr Asp Glu Lys
225                 230                 235                 240

His Tyr Ile Glu Ala Phe Arg Pro Leu Leu Glu Ala Arg Gly Phe Pro
            245                 250                 255

Ala Gln Phe Ile Val Asp Gln Gly Arg Ser Gly Lys Gln Pro Thr Gly
        260                 265                 270

Gln Lys Glu Trp Gly His Trp Cys Asn Ala Ile Gly Thr Gly Phe Gly
    275                 280                 285

Met Arg Pro Thr Ala Asn Thr Gly His Gln Tyr Val Asp Ala Phe Val
290                 295                 300
```

```
Trp Val Lys Pro Gly Gly Glu Cys Asp Gly Thr Ser Asp Thr Thr Ala
305                 310                 315                 320

Ala Arg Tyr Asp Tyr His Cys Gly Leu Glu Asp Ala Leu Lys Pro Ala
                325                 330                 335

Pro Glu Ala Gly Gln Trp Phe Asn Glu Tyr Phe Ile Gln Leu Leu Arg
            340                 345                 350

Asn Ala Asn Pro Pro Phe
            355

<210> SEQ ID NO 22
<211> LENGTH: 357
<212> TYPE: PRT
<213> ORGANISM: Artificial Sequence
<220> FEATURE:
<223> OTHER INFORMATION: Chimeric CBH II Polypeptide

<400> SEQUENCE: 22

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
            100                 105                 110

Arg Ile Arg Glu Ile Leu Ile Ser Phe Ser Asp Val Arg Thr Ile Leu
        115                 120                 125

Val Ile Glu Pro Asp Ser Leu Ala Asn Met Val Thr Asn Met Asn Val
130                 135                 140

Pro Lys Cys Ser Gly Ala Ala Ser Thr Tyr Lys Glu Leu Thr Val Tyr
145                 150                 155                 160

Ala Leu Lys Gln Leu Asn Leu Pro His Val Ala Met Tyr Met Asp Ala
                165                 170                 175

Gly His Ala Gly Trp Leu Gly Trp Pro Ala Asn Ile Gln Pro Ala Ala
            180                 185                 190

Glu Leu Phe Ala Gln Ile Tyr Arg Asp Ala Gly Arg Pro Ala Ala Val
        195                 200                 205

Arg Gly Leu Ala Thr Asn Val Ala Asn Tyr Asn Ala Trp Ser Val Ser
210                 215                 220

Ser Pro Pro Pro Tyr Thr Ser Pro Asn Pro Asn Tyr Asp Glu Lys His
225                 230                 235                 240

Tyr Ile Glu Ala Phe Arg Pro Leu Leu Glu Ala Arg Gly Phe Pro Ala
                245                 250                 255

Gln Phe Ile Val Asp Gln Gly Arg Ser Gly Lys Gln Pro Thr Gly Gln
            260                 265                 270

Lys Glu Trp Gly His Trp Cys Asn Ala Ile Gly Thr Gly Phe Gly Met
        275                 280                 285

Arg Pro Thr Ala Asn Thr Gly His Gln Tyr Val Asp Ala Phe Val Trp
290                 295                 300
```

```
Val Lys Pro Gly Gly Glu Cys Asp Gly Thr Ser Asp Thr Thr Ala Ala
305                 310                 315                 320

Arg Tyr Asp Tyr His Cys Gly Leu Glu Asp Ala Leu Lys Pro Ala Pro
                325                 330                 335

Glu Ala Gly Gln Trp Phe Asn Glu Tyr Phe Ile Gln Leu Leu Arg Asn
            340                 345                 350

Ala Asn Pro Pro Phe
            355

<210> SEQ ID NO 23
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 23

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Lys Glu Leu Thr
145                 150                 155                 160

Val Tyr Ala Leu Lys Gln Leu Asn Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Gln Ile Tyr Arg Asp Ala Gly Arg Pro Ala
        195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Ser
305                 310                 315                 320

Ala Ala Arg Tyr Asp Tyr His Cys Gly Leu Ser Asp Ala Leu Thr Pro
                325                 330                 335

Ala Pro Glu Ala Gly Gln Trp Phe Gln Ala Tyr Phe Glu Gln Leu Leu
            340                 345                 350

Ile Asn Ala Asn Pro Pro Phe
            355

<210> SEQ ID NO 24
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 24

Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
            20                  25                  30

Ala Lys Ala Ala Lys Val Ala Glu Val Pro Ser Phe Gln Trp Leu Asp
        35                  40                  45

Arg Asn Val Thr Val Asp Thr Leu Phe Ser Gly Thr Leu Ala Glu Ile
50                  55                  60

Arg Ala Ala Asn Gln Arg Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Lys Glu Leu Thr
145                 150                 155                 160

Val Tyr Ala Leu Lys Gln Leu Asn Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Gln Ile Tyr Arg Asp Ala Gly Arg Pro Ala
        195                 200                 205

Ala Val Arg Gly Leu Ala Thr Asn Val Ala Asn Tyr Asn Ala Trp Ser
210                 215                 220

Val Ser Ser Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
                245                 250                 255

Pro Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
        340                 345                 350

Thr Asn Ala Asn Pro Ser Phe Leu
        355                 360

<210> SEQ ID NO 25
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 25

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
50                  55                  60

Ile Arg Glu Ala Asn Gln Ala Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Tyr Lys Arg
            100                 105                 110

Tyr Ile Asp Arg Ile Arg Glu Leu Leu Ile Gln Tyr Ser Asp Ile Arg
            115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
290                 295                 300
```

```
Phe Val Trp Val Lys Pro Gly Gly Glu Ser Asp Gly Thr Ser Asp Thr
305                 310                 315                 320

Ser Ala Ala Arg Tyr Asp Tyr His Cys Gly Leu Ser Asp Ala Leu Thr
            325                 330                 335

Pro Ala Pro Glu Ala Gly Gln Trp Phe Gln Ala Tyr Phe Glu Gln Leu
        340                 345                 350

Leu Ile Asn Ala Asn Pro Pro Phe
    355                 360
```

<210> SEQ ID NO 26
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 26

```
Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Gln Trp Leu Asp
        35                  40                  45

Arg Asn Val Thr Val Asp Thr Leu Phe Ser Gly Thr Leu Ala Glu Ile
50                  55                  60

Arg Ala Ala Asn Gln Arg Gly Ala Asn Pro Pro Tyr Ala Gly Ile Phe
65                  70                  75                  80

Val Val Tyr Asp Leu Pro Asp Arg Asp Cys Ala Ala Ala Ala Ser Asn
                85                  90                  95

Gly Glu Trp Ser Ile Ala Asn Asn Gly Ala Asn Asn Tyr Lys Arg Tyr
            100                 105                 110

Ile Asp Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Ser
305                 310                 315                 320

Ala Ala Arg Tyr Asp Tyr His Cys Gly Leu Ser Asp Ala Leu Thr Pro
            325                 330                 335

Ala Pro Glu Ala Gly Gln Trp Phe Gln Ala Tyr Phe Glu Gln Leu Leu
        340                 345                 350

Ile Asn Ala Asn Pro Pro Phe
            355

<210> SEQ ID NO 27
<211> LENGTH: 358
<212> TYPE: PRT
<213> ORGANISM: Artificial Sequence
<220> FEATURE:
<223> OTHER INFORMATION: Chimeric CBH II Polypeptide

<400> SEQUENCE: 27

Gly Asn Pro Phe Ser Gly Val Gln Leu Trp Ala Asn Thr Tyr Tyr Ser
1               5                   10                  15

Ser Glu Val His Thr Leu Ala Ile Pro Ser Leu Ser Pro Glu Leu Ala
            20                  25                  30

Ala Lys Ala Ala Lys Val Ala Glu Val Pro Ser Phe Gln Trp Leu Asp
        35                  40                  45

Arg Asn Val Thr Val Asp Thr Leu Phe Ser Gly Thr Leu Ala Glu Ile
50                  55                  60

Arg Ala Ala Asn Gln Arg Gly Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
            100                 105                 110

Arg Ile Arg Glu Ile Leu Ile Ser Phe Ser Asp Val Arg Thr Ile Leu
        115                 120                 125

Val Ile Glu Pro Asp Ser Leu Ala Asn Met Val Thr Asn Met Asn Val
130                 135                 140

Pro Lys Cys Ser Gly Ala Ala Ser Thr Tyr Lys Glu Leu Thr Val Tyr
145                 150                 155                 160

Ala Leu Lys Gln Leu Asn Leu Pro His Val Ala Met Tyr Met Asp Ala
                165                 170                 175

Gly His Ala Gly Trp Leu Gly Trp Pro Ala Asn Ile Gln Pro Ala Ala
            180                 185                 190

Glu Leu Phe Ala Gln Ile Tyr Arg Asp Ala Gly Arg Pro Ala Ala Val
        195                 200                 205

Arg Gly Leu Ala Thr Asn Val Ala Asn Tyr Asn Ala Trp Ser Ile Ala
210                 215                 220

Ser Pro Pro Ser Tyr Thr Ser Pro Asn Pro Asn Tyr Asp Glu Lys His
225                 230                 235                 240

Tyr Ile Glu Ala Phe Ala Pro Leu Leu Arg Asn Gln Gly Phe Asp Ala
                245                 250                 255

Lys Phe Ile Val Asp Thr Gly Arg Asn Gly Lys Gln Pro Thr Gly Gln
            260                 265                 270

Leu Glu Trp Gly His Trp Cys Asn Val Lys Gly Thr Gly Phe Gly Val
        275                 280                 285

Arg Pro Thr Ala Asn Thr Gly His Glu Leu Val Asp Ala Phe Val Trp
290                 295                 300
```

```
Val Lys Pro Gly Gly Glu Ser Asp Gly Thr Ser Asp Ser Ser Ala Pro
305                 310                 315                 320

Arg Phe Asp Ser His Cys Ala Leu Pro Asp Ala Leu Gln Pro Ala Pro
                325                 330                 335

Gln Ala Gly Ala Trp Phe Gln Ala Tyr Phe Val Gln Leu Leu Thr Asn
                340                 345                 350

Ala Asn Pro Ser Phe Leu
                355

<210> SEQ ID NO 28
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 28

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
            35                  40                  45

Asp Arg Asn Val Thr Val Asp Thr Leu Phe Ser Gly Thr Leu Ala Glu
        50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Leu Leu Ile Gln Tyr Ser Asp Ile Arg
        115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Thr Tyr Lys Glu Leu
145                 150                 155                 160

Thr Val Tyr Ala Leu Lys Gln Leu Asn Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Gln Ile Tyr Arg Asp Ala Gly Arg Pro
        195                 200                 205

Ala Ala Val Arg Gly Leu Ala Thr Asn Val Ala Asn Tyr Asn Gly Trp
210                 215                 220

Asn Ile Thr Ser Pro Pro Ser Tyr Thr Gln Gly Asn Ala Val Tyr Asn
225                 230                 235                 240

Glu Lys Leu Tyr Ile His Ala Ile Gly Pro Leu Leu Ala Asn His Gly
                245                 250                 255

Trp Ser Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
        340                 345                 350

Leu Thr Asn Ala Asn Pro Ser Phe Leu
    355                 360

<210> SEQ ID NO 29
<211> LENGTH: 357
<212> TYPE: PRT
<213> ORGANISM: Artificial Sequence
<220> FEATURE:
<223> OTHER INFORMATION: Chimeric CBH II Polypeptide

<400> SEQUENCE: 29

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Met Trp Leu Asp
        35                  40                  45

Thr Leu Asp Lys Thr Pro Leu Met Glu Gln Thr Leu Ala Asp Ile Arg
50                  55                  60

Thr Ala Asn Lys Asn Gly Gly Asn Tyr Ala Gly Gln Phe Val Val Tyr
65                  70                  75                  80

Asp Leu Pro Asp Arg Asp Cys Ala Ala Leu Ala Ser Asn Gly Glu Tyr
            85                  90                  95

Ser Ile Ala Asp Gly Gly Val Ala Lys Tyr Lys Asn Tyr Ile Asp Arg
        100                 105                 110

Ile Arg Glu Leu Leu Ile Gln Tyr Ser Asp Ile Arg Thr Ile Leu Val
    115                 120                 125

Ile Glu Pro Asp Ser Leu Ala Asn Met Val Thr Asn Met Asn Val Gln
130                 135                 140

Lys Cys Ser Asn Ala Ala Ser Ala Tyr Leu Glu Cys Ile Asn Tyr Ala
145                 150                 155                 160

Val Thr Gln Leu Asn Leu Pro Asn Val Ala Met Tyr Leu Asp Ala Gly
            165                 170                 175

His Ala Gly Trp Leu Gly Trp Pro Ala Asn Gln Asp Pro Ala Ala Gln
        180                 185                 190

Leu Phe Ala Asn Val Tyr Lys Asn Ala Ser Ser Pro Arg Ala Leu Arg
    195                 200                 205

Gly Leu Ala Thr Asn Val Ala Asn Tyr Asn Ala Trp Ser Val Ser Ser
210                 215                 220

Pro Pro Pro Tyr Thr Ser Pro Asn Pro Asn Tyr Asp Glu Lys His Tyr
225                 230                 235                 240

Ile Glu Ala Phe Arg Pro Leu Leu Glu Ala Arg Gly Phe Pro Ala Lys
            245                 250                 255

Phe Ile Val Asp Thr Gly Arg Asn Gly Lys Gln Pro Thr Gly Gln Leu
        260                 265                 270

Glu Trp Gly His Trp Cys Asn Val Lys Gly Thr Gly Phe Gly Val Arg
    275                 280                 285

Pro Thr Ala Asn Thr Gly His Glu Leu Val Asp Ala Phe Val Trp Val
290                 295                 300
```

```
Lys Pro Gly Gly Glu Ser Asp Gly Thr Ser Asp Ser Ser Ala Pro Arg
305                 310                 315                 320

Phe Asp Ser His Cys Ala Leu Pro Asp Ala Leu Gln Pro Ala Pro Gln
            325                 330                 335

Ala Gly Ala Trp Phe Gln Ala Tyr Phe Val Gln Leu Leu Thr Asn Ala
        340                 345                 350

Asn Pro Ser Phe Leu
        355

<210> SEQ ID NO 30
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 30

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Lys Glu Leu
145                 150                 155                 160

Thr Val Tyr Ala Leu Lys Gln Leu Asn Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Gln Ile Tyr Arg Asp Ala Gly Arg Pro
        195                 200                 205

Ala Ala Val Arg Gly Leu Ala Thr Asn Val Ala Asn Tyr Asn Ala Trp
    210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
        340                 345                 350

Leu Thr Asn Ala Asn Pro Ser Phe Leu
    355                 360
```

<210> SEQ ID NO 31
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 31

```
Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Gln Trp Leu Asp
        35                  40                  45

Arg Asn Val Thr Val Asp Thr Leu Leu Val Gln Thr Leu Ser Glu Ile
50                  55                  60

Arg Glu Ala Asn Gln Ala Gly Ala Asn Pro Pro Tyr Ala Gly Ile Phe
65                  70                  75                  80

Val Val Tyr Asp Leu Pro Asp Arg Asp Cys Ala Ala Ala Ala Ser Asn
                85                  90                  95

Gly Glu Trp Ser Ile Ala Asn Asn Gly Ala Asn Asn Tyr Lys Arg Tyr
            100                 105                 110

Ile Asp Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Lys Glu Leu Thr
145                 150                 155                 160

Val Tyr Ala Leu Lys Gln Leu Asn Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Gln Ile Tyr Arg Asp Ala Gly Arg Pro Ala
        195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
                325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355

<210> SEQ ID NO 32
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 32

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
                20                  25                  30

Thr Ala Ala Ala Val Ala Lys Val Pro Ser Phe Gln Trp Leu Asp
            35                  40                  45

Arg Asn Val Thr Val Asp Thr Leu Leu Val Gln Thr Leu Ser Glu Ile
50                  55                  60

Arg Glu Ala Asn Gln Ala Gly Ala Asn Pro Pro Tyr Ala Gly Ile Phe
65                  70                  75                  80

Val Val Tyr Asp Leu Pro Asp Arg Asp Cys Ala Ala Ala Ser Asn
                85                  90                  95

Gly Glu Trp Ser Ile Ala Asn Asn Gly Ala Asn Asn Tyr Lys Arg Tyr
                100                 105                 110

Ile Asp Arg Ile Arg Glu Ile Leu Ile Ser Phe Ser Asp Val Arg Thr
            115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Val Ser Ser Pro Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
                245                 250                 255

Pro Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355
```

<210> SEQ ID NO 33
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 33

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Pro Tyr Ala Gly Ile Phe
65                  70                  75                  80

Val Val Tyr Asp Leu Pro Asp Arg Asp Cys Ala Ala Ala Ser Asn
            85                  90                  95

Gly Glu Trp Ser Ile Ala Asn Asn Gly Ala Asn Asn Tyr Lys Arg Tyr
            100                 105                 110

Ile Asp Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Ala Tyr Leu Glu Cys Ile
145                 150                 155                 160

Asn Tyr Ala Val Thr Gln Leu Asn Leu Pro Asn Val Ala Met Tyr Leu
            165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
        195                 200                 205

Ala Leu Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
            245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355

<210> SEQ ID NO 34
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 34

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
    210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 35
<211> LENGTH: 358
<212> TYPE: PRT
<213> ORGANISM: Artificial Sequence
<220> FEATURE:
<223> OTHER INFORMATION: Chimeric CBH II Polypeptide

<400> SEQUENCE: 35

Gly Asn Pro Phe Val Gly Val Thr Pro Trp Ala Asn Ala Tyr Tyr Ala
1               5                   10                  15

Ser Glu Val Ser Ser Leu Ala Ile Pro Ser Leu Thr Gly Ala Met Ala
            20                  25                  30

Thr Ala Ala Ala Val Ala Lys Val Pro Ser Phe Met Trp Leu Asp
        35                  40                  45

Thr Leu Asp Lys Thr Pro Leu Met Glu Gln Thr Leu Ala Asp Ile Arg
    50                  55                  60

Thr Ala Asn Lys Asn Gly Ala Asn Pro Pro Tyr Ala Gly Ile Phe Val
65                  70                  75                  80

Val Tyr Asp Leu Pro Asp Arg Asp Cys Ala Ala Ala Ser Asn Gly
                85                  90                  95

Glu Trp Ser Ile Ala Asn Asn Gly Ala Asn Tyr Lys Arg Tyr Ile
                100                 105                 110

Asp Arg Ile Arg Glu Ile Leu Ile Ser Phe Ser Asp Val Arg Thr Ile
            115                 120                 125

Leu Val Ile Glu Pro Asp Ser Leu Ala Asn Met Val Thr Asn Met Asn
    130                 135                 140

Val Pro Lys Cys Ser Gly Ala Ala Ser Thr Tyr Arg Glu Leu Thr Ile
145                 150                 155                 160

Tyr Ala Leu Lys Gln Leu Asp Leu Pro His Val Ala Met Tyr Met Asp
                165                 170                 175

Ala Gly His Ala Gly Trp Leu Gly Trp Pro Ala Asn Ile Gln Pro Ala
            180                 185                 190

Ala Glu Leu Phe Ala Lys Ile Tyr Glu Asp Ala Gly Lys Pro Arg Ala
        195                 200                 205

Val Arg Gly Leu Ala Thr Asn Val Ala Asn Tyr Asn Ala Trp Ser Ile
    210                 215                 220

Ala Ser Pro Pro Ser Tyr Thr Ser Pro Asn Pro Asn Tyr Asp Glu Lys
225                 230                 235                 240

His Tyr Ile Glu Ala Phe Ala Pro Leu Leu Arg Asn Gln Gly Phe Asp
                245                 250                 255

Ala Lys Phe Ile Val Asp Thr Gly Arg Asn Gly Lys Gln Pro Thr Gly
            260                 265                 270

Gln Leu Glu Trp Gly His Trp Cys Asn Val Lys Gly Thr Gly Phe Gly
        275                 280                 285

Val Arg Pro Thr Ala Asn Thr Gly His Glu Leu Val Asp Ala Phe Val
    290                 295                 300
```

Trp Val Lys Pro Gly Gly Glu Ser Asp Gly Thr Ser Asp Thr Thr Ala
305                 310                 315                 320

Ala Arg Tyr Asp Tyr His Cys Gly Leu Glu Asp Ala Leu Lys Pro Ala
        325                 330                 335

Pro Glu Ala Gly Gln Trp Phe Asn Glu Tyr Phe Ile Gln Leu Leu Arg
            340                 345                 350

Asn Ala Asn Pro Pro Phe
            355

<210> SEQ ID NO 36
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 36

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
            165                 170                 175

Asp Ala Gly His Ala Gly Trp Leu Gly Trp Pro Ala Asn Ile Gln Pro
        180                 185                 190

Ala Ala Glu Leu Phe Ala Lys Ile Tyr Glu Asp Ala Gly Lys Pro Arg
    195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
            245                 250                 255

Asp Ala Lys Phe Ile Val Asp Thr Gly Arg Asn Gly Lys Gln Pro Thr
        260                 265                 270

Gly Gln Leu Glu Trp Gly His Trp Cys Asn Val Lys Gly Thr Gly Phe
    275                 280                 285

Gly Val Arg Pro Thr Ala Asn Thr Gly His Glu Leu Val Asp Ala Phe
290                 295                 300

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360
```

<210> SEQ ID NO 37
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 37

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Ile Leu Ile Ser Phe Ser Asp Val Arg Thr
            115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Ala Tyr Leu Glu Cys Ile
145                 150                 155                 160

Asn Tyr Ala Val Thr Gln Leu Asn Leu Pro Asn Val Ala Met Tyr Leu
                165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
            195                 200                 205

Ala Leu Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
            275                 280                 285

Gly Val Arg Pro Thr Ala Asn Thr Gly His Glu Leu Val Asp Ala Phe
290                 295                 300
```

Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 38
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 38

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
            115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Arg Glu Leu Thr
145                 150                 155                 160

Ile Tyr Ala Leu Lys Gln Leu Asp Leu Pro His Val Ala Met Tyr Met
            165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
            195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
            245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
            275                 280                 285

Gly Val Arg Pro Thr Ala Asn Thr Gly His Glu Leu Val Asp Ala Phe
290                 295                 300

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355
```

<210> SEQ ID NO 39
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 39

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
            85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
            115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Arg Glu Leu Thr
145                 150                 155                 160

Ile Tyr Ala Leu Lys Gln Leu Asp Leu Pro His Val Ala Met Tyr Met
            165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
            195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
            245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
            275                 280                 285

Gly Val Arg Pro Thr Ala Asn Thr Gly His Glu Leu Val Asp Ala Phe
290                 295                 300
```

Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 40
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 40

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Pro Tyr Ala Gly Ile Phe
65                  70                  75                  80

Val Val Tyr Asp Leu Pro Asp Arg Asp Cys Ala Ala Ala Ser Asn
                85                  90                  95

Gly Glu Trp Ser Ile Ala Asn Asn Gly Ala Asn Asn Tyr Lys Arg Tyr
                100                 105                 110

Ile Asp Arg Ile Arg Glu Leu Leu Ile Gln Tyr Ser Asp Ile Arg Thr
            115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Ala Tyr Leu Glu Cys Ile
145                 150                 155                 160

Asn Tyr Ala Val Thr Gln Leu Asn Leu Pro Asn Val Ala Met Tyr Leu
                165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
            195                 200                 205

Ala Leu Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
            275                 280                 285

Gly Val Arg Pro Thr Ala Asn Thr Gly His Glu Leu Val Asp Ala Phe
290                 295                 300

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 41
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 41

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Val Ser Ser Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
                245                 250                 255

Pro Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
            340                 345                 350

Arg Asn Ala Asn Pro Pro Phe
            355
```

<210> SEQ ID NO 42
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 42

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Pro Tyr Ala Gly Ile Phe
65                  70                  75                  80

Val Val Tyr Asp Leu Pro Asp Arg Asp Cys Ala Ala Ala Ala Ser Asn
                85                  90                  95

Gly Glu Trp Ser Ile Ala Asn Asn Gly Ala Asn Asn Tyr Lys Arg Tyr
            100                 105                 110

Ile Asp Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 43
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 43

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Leu Leu Ile Gln Tyr Ser Asp Ile Arg
        115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
    210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

-continued

```
Phe Val Trp Val Lys Pro Gly Gly Glu Ser Asp Gly Thr Ser Asp Thr
305                 310                 315                 320

Thr Ala Ala Arg Tyr Asp Tyr His Cys Gly Leu Glu Asp Ala Leu Lys
            325                 330                 335

Pro Ala Pro Glu Ala Gly Gln Trp Phe Asn Glu Tyr Phe Ile Gln Leu
        340                 345                 350

Leu Arg Asn Ala Asn Pro Pro Phe
        355                 360

<210> SEQ ID NO 44
<211> LENGTH: 359
<212> TYPE: PRT
<213> ORGANISM: Artificial Sequence
<220> FEATURE:
<223> OTHER INFORMATION: Chimeric CBH II Polypeptide

<400> SEQUENCE: 44

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Ala Tyr Leu Glu Cys Ile
145                 150                 155                 160

Asn Tyr Ala Val Thr Gln Leu Asn Leu Pro Asn Val Ala Met Tyr Leu
                165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
        195                 200                 205

Ala Leu Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

-continued

```
Val Trp Val Lys Pro Gly Gly Glu Ser Asp Gly Thr Ser Asp Thr Thr
305                 310                 315                 320

Ala Ala Arg Tyr Asp Tyr His Cys Gly Leu Glu Asp Ala Leu Lys Pro
            325                 330                 335

Ala Pro Glu Ala Gly Gln Trp Phe Asn Glu Tyr Phe Ile Gln Leu Leu
        340                 345                 350

Arg Asn Ala Asn Pro Pro Phe
        355

<210> SEQ ID NO 45
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 45

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Ala Tyr Leu Glu Cys Ile
145                 150                 155                 160

Asn Tyr Ala Val Thr Gln Leu Asn Leu Pro Asn Val Ala Met Tyr Leu
                165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
        195                 200                 205

Ala Leu Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 46
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 46

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
            35                  40                  45

Asp Arg Asn Val Thr Val Asp Thr Leu Phe Ser Gly Thr Leu Ala Glu
        50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Leu Leu Ile Gln Tyr Ser Asp Ile Arg
        115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 47
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 47

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ser Asn
            85                  90                  95

Gly Glu Trp Ala Ile Ala Asn Asn Gly Val Asn Asn Tyr Lys Ala Tyr
            100                 105                 110

Ile Asn Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Ala Tyr Leu Glu Cys Ile
145                 150                 155                 160

Asn Tyr Ala Val Thr Gln Leu Asn Leu Pro Asn Val Ala Met Tyr Leu
            165                 170                 175

Asp Ala Gly His Ala Gly Trp Leu Gly Trp Pro Ala Asn Gln Asp Pro
            180                 185                 190

Ala Ala Gln Leu Phe Ala Asn Val Tyr Lys Asn Ala Ser Ser Pro Arg
        195                 200                 205

Ala Leu Arg Gly Leu Ala Thr Asn Val Ala Asn Tyr Asn Ala Trp Ser
210                 215                 220

Val Ser Ser Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
            245                 250                 255

Pro Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360
```

<210> SEQ ID NO 48
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 48

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Thr Ile Arg Gln Ile Val Val Glu Tyr Ser Asp Ile Arg
        115                 120                 125

Thr Leu Leu Val Ile Glu Pro Asp Ser Leu Ala Asn Leu Val Thr Asn
130                 135                 140

Leu Gly Thr Pro Lys Cys Ala Asn Ala Gln Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
                325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 49
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 49

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Leu Leu Ile Gln Tyr Ser Asp Ile Arg
        115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360
```

<210> SEQ ID NO 50
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 50

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Pro Tyr Ala Gly Ile Phe
65                  70                  75                  80

Val Val Tyr Asp Leu Pro Asp Arg Asp Cys Ala Ala Ala Ala Ser Asn
                85                  90                  95

Gly Glu Trp Ser Ile Ala Asn Asn Gly Ala Asn Asn Tyr Lys Arg Tyr
            100                 105                 110

Ile Asp Arg Ile Arg Glu Leu Leu Ile Gln Tyr Ser Asp Ile Arg Thr
        115                 120                 125

Ile Leu Val Ile Glu Pro Asp Ser Leu Ala Asn Met Val Thr Asn Met
130                 135                 140

Asn Val Gln Lys Cys Ser Asn Ala Ala Ser Thr Tyr Arg Glu Leu Thr
145                 150                 155                 160

Ile Tyr Ala Leu Lys Gln Leu Asp Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Lys Ile Tyr Glu Asp Ala Gly Lys Pro Arg
        195                 200                 205

Ala Val Arg Gly Leu Ala Thr Asn Val Ala Asn Tyr Asn Ala Trp Ser
210                 215                 220

Ile Ala Ser Pro Pro Ser Tyr Thr Ser Pro Asn Pro Asn Tyr Asp Glu
225                 230                 235                 240

Lys His Tyr Ile Glu Ala Phe Ala Pro Leu Leu Arg Asn Gln Gly Phe
                245                 250                 255

Asp Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

```
Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 51
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 51

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Tyr Lys Arg
            100                 105                 110

Tyr Ile Asp Arg Ile Arg Glu Ile Leu Ile Ser Phe Ser Asp Val Arg
            115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
            195                 200                 205

Arg Ala Leu Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
            275                 280                 285

Phe Gly Val Arg Pro Thr Ala Asn Thr Gly His Glu Leu Val Asp Ala
        290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360
```

<210> SEQ ID NO 52
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 52

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Lys Glu Leu
145                 150                 155                 160

Thr Val Tyr Ala Leu Lys Gln Leu Asn Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Gln Ile Tyr Arg Asp Ala Gly Arg Pro
        195                 200                 205

Ala Ala Val Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 53
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 53

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Lys Glu Leu
145                 150                 155                 160

Thr Val Tyr Ala Leu Lys Gln Leu Asn Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Gln Ile Tyr Arg Asp Ala Gly Arg Pro
        195                 200                 205

Ala Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 54
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 54

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
    210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 55
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 55

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Ala Asn Pro Gln Tyr Ala Ala Gln Ile
65                  70                  75                  80

Val Val Tyr Asp Leu Pro Asp Arg Asp Cys Ala Ala Ala Ala Ser Asn
                85                  90                  95

Gly Glu Trp Ala Ile Ala Asn Asn Gly Val Asn Asn Tyr Lys Ala Tyr
            100                 105                 110

Ile Asn Arg Ile Arg Glu Ile Leu Ile Ser Phe Ser Asp Val Arg Thr
        115                 120                 125

Ile Leu Val Ile Glu Pro Asp Ser Leu Ala Asn Met Val Thr Asn Met
130                 135                 140

Asn Val Pro Lys Cys Ser Gly Ala Ala Ser Thr Tyr Lys Glu Leu Thr
145                 150                 155                 160

Val Tyr Ala Leu Lys Gln Leu Asn Leu Pro His Val Ala Met Tyr Met
                165                 170                 175

Asp Ala Gly His Ala Gly Trp Leu Gly Trp Pro Ala Asn Ile Gln Pro
            180                 185                 190

Ala Ala Glu Leu Phe Ala Gln Ile Tyr Arg Asp Ala Gly Arg Pro Ala
        195                 200                 205

Ala Val Arg Gly Leu Ala Thr Asn Val Ala Asn Tyr Asn Ala Trp Ser
210                 215                 220

Val Ser Ser Pro Pro Tyr Thr Ser Pro Asn Pro Asn Tyr Asp Glu
225                 230                 235                 240

Lys His Tyr Ile Glu Ala Phe Arg Pro Leu Leu Glu Ala Arg Gly Phe
                245                 250                 255

Pro Ala Lys Phe Ile Val Asp Thr Gly Arg Asn Gly Lys Gln Pro Thr
            260                 265                 270

Gly Gln Leu Glu Trp Gly His Trp Cys Asn Val Lys Gly Thr Gly Phe
        275                 280                 285

Gly Val Arg Pro Thr Ala Asn Thr Gly His Glu Leu Val Asp Ala Phe
290                 295                 300
```

Val Trp Val Lys Pro Gly Gly Glu Ser Asp Gly Thr Ser Asp Ser Ser
305                 310                 315                 320

Ala Pro Arg Phe Asp Ser His Cys Ala Leu Pro Asp Ala Leu Gln Pro
            325                 330                 335

Ala Pro Gln Ala Gly Ala Trp Phe Gln Ala Tyr Phe Val Gln Leu Leu
            340                 345                 350

Thr Asn Ala Asn Pro Ser Phe Leu
            355                 360

<210> SEQ ID NO 56
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 56

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Leu Leu Ile Gln Tyr Ser Asp Ile Arg
        115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Ala Tyr Leu Glu Cys
145                 150                 155                 160

Ile Asn Tyr Ala Val Thr Gln Leu Asn Leu Pro Asn Val Ala Met Tyr
                165                 170                 175

Leu Asp Ala Gly His Ala Gly Trp Leu Gly Trp Pro Ala Asn Gln Asp
            180                 185                 190

Pro Ala Ala Gln Leu Phe Ala Asn Val Tyr Lys Asn Ala Ser Ser Pro
        195                 200                 205

Arg Ala Leu Arg Gly Leu Ala Thr Asn Val Ala Asn Tyr Asn Ala Trp
    210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360
```

<210> SEQ ID NO 57
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 57

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Leu Val Gln Thr Leu Ser Glu
    50                  55                  60

Ile Arg Glu Ala Asn Gln Ala Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Gly Thr Ser Asp Ser
305                 310                 315                 320

Ser Ala Pro Arg Phe Asp Ser His Cys Ala Leu Pro Asp Ala Leu Gln
                325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360
```

<210> SEQ ID NO 58
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 58

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
            35                  40                  45

Asp Arg Asn Val Thr Val Asp Thr Leu Phe Ser Gly Thr Leu Ala Glu
50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Leu Leu Ile Gln Tyr Ser Asp Ile Arg
            115                 120                 125

Thr Ile Leu Val Ile Glu Pro Asp Ser Leu Ala Asn Met Val Thr Asn
130                 135                 140

Met Asn Val Gln Lys Cys Ser Asn Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
            195                 200                 205

Arg Ala Val Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
            275                 280                 285

Phe Gly Val Arg Pro Thr Ala Asn Thr Gly His Glu Leu Val Asp Ala
            290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
                325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
                355                 360

<210> SEQ ID NO 59
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 59

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
            35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Gln Tyr Ala Ala Gln
65                  70                  75                  80

Ile Val Val Tyr Asp Leu Pro Asp Arg Asp Cys Ala Ala Ala Ala Ser
                85                  90                  95

Asn Gly Glu Trp Ala Ile Ala Asn Asn Gly Val Asn Asn Tyr Lys Ala
            100                 105                 110

Tyr Ile Asn Arg Ile Arg Glu Ile Leu Ile Ser Phe Ser Asp Val Arg
    115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
    195                 200                 205

Arg Ala Val Arg Gly Leu Ala Thr Asn Val Ala Asn Tyr Asn Ala Trp
210                 215                 220

Ser Val Ser Ser Pro Pro Tyr Thr Ser Pro Asn Pro Asn Tyr Asp
225                 230                 235                 240

Glu Lys His Tyr Ile Glu Ala Phe Arg Pro Leu Leu Glu Ala Arg Gly
                245                 250                 255

Phe Pro Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
    275                 280                 285

Phe Gly Val Arg Pro Thr Ala Asn Thr Gly His Glu Leu Val Asp Ala
290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
        340                 345                 350

Leu Thr Asn Ala Asn Pro Ser Phe Leu
    355                 360
```

<210> SEQ ID NO 60
<211> LENGTH: 358
<212> TYPE: PRT
<213> ORGANISM: Artificial Sequence
<220> FEATURE:
<223> OTHER INFORMATION: Chimeric CBH II Polypeptide

<400> SEQUENCE: 60

```
Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Met Trp Leu
        35                  40                  45

Asp Thr Leu Asp Lys Thr Pro Leu Met Glu Gln Thr Leu Ala Asp Ile
50                  55                  60

Arg Thr Ala Asn Lys Asn Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
            100                 105                 110

Thr Ile Arg Gln Ile Val Val Glu Tyr Ser Asp Ile Arg Thr Leu Leu
        115                 120                 125

Val Ile Glu Pro Asp Ser Leu Ala Asn Leu Val Thr Asn Leu Gly Thr
130                 135                 140

Pro Lys Cys Ala Asn Ala Gln Ser Ala Tyr Leu Glu Cys Ile Asn Tyr
145                 150                 155                 160

Ala Val Thr Gln Leu Asn Leu Pro Asn Val Ala Met Tyr Leu Asp Ala
                165                 170                 175

Gly His Ala Gly Trp Leu Gly Trp Pro Ala Asn Gln Asp Pro Ala Ala
            180                 185                 190

Gln Leu Phe Ala Asn Val Tyr Lys Asn Ala Ser Ser Pro Arg Ala Leu
        195                 200                 205

Arg Gly Leu Ala Thr Asn Val Ala Asn Tyr Asn Ala Trp Ser Val Ser
210                 215                 220

Ser Pro Pro Pro Tyr Thr Ser Pro Asn Pro Asn Tyr Asp Glu Lys His
225                 230                 235                 240

Tyr Ile Glu Ala Phe Arg Pro Leu Leu Glu Ala Arg Gly Phe Pro Ala
                245                 250                 255

Lys Phe Ile Val Asp Thr Gly Arg Asn Gly Lys Gln Pro Thr Gly Gln
            260                 265                 270

Leu Glu Trp Gly His Trp Cys Asn Val Lys Gly Thr Gly Phe Gly Val
        275                 280                 285

Arg Pro Thr Ala Asn Thr Gly His Glu Leu Val Asp Ala Phe Val Trp
290                 295                 300
```

```
Val Lys Pro Gly Gly Glu Ser Asp Gly Thr Ser Asp Ser Ser Ala Pro
305                 310                 315                 320

Arg Phe Asp Ser His Cys Ala Leu Pro Asp Ala Leu Gln Pro Ala Pro
                325                 330                 335

Gln Ala Gly Ala Trp Phe Gln Ala Tyr Phe Val Gln Leu Leu Thr Asn
                340                 345                 350

Ala Asn Pro Ser Phe Leu
            355

<210> SEQ ID NO 61
<211> LENGTH: 358
<212> TYPE: PRT
<213> ORGANISM: Artificial Sequence
<220> FEATURE:
<223> OTHER INFORMATION: Chimeric CBH II Polypeptide

<400> SEQUENCE: 61

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Met Trp Leu
            35                  40                  45

Asp Thr Leu Asp Lys Thr Pro Leu Met Glu Gln Thr Leu Ala Asp Ile
    50                  55                  60

Arg Thr Ala Asn Lys Asn Gly Asn Tyr Ala Gly Gln Phe Val Val
65                  70                  75                  80

Tyr Asp Leu Pro Asp Arg Asp Cys Ala Ala Leu Ala Ser Asn Gly Glu
                85                  90                  95

Tyr Ser Ile Ala Asp Gly Gly Val Ala Lys Tyr Lys Asn Tyr Ile Asp
                100                 105                 110

Thr Ile Arg Gln Ile Val Val Glu Tyr Ser Asp Ile Arg Thr Leu Leu
            115                 120                 125

Val Ile Glu Pro Asp Ser Leu Ala Asn Leu Val Thr Asn Leu Gly Thr
130                 135                 140

Pro Lys Cys Ala Asn Ala Gln Ser Ala Tyr Leu Glu Cys Ile Asn Tyr
145                 150                 155                 160

Ala Val Thr Gln Leu Asn Leu Pro Asn Val Ala Met Tyr Leu Asp Ala
                165                 170                 175

Gly His Ala Gly Trp Leu Gly Trp Pro Ala Asn Gln Asp Pro Ala Ala
                180                 185                 190

Gln Leu Phe Ala Asn Val Tyr Lys Asn Ala Ser Ser Pro Arg Ala Leu
            195                 200                 205

Arg Gly Leu Ala Thr Asn Val Ala Asn Tyr Asn Ala Trp Ser Ile Ala
210                 215                 220

Ser Pro Pro Ser Tyr Thr Ser Pro Asn Pro Asn Tyr Asp Glu Lys His
225                 230                 235                 240

Tyr Ile Glu Ala Phe Ala Pro Leu Leu Arg Asn Gln Gly Phe Asp Ala
                245                 250                 255

Lys Phe Ile Val Asp Thr Gly Arg Asn Gly Lys Gln Pro Thr Gly Gln
                260                 265                 270

Leu Glu Trp Gly His Trp Cys Asn Val Lys Gly Thr Gly Phe Gly Val
            275                 280                 285

Arg Pro Thr Ala Asn Thr Gly His Glu Leu Val Asp Ala Phe Val Trp
290                 295                 300
```

```
Val Lys Pro Gly Gly Glu Ser Asp Gly Thr Ser Asp Ser Ser Ala Pro
305                 310                 315                 320

Arg Phe Asp Ser His Cys Ala Leu Pro Asp Ala Leu Gln Pro Ala Pro
                325                 330                 335

Gln Ala Gly Ala Trp Phe Gln Ala Tyr Phe Val Gln Leu Leu Thr Asn
            340                 345                 350

Ala Asn Pro Ser Phe Leu
            355

<210> SEQ ID NO 62
<211> LENGTH: 361
<212> TYPE: PRT
<213> ORGANISM: Artificial Sequence
<220> FEATURE:
<223> OTHER INFORMATION: Chimeric CBH II Polypeptide

<400> SEQUENCE: 62

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
            20                  25                  30

Arg Ala Ala Ser Ala Val Ala Glu Val Pro Ser Phe Gln Trp Leu
        35                  40                  45

Asp Arg Asn Val Thr Val Asp Thr Leu Phe Ser Gly Thr Leu Ala Glu
    50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Asn Tyr Lys Arg
            100                 105                 110

Tyr Ile Asp Arg Ile Arg Glu Ile Leu Ile Ser Phe Ser Asp Val Arg
        115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
        195                 200                 205

Arg Ala Val Arg Gly Leu Ala Thr Asn Val Ala Asn Tyr Asn Ala Trp
    210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
        275                 280                 285

Phe Gly Val Arg Pro Thr Ala Asn Thr Gly His Glu Leu Val Asp Ala
    290                 295                 300
```

```
Phe Val Trp Val Lys Pro Gly Gly Glu Ser Asp Gly Thr Ser Asp Ser
305                 310                 315                 320

Ser Ala Pro Arg Phe Asp Ser His Cys Ala Leu Pro Asp Ala Leu Gln
            325                 330                 335

Pro Ala Pro Gln Ala Gly Ala Trp Phe Gln Ala Tyr Phe Val Gln Leu
            340                 345                 350

Leu Thr Asn Ala Asn Pro Ser Phe Leu
            355                 360

<210> SEQ ID NO 63
<211> LENGTH: 360
<212> TYPE: PRT
<213> ORGANISM: Artificial Sequence
<220> FEATURE:
<223> OTHER INFORMATION: Chimeric CBH II Polypeptide

<400> SEQUENCE: 63

Gly Asn Pro Phe Glu Gly Val Gln Leu Trp Ala Asn Asn Tyr Tyr Arg
1               5                   10                  15

Ser Glu Val His Thr Leu Ala Ile Pro Gln Ile Thr Asp Pro Ala Leu
                20                  25                  30

Arg Ala Ala Ser Ala Val Ala Glu Val Pro Ser Phe Gln Trp Leu
            35                  40                  45

Asp Arg Asn Val Thr Val Asp Thr Leu Phe Ser Gly Thr Leu Ala Glu
50                  55                  60

Ile Arg Ala Ala Asn Gln Arg Gly Ala Asn Pro Pro Tyr Ala Gly Ile
65                  70                  75                  80

Phe Val Val Tyr Asp Leu Pro Asp Arg Asp Cys Ala Ala Ala Ala Ser
                85                  90                  95

Asn Gly Glu Trp Ser Ile Ala Asn Asn Gly Ala Asn Tyr Lys Arg
            100                 105                 110

Tyr Ile Asp Arg Ile Arg Glu Ile Leu Ile Ser Phe Ser Asp Val Arg
            115                 120                 125

Thr Ile Leu Val Ile Glu Pro Asp Ser Leu Ala Asn Met Val Thr Asn
130                 135                 140

Met Asn Val Pro Lys Cys Ser Gly Ala Ala Ser Thr Tyr Arg Glu Leu
145                 150                 155                 160

Thr Ile Tyr Ala Leu Lys Gln Leu Asp Leu Pro His Val Ala Met Tyr
                165                 170                 175

Met Asp Ala Gly His Ala Gly Trp Leu Gly Trp Pro Ala Asn Ile Gln
            180                 185                 190

Pro Ala Ala Glu Leu Phe Ala Lys Ile Tyr Glu Asp Ala Gly Lys Pro
            195                 200                 205

Arg Ala Val Arg Gly Leu Ala Thr Asn Val Ala Asn Tyr Asn Ala Trp
210                 215                 220

Ser Ile Ala Ser Pro Pro Ser Tyr Thr Ser Pro Asn Pro Asn Tyr Asp
225                 230                 235                 240

Glu Lys His Tyr Ile Glu Ala Phe Ala Pro Leu Leu Arg Asn Gln Gly
                245                 250                 255

Phe Asp Ala Lys Phe Ile Val Asp Thr Gly Arg Asn Gly Lys Gln Pro
            260                 265                 270

Thr Gly Gln Leu Glu Trp Gly His Trp Cys Asn Val Lys Gly Thr Gly
            275                 280                 285

Phe Gly Val Arg Pro Thr Ala Asn Thr Gly His Glu Leu Val Asp Ala
        290                 295                 300
```

```
Phe Val Trp Val Lys Pro Gly Gly Glu Ser Asp Gly Thr Ser Asp Thr
305                 310                 315                 320

Thr Ala Ala Arg Tyr Asp Tyr His Cys Gly Leu Glu Asp Ala Leu Lys
                325                 330                 335

Pro Ala Pro Glu Ala Gly Gln Trp Phe Asn Glu Tyr Phe Ile Gln Leu
            340                 345                 350

Leu Arg Asn Ala Asn Pro Pro Phe
355                 360

<210> SEQ ID NO 64
<211> LENGTH: 447
<212> TYPE: PRT
<213> ORGANISM: Trichoderma reesei

<400> SEQUENCE: 64

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320
```

```
Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Ser His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 65
<211> LENGTH: 453
<212> TYPE: PRT
<213> ORGANISM: Humicola insolens

<400> SEQUENCE: 65

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
            35                  40                  45

Thr Ser Thr Ser Ser Ser Thr Thr Ser Arg Ala Thr Ser Thr Thr
        50                  55                  60

Ser Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
            85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
            115                 120                 125

Ala Ser Ala Val Ala Glu Val Pro Ser Phe Gln Trp Leu Asp Arg Asn
            130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
            165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
            195                 200                 205

Arg Ile Arg Glu Ile Leu Ile Ser Phe Ser Asp Val Arg Thr Ile Leu
            210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
```

```
                    245                 250                 255
Ala Leu Lys Gln Leu Asp Leu Pro His Val Ala Met Tyr Met Asp Ala
                260                 265                 270

Gly His Ala Gly Trp Leu Gly Trp Pro Ala Asn Ile Gln Pro Ala Ala
            275                 280                 285

Glu Leu Phe Ala Lys Ile Tyr Glu Asp Ala Gly Lys Pro Arg Ala Val
        290                 295                 300

Arg Gly Leu Ala Thr Asn Val Ala Asn Tyr Asn Ala Trp Ser Ile Ser
305                 310                 315                 320

Ser Pro Pro Tyr Thr Ser Pro Asn Pro Asn Tyr Asp Glu Lys His
                325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
                355                 360                 365

Lys Glu Trp Gly His Trp Cys Asn Ala Ile Gly Thr Gly Phe Gly Met
            370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Tyr His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
            435                 440                 445

Ala Asn Pro Pro Phe
450

<210> SEQ ID NO 66
<211> LENGTH: 440
<212> TYPE: PRT
<213> ORGANISM: Phanerochaete chrysosporium

<400> SEQUENCE: 66

Ala Ser Ser Glu Trp Gly Gln Cys Gly Gly Ile Gly Trp Thr Gly Pro
1               5                   10                  15

Thr Thr Cys Val Ser Gly Thr Cys Thr Val Leu Asn Pro Tyr Tyr
                20                  25                  30

Ser Gln Cys Leu Pro Gly Ser Ala Val Thr Thr Ser Val Ile Thr
            35                  40                  45

Ser His Ser Ser Ser Val Ser Ser Val Ser Ser His Ser Gly Ser Ser
        50                  55                  60

Thr Ser Thr Ser Ser Pro Thr Gly Pro Thr Gly Thr Asn Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Lys Gln Ile Thr Asp
                100                 105                 110

Pro Thr Leu Ser Ser Lys Ala Ala Ser Val Ala Asn Ile Pro Thr Phe
            115                 120                 125

Thr Trp Leu Asp Ser Val Ala Lys Ile Pro Asp Leu Gly Thr Tyr Leu
        130                 135                 140

Ala Ser Ala Ser Ala Leu Gly Lys Ser Thr Gly Thr Lys Gln Leu Val
145                 150                 155                 160
```

```
Gln Ile Val Ile Tyr Asp Leu Pro Asp Arg Asp Cys Ala Ala Lys Ala
                165                 170                 175

Ser Asn Gly Glu Phe Ser Ile Ala Asn Gly Gln Ala Asn Tyr Glu
            180                 185                 190

Asn Tyr Ile Asp Gln Ile Val Ala Gln Ile Gln Gln Phe Pro Asp Val
                195                 200                 205

Arg Val Val Ala Val Ile Glu Pro Asp Ser Leu Ala Asn Leu Val Thr
                210                 215                 220

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
                245                 250                 255

Tyr Met Asp Ala Gly His Ala Gly Trp Leu Gly Trp Pro Ala Asn Leu
                260                 265                 270

Ser Pro Ala Ala Gln Leu Phe Thr Gln Val Trp Gln Asn Ala Gly Lys
                275                 280                 285

Ser Pro Phe Ile Lys Gly Leu Ala Thr Asn Val Ala Asn Tyr Asn Ala
                290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
                325                 330                 335

Gly Trp Asp Ala Thr Phe Ile Val Asp Gln Gly Arg Ser Gly Val Gln
                340                 345                 350

Asn Ile Arg Gln Gln Trp Gly Asp Trp Cys Asn Ile Lys Gly Ala Gly
                355                 360                 365

Phe Gly Thr Arg Pro Thr Thr Asn Thr Gly Ser Gln Phe Ile Asp Ser
                370                 375                 380

Ile Val Trp Val Lys Pro Gly Gly Glu Cys Asp Gly Thr Ser Asn Ser
385                 390                 395                 400

Ser Ser Pro Arg Tyr Asp Ser Thr Cys Ser Leu Pro Asp Ala Ala Gln
                405                 410                 415

Pro Ala Pro Glu Ala Gly Thr Trp Phe Gln Ala Tyr Phe Gln Thr Leu
                420                 425                 430

Val Ser Ala Ala Asn Pro Pro Leu
            435                 440

<210> SEQ ID NO 67
<211> LENGTH: 447
<212> TYPE: PRT
<213> ORGANISM: Trichoderma reesei

<400> SEQUENCE: 67

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
                20                  25                  30

Tyr Tyr Ser Gln Cys Leu Pro Gly Ala Ala Ser Ser Ser Ser Ser Thr
            35                  40                  45

Arg Ala Ala Ser Thr Thr Ser Arg Val Ser Pro Thr Thr Ser Arg Ser
        50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95
```

```
Thr Pro Trp Ala Asn Ala Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
            130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
            210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 68
<211> LENGTH: 447
<212> TYPE: PRT
<213> ORGANISM: Trichoderma reesei

<400> SEQUENCE: 68

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
```

```
                20                  25                  30
Tyr Tyr Ser Gln Cys Leu Pro Gly Ala Ala Ser Ser Ser Ser Thr
            35                  40                  45

Arg Ala Ala Ser Thr Thr Ser Arg Val Ser Pro Thr Thr Ser Arg Ser
 50                  55                  60

Ser Ser Ala Thr Pro Pro Gly Ser Thr Thr Arg Val Pro Pro
 65                  70                  75                  80

Val Glu Ser Gly Thr Ala Thr Tyr Ser Gly Asn Pro Phe Val Gly Val
                    85                  90                  95

Thr Pro Trp Ala Asn Ala Tyr Tyr Ala Ser Glu Val Ser Ser Leu Ala
                100                 105                 110

Ile Pro Ser Leu Thr Gly Ala Met Ala Thr Ala Ala Ala Val Ala
                115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                    165                 170                 175

Ala Ala Leu Ala Ser Asn Gly Glu Tyr Ser Ile Ala Asp Gly Gly Val
                180                 185                 190

Ala Lys Tyr Lys Asn Tyr Ile Asp Thr Ile Arg Gln Ile Val Val Glu
                195                 200                 205

Tyr Ser Asp Ile Arg Thr Leu Leu Val Ile Glu Pro Asp Ser Leu Ala
            210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
                260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Ser Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                    325                 330                 335

Leu Ala Asn His Gly Trp Ser Asn Ala Phe Phe Ile Thr Asp Gln Gly
                340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                    405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445
```

<210> SEQ ID NO 69
<211> LENGTH: 447
<212> TYPE: PRT
<213> ORGANISM: Trichoderma reesei

<400> SEQUENCE: 69

| | | | | | | | | | | | | | | | |
|---|---|---|---|---|---|---|---|---|---|---|---|---|---|---|---|
| Gln | Ala | Cys | Ser | Ser | Val | Trp | Gly | Gln | Cys | Gly | Gly | Gln | Asn | Trp | Ser |
| 1 | | | | 5 | | | | | 10 | | | | | 15 | |
| Gly | Pro | Thr | Cys | Cys | Ala | Ser | Gly | Ser | Thr | Cys | Val | Tyr | Ser | Asn | Asp |
| | | | 20 | | | | | 25 | | | | | 30 | | |
| Tyr | Tyr | Ser | Gln | Cys | Leu | Pro | Gly | Ala | Ala | Ser | Ser | Ser | Ser | Ser | Thr |
| | | 35 | | | | | 40 | | | | | 45 | | | |
| Arg | Ala | Ala | Ser | Thr | Thr | Ser | Arg | Val | Ser | Pro | Thr | Thr | Ser | Arg | Ser |
| | 50 | | | | | 55 | | | | | 60 | | | | |
| Ser | Ser | Ala | Thr | Pro | Pro | Pro | Gly | Ser | Thr | Thr | Thr | Arg | Val | Pro | Pro |
| 65 | | | | | 70 | | | | | 75 | | | | | 80 |
| Val | Gly | Ser | Gly | Thr | Ala | Thr | Tyr | Ser | Gly | Asn | Pro | Phe | Val | Gly | Val |
| | | | | 85 | | | | | 90 | | | | | 95 | |
| Thr | Pro | Trp | Ala | Asn | Ala | Tyr | Tyr | Ala | Ser | Glu | Val | Ser | Ser | Leu | Ala |
| | | | 100 | | | | | 105 | | | | | 110 | | |
| Ile | Pro | Ser | Leu | Thr | Gly | Ala | Met | Ala | Thr | Ala | Ala | Ala | Ala | Val | Ala |
| | | 115 | | | | | 120 | | | | | 125 | | | |
| Lys | Val | Pro | Ser | Phe | Met | Trp | Leu | Asp | Thr | Leu | Asp | Lys | Thr | Pro | Leu |
| | 130 | | | | | 135 | | | | | 140 | | | | |
| Met | Glu | Gln | Thr | Leu | Ala | Asp | Ile | Arg | Thr | Ala | Asn | Lys | Asn | Gly | Gly |
| 145 | | | | | 150 | | | | | 155 | | | | | 160 |
| Asn | Tyr | Ala | Gly | Gln | Phe | Val | Val | Tyr | Asp | Leu | Pro | Asp | Arg | Asp | Cys |
| | | | | 165 | | | | | 170 | | | | | 175 | |
| Ala | Ala | Leu | Ala | Ser | Asn | Gly | Glu | Tyr | Ser | Ile | Ala | Asp | Gly | Gly | Val |
| | | | 180 | | | | | 185 | | | | | 190 | | |
| Ala | Lys | Tyr | Lys | Asn | Tyr | Ile | Asp | Thr | Ile | Arg | Gln | Ile | Val | Val | Glu |
| | | 195 | | | | | 200 | | | | | 205 | | | |
| Tyr | Ser | Asp | Ile | Arg | Thr | Leu | Leu | Val | Ile | Glu | Pro | Asp | Ser | Leu | Ala |
| | 210 | | | | | 215 | | | | | 220 | | | | |
| Asn | Leu | Val | Thr | Asn | Leu | Ser | Thr | Pro | Lys | Cys | Ala | Asn | Ala | Gln | Ser |
| 225 | | | | | 230 | | | | | 235 | | | | | 240 |
| Ala | Tyr | Leu | Glu | Cys | Ile | Asn | Tyr | Ala | Val | Thr | Gln | Leu | Asn | Leu | Pro |
| | | | | 245 | | | | | 250 | | | | | 255 | |
| Asn | Val | Ala | Met | Tyr | Leu | Asp | Ala | Gly | His | Ala | Gly | Trp | Leu | Gly | Trp |
| | | | 260 | | | | | 265 | | | | | 270 | | |
| Pro | Ala | Asn | Gln | Asp | Pro | Ala | Ala | Gln | Leu | Phe | Ala | Asn | Val | Tyr | Lys |
| | | 275 | | | | | 280 | | | | | 285 | | | |
| Asn | Ala | Ser | Ser | Pro | Arg | Ala | Leu | Arg | Gly | Leu | Ala | Thr | Asn | Val | Ala |
| | 290 | | | | | 295 | | | | | 300 | | | | |
| Asn | Tyr | Asn | Gly | Trp | Asn | Ile | Thr | Ser | Pro | Pro | Ser | Tyr | Thr | Gln | Gly |
| 305 | | | | | 310 | | | | | 315 | | | | | 320 |
| Asn | Ala | Val | Tyr | Asn | Glu | Lys | Leu | Tyr | Ile | His | Ala | Ile | Gly | Pro | Leu |
| | | | | 325 | | | | | 330 | | | | | 335 | |
| Leu | Ala | Asn | His | Gly | Trp | Ser | Asn | Ala | Phe | Phe | Ile | Thr | Asp | Gln | Gly |
| | | | 340 | | | | | 345 | | | | | 350 | | |
| Arg | Ser | Gly | Lys | Gln | Pro | Thr | Gly | Gln | Gln | Gln | Trp | Gly | Asp | Trp | Cys |
| | | 355 | | | | | 360 | | | | | 365 | | | |
| Asn | Val | Ile | Gly | Thr | Gly | Phe | Gly | Ile | Arg | Pro | Ser | Ala | Asn | Thr | Gly |

```
            370                 375                 380
Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
                420                 425                 430

Ala Tyr Phe Val Gln Leu Leu Thr Asn Ala Asn Pro Ser Phe Leu
            435                 440                 445

<210> SEQ ID NO 70
<211> LENGTH: 447
<212> TYPE: PRT
<213> ORGANISM: Trichoderma reesei

<400> SEQUENCE: 70

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300
```

```
Ser Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 71
<211> LENGTH: 447
<212> TYPE: PRT
<213> ORGANISM: Trichoderma reesei

<400> SEQUENCE: 71

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Gly Thr Pro Lys Cys Ala Asn Ala Gln Ser
225                 230                 235                 240
```

```
Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 72
<211> LENGTH: 447
<212> TYPE: PRT
<213> ORGANISM: Trichoderma reesei

<400> SEQUENCE: 72

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
    130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
```

```
                165                 170                 175
Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
            195                 200                 205

Tyr Ser Asp Ile Arg Thr Leu Leu Val Ile Glu Pro Asp Ser Leu Ala
        210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
            275                 280                 285

Asn Ala Ser Ser Pro Arg Ala Leu Arg Gly Leu Ala Thr Asn Val Ala
            290                 295                 300

Ser Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
            355                 360                 365

Asn Val Ile Gly Thr Gly Phe Gly Ile Arg Pro Ser Ala Asn Thr Gly
            370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Arg Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445

<210> SEQ ID NO 73
<211> LENGTH: 447
<212> TYPE: PRT
<213> ORGANISM: Trichoderma reesei

<400> SEQUENCE: 73

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30

Tyr Tyr Ser Gln Cys Leu Pro Gly Ala Ala Ser Ser Ser Ser Ser Thr
        35                  40                  45

Arg Ala Ala Ser Thr Thr Ser Arg Val Ser Pro Thr Thr Ser Arg Ser
    50                  55                  60

Ser Ser Ala Thr Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
            85                  90                  95
```

-continued

```
Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
        115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
    210                 215                 220

Asn Leu Val Thr Asn Leu Ser Thr Pro Lys Cys Ala Asn Ala Gln Ser
225                 230                 235                 240

Ala Tyr Leu Glu Cys Ile Asn Tyr Ala Val Thr Gln Leu Asn Leu Pro
                245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
    290                 295                 300

Asn Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
                325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
    370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 74
<211> LENGTH: 447
<212> TYPE: PRT
<213> ORGANISM: Trichoderma reesei

<400> SEQUENCE: 74

Gln Ala Cys Ser Ser Val Trp Gly Gln Cys Gly Gly Gln Asn Trp Ser
1               5                   10                  15

Gly Pro Thr Cys Cys Ala Ser Gly Ser Thr Cys Val Tyr Ser Asn Asp
            20                  25                  30
```

```
Tyr Tyr Ser Gln Cys Leu Pro Gly Ala Ala Ser Ser Ser Ser Thr
        35              40                  45

Arg Ala Ala Ser Thr Thr Ser Arg Val Ser Pro Thr Thr Ser Arg Ser
50                      55                      60

Ser Ser Ala Thr Pro Pro Pro Gly Ser Thr Thr Thr Arg Val Pro Pro
65                  70                  75                  80

Val Gly Ser Gly Thr Ala Thr Tyr Ser Gly Asn Pro Phe Val Gly Val
                85                  90                  95

Thr Pro Trp Ala Asn Ala Tyr Tyr Ala Ser Glu Val Ser Ser Leu Ala
            100                 105                 110

Ile Pro Ser Leu Thr Gly Ala Met Ala Thr Ala Ala Ala Val Ala
            115                 120                 125

Lys Val Pro Ser Phe Met Trp Leu Asp Thr Leu Asp Lys Thr Pro Leu
130                 135                 140

Met Glu Gln Thr Leu Ala Asp Ile Arg Thr Ala Asn Lys Asn Gly Gly
145                 150                 155                 160

Asn Tyr Ala Gly Gln Phe Val Val Tyr Asp Leu Pro Asp Arg Asp Cys
                165                 170                 175

Ala Ala Leu Ala Ser Asn Gly Glu Tyr Ser Ile Ala Asp Gly Gly Val
            180                 185                 190

Ala Lys Tyr Lys Asn Tyr Ile Asp Thr Ile Arg Gln Ile Val Val Glu
        195                 200                 205

Tyr Ser Asp Ile Arg Thr Leu Leu Val Ile Glu Pro Asp Ser Leu Ala
        210                 215                 220

Asn Leu Val Thr Asn Leu Gly Thr Pro Lys Cys Ala Asn Ala Gln Ser
225                 230                 235                 240

Ala Tyr Leu Glu Cys Ile Asn Tyr Ala Val Thr Gln Leu Asn Leu Pro
            245                 250                 255

Asn Val Ala Met Tyr Leu Asp Ala Gly His Ala Gly Trp Leu Gly Trp
            260                 265                 270

Pro Ala Asn Gln Asp Pro Ala Ala Gln Leu Phe Ala Asn Val Tyr Lys
        275                 280                 285

Asn Ala Ser Ser Pro Arg Ala Leu Arg Gly Leu Ala Thr Asn Val Ala
        290                 295                 300

Ser Tyr Asn Gly Trp Asn Ile Thr Ser Pro Pro Ser Tyr Thr Gln Gly
305                 310                 315                 320

Asn Ala Val Tyr Asn Glu Lys Leu Tyr Ile His Ala Ile Gly Pro Leu
            325                 330                 335

Leu Ala Asn His Gly Trp Ser Asn Ala Phe Phe Ile Thr Asp Gln Gly
            340                 345                 350

Arg Ser Gly Lys Gln Pro Thr Gly Gln Gln Gln Trp Gly Asp Trp Cys
        355                 360                 365

Asn Val Ile Gly Thr Gly Phe Gly Ile Arg Pro Ser Ala Asn Thr Gly
        370                 375                 380

Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
                405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
            435                 440                 445
```

<210> SEQ ID NO 75
<211> LENGTH: 447
<212> TYPE: PRT
<213> ORGANISM: Trichoderma reesei

<400> SEQUENCE: 75

| | | | | | | | | | | | | | | |
|---|---|---|---|---|---|---|---|---|---|---|---|---|---|---|
| Gln | Ala | Cys | Ser | Ser | Val | Trp | Gly | Gln | Cys | Gly | Gly | Gln | Asn | Trp Ser |
| 1 | | | | 5 | | | | | 10 | | | | | 15 |
| Gly | Pro | Thr | Cys | Cys | Ala | Ser | Gly | Ser | Thr | Cys | Val | Tyr | Ser | Asn Asp |
| | | | 20 | | | | | 25 | | | | | 30 | |
| Tyr | Tyr | Ser | Gln | Cys | Leu | Pro | Gly | Ala | Ala | Ser | Ser | Ser | Ser | Thr |
| | | 35 | | | | | 40 | | | | | 45 | | |
| Arg | Ala | Ala | Ser | Thr | Thr | Ser | Arg | Val | Ser | Pro | Thr | Thr | Ser | Arg Ser |
| | 50 | | | | | 55 | | | | | 60 | | | |
| Ser | Ser | Ala | Thr | Pro | Pro | Pro | Gly | Ser | Thr | Thr | Thr | Arg | Val | Pro Pro |
| 65 | | | | | 70 | | | | | 75 | | | | | 80 |
| Val | Gly | Ser | Gly | Thr | Ala | Thr | Tyr | Ser | Gly | Asn | Pro | Phe | Val | Gly Val |
| | | | | 85 | | | | | 90 | | | | | 95 |
| Thr | Pro | Trp | Ala | Asn | Ala | Tyr | Tyr | Ala | Ser | Glu | Val | Ser | Ser | Leu Ala |
| | | | 100 | | | | | 105 | | | | | 110 | |
| Ile | Pro | Ser | Leu | Thr | Gly | Ala | Met | Ala | Thr | Ala | Ala | Ala | Val | Ala |
| | | 115 | | | | | 120 | | | | | 125 | | |
| Lys | Val | Pro | Ser | Phe | Met | Trp | Leu | Asp | Thr | Leu | Asp | Lys | Thr | Pro Leu |
| | 130 | | | | | 135 | | | | | 140 | | | |
| Met | Glu | Gln | Thr | Leu | Ala | Asp | Ile | Arg | Thr | Ala | Asn | Lys | Asn | Gly Gly |
| 145 | | | | | 150 | | | | | 155 | | | | | 160 |
| Asn | Tyr | Ala | Gly | Gln | Phe | Val | Val | Tyr | Asp | Leu | Pro | Asp | Arg | Asp Cys |
| | | | | 165 | | | | | 170 | | | | | 175 |
| Ala | Ala | Leu | Ala | Ser | Asn | Gly | Glu | Tyr | Ser | Ile | Ala | Asp | Gly | Gly Val |
| | | | 180 | | | | | 185 | | | | | 190 | |
| Ala | Lys | Tyr | Lys | Asn | Tyr | Ile | Asp | Thr | Ile | Arg | Gln | Ile | Val | Val Glu |
| | | 195 | | | | | 200 | | | | | 205 | | |
| Tyr | Ser | Asp | Ile | Arg | Thr | Leu | Leu | Val | Ile | Glu | Pro | Asp | Ser | Leu Ala |
| | 210 | | | | | 215 | | | | | 220 | | | |
| Asn | Leu | Val | Thr | Asn | Leu | Ser | Thr | Pro | Lys | Cys | Ala | Asn | Ala | Gln Ser |
| 225 | | | | | 230 | | | | | 235 | | | | | 240 |
| Ala | Tyr | Leu | Glu | Cys | Ile | Asn | Tyr | Ala | Val | Thr | Gln | Leu | Asn | Leu Pro |
| | | | | 245 | | | | | 250 | | | | | 255 |
| Asn | Val | Ala | Met | Tyr | Leu | Asp | Ala | Gly | His | Ala | Gly | Trp | Leu | Gly Trp |
| | | | 260 | | | | | 265 | | | | | 270 | |
| Pro | Ala | Asn | Gln | Asp | Pro | Ala | Ala | Gln | Leu | Phe | Ala | Asn | Val | Tyr Lys |
| | | 275 | | | | | 280 | | | | | 285 | | |
| Asn | Ala | Ser | Ser | Pro | Arg | Ala | Leu | Arg | Gly | Leu | Ala | Thr | Asn | Val Ala |
| | 290 | | | | | 295 | | | | | 300 | | | |
| Ser | Tyr | Asn | Gly | Trp | Asn | Ile | Thr | Ser | Pro | Pro | Ser | Tyr | Thr | Gln Gly |
| 305 | | | | | 310 | | | | | 315 | | | | | 320 |
| Asn | Ala | Val | Tyr | Asn | Glu | Lys | Leu | Tyr | Ile | His | Ala | Ile | Gly | Pro Leu |
| | | | | 325 | | | | | 330 | | | | | 335 |
| Leu | Ala | Asn | His | Gly | Trp | Ser | Asn | Ala | Phe | Phe | Ile | Thr | Asp | Gln Gly |
| | | | 340 | | | | | 345 | | | | | 350 | |
| Arg | Ser | Gly | Lys | Gln | Pro | Thr | Gly | Gln | Gln | Gln | Trp | Gly | Asp | Trp Cys |
| | | 355 | | | | | 360 | | | | | 365 | | |
| Asn | Val | Ile | Gly | Thr | Gly | Phe | Gly | Ile | Arg | Pro | Ser | Ala | Asn | Thr Gly |
| | 370 | | | | | 375 | | | | | 380 | | | |

```
Asp Ser Leu Leu Asp Ser Phe Val Trp Val Lys Pro Gly Gly Glu Cys
385                 390                 395                 400

Asp Gly Thr Ser Asp Ser Ser Ala Pro Gln Phe Asp Pro His Cys Ala
            405                 410                 415

Leu Pro Asp Ala Leu Gln Pro Ala Pro Gln Ala Gly Ala Trp Phe Gln
            420                 425                 430

Ala Tyr Phe Val Gln Leu Leu Thr Asn Ala Asn Pro Ser Phe Leu
        435                 440                 445

<210> SEQ ID NO 76
<211> LENGTH: 453
<212> TYPE: PRT
<213> ORGANISM: Humicola insolens

<400> SEQUENCE: 76

Ala Ser Cys Ala Pro Thr Trp Gly Gln Cys Gly Gly Ile Gly Phe Asn
1               5                   10                  15

Gly Pro Thr Cys Cys Gln Ser Gly Ser Thr Cys Val Lys Gln Asn Asp
            20                  25                  30

Trp Tyr Ser Gln Cys Leu Pro Gly Ser Gln Val Thr Thr Thr Ser Thr
        35                  40                  45

Thr Ser Thr Ser Ser Ser Ser Thr Thr Ser Arg Ala Thr Ser Thr Thr
50                  55                  60

Ser Thr Gly Gly Val Thr Ser Ile Thr Thr Ala Pro Thr Arg Thr Val
65                  70                  75                  80

Thr Ile Pro Gly Gly Ala Thr Thr Thr Ala Ser Tyr Asn Gly Asn Pro
                85                  90                  95

Phe Glu Gly Val Gln Leu Trp Ala Asn Asn Tyr Tyr Arg Ser Glu Val
            100                 105                 110

His Thr Leu Ala Ile Pro Gln Ile Thr Asp Pro Ala Leu Arg Ala Ala
        115                 120                 125

Ala Ser Ala Val Ala Glu Val Pro Ser Phe Gln Trp Leu Asp Arg Asn
    130                 135                 140

Val Thr Val Asp Thr Leu Leu Val Glu Thr Leu Ser Glu Ile Arg Ala
145                 150                 155                 160

Ala Asn Gln Ala Gly Ala Asn Pro Pro Tyr Ala Ala Gln Ile Val Val
                165                 170                 175

Tyr Asp Leu Pro Asp Arg Asp Cys Ala Ala Ala Ser Asn Gly Glu
            180                 185                 190

Trp Ala Ile Ala Asn Asn Gly Ala Asn Asn Tyr Lys Gly Tyr Ile Asn
        195                 200                 205

Arg Ile Arg Glu Ile Leu Ile Ser Phe Ser Asp Val Arg Thr Ile Leu
    210                 215                 220

Val Ile Glu Pro Asp Ser Leu Ala Asn Met Val Thr Asn Met Asn Val
225                 230                 235                 240

Ala Lys Cys Ser Gly Ala Ala Ser Thr Tyr Arg Glu Leu Thr Ile Tyr
                245                 250                 255

Ala Leu Lys Gln Leu Asp Leu Pro His Val Ala Met Tyr Met Asp Ala
            260                 265                 270

Gly His Ala Gly Trp Leu Gly Trp Pro Ala Asn Ile Gln Pro Ala Ala
        275                 280                 285

Glu Leu Phe Ala Lys Ile Tyr Glu Asp Ala Gly Lys Pro Arg Ala Val
    290                 295                 300

Arg Gly Leu Ala Thr Asn Val Ala Asn Tyr Asn Ala Trp Ser Ile Ser
```

```
                305                 310                 315                 320
Ser Pro Pro Tyr Thr Ser Pro Asn Pro Asn Tyr Asp Glu Lys His
                    325                 330                 335

Tyr Ile Glu Ala Phe Arg Pro Leu Leu Glu Ala Arg Gly Phe Pro Ala
                340                 345                 350

Gln Phe Ile Val Asp Gln Gly Arg Ser Gly Lys Gln Pro Thr Gly Gln
                355                 360                 365

Lys Glu Trp Gly His Trp Cys Asn Ala Ile Thr Gly Phe Gly Met
370                 375                 380

Arg Pro Thr Ala Asn Thr Gly His Gln Tyr Val Asp Ala Phe Val Trp
385                 390                 395                 400

Val Lys Pro Gly Gly Glu Cys Asp Gly Thr Ser Asp Thr Thr Ala Ala
                405                 410                 415

Arg Tyr Asp Pro His Cys Gly Leu Glu Asp Ala Leu Lys Pro Ala Pro
                420                 425                 430

Glu Ala Gly Gln Trp Phe Gln Ala Tyr Phe Glu Gln Leu Leu Arg Asn
                435                 440                 445

Ala Asn Pro Pro Phe
450

<210> SEQ ID NO 77
<211> LENGTH: 440
<212> TYPE: PRT
<213> ORGANISM: Phanerochaete chrysosporium

<400> SEQUENCE: 77

Ala Ser Ser Glu Trp Gly Gln Cys Gly Gly Ile Gly Trp Thr Gly Pro
1               5                   10                  15

Thr Thr Cys Val Ser Gly Thr Thr Cys Thr Val Leu Asn Pro Tyr Tyr
                20                  25                  30

Ser Gln Cys Leu Pro Gly Ser Ala Val Thr Thr Ser Val Ile Thr
                35                  40                  45

Ser His Ser Ser Ser Val Ser Ser Val Ser Ser His Ser Gly Ser Ser
            50                  55                  60

Thr Ser Thr Ser Ser Pro Thr Gly Pro Thr Gly Thr Asn Pro Pro Pro
65                  70                  75                  80

Pro Pro Ser Ala Asn Asn Pro Trp Thr Gly Phe Gln Ile Phe Leu Ser
                85                  90                  95

Pro Tyr Tyr Ala Asn Glu Val Ala Ala Ala Ala Lys Gln Ile Thr Asp
                100                 105                 110

Pro Thr Leu Ser Ser Lys Ala Ala Ser Val Ala Asn Ile Pro Thr Phe
                115                 120                 125

Thr Trp Leu Asp Ser Val Ala Lys Ile Pro Asp Leu Gly Thr Tyr Leu
            130                 135                 140

Ala Ser Ala Ser Ala Leu Gly Lys Ser Thr Gly Thr Lys Gln Leu Val
145                 150                 155                 160

Gln Ile Val Ile Tyr Asp Leu Pro Asp Arg Asp Cys Ala Ala Lys Ala
                165                 170                 175

Ser Asn Gly Glu Phe Ser Ile Ala Asn Asn Gly Gln Ala Asn Tyr Glu
                180                 185                 190

Asn Tyr Ile Asp Gln Ile Val Ala Gln Ile Gln Gln Phe Pro Asp Val
                195                 200                 205

Arg Val Val Ala Val Ile Glu Pro Asp Ser Leu Ala Asn Leu Val Thr
            210                 215                 220
```

Asn Leu Asn Val Gln Lys Cys Ala Asn Ala Lys Thr Thr Tyr Leu Ala
225                 230                 235                 240

Cys Val Asn Tyr Ala Leu Thr Asn Leu Ala Lys Val Gly Val Tyr Met
            245                 250                 255

Tyr Met Asp Ala Gly His Ala Gly Trp Leu Gly Trp Pro Ala Asn Leu
            260                 265                 270

Ser Pro Ala Ala Gln Leu Phe Thr Gln Val Trp Gln Asn Ala Gly Lys
        275                 280                 285

Ser Pro Phe Ile Lys Gly Leu Ala Thr Asn Val Ala Asn Tyr Asn Ala
        290                 295                 300

Leu Gln Ala Ala Ser Pro Asp Pro Ile Thr Gln Gly Asn Pro Asn Tyr
305                 310                 315                 320

Asp Glu Ile His Tyr Ile Asn Ala Leu Ala Pro Leu Leu Gln Gln Ala
            325                 330                 335

Gly Trp Asp Ala Thr Phe Ile Val Asp Gln Gly Arg Ser Gly Val Gln
            340                 345                 350

Asn Ile Arg Gln Gln Trp Gly Asp Trp Cys Asn Ile Lys Gly Ala Gly
        355                 360                 365

Phe Gly Thr Arg Pro Thr Thr Asn Thr Gly Ser Gln Phe Ile Asp Ser
370                 375                 380

Ile Val Trp Val Lys Pro Gly Gly Glu Cys Asp Gly Thr Ser Asn Ser
385                 390                 395                 400

Ser Ser Pro Arg Tyr Asp Pro Thr Cys Ser Leu Pro Asp Ala Ala Gln
            405                 410                 415

Pro Ala Pro Glu Ala Gly Thr Trp Phe Gln Ala Tyr Phe Gln Thr Leu
            420                 425                 430

Val Ser Ala Ala Asn Pro Pro Leu
        435                 440

<210> SEQ ID NO 78
<211> LENGTH: 459
<212> TYPE: PRT
<213> ORGANISM: Trichoderma reesei

<400> SEQUENCE: 78

Asp Tyr Lys Asp Asp Asp Lys Glu Phe Leu Glu Ala Ser Cys Ser
1               5                   10                  15

Ser Val Trp Gly Gln Cys Gly Gly Gln Asn Trp Ser Gly Pro Thr Cys
            20                  25                  30

Cys Ala Ser Gly Ser Thr Cys Val Tyr Ser Asn Asp Tyr Tyr Ser Gln
        35                  40                  45

Cys Leu Pro Gly Ala Ala Ser Ser Ser Ser Thr Arg Ala Ala Ser
50                  55                  60

Thr Thr Ser Arg Val Ser Pro Thr Thr Ser Arg Ser Ser Ser Ala Thr
65                  70                  75                  80

Pro Pro Pro Gly Ser Thr Thr Thr Arg Val Pro Pro Val Gly Ser Gly
            85                  90                  95

Thr Ala Thr Tyr Ser Gly Asn Pro Phe Val Gly Val Thr Pro Trp Ala
        100                 105                 110

Asn Ala Tyr Tyr Ala Ser Glu Val Ser Ser Leu Ala Ile Pro Ser Leu
        115                 120                 125

Thr Gly Ala Met Ala Thr Ala Ala Ala Val Ala Lys Val Pro Ser
130                 135                 140

Phe Met Trp Leu Asp Thr Leu Asp Lys Thr Pro Leu Met Glu Gln Thr
145                 150                 155                 160

```
Leu Ala Asp Ile Arg Thr Ala Asn Lys Asn Gly Gly Asn Tyr Ala Gly
            165                 170                 175

Gln Phe Val Val Tyr Asp Leu Pro Asp Arg Asp Cys Ala Ala Leu Ala
        180                 185                 190

Ser Asn Gly Glu Tyr Ser Ile Ala Asp Gly Val Ala Lys Tyr Lys
    195                 200                 205

Asn Tyr Ile Asp Thr Ile Arg Gln Ile Val Glu Tyr Ser Asp Ile
        210                 215                 220

Arg Thr Leu Leu Val Ile Glu Pro Asp Ser Leu Ala Asn Leu Val Thr
225                 230                 235                 240

Asn Leu Gly Thr Pro Lys Cys Ala Asn Ala Gln Ser Ala Tyr Leu Glu
            245                 250                 255

Cys Ile Asn Tyr Ala Val Thr Gln Leu Asn Leu Pro Asn Val Ala Met
            260                 265                 270

Tyr Leu Asp Ala Gly His Ala Gly Trp Leu Gly Trp Pro Ala Asn Gln
        275                 280                 285

Asp Pro Ala Ala Gln Leu Phe Ala Asn Val Tyr Lys Asn Ala Ser Ser
    290                 295                 300

Pro Arg Ala Leu Arg Gly Leu Ala Thr Asn Val Ala Asn Tyr Asn Gly
305                 310                 315                 320

Trp Asn Ile Thr Ser Pro Pro Ser Tyr Thr Gln Gly Asn Ala Val Tyr
            325                 330                 335

Asn Glu Lys Leu Tyr Ile His Ala Ile Gly Pro Leu Leu Ala Asn His
            340                 345                 350

Gly Trp Ser Asn Ala Phe Phe Ile Thr Asp Gln Gly Arg Ser Gly Lys
        355                 360                 365

Gln Pro Thr Gly Gln Gln Gln Trp Gly Asp Trp Cys Asn Val Ile Gly
    370                 375                 380

Thr Gly Phe Gly Ile Arg Pro Ser Ala Asn Thr Gly Asp Ser Leu Leu
385                 390                 395                 400

Asp Ser Phe Val Trp Val Lys Pro Gly Gly Glu Cys Asp Gly Thr Ser
            405                 410                 415

Asp Ser Ser Ala Pro Arg Phe Asp Ser His Cys Ala Leu Pro Asp Ala
            420                 425                 430

Leu Gln Pro Ala Pro Gln Ala Gly Ala Trp Phe Gln Ala Tyr Phe Val
        435                 440                 445

Gln Leu Leu Thr Asn Ala Asn Pro Ser Phe Leu
    450                 455

<210> SEQ ID NO 79
<211> LENGTH: 484
<212> TYPE: PRT
<213> ORGANISM: Podospora anserina

<400> SEQUENCE: 79

Met Ala Lys Arg Leu Leu Leu Thr Ala Ala Leu Ala Ala Thr Thr Leu
1               5                   10                  15

Ala Ala Pro Val Ile Glu Glu Arg Gln Asn Cys Gly Ser Val Trp Ser
            20                  25                  30

Gln Cys Gly Gly Gln Gly Trp Thr Gly Ala Thr Cys Cys Ala Ser Gly
        35                  40                  45

Ser Thr Cys Val Ala Gln Asn Gln Trp Tyr Ser Gln Cys Leu Pro Gly
    50                  55                  60

Ser Gln Val Thr Thr Thr Ala Gln Ala Pro Ser Ser Thr Arg Thr Thr
```

```
                65                  70                  75                  80
        Thr Ser Ser Ser Arg Pro Thr Ser Ser Ile Ser Thr Ser Ala
                        85                  90                  95
        Val Asn Val Pro Thr Thr Thr Ser Ala Gly Ala Ser Val Thr Val
                        100                 105                 110
        Pro Pro Gly Gly Gly Ala Ser Ser Thr Ala Ser Tyr Ser Gly Asn Pro
                        115                 120                 125
        Phe Leu Gly Val Gln Gln Trp Ala Asn Ser Tyr Tyr Ser Ser Glu Val
                        130                 135                 140
        His Thr Leu Ala Ile Pro Ser Leu Thr Gly Pro Met Ala Thr Lys Ala
        145                 150                 155                 160
        Ala Ala Val Ala Lys Val Pro Ser Phe Gln Trp Met Asp Arg Asn Val
                        165                 170                 175
        Thr Val Asp Thr Leu Phe Ser Gly Thr Leu Ala Asp Ile Arg Ala Ala
                        180                 185                 190
        Asn Arg Ala Gly Ala Asn Pro Pro Tyr Ala Gly Ile Phe Val Val Tyr
                        195                 200                 205
        Asp Leu Pro Asp Arg Asp Cys Ala Ala Ala Ser Asn Gly Glu Trp
                        210                 215                 220
        Ala Ile Ala Asp Gly Gly Ala Ala Lys Tyr Lys Ala Tyr Ile Asp Arg
        225                 230                 235                 240
        Ile Arg His His Leu Val Gln Tyr Ser Asp Ile Arg Thr Ile Leu Val
                        245                 250                 255
        Ile Glu Pro Asp Ser Leu Ala Asn Met Val Thr Asn Met Asn Val Pro
                        260                 265                 270
        Lys Cys Gln Gly Ala Ala Asn Thr Tyr Lys Glu Leu Thr Val Tyr Ala
                        275                 280                 285
        Leu Lys Gln Leu Asn Leu Pro Asn Val Ala Met Tyr Leu Asp Ala Gly
                        290                 295                 300
        His Ala Gly Trp Leu Gly Trp Pro Ala Asn Ile Gly Pro Ala Ala Glu
        305                 310                 315                 320
        Leu Phe Ala Gly Ile Tyr Lys Asp Ala Gly Arg Pro Thr Ser Leu Arg
                        325                 330                 335
        Gly Leu Ala Thr Asn Val Ala Asn Tyr Asn Gly Trp Ser Leu Ser Ser
                        340                 345                 350
        Ala Pro Ser Tyr Thr Thr Pro Asn Pro Asn Phe Asp Glu Lys Arg Phe
                        355                 360                 365
        Val Gln Ala Phe Ser Pro Leu Leu Thr Ala Ala Gly Phe Pro Ala His
                        370                 375                 380
        Phe Ile Thr Asp Thr Gly Arg Ser Gly Lys Gln Pro Thr Gly Gln Leu
        385                 390                 395                 400
        Glu Trp Gly His Trp Cys Asn Ala Ile Gly Thr Gly Phe Gly Pro Arg
                        405                 410                 415
        Pro Thr Thr Asp Thr Gly Leu Asp Ile Glu Asp Ala Phe Val Trp Ile
                        420                 425                 430
        Lys Pro Gly Gly Glu Cys Asp Gly Thr Ser Asp Thr Thr Ala Ala Arg
                        435                 440                 445
        Tyr Asp His His Cys Gly Phe Ala Asp Ala Leu Lys Pro Ala Pro Glu
                        450                 455                 460
        Ala Gly Gln Trp Phe Gln Ala Tyr Phe Glu Gln Leu Leu Thr Asn Ala
        465                 470                 475                 480
        Asn Pro Pro Phe
```

<210> SEQ ID NO 80
<211> LENGTH: 485
<212> TYPE: PRT
<213> ORGANISM: Chaetomium Globosum

<400> SEQUENCE: 80

```
Met Ala Ala Lys Leu Phe Leu Ala Ala Leu Ala Ala Thr Ala Leu
1               5                   10                  15

Ala Ala Pro Val Val Glu Glu Arg Gln Asn Cys Ala Thr Leu Trp Gly
                20                  25                  30

Gln Cys Gly Gly Asn Gly Trp Asn Gly Ala Thr Cys Cys Ala Ser Gly
            35                  40                  45

Ser Thr Cys Thr Lys Gln Asn Asp Trp Tyr Ser Gln Cys Leu Pro Gly
    50                  55                  60

Gly Ala Val Thr Thr Pro Gly Thr Thr Thr Lys Pro Thr Ser Thr Ser
65                  70                  75                  80

Thr Ser Thr Ser Thr Ser Ser Arg Ser Thr Ser Thr Ser Gln Gly Gly
                85                  90                  95

Gly Val Ser Ser Thr Ser Ser Pro Pro Val Val Thr Asn Pro Pro
                100                 105                 110

Thr Ser Ile Pro Gly Gly Ala Ser Ser Thr Ala Ser Tyr Thr Gly Asn
            115                 120                 125

Pro Phe Ser Gly Val Gln Met Trp Ala Asn Asp Tyr Tyr Arg Ser Glu
    130                 135                 140

Val His Thr Leu Ala Met Pro Ser Leu Thr Gly Ala Met Ala Thr Lys
145                 150                 155                 160

Ala Ala Lys Val Ala Glu Val Pro Ser Tyr Gln Trp Met Asp Arg Asn
                165                 170                 175

Val Thr Val Asp Thr Leu Phe Ser Gly Thr Leu Ala Gln Ile Arg Ala
            180                 185                 190

Ala Asn Gln Ala Gly Ala Ser Pro Pro Tyr Ala Gly Ile Phe Val Val
        195                 200                 205

Tyr Asp Leu Pro Asp Arg Asp Cys Ala Ala Ala Ser Asn Gly Glu
    210                 215                 220

Trp Ser Ile Ala Asn Gly Gly Ala Ala Asn Tyr Lys Ala Tyr Ile Lys
225                 230                 235                 240

Arg Ile Arg Glu Leu Ile Ile Gln Tyr Ser Asp Ile Arg Met Leu Leu
                245                 250                 255

Val Ile Glu Pro Asp Ser Leu Ala Asn Met Val Thr Asn Met Gly Val
            260                 265                 270

Ala Lys Cys Ala Gly Ala Ala Ser Thr Tyr Lys Glu Leu Thr Ile His
        275                 280                 285

Ala Leu Lys Glu Leu Asn Leu Pro Asn Val Ala Met Tyr Leu Asp Ala
    290                 295                 300

Gly His Ala Gly Trp Leu Gly Trp Pro Ala Asn Ile Gln Pro Ala Ala
305                 310                 315                 320

Asp Leu Phe Ala Thr Leu Tyr Lys Asp Ala Gly Arg Pro Ala Ala Val
                325                 330                 335

Arg Gly Leu Ala Thr Asn Val Ala Asn Tyr Asn Ala Trp Ser Val Ser
            340                 345                 350

Ser Ala Pro Ala Tyr Thr Ser Pro Asn Pro Asn Tyr Asp Glu Lys His
        355                 360                 365

Tyr Val Glu Ala Phe Ser Pro Leu Leu Thr Ala Ala Gly Phe Pro Ala
    370                 375                 380
```

-continued

```
His Phe Ile Thr Asp Thr Gly Arg Ser Gly Lys Gln Pro Thr Gly Gln
385                 390                 395                 400

Leu Glu Trp Gly His Trp Cys Asn Ala Val Gly Thr Gly Phe Gly Gln
            405                 410                 415

Arg Pro Ser Ala Asn Thr Gly His Asp Leu Leu Asp Ala Phe Val Trp
        420                 425                 430

Ile Lys Pro Gly Gly Glu Cys Asp Gly Thr Ser Asp Thr Thr Ala Ala
    435                 440                 445

Arg Tyr Asp His Asn Cys Gly Leu Ala Asp Ala Leu Lys Pro Ala Pro
450                 455                 460

Glu Ala Gly Gln Trp Phe Gln Ala Tyr Phe Glu Gln Leu Leu Thr Asn
465                 470                 475                 480

Ala Asn Pro Pro Phe
                485

<210> SEQ ID NO 81
<211> LENGTH: 487
<212> TYPE: PRT
<213> ORGANISM: Magnaporthe grisea

<400> SEQUENCE: 81

Met Ala Ser Lys Leu Phe Leu Ala Ala Leu Leu Gln Gly Ala Leu
1               5                   10                  15

Ser Ser Pro Leu Ala Val Glu Glu Arg Gln Ala Cys Ala Ala Gln Trp
            20                  25                  30

Gly Gln Cys Gly Gly Gln Asp Tyr Thr Gly Pro Thr Cys Cys Gln Ser
        35                  40                  45

Gly Ser Thr Cys Val Val Ser Asn Gln Trp Tyr Ser Gln Cys Leu Pro
    50                  55                  60

Gly Ser Ser Asn Pro Thr Thr Thr Ser Arg Thr Ser Thr Ser Ser Ser
65                  70                  75                  80

Ser Ser Thr Ser Arg Thr Ser Ser Thr Ser Arg Pro Pro Ser Ser
                85                  90                  95

Val Pro Thr Thr Pro Thr Ser Val Pro Pro Thr Ile Thr Thr Thr Pro
            100                 105                 110

Thr Thr Thr Pro Thr Gly Gly Ser Gly Pro Gly Thr Thr Ala Ser Phe
        115                 120                 125

Thr Gly Asn Pro Phe Ala Gly Val Asn Leu Phe Pro Asn Lys Phe Tyr
    130                 135                 140

Ser Ser Glu Val His Thr Leu Ala Ile Pro Ser Leu Thr Gly Ser Leu
145                 150                 155                 160

Val Ala Lys Ala Ser Ala Val Ala Gln Val Pro Ser Phe Gln Trp Leu
                165                 170                 175

Asp Ile Ala Ala Lys Val Glu Thr Leu Met Pro Gly Ala Leu Ala Asp
            180                 185                 190

Val Arg Ala Ala Asn Ala Gly Gly Asn Tyr Ala Ala Gln Leu Val
        195                 200                 205

Val Tyr Asp Leu Pro Asp Arg Asp Cys Ala Ala Ala Ser Asn Gly
    210                 215                 220

Glu Phe Ser Ile Ala Asp Gly Gly Val Val Lys Tyr Lys Ala Tyr Ile
225                 230                 235                 240

Asp Ala Ile Arg Lys Gln Leu Leu Ala Tyr Ser Asp Val Arg Thr Ile
                245                 250                 255

Leu Val Ile Glu Pro Asp Ser Leu Ala Asn Met Val Thr Asn Met Gly
```

```
               260                 265                 270
Val Pro Lys Cys Ala Gly Ala Lys Asp Ala Tyr Leu Glu Cys Thr Ile
            275                 280                 285

Tyr Ala Val Lys Gln Leu Asn Leu Pro His Val Ala Met Tyr Leu Asp
            290                 295                 300

Gly Gly His Ala Gly Trp Leu Gly Trp Pro Ala Asn Leu Gln Pro Ala
305                 310                 315                 320

Ala Asp Leu Phe Gly Lys Leu Tyr Ala Asp Ala Gly Lys Pro Ser Gln
            325                 330                 335

Leu Arg Gly Met Ala Thr Asn Val Ala Asn Tyr Asn Ala Trp Asp Leu
            340                 345                 350

Thr Thr Ala Pro Ser Tyr Thr Thr Pro Asn Pro Asn Phe Asp Glu Lys
            355                 360                 365

Lys Tyr Ile Ser Ala Phe Ala Pro Leu Leu Ala Ala Lys Gly Trp Ser
            370                 375                 380

Ala His Phe Ile Ile Asp Gln Gly Arg Ser Gly Lys Gln Pro Thr Gly
385                 390                 395                 400

Gln Lys Glu Trp Gly His Trp Cys Asn Gln Gln Gly Val Gly Phe Gly
            405                 410                 415

Arg Arg Pro Ser Ala Asn Thr Gly Ser Glu Leu Ala Asp Ala Phe Val
            420                 425                 430

Trp Ile Lys Pro Gly Gly Glu Cys Asp Gly Val Ser Asp Pro Thr Ala
            435                 440                 445

Pro Arg Phe Asp His Phe Cys Gly Thr Asp Tyr Gly Ala Met Ser Asp
            450                 455                 460

Ala Pro Gln Ala Gly Gln Trp Phe Gln Lys Tyr Phe Glu Met Leu Leu
465                 470                 475                 480

Thr Asn Ala Asn Pro Pro Leu
            485

<210> SEQ ID NO 82
<211> LENGTH: 421
<212> TYPE: PRT
<213> ORGANISM: Sclerotinia sclerotiorum

<400> SEQUENCE: 82

Met Gly Leu Lys Asn Val Leu Ala Ala Ala Val Ala Pro Thr
1               5                   10                  15

Val Tyr Ala Gln Gly Ala Gly Tyr Ser Gln Cys Gly Gly Gln Gly Trp
            20                  25                  30

Ser Gly Ala Thr Thr Cys Val Ser Gly Phe Thr Cys Thr Tyr Thr Asn
            35                  40                  45

Glu Tyr Tyr Ser Gln Cys Leu Pro Gly Ser Gly Gly Ala Ser Ser
50                  55                  60

Ser Arg Pro Thr Thr Thr Ala Pro Thr Thr Ile Val Thr Ser Thr Lys
65                  70                  75                  80

Ala Ser Thr Thr Thr Gly Ser Ser Ala Thr Thr Ala Ala Pro Ala
            85                  90                  95

Ala Gly Asn Pro Phe Val Gly Lys Ala Leu Tyr Val Asn Pro Tyr Tyr
            100                 105                 110

Ala Ser Glu Ile Ser Ala Ser Ala Ile Pro Ser Leu Thr Gly Ala Met
            115                 120                 125

Ala Thr Lys Ala Ala Ala Val Ala Lys Val Pro Thr Phe Phe Trp Leu
            130                 135                 140
```

```
Asp Thr Ala Asp Lys Val Pro Thr Met Gly Thr Tyr Leu Ser Asn Ile
145                 150                 155                 160

Arg Ala Leu Asn Lys Ala Gly Ala Asn Pro Pro Val Ala Gly Thr Phe
                165                 170                 175

Val Val Tyr Asp Leu Pro Asp Arg Asp Cys Ala Ala Ala Ala Ser Asn
            180                 185                 190

Gly Glu Tyr Ser Ile Ala Asn Asn Gly Val Ala Asn Tyr Lys Ala Tyr
        195                 200                 205

Ile Asp Ser Ile Val Thr Ile Leu Lys Asn Tyr Ser Asp Thr Ser Val
    210                 215                 220

Ile Leu Ile Ile Val Asp Leu Pro Asn Val Ser Met Tyr Leu Asp Ala
225                 230                 235                 240

Gly His Ala Gly Trp Leu Gly Trp Ser Ala Asn Ile Gly Pro Ala Ala
                245                 250                 255

Gln Leu Phe Gly Gln Val Tyr Lys Ala Ala Gly Ser Pro Ser Gln Val
            260                 265                 270

Arg Gly Leu Ala Thr Asn Val Ala Asn Tyr Asn Ala Trp Thr Ser Ser
        275                 280                 285

Ser Cys Pro Ser Tyr Thr Ser Gly Asp Ser Asn Cys Asn Glu Lys Leu
    290                 295                 300

Tyr Ile Asn Ala Leu Ala Pro Leu Leu Thr Ala Gln Gly Phe Pro Ala
305                 310                 315                 320

His Phe Ile Met Asp Thr Gly Arg Asn Gly Val Gln Pro Thr Ala Gln
                325                 330                 335

Gln Ala Trp Gly Asp Trp Cys Asn Val Ile Gly Thr Gly Phe Gly Val
            340                 345                 350

Arg Pro Thr Thr Asn Thr Gly Asp Ala Leu Glu Asp Ala Phe Val Trp
        355                 360                 365

Val Lys Pro Gly Gly Glu Ala Asp Gly Thr Ser Asn Thr Thr Ala Ala
    370                 375                 380

Arg Tyr Asp Phe His Cys Gly Leu Ser Asp Ala Leu Gln Pro Ala Pro
385                 390                 395                 400

Glu Ala Gly Thr Trp Phe Gln Ala Tyr Phe Ala Gln Leu Leu Thr Asn
                405                 410                 415

Ala Asn Pro Ser Phe
            420

<210> SEQ ID NO 83
<211> LENGTH: 449
<212> TYPE: PRT
<213> ORGANISM: Phaeosphaeria nodorum

<400> SEQUENCE: 83

Met Lys Ala Val Ser Phe Leu Ala Val Ala Ala Leu Ala Pro Ala Ile
1               5                   10                  15

Lys Ala Gln Ala Ser Leu Tyr Gln Gln Cys Gly Gly Thr Gly Phe Ser
                20                  25                  30

Gly Ser Thr Thr Cys Val Ser Gly Ala Tyr Cys Ser Lys Val Asn Asp
            35                  40                  45

Ser Ala Thr Ser Ala Ala Pro Ala Pro Thr Thr Phe Lys Thr Ser Lys
        50                  55                  60

Thr Val Gly Ser Pro Ala Thr Gly Ser Ser Thr Gly Ser Ser Ala
65                  70                  75                  80

Thr Gly Thr Ala Ser Pro Gly Asp Gly Ser Asn Pro Leu Lys Gly Lys
                85                  90                  95
```

```
Asn Phe Tyr Ala Asn Ser Tyr Ala Ser Glu Ile Asn Asn Leu Ala
            100                 105                 110

Ala Pro Ser Leu Val Ala Ala Gly Asn Ala Ala Leu Ala Lys Ala
            115                 120                 125

Ser Asn Val Ala Lys Val Gly Thr Phe Tyr Trp Leu Asp Val Arg Ala
130                 135                 140

Lys Val Pro Ile Ile Ser Thr Phe Ala Lys Asp Val Gln Lys Arg Asn
145                 150                 155                 160

Ala Ala Gly Ala Asn Glu Val Leu Pro Leu Val Val Tyr Asp Leu Pro
                165                 170                 175

Glu Arg Asp Cys Ala Ala Leu Ala Ser Asn Gly Glu Leu Ser Leu Ala
            180                 185                 190

Asn Asn Gly Thr Ala Leu Tyr Gln Glu Tyr Ile Asp Met Ile Ala Ala
            195                 200                 205

Gln Ile Lys Gln Phe Pro Asp Val Thr Phe Leu Leu Val Glu Pro
210                 215                 220

Asp Ser Leu Ala Asn Leu Val Thr Asn Leu Asn Val Ala Lys Cys Ala
225                 230                 235                 240

Asn Ala Ala Thr Ala Tyr Lys Thr Leu Thr Ala Tyr Ala Ile Lys Thr
                245                 250                 255

Leu Asn Leu Lys Asn Val Ile Met Tyr Leu Asp Ala Gly His Ala Gly
            260                 265                 270

Trp Leu Gly Trp Thr Ala Asn Ile Glu Pro Ala Ala Glu Leu Phe Gly
            275                 280                 285

Ala Leu Tyr Lys Ser Ala Gly Ser Pro Ala Ala Val Arg Gly Leu Val
            290                 295                 300

Thr Asn Val Ala Asn Tyr Asn Ala Trp Ser Ile Ala Thr Cys Pro Ser
305                 310                 315                 320

Tyr Thr Gln Gly Asn Thr Asn Cys Asp Glu Lys Arg Tyr Val Asn Ala
                325                 330                 335

Leu Ala Pro Leu Leu Val Lys Asn Gly Phe Pro Ala His Phe Leu Thr
            340                 345                 350

Asp Thr Gly Arg Asn Gly Val Gln Pro Thr Lys Gln Ala Trp Gly
            355                 360                 365

Asp Trp Cys Asn Val Ile Gly Thr Gly Phe Gly Ile Arg Pro Ser Ser
            370                 375                 380

Thr Thr Asp Asp Pro Leu Leu Asp Ala Tyr Val Trp Val Lys Pro Gly
385                 390                 395                 400

Gly Glu Gly Asp Gly Thr Ser Asp Thr Ser Ala Val Arg Tyr Asp Ala
                405                 410                 415

His Cys Gly Tyr Ala Asp Ala Leu Lys Pro Ala Pro Glu Ala Gly Ser
            420                 425                 430

Trp Phe Gln Ala Tyr Phe Val Gln Leu Leu Ser Asn Ala Ser Pro Ala
            435                 440                 445

Phe

<210> SEQ ID NO 84
<211> LENGTH: 438
<212> TYPE: PRT
<213> ORGANISM: Agaricus bisporus

<400> SEQUENCE: 84

Met Phe Lys Phe Ala Ala Leu Leu Ala Leu Ala Ser Leu Val Pro Gly
1               5                   10                  15
```

```
Phe Val Gln Ala Gln Ser Pro Val Trp Gly Gln Cys Gly Gly Asn Gly
             20                  25                  30

Trp Thr Gly Pro Thr Thr Cys Ala Ser Gly Ser Thr Cys Val Lys Gln
         35                  40                  45

Asn Asp Phe Tyr Ser Gln Cys Leu Pro Asn Asn Gln Ala Pro Pro Ser
     50                  55                  60

Thr Thr Thr Gln Pro Gly Thr Thr Pro Pro Ala Thr Thr Thr Ser Gly
 65                  70                  75                  80

Gly Thr Gly Pro Thr Ser Gly Ala Gly Asn Pro Tyr Thr Gly Lys Thr
                 85                  90                  95

Val Trp Leu Ser Pro Phe Tyr Ala Asp Glu Val Ala Gln Ala Ala
                100                 105                 110

Asp Ile Ser Asn Pro Ser Leu Ala Thr Lys Ala Ala Ser Val Ala Lys
             115                 120                 125

Ile Pro Thr Phe Thr Trp Phe Asp Thr Val Ala Lys Val Pro Asp Leu
 130                 135                 140

Gly Gly Tyr Leu Ala Asp Ala Gln Ser Lys Asn Gln Leu Val Gln Ile
145                 150                 155                 160

Val Val Tyr Asp Leu Pro Asp Arg Asp Cys Ala Ala Leu Ala Ser Asn
                165                 170                 175

Gly Glu Phe Ser Leu Ala Asn Asp Gly Leu Asn Lys Tyr Lys Asn Tyr
                180                 185                 190

Val Asp Gln Ile Ala Ala Gln Ile Lys Gln Phe Pro Asp Val Ser Val
             195                 200                 205

Val Ala Val Ile Glu Pro Asp Ser Leu Ala Asn Leu Val Thr Asn Leu
         210                 215                 220

Asn Val Gln Lys Cys Ala Asn Ala Gln Ser Ala Tyr Lys Glu Gly Val
225                 230                 235                 240

Ile Tyr Ala Ile Gln Lys Leu Asp Ala Val Gly Val Thr Met Tyr Ile
                245                 250                 255

Asp Ala Gly His Ala Gly Trp Leu Gly Trp Pro Ala Asn Leu Ser Pro
             260                 265                 270

Ala Ala Gln Leu Phe Ala Gln Ile Tyr Arg Asp Ala Gly Ser Pro Arg
         275                 280                 285

Asn Leu Arg Gly Ile Ala Thr Asn Val Ala Asn Phe Asn Ala Leu Arg
     290                 295                 300

Ala Ser Ser Pro Asp Pro Ile Thr Gln Gly Asn Ser Asn Tyr Asp Glu
305                 310                 315                 320

Ile His Tyr Ile Glu Ala Leu Ala Pro Met Leu Ser Asn Ala Gly Phe
                325                 330                 335

Pro Ala His Phe Ile Val Asp Gln Gly Arg Ser Gly Val Gln Asn Ile
             340                 345                 350

Arg Asp Gln Trp Gly Asp Trp Cys Asn Val Lys Gly Ala Gly Phe Gly
         355                 360                 365

Gln Arg Pro Thr Thr Asn Thr Gly Ser Ser Leu Ile Asp Ala Ile Val
     370                 375                 380

Trp Val Lys Pro Gly Gly Glu Cys Asp Gly Thr Ser Asp Ser Ser Ser
385                 390                 395                 400

Pro Arg Phe Asp Ser His Cys Ser Leu Ser Asp Ala His Gln Pro Ala
                405                 410                 415

Pro Glu Ala Gly Thr Trp Phe Gln Ala Tyr Phe Glu Thr Leu Val Ala
             420                 425                 430
```

Asn Ala Asn Pro Ala Leu
        435

<210> SEQ ID NO 85
<211> LENGTH: 443
<212> TYPE: PRT
<213> ORGANISM: Lentinula edodes

<400> SEQUENCE: 85

Met Lys Ile Thr Ser Thr Gly Leu Leu Ala Leu Ser Ser Leu Leu Pro
1               5                   10                  15

Phe Ala Leu Gly Gln Ser Gln Leu Tyr Ala Gln Cys Gly Gly Ile Gly
            20                  25                  30

Trp Ser Gly Ala Thr Thr Cys Val Ser Gly Ala Thr Cys Thr Val Val
        35                  40                  45

Asn Ala Tyr Tyr Ser Gln Cys Leu Pro Gly Ser Ala Ser Ala Pro Pro
    50                  55                  60

Thr Ser Thr Ser Ser Ile Gly Thr Gly Thr Thr Ser Ser Ala Pro
65                  70                  75                  80

Gly Ser Thr Gly Thr Thr Thr Pro Ala Ala Gly Asn Pro Phe Thr Glu
                85                  90                  95

Gln Ile Tyr Leu Ser Pro Tyr Tyr Ala Asn Glu Ile Ala Ala Ala Val
            100                 105                 110

Thr Gln Ile Ser Asp Pro Thr Thr Ala Ala Ala Ala Lys Val Ala
        115                 120                 125

Asn Ile Pro Thr Phe Ile Trp Leu Asp Gln Val Ala Lys Val Pro Asp
    130                 135                 140

Leu Gly Thr Tyr Leu Ala Asp Ala Ser Ala Lys Gln Lys Ser Glu Gly
145                 150                 155                 160

Lys Asn Tyr Leu Val Gln Ile Val Val Tyr Asp Leu Pro Asp Arg Asp
                165                 170                 175

Cys Ala Ala Leu Ala Ser Asn Gly Glu Phe Thr Ile Ala Asp Asn Gly
            180                 185                 190

Glu Ala Asn Tyr His Asp Tyr Ile Asp Gln Ile Val Ala Gln Ile Lys
        195                 200                 205

Gln Tyr Pro Asp Val His Val Val Ala Val Ile Glu Pro Asp Ser Leu
    210                 215                 220

Ala Asn Leu Val Thr Asn Leu Ser Val Ala Lys Cys Ala Asn Ala Gln
225                 230                 235                 240

Thr Thr Tyr Leu Glu Cys Val Thr Tyr Ala Met Gln Gln Leu Ser Ala
                245                 250                 255

Val Gly Val Thr Met Tyr Leu Asp Ala Gly His Ala Gly Trp Leu Gly
            260                 265                 270

Trp Pro Ala Asn Leu Ser Pro Ala Gln Leu Phe Thr Ser Leu Tyr
        275                 280                 285

Ser Asn Ala Gly Ser Pro Ser Gly Val Arg Gly Leu Ala Thr Asn Val
    290                 295                 300

Ala Asn Tyr Asn Ala Leu Val Ala Thr Thr Pro Asp Pro Ile Thr Gln
305                 310                 315                 320

Gly Asp Pro Asn Tyr Asp Glu Met Leu Tyr Ile Glu Ala Leu Ala Pro
                325                 330                 335

Leu Leu Gly Ser Phe Pro Ala His Phe Ile Val Asp Gln Gly Arg Ser
            340                 345                 350

Gly Val Gln Asp Ile Arg Gln Gln Trp Gly Asp Trp Cys Asn Val Leu
        355                 360                 365

```
Gly Ala Gly Phe Gly Thr Gln Pro Thr Thr Asn Thr Gly Ser Ser Leu
        370                 375                 380

Ile Asp Ser Ile Val Trp Val Lys Pro Gly Gly Glu Cys Asp Gly Thr
385                 390                 395                 400

Ser Asn Thr Ser Ser Pro Arg Tyr Asp Ala His Cys Gly Leu Pro Asp
                405                 410                 415

Ala Thr Pro Asn Ala Pro Glu Ala Gly Thr Trp Phe Gln Ala Tyr Phe
            420                 425                 430

Glu Thr Leu Val Glu Lys Ala Asn Pro Pro Leu
        435                 440

<210> SEQ ID NO 86
<211> LENGTH: 460
<212> TYPE: PRT
<213> ORGANISM: Coniophora puteana

<400> SEQUENCE: 86

Met Phe Lys Phe Ala Ala Leu Ser Ala Phe Val Ala Leu Val Pro Leu
1               5                   10                  15

Leu Val Asn Ala Gln Val Ala Ala Tyr Gly Gln Cys Gly Gly Gln Asp
            20                  25                  30

Trp Thr Gly Ala Thr Ala Cys Ala Ser Gly Thr Ala Cys Thr Lys Val
        35                  40                  45

Asn Asp Tyr Tyr Tyr Gln Cys Leu Pro Gly Ser Ser Gly Ser Ser Val
    50                  55                  60

Ser Gly Gly Ser Gly Ser Gly Ser Thr Ser Ala Pro Ser Pro Thr Ser
65                  70                  75                  80

Thr Val Pro Thr Ser Thr Ser Ala Ser Thr Ala Pro Ser Ser Thr
                85                  90                  95

Ser Thr Ser Ser Ala Ala Ser Ser Asp Asn Pro Tyr Thr Gly Tyr Gln
                100                 105                 110

Ile Phe Leu Asn Pro Glu Tyr Ala Ser Glu Val Gln Ala Ala Ile Pro
            115                 120                 125

Ser Ile Thr Asp Ser Ala Val Ala Ala Lys Ala Leu Lys Val Ala Glu
        130                 135                 140

Val Pro Val Phe Phe Trp Leu Asp Gln Val Ala Lys Val Pro Asp Leu
145                 150                 155                 160

Glu Thr Tyr Leu Ala Ala Ala Asp Lys Gln Gly Lys Ser Ser Gly Gln
                165                 170                 175

Lys Gln Leu Leu Gln Ile Val Val Tyr Asp Leu Pro Asp Arg Asp Cys
            180                 185                 190

Ala Ala Asn Ala Ser Asn Gly Glu Phe Ser Ile Ser Asp Asp Gly Gln
        195                 200                 205

Ala Lys Tyr Glu Asn Tyr Ile Asp Gln Ile Val Ala Ile Val Lys Lys
    210                 215                 220

Tyr Pro Asp Val Arg Val Val Ala Val Val Glu Pro Asp Ser Met Gly
225                 230                 235                 240

Asn Leu Val Thr Asn Met Asp Leu Pro Lys Cys Ser Ala Ala Ala Pro
                245                 250                 255

Thr Tyr Lys Thr Cys Ile Asn Tyr Ala Ile Ala Gln Leu Ser Ser Ala
                260                 265                 270

Gly Val Tyr Met Tyr Val Asp Ala Gly His Ala Gly Trp Leu Gly Trp
            275                 280                 285

Pro Asn Asn Leu Ala Pro Ala Ala Gln Leu Phe Gly Glu Leu Tyr Glu
```

```
            290                 295                 300
Thr Ser Gly Lys Ser Ala Tyr Phe Arg Gly Leu Ala Thr Asn Val Ala
305                 310                 315                 320

Asn Tyr Asn Ala Leu Asn Thr Ser Ser Pro Asp Pro Cys Thr Gln Asn
                325                 330                 335

Ala Pro Asn Tyr Asp Glu Met Leu Tyr Ile Asn Ala Leu Ser Pro Leu
            340                 345                 350

Leu Gln Gln Gly Phe Ser Ala Gln Phe Ile Val Asp Gln Gly Arg
        355                 360                 365

Ser Gly Val Gln Asn Ile Arg Asn Ala Trp Gly Asp Trp Cys Asn Ile
    370                 375                 380

Lys Gly Ala Gly Phe Gly Ile Arg Pro Thr Thr Asp Thr Gly Ser Pro
385                 390                 395                 400

Leu Ile Asp Ser Ile Val Trp Val Lys Pro Gly Gly Glu Cys Asp Gly
                405                 410                 415

Thr Ser Asn Ser Ser Ala Pro Arg Tyr Asp Ser Thr Cys Ser Leu Ser
            420                 425                 430

Asp Ser Leu Gln Pro Ala Pro Glu Ala Gly Thr Trp Phe Gln Gln Tyr
        435                 440                 445

Phe Glu Ala Leu Val Thr Asn Ala Val Pro Ser Leu
450                 455                 460
```

<210> SEQ ID NO 87
<211> LENGTH: 442
<212> TYPE: PRT
<213> ORGANISM: Volvariella volvacea

<400> SEQUENCE: 87

```
Met Ser Arg Phe Ser Ala Leu Thr Ala Leu Leu Ser Leu Pro Leu
1               5                   10                  15

Leu Ala Ile Ala Gln Ser Pro Leu Tyr Gly Gln Cys Gly Gly Asn Gly
            20                  25                  30

Trp Thr Gly Pro Lys Thr Cys Val Ser Gly Ala Thr Cys Thr Val Ile
        35                  40                  45

Asn Asp Trp Tyr Trp Gln Cys Leu Pro Gly Asn Gly Pro Thr Ser Ser
    50                  55                  60

Ser Pro Thr Ser Thr Pro Thr Thr Thr Thr Thr Gly Gly Pro Gln
65                  70                  75                  80

Pro Thr Val Pro Ala Ala Gly Asn Pro Tyr Thr Gly Tyr Glu Ile Tyr
                85                  90                  95

Leu Ser Pro Tyr Tyr Ala Ala Glu Ala Gln Ala Ala Ala Gln Ile
            100                 105                 110

Ser Asp Ala Thr Gln Lys Ala Lys Ala Leu Lys Val Ala Gln Ile Pro
        115                 120                 125

Thr Phe Thr Trp Phe Asp Val Ile Ala Lys Thr Ser Thr Leu Gly Asp
130                 135                 140

Tyr Leu Ala Glu Ala Ser Ala Leu Gly Lys Ser Ser Gly Lys Lys Tyr
145                 150                 155                 160

Leu Val Gln Ile Val Val Tyr Asp Leu Pro Asp Arg Asp Cys Ala Ala
                165                 170                 175

Leu Ala Ser Asn Gly Glu Phe Ser Ile Ala Asn Asn Gly Leu Asn Asn
            180                 185                 190

Tyr Lys Gly Tyr Ile Asp Gln Leu Val Ala Gln Ile Lys Lys Tyr Pro
        195                 200                 205
```

```
Asp Val Arg Val Val Ala Val Ile Glu Pro Asp Ser Leu Ala Asn Leu
    210                 215                 220

Val Thr Asn Leu Asn Val Ser Lys Cys Ala Asn Ala Gln Thr Ala Tyr
225                 230                 235                 240

Lys Ala Gly Val Thr Tyr Ala Leu Gln Gln Leu Asn Ser Val Gly Val
                245                 250                 255

Tyr Met Tyr Leu Asp Ala Gly His Ala Gly Trp Leu Gly Trp Pro Ala
                260                 265                 270

Asn Leu Asn Pro Ala Ala Gln Leu Phe Ser Gln Leu Tyr Arg Asp Ala
                275                 280                 285

Gly Ser Pro Gln Tyr Val Arg Gly Leu Ala Thr Asn Val Ala Asn Tyr
            290                 295                 300

Asn Ala Leu Ser Ala Ser Ser Pro Asp Pro Val Thr Gln Gly Asn Pro
305                 310                 315                 320

Asn Tyr Asp Glu Leu His Tyr Ile Asn Ala Leu Ala Pro Ala Leu Gln
                325                 330                 335

Ser Gly Gly Phe Pro Ala His Phe Ile Val Asp Gln Gly Arg Ser Gly
                340                 345                 350

Val Gln Asn Ile Arg Gln Gln Trp Gly Asp Trp Cys Asn Val Lys Gly
            355                 360                 365

Ala Gly Phe Gly Gln Arg Pro Thr Leu Ser Thr Gly Ser Ser Leu Ile
        370                 375                 380

Asp Ala Ile Val Trp Ile Lys Pro Gly Gly Glu Cys Asp Gly Thr Thr
385                 390                 395                 400

Asn Thr Ser Ser Pro Arg Tyr Asp Ser His Cys Gly Leu Ser Asp Ala
                405                 410                 415

Thr Pro Asn Ala Pro Glu Ala Gly Gln Trp Phe Gln Ala Tyr Phe Glu
            420                 425                 430

Thr Leu Val Arg Asn Ala Ser Pro Pro Leu
            435                 440

<210> SEQ ID NO 88
<211> LENGTH: 389
<212> TYPE: PRT
<213> ORGANISM: Coniophora puteana

<400> SEQUENCE: 88

Met Phe Ser Pro Val Val Leu Gly Ala Leu Ala Leu Leu Pro Ala
1               5                   10                  15

Ala Val Gln Ala Met Pro Ala Ser Thr Gln Ala Arg Ala Ala Asp Ala
            20                  25                  30

Thr Ala Asn Pro Tyr Thr Gly Tyr Thr Ile Phe Lys Asn Pro Glu Tyr
        35                  40                  45

Val Ala Glu Val Gln Ala Ala Val Gln Gln Ile Ser Asp Ser Ser Leu
    50                  55                  60

Ala Ser Ala Ala Ala Gly Val Glu Asp Val Pro Val Phe Phe Trp Leu
65                  70                  75                  80

Asp Gln Val Ala Lys Val Pro Asn Leu Thr Thr Tyr Leu Ala Ala Ala
                85                  90                  95

Asp Ala Glu Ala Lys Ser Ser Gly Ser Gln Gln Leu Phe Gln Ile Val
            100                 105                 110

Val Tyr Asp Leu Pro Asp Arg Asp Cys Ala Ala Ala Ser Asn Gly
        115                 120                 125

Glu Phe Ser Ile Ser Asp Asn Gly Gln Ala Asn Tyr Glu Asn Tyr Ile
    130                 135                 140
```

Asp Gln Ile Val Ala Ser Ile Lys Gln Tyr Pro Asp Val Arg Val
145                 150                 155                 160

Ala Val Val Glu Pro Asp Ser Met Ala Asn Leu Val Thr Asn Leu Ser
                165                 170                 175

Val Gln Lys Cys Ala Asp Ala Glu Ser Thr Tyr Lys Thr Cys Val Ala
            180                 185                 190

Tyr Ala Ile Glu Gln Leu Ala Thr Val Gly Val Tyr Met Tyr Leu Asp
        195                 200                 205

Ala Gly His Ala Gly Trp Leu Gly Trp Pro Ala Asn Leu Ser Pro Ala
    210                 215                 220

Ala Glu Leu Phe Ala Gln Met Tyr Ser Thr Thr Gly Ser Ser Pro Tyr
225                 230                 235                 240

Phe Arg Gly Leu Ala Thr Asn Val Ala Asn Tyr Asn Ser Leu Thr Thr
                245                 250                 255

Asp Ser Pro Asp Pro Ile Thr Ser Gly Asp Ser Asn Tyr Asp Glu Leu
            260                 265                 270

Leu Tyr Ile Glu Ala Leu Ser Pro Leu Leu Val Asp Asn Gly Phe Pro
        275                 280                 285

Ala Gln Phe Ile Val Glu Gln Ala Arg Ser Gly Val Gln Asn Ile Arg
    290                 295                 300

Ser Ala Trp Gly Asp Trp Cys Asn Val Lys Gly Ala Gly Phe Gly Leu
305                 310                 315                 320

Arg Pro Ser Thr Asp Thr Pro Ser Ser Leu Ile Asp Ser Ile Val Trp
                325                 330                 335

Val Lys Pro Gly Gly Glu Ala Asp Gly Thr Ser Asn Ser Ser Ala Ala
            340                 345                 350

Arg Tyr Asp Tyr His Cys Ser Leu Ser Asp Ala Leu Gln Pro Ala Pro
        355                 360                 365

Glu Ala Gly Thr Trp Phe Gln Thr Tyr Phe Glu Asp Leu Val Ser Gly
    370                 375                 380

Ala Asn Pro Ala Phe
385

<210> SEQ ID NO 89
<211> LENGTH: 454
<212> TYPE: PRT
<213> ORGANISM: Coprinopsis cinerea okayama

<400> SEQUENCE: 89

Met Leu Lys Gly Ser Lys Phe Phe Ala Leu Ser Leu Ala Leu Leu Pro
1               5                   10                  15

Ala Leu Val Gln Ala Gln Arg Pro Leu Tyr Ala Gln Cys Gly Gly Thr
            20                  25                  30

Gly Trp Thr Gly Glu Thr Thr Cys Val Ser Gly Ala Val Cys Glu Val
        35                  40                  45

Ile Asn Gln Trp Tyr His Gln Cys Leu Pro Gly Ser Asn Gln Pro Gln
    50                  55                  60

Pro Pro Val Thr Thr Gln Pro Pro Val Val Pro Thr Thr Ser Gln
65                  70                  75                  80

Pro Pro Val Val Pro Thr Asn Pro Pro Gly Gly Thr Pro Val Pro
            85                  90                  95

Ser Thr Gly Asn Pro Phe Glu Gly Tyr Asp Ile Tyr Leu Ser Pro Tyr
        100                 105                 110

Tyr Ala Glu Glu Val Glu Ala Ala Ala Met Ile Asp Asp Pro Val

```
            115                 120                 125
Leu Lys Ala Lys Ala Leu Lys Val Lys Glu Ile Pro Thr Phe Ile Trp
130                 135                 140

Phe Asp Val Val Arg Lys Thr Pro Asp Leu Gly Arg Tyr Leu Ala Asp
145                 150                 155                 160

Ala Thr Ala Ile Gln Gln Arg Thr Gly Arg Lys Gln Leu Val Gln Ile
                165                 170                 175

Val Val Tyr Asp Leu Pro Asp Arg Asp Cys Ala Ala Ala Ser Asn
            180                 185                 190

Gly Glu Phe Ser Leu Ala Asp Gly Met Glu Lys Tyr Lys Asp Tyr
        195                 200                 205

Val Asp Arg Leu Ala Ser Glu Ile Arg Lys Tyr Pro Asp Val Arg Ile
210                 215                 220

Val Ala Val Ile Glu Pro Asp Ser Leu Ala Asn Met Val Thr Asn Met
225                 230                 235                 240

Asn Val Ala Lys Cys Arg Gly Ala Glu Ala Tyr Lys Glu Gly Val
            245                 250                 255

Ile Tyr Ala Leu Arg Gln Leu Ser Ala Leu Gly Val Tyr Ser Tyr Val
                260                 265                 270

Asp Ala Gly His Ala Gly Trp Leu Gly Trp Asn Ala Asn Leu Ala Pro
            275                 280                 285

Ser Ala Arg Leu Phe Ala Gln Ile Tyr Lys Asp Ala Gly Arg Ser Ala
290                 295                 300

Phe Ile Arg Gly Leu Ala Thr Asn Val Ser Asn Tyr Asn Ala Leu Ser
305                 310                 315                 320

Ala Thr Thr Arg Asp Pro Val Thr Gln Gly Asn Asp Asn Tyr Asp Glu
                325                 330                 335

Leu Arg Phe Ile Asn Ala Leu Ala Pro Leu Leu Arg Asn Glu Gly Trp
            340                 345                 350

Asp Ala Lys Phe Ile Val Asp Gln Gly Arg Ser Gly Val Gln Asn Ile
            355                 360                 365

Arg Gln Glu Trp Gly Asn Trp Cys Asn Val Tyr Gly Ala Gly Phe Gly
370                 375                 380

Met Arg Pro Thr Leu Asn Thr Pro Ser Ser Ala Ile Asp Ala Ile Val
385                 390                 395                 400

Trp Ile Lys Pro Gly Gly Glu Ala Asp Gly Thr Ser Asp Thr Ser Ala
                405                 410                 415

Pro Arg Tyr Asp Thr His Cys Gly Lys Ser Asp Ser His Lys Pro Ala
            420                 425                 430

Pro Glu Ala Gly Thr Trp Phe Gln Glu Tyr Phe Val Asn Leu Val Lys
        435                 440                 445

Asn Ala Asn Pro Pro Leu
    450

<210> SEQ ID NO 90
<211> LENGTH: 361
<212> TYPE: PRT
<213> ORGANISM: Moniliophthora perniciosa

<400> SEQUENCE: 90

Ile Pro Gly Ser Asp Pro Gly Asn Pro Gly Pro Thr Ser Ser Thr
1               5                   10                  15

Leu Ser Thr Ala Ala Pro Thr Asn Thr Gln Ser Pro Val Glu
            20                  25                  30
```

```
Asp Asn Pro Tyr Thr Gly Tyr Thr Ile Tyr Leu Ser Pro Tyr Tyr Ala
            35                  40                  45

Asp Glu Ile Asp Ala Ala Ala Lys Ile Thr Asp Pro Thr Leu Lys
 50                  55                  60

Val Gln Ala Leu Lys Val Lys Glu Ile Pro Thr Phe Ile Trp Phe Asp
 65                  70                  75                  80

Thr Thr Ala Lys Leu Ser Thr Leu Glu Pro Tyr Leu Lys Asp Ala Ser
                85                  90                  95

Ala Lys Gly Lys Ala Glu Gly Lys Lys Tyr Leu Leu Gln Ile Val Val
            100                 105                 110

Tyr Thr Leu Pro Glu Arg Asp Cys Ala Ala Leu Ala Ser Asn Gly Glu
            115                 120                 125

Leu Ser Ile Asp Asn Gly Gly Glu Val Lys Ser Arg Glu Tyr Ile Asp
            130                 135                 140

Thr Met Val Ala Thr Ile Lys Lys Tyr Pro Asp Val Arg Val Val Ala
145                 150                 155                 160

Val Val Glu Pro Asp Ser Leu Ala Asn Leu Val Thr Asn Leu Asn Val
                165                 170                 175

Gln Lys Cys Ser Lys Ala Gln Thr Ile Tyr Lys Thr Ser Thr Gln Tyr
            180                 185                 190

Ala Leu Lys Gln Leu Asp Thr Ala Gly Val Tyr Met Tyr Leu Asp Ala
            195                 200                 205

Gly His Ala Gly Trp Leu Gly Trp Pro Ala Asn Leu Thr Pro Thr Ala
            210                 215                 220

Gln Leu Phe Gln Gln Val Trp Gln Asp Ala Gly Ser Pro Lys Phe Val
225                 230                 235                 240

Arg Gly Leu Ala Thr Asn Val Ala Asn Phe Asn Ala Leu Arg Ala Ala
                245                 250                 255

Ser Pro Asp Pro Val Thr Ser Gln Asn Pro Asn Tyr Asp Glu Ile His
            260                 265                 270

Tyr Ile Glu Gly Arg Ala Gly Gln Gln Asn Leu Arg Lys Glu Trp Gly
            275                 280                 285

Asp Trp Cys Asn Val Lys Gly Ala Gly Phe Gly Thr Arg Pro Thr Thr
290                 295                 300

Asn Thr Gly Ser Ser Leu Ile Asp Ser Ile Val Trp Val Lys Pro Gly
305                 310                 315                 320

Gly Glu Ser Ala Arg Phe Asp Ala Lys Cys Val Ser Ala Ser Ser His
                325                 330                 335

Val Pro Ala Pro Glu Ala Gly Thr Trp Phe Gln Glu Tyr Phe Glu Ala
            340                 345                 350

Leu Val Arg Asn Ala Asn Pro Ala Leu
            355                 360

<210> SEQ ID NO 91
<211> LENGTH: 460
<212> TYPE: PRT
<213> ORGANISM: Piromyces rhizinflatus

<400> SEQUENCE: 91

Met Lys Phe Ser Thr Leu Ile Gly Thr Leu Phe Ala Thr Gly Ala Leu
 1               5                  10                  15

Ala Ser Ser Cys His Arg Asp Tyr Pro Cys Cys Asn Asp Cys Asn Val
            20                  25                  30

Val Tyr Gln Asp Trp Glu Arg Asp Trp Gly Val Leu Asn Gly Gln Glu
            35                  40                  45
```

```
Trp Cys Phe Ile Asp Lys Asn Arg Cys Asn Gly Gly Tyr Cys Lys
 50                  55                  60

Phe Glu Ser Leu Gly Tyr Pro Cys Cys Asn Gly Cys Asp Val Tyr
 65                  70                  75                  80

Thr Asp Asn Asp Gly Arg Trp Gly Val Glu Asn Gly Asn Trp Cys Gly
                 85                  90                  95

Ile Arg Asp Asp Lys Cys Asn Gly Tyr Gln Gln Pro Arg Thr Thr Thr
                100                 105                 110

Thr Thr Arg Thr Thr Thr Arg Thr Thr Thr Gln Arg Pro Val Gln
                115                 120                 125

Thr Asn Val Ser Asp Asn Phe Phe Glu Asn Thr Leu Tyr Ser Asn Phe
                130                 135                 140

Lys Phe Gln Gly Glu Val Gln Ser Ser Ile Gln Lys Leu Ser Gly Asp
145                 150                 155                 160

Met Ala Lys Lys Ala Glu Lys Val Lys Tyr Val Pro Thr Ala Val Trp
                165                 170                 175

Leu Ala Trp Glu Gly Ala Pro Arg Glu Val Pro Gln Tyr Leu Asp Asp
                180                 185                 190

Ala Gly Ser Lys Thr Val Phe Val Leu Tyr Met Ile Pro Thr Arg
                195                 200                 205

Asp Cys Asn Ala Asn Ala Ser Val Gly Gly Ser Ala Thr Leu Glu Lys
210                 215                 220

Tyr Lys Gly Tyr Ile Asp Asn Ile Tyr Asn Thr Phe Asn Gln Tyr Pro
225                 230                 235                 240

Asn Ser Lys Ile Val Met Ile Leu Glu Pro Asp Thr Ile Gly Asn Leu
                245                 250                 255

Val Thr Ala Asn Asn Ala Asn Cys Met Asn Val Gln Asn Leu His Lys
                260                 265                 270

Gln Gly Leu Ala Tyr Ala Ile Ser Lys Phe Gly Thr Gln Lys Asn Val
                275                 280                 285

Arg Val Tyr Leu Asp Ala Ala His Gly Ala Trp Leu Ser Ser His Ala
                290                 295                 300

Asp Lys Thr Ala Gln Val Ile Lys Glu Ile Leu Asn Asn Ala Gly Ser
305                 310                 315                 320

Gly Lys Leu Arg Gly Ile Thr Thr Asn Val Ser Asn Tyr Gln Thr Val
                325                 330                 335

Asn Asp Glu Tyr Ser Tyr Gln Met Arg Leu Asn Ser Ala Leu Gln Asn
                340                 345                 350

Leu Gly Val Arg Asp Leu His Tyr Ile Ile Asp Thr Ser Arg Asn Gly
                355                 360                 365

Ala Asn Ile Ala Gln Gln Phe Asn Gln Ser Gly Thr Trp Cys Asn Phe
370                 375                 380

Lys Gly Ala Gly Leu Gly Ala Arg Pro Gln Ala Asn Pro Asp Ser Ser
385                 390                 395                 400

Lys Pro Leu Leu Asp Ala Tyr Met Trp Ile Lys Thr Pro Gly Glu Ala
                405                 410                 415

Asp Gly Ser Ser Ser Gly Ser Arg Ala Asp Pro Val Cys Gly Arg Trp
                420                 425                 430

Asp Ser Leu Gln Gly Ala Pro Asp Ala Gly Ser Trp Phe His Asp Tyr
                435                 440                 445

Phe Val Met Leu Leu Gln Asn Ala Asn Pro Pro Phe
450                 455                 460
```

<210> SEQ ID NO 92
<211> LENGTH: 518
<212> TYPE: PRT
<213> ORGANISM: Piromyces rhizinflatus

<400> SEQUENCE: 92

```
Met Lys Phe Ile Val Cys Ala Ser Ile Leu Ser Leu Gly Leu Phe Lys
1               5                   10                  15

Phe Ala Asp Ala Ala Cys Ala Gly Pro Tyr Ala Gln Cys Gly Gly Asn
            20                  25                  30

Asn Phe Asn Gly Glu Asn Cys Cys Gln Ser Gly Tyr Lys Cys Val Ala
        35                  40                  45

Ile Asn Glu Trp Tyr Ser Gln Cys Gln Glu Gly Ala Ala Glu Pro Glu
    50                  55                  60

Pro Val Pro Gln Ser Ser Ala Ala Asp Asp Gln Trp Asn Asn Asn Asn
65                  70                  75                  80

Gln Trp Asn Asn Asn Gln Gln Asn Asn Gln Trp Asn Asn Pro Trp Asp
                85                  90                  95

Asn Asn Asn Asn Gln Trp Asn Asn Gln Trp Asn Asn Gln Gln
            100                 105                 110

Asn Asn Gln Trp Asn Asn Asn Gln Gln Asn Asn Gln Trp Asp Asn
            115                 120                 125

Asn Asn Gln Trp Asn Asn Asn Gln Trp Asn Asn Gln Gln Gln Asn
        130                 135                 140

Asn Gln Gln Gln Asn Asn Gln Gln Asn Asn Gln Trp Asn Asn Asn
145                 150                 155                 160

Asn Gln Trp Asn Asn Asn Gln Gln Asn Asn Gln Gln Gln Asn Asn
                165                 170                 175

Gln Ala Pro Ala Gln Ser Asn Gly Gly Ala Ser Gly Ser Ser Gln
            180                 185                 190

Asn Phe Phe Thr Asn Glu Ile Tyr Ala Asn Pro Arg Phe Ile Glu Glu
            195                 200                 205

Ile Asp Ser Ser Ile Pro Lys Leu Thr Pro Glu Leu Ala Ala Lys Ala
    210                 215                 220

Glu Lys Val Lys Gln Val Pro Thr Ala Val Trp Leu Ala Trp Asp Gly
225                 230                 235                 240

Ala Pro Gly Glu Val Glu Gly His Leu Lys Ala Ala Gly Ser Lys Thr
                245                 250                 255

Val Val Phe Ile Leu Tyr Met Ile Pro Thr Arg Asp Cys Asn Ser Asn
            260                 265                 270

Ala Ser Ala Gly Gly Ala Ser Asp Leu Asn Lys Tyr Lys Gly Tyr Val
        275                 280                 285

Asp Asp Ile Ala Gly Thr Ile Lys Ser His Pro Glu Ser Lys Val Val
    290                 295                 300

Met Ile Val Glu Pro Asp Thr Leu Gly Asn Leu Val Thr Gly Ser Ser
305                 310                 315                 320

Glu Ala Cys Lys Asn Val His Ser Leu His Lys Ser Ala Leu Ser Tyr
                325                 330                 335

Ala Val Asn Val Phe Gly Ala Met Ser Asn Val Ser Val Tyr Leu Asp
            340                 345                 350

Ala Ala His Gly Lys Trp Leu Gly Gly Ser Thr Asp Lys Val Ala Ser
        355                 360                 365

Val Leu Lys Glu Ile Leu Asp Asn Ala Pro Asn Gly Lys Ile Arg Gly
    370                 375                 380
```

```
Leu Ser Thr Asn Val Ser Asn Tyr Gln Pro Leu Ser Glu Ala Gln
385                 390                 395                 400

Tyr His Gln Gly Leu Ser Ser Ala Leu Ala Ala Val Gly Tyr Pro Gly
            405                 410                 415

Met Lys Phe Val Val Asp Thr Gly Arg Asn Gly Val Asp Val Ser Ser
        420                 425                 430

Thr Phe Ser Ile Asn Glu Thr Trp Cys Asn Phe Val Gly Thr Gly Phe
    435                 440                 445

Gly Glu Arg Pro Gln Gly Asn Pro Ser Gly Tyr Pro Leu Leu Asp Ala
        450                 455                 460

Phe Met Trp Leu Lys Thr Pro Gly Glu Ala Asp Gly Ser Ala Thr Gly
465                 470                 475                 480

Ser Arg Ala Asp Pro Val Cys Ala Arg Gln Asp Ser Leu Gln Gly Ala
            485                 490                 495

Pro Asp Ala Gly Gln Trp Phe His Glu Tyr Phe Val Gln Leu Leu Glu
        500                 505                 510

Asn Ala Lys Pro Gly Phe
            515

<210> SEQ ID NO 93
<211> LENGTH: 376
<212> TYPE: PRT
<213> ORGANISM: Piromyces rhizinflatus

<400> SEQUENCE: 93

Glu Thr Leu Pro Gln Gln Ser Asn Ser Ala Lys Thr Leu Pro Gln Gln
1               5                   10                  15

Ser Asp Ser Ala Lys Thr Ile Pro Gln Pro Thr Ser Ala Glu Ser Gln
            20                  25                  30

Thr Ser Lys Thr Leu Pro Gln Thr Gly Gly Ser Gly Asn Gly Ser Ser
        35                  40                  45

Gln Asn Phe Phe Leu Asn Glu Ile Tyr Ala Asn Pro Lys Phe Ile Glu
    50                  55                  60

Glu Val Glu Asp Ser Ile Glu Lys Leu Thr Pro Glu Leu Gln Ala Lys
65                  70                  75                  80

Ala Glu Lys Val Lys Asp Val Pro Thr Ala Val Trp Leu Ala Trp Asp
                85                  90                  95

Gly Ser Pro Gly Glu Val Glu Gly His Leu Val Ala Ala Gly Ser Lys
            100                 105                 110

Thr Val Val Phe Leu Leu Tyr Met Ile Pro Thr Arg Asp Cys Asn Ser
        115                 120                 125

Asn Ala Ser Ala Gly Gly Ala Ala Ser Leu Asp Lys Tyr Lys Gly Tyr
    130                 135                 140

Ile Asp Asp Ile Ser Asn Thr Ile Lys Ser His Pro Glu Ser Lys Val
145                 150                 155                 160

Val Met Val Val Glu Pro Asp Thr Leu Gly Asn Leu Val Thr Gly Asn
                165                 170                 175

Ser Glu Ala Cys Lys Asn Val His Thr Leu His Lys Asn Ala Leu Ser
            180                 185                 190

Tyr Ala Val Asp Val Phe Gly Ala Met Ser Asn Val Ser Val Tyr Leu
        195                 200                 205

Asp Ala Ala His Gly Met Trp Leu Gly Pro His Thr Asp Lys Val Ala
    210                 215                 220

Ser Val Ile Lys Glu Ile Leu Asn Asn Ala Pro Asn Gly Lys Ile Arg
```

```
                225                 230                 235                 240
Gly Leu Ser Thr Asn Val Ser Asn Tyr Gln Pro Val Ser Ser Glu Tyr
                    245                 250                 255

Gln Tyr His Gln Lys Leu Ala Ala Ser Leu Ala Ala Val Gly Val Asn
                    260                 265                 270

Asp Val His Phe Ile Val Asp Thr Gly Arg Ser Gly Val Asp Val Thr
                    275                 280                 285

Glu Thr Phe Ser Lys Gln Gln Thr Trp Cys Asn Phe Ile Gly Ala Gly
                    290                 295                 300

Leu Gly Pro Arg Pro Gln Gly Asn Pro Asp Ala Ser Met Pro Leu Leu
305                 310                 315                 320

Asp Ala Tyr Met Trp Leu Lys Thr Pro Gly Glu Ala Asp Gly Ser Ala
                    325                 330                 335

Val Gly Asp Arg Ala Asp Pro Val Cys Ser His Glu Asp Ser Leu Gln
                    340                 345                 350

Val Ala Pro Asp Ala Gly Gln Trp Phe His Asp Tyr Phe Val Leu Leu
                    355                 360                 365

Leu Lys Asn Ala Asn Pro Pro Phe
    370                 375

<210> SEQ ID NO 94
<211> LENGTH: 463
<212> TYPE: PRT
<213> ORGANISM: Piromyces rhizinflatus

<400> SEQUENCE: 94

Met Lys Phe Leu Ser Leu Ile Gly Thr Leu Phe Ala Thr Gly Ala Leu
1               5                   10                  15

Ala Ser Gln Cys His Pro Asn Trp Pro Cys Cys Leu Asn Cys Asp Val
                20                  25                  30

Val Tyr Gln Asp Gly Glu Gly Asp Trp Gly Val Leu Asn Asn Asp Trp
                35                  40                  45

Cys Phe Ile Ser Lys Ser Arg Cys Gly Asn Asn Asn Asn Asn Asn Asn
        50                  55                  60

Gly Tyr Cys Lys Phe Gln Ser Leu Gly Tyr Pro Cys Cys Ser Gly Cys
65                  70                  75                  80

Gln Val Val Tyr Thr Asp Gly Asp Gly Asn Trp Gly Val Glu Asn Gly
                85                  90                  95

Asn Trp Cys Gly Ile Arg Asp Glu Gln Cys Gly Gly Gly Asn Asn Trp
                100                 105                 110

Gln Gln Pro Thr Thr Arg Thr Thr Thr Arg Thr Thr Thr Arg Thr
                115                 120                 125

Gln Asn Asn Arg Pro Thr Ser Asp Asn Phe Phe Asp Asn Thr Leu Tyr
    130                 135                 140

Ser Asn Tyr Lys Phe Gln Asp Glu Val Gln Ser Ser Ile Asn Lys Leu
145                 150                 155                 160

Ser Gly Gln Met Ala Glu Lys Ala Lys Lys Val Lys Tyr Val Pro Thr
                165                 170                 175

Ala Ala Trp Leu Ala Trp Ser Gly Ala Pro Asp Glu Val Pro Arg Tyr
                180                 185                 190

Leu Gln Glu Ala Gly Ser Asp Thr Val Val Phe Val Leu Tyr Met Ile
                195                 200                 205

Pro Thr Arg Asp Cys Asn Ala Asn Ala Ser Ala Gly Gly Ser Ala Asn
    210                 215                 220
```

-continued

```
Leu Asp Thr Tyr Lys Gly Tyr Val Asn Lys Ile Tyr Asn Thr Ile Asn
225                 230                 235                 240

Gln Tyr Pro Asn Ser Arg Ile Val Met Ile Leu Glu Pro Asp Thr Ile
            245                 250                 255

Gly Asn Leu Val Thr Ala Asn Asn Gln Asn Cys Gln Asn Val Gln Asn
        260                 265                 270

Leu His Lys Asn Ala Leu Ala Tyr Ala Ile Ser Lys Phe Gly Thr Gln
    275                 280                 285

Ser Asn Val Ser Val Tyr Leu Asp Ala Ala His Gly Ala Trp Leu Ser
290                 295                 300

Pro His Ala Asp Lys Thr Ala Gln Val Ile Lys Glu Ile Leu Ser Lys
305                 310                 315                 320

Ala Gly Asn Gly Lys Ile Arg Gly Ile Ser Thr Asn Val Ser Asn Tyr
                325                 330                 335

Gln Thr Ile Asp Asp Glu Tyr Asn Tyr His Gln Arg Leu Asn Ser Ala
            340                 345                 350

Leu Gln Asn Leu Gly Val Ser Asn Met His Phe Ile Val Asp Thr Ser
        355                 360                 365

Arg Asn Gly Ala Asn Ile Ala Ser Gln Phe Asn Gln Ser Gly Thr Trp
    370                 375                 380

Cys Asn Phe Lys Gly Ala Gly Leu Gly Gln Arg Pro Lys Gly Ser Pro
385                 390                 395                 400

Asp Pro Ser Lys Pro Leu Leu Asp Ala Tyr Met Trp Ile Lys Thr Pro
                405                 410                 415

Gly Glu Ala Asp Gly Ser Ser Ser Gly Ala Arg Ala Asp Pro Val Cys
            420                 425                 430

Gly Arg Trp Asp Ser Leu Gln Gly Ala Pro Asp Ala Gly Ser Trp Phe
        435                 440                 445

His Asp Tyr Phe Val Met Leu Leu Gln Asn Ala Asn Pro Ser Phe
    450                 455                 460

<210> SEQ ID NO 95
<211> LENGTH: 510
<212> TYPE: PRT
<213> ORGANISM: Neocallimastix frontalis

<400> SEQUENCE: 95

Met Lys Phe Ile Val Phe Ala Ser Ile Leu Ser Ser Gly Ile Ile Lys
1               5                   10                  15

Leu Ser Asn Ala Ala Cys Gly Gly Pro Tyr Ala Gln Cys Gly Gly Ser
            20                  25                  30

Gly Phe Ser Gly Glu Ala Cys Cys Gln Asp Gly Tyr Lys Cys Val Ala
        35                  40                  45

Met Asn Glu Trp Tyr Ser Gln Cys Gln Ala Gly Ser Asp Ala Pro Ala
    50                  55                  60

Asn Ser Ala Ala Pro Val Asn Ser Ala Val Gly Asn Asp Asn Asn
65                  70                  75                  80

Asn Asn Asn Gln Trp Asn Asn Gln Trp Asn Asn Gly Trp Asn Trp
                85                  90                  95

Gly Asn Gly Asn Asn Glu Ala Gln Asn Pro Trp Asn Asn Asn Gly Trp
            100                 105                 110

Ser Trp Glu Gly Gly Asn Asn Gly Asn Gln Asp Gln Asn Gln Trp Asp
        115                 120                 125

Asn Asn Gly Trp Pro Trp Gly Gly Asn Asn Gly Asn Gln Gly Pro Val
    130                 135                 140
```

Gln Val Asn Ile Gly Glu Asn Asn Gln Asn Gln Asn Pro Ala Asn
145                 150                 155                 160

Asp Ala Pro Ala Pro Pro Ala Gln Gly Gln Ala Pro Ala Pro Ala
            165                 170                 175

Pro Ala Ala Ala Gly Gly Ser Gly Ser Ser Gln Asn Phe Phe Gln
            180                 185                 190

Asn Glu Ile Tyr Ala Asn Pro Lys Phe Ile Glu Glu Val Asp Ser Ser
            195                 200                 205

Ile Ala Lys Leu Asp Gly Glu Leu Lys Ala Lys Ala Glu Lys Val Lys
210                 215                 220

Ser Val Pro Thr Ala Val Trp Leu Ala Trp Asp Gly Ala Pro Gly Glu
225                 230                 235                 240

Val Ala Gln His Leu Glu Ala Ala Gly Ser Lys Thr Val Val Phe Ile
            245                 250                 255

Met Tyr Met Ile Pro Thr Arg Asp Cys Asn Ala Asn Ala Ser Ala Gly
            260                 265                 270

Gly Ala Ser Asn Leu Gln Thr Tyr Lys Gly Tyr Val Asp Ser Ile Ser
            275                 280                 285

Asn Thr Ile Lys Lys Tyr Pro Asn Ser Lys Val Val Met Ile Leu Glu
290                 295                 300

Pro Asp Thr Leu Gly Asn Leu Val Thr Ala Asn Ser Glu Asn Cys Lys
305                 310                 315                 320

Asn Val His Gln Leu His Lys Asp Ala Leu Ser Tyr Gly Val Asn Val
            325                 330                 335

Phe Gly Ser Met Ser Asn Val Ser Val Tyr Leu Asp Ala Ala His Gly
            340                 345                 350

Ala Trp Leu Gly Asp Ser Thr Asp Lys Val Ala Ala Val Val Lys Glu
            355                 360                 365

Ile Leu Ser Asn Ala Pro Asn Gly Lys Ile Arg Gly Leu Ser Thr Asn
370                 375                 380

Ile Ser Asn Tyr Gln Pro Val Asp Ser Glu Tyr Gly Tyr His Gln Lys
385                 390                 395                 400

Leu Ala Ser Ala Leu Ser Ala Ala Gly Tyr Pro Asp Met His Phe Val
            405                 410                 415

Val Asp Thr Gly Arg Asp Gly Val Ala Ile Ser Ser Gly Thr Trp Cys
            420                 425                 430

Asn Leu Ile Gly Thr Gly Phe Gly Glu Arg Pro Lys Gly Asn Pro Asn
            435                 440                 445

Pro Gly Met Pro Leu Leu Asp Ala Tyr Met Trp Leu Lys Thr Pro Gly
            450                 455                 460

Glu Ala Asp Gly Ser Ser Thr Gly Ala Arg Ala Asp Pro Val Cys Ala
465                 470                 475                 480

Lys Ser Asp Ser Leu Pro Gly Ala Pro Asp Ala Gly Gln Trp Phe His
            485                 490                 495

Asp Tyr Phe Val Gln Leu Leu Lys Asn Ala Lys Pro Ala Phe
            500                 505                 510

<210> SEQ ID NO 96
<211> LENGTH: 459
<212> TYPE: PRT
<213> ORGANISM: Orpinomyces sp. PC-2

<400> SEQUENCE: 96

Met Lys Phe Ser Thr Val Leu Ala Thr Leu Phe Ala Thr Gly Ala Leu

-continued

```
1               5                   10                  15
Ala Ser Glu Cys His Trp Gln Tyr Pro Cys Cys Lys Asp Cys Thr Val
            20                  25                  30
Tyr Tyr Thr Asp Thr Glu Gly Lys Trp Gly Val Leu Asn Asn Asp Trp
                35                  40                  45
Cys Met Ile Asp Asn Arg Arg Cys Ser Ser Asn Asn Asn Asn Cys Ser
            50                  55                  60
Ser Ser Ile Thr Ser Gln Gly Tyr Pro Cys Cys Ser Asn Asn Asn Cys
65                  70                  75                  80
Lys Val Glu Tyr Thr Asp Asn Asp Gly Lys Trp Gly Val Glu Asn Asn
                85                  90                  95
Asn Trp Cys Gly Ile Ser Asn Ser Cys Gly Gly Gln Gln Gln Gln Gln
                100                 105                 110
Pro Thr Gln Pro Thr Gln Pro Thr Gln Pro Gln Pro Thr Gln Pro
            115                 120                 125
Ser Ser Asp Asn Phe Phe Glu Asn Glu Ile Tyr Ser Asn Tyr Lys Phe
            130                 135                 140
Gln Gly Glu Val Asp Ile Ser Ile Lys Lys Leu Asn Gly Asp Leu Lys
145                 150                 155                 160
Ala Lys Ala Glu Lys Val Lys Tyr Val Pro Thr Ala Val Trp Leu Ala
                165                 170                 175
Trp Asp Gly Ala Pro Gln Glu Val Pro Arg Tyr Leu Gln Glu Ala Gly
            180                 185                 190
Asn Lys Thr Val Val Phe Val Leu Tyr Met Ile Pro Thr Arg Asp Cys
                195                 200                 205
Gly Ala Asn Ala Ser Ala Gly Gly Ser Ala Thr Ile Asp Lys Tyr Lys
            210                 215                 220
Gly Tyr Ile Asn Asn Ile Tyr Asn Thr Ser Asn Gln Tyr Lys Asn Ser
225                 230                 235                 240
Lys Ile Val Met Ile Leu Glu Pro Asp Thr Ile Gly Asn Leu Val Thr
                245                 250                 255
Asn Asn Asn Asp Asn Cys Arg Asn Val Arg Asn Met His Lys Gln Ala
                260                 265                 270
Leu Ser Tyr Ala Ile Ser Lys Phe Gly Thr Gln Ser His Val Lys Val
            275                 280                 285
Tyr Leu Asp Ala Ala His Gly Ala Trp Leu Asn Gln Tyr Ala Asp Gln
            290                 295                 300
Thr Ala Asn Val Ile Lys Glu Ile Leu Asn Asn Ala Gly Ser Gly Lys
305                 310                 315                 320
Leu Arg Gly Ile Ser Thr Asn Val Ser Asn Tyr Gln Ser Ile Glu Ser
                325                 330                 335
Glu Tyr Lys Tyr His Gln Asn Leu Asn Arg Ala Leu Glu Ser Lys Gly
            340                 345                 350
Val Arg Gly Leu Lys Phe Ile Val Asp Thr Ser Arg Asn Gly Ala Asn
            355                 360                 365
Val Glu Gly Ala Phe Asn Ala Ser Gly Thr Trp Cys Asn Phe Lys Gly
            370                 375                 380
Ala Gly Leu Gly Gln Arg Pro Lys Gly Asn Pro Asn Pro Gly Ser Met
385                 390                 395                 400
Pro Leu Leu Asp Ala Tyr Met Trp Ile Lys Thr Pro Gly Glu Ala Asp
                405                 410                 415
Gly Ser Ser Gln Gly Ser Arg Ala Asp Pro Val Cys Ala Arg Gly Asp
            420                 425                 430
```

```
Ser Leu Gln Gly Ala Pro Asp Ala Gly Ser Trp Phe His Glu Tyr Phe
        435                 440                 445

Thr Met Leu Ile Gln Asn Ala Asn Pro Pro Phe
        450                 455
```

<210> SEQ ID NO 97
<211> LENGTH: 345
<212> TYPE: PRT
<213> ORGANISM: Piromyces rhizinflatus

<400> SEQUENCE: 97

```
Thr Ala Val Trp Leu Ala Trp Asp Gly Ala Pro Gly Glu Val Glu Gly
1               5                   10                  15

His Leu Lys Asn Ala Gly Asp Lys Thr Ile Val Phe Ile Leu Tyr Met
            20                  25                  30

Ile Pro Thr Arg Asp Cys Asn Ser Lys Ala Ser Ala Gly Gly Ala Ser
        35                  40                  45

Asn Leu Lys Lys Tyr Gln Gly Tyr Val Asp Ser Ile Ala Asn Thr Ile
    50                  55                  60

Ser Lys His Pro Glu Ser Lys Val Val Met Val Ile Glu Pro Asp Thr
65                  70                  75                  80

Leu Gly Asn Leu Ile Thr Gly Glu Thr Glu Glu Cys Lys Thr Val His
                85                  90                  95

Thr Leu His Lys Asp Ala Leu Ala Tyr Ala Val Asn Val Phe Gly Asp
            100                 105                 110

Met Ser Asn Val Ser Ala Tyr Leu Asp Ala Ala His Gly Lys Trp Leu
        115                 120                 125

Gly Trp Ala Ala Gly Lys Thr Ala Ala Val Ile Lys Glu Ile Leu Asp
    130                 135                 140

Asn Ala Pro Asn Gly Asn Ile Arg Gly Phe Ser Thr Asn Val Ser Asn
145                 150                 155                 160

Tyr Gln Pro Ile Glu Ser Glu Tyr Glu Tyr His Glu Lys Leu Asn Ala
                165                 170                 175

Ala Leu Glu Asp Leu Gly Ile Thr Gly Lys Lys Phe Ile Val Asp Thr
            180                 185                 190

Gly Arg Ser Gly Val Asp Val Thr Glu Glu Phe Asn Leu Asn Gln Thr
        195                 200                 205

Trp Cys Asn Leu Ile Tyr Ala Gly Leu Gly Glu Pro Ser Arg Gly Ser
    210                 215                 220

Pro Asp Pro Glu Lys Phe Pro Leu Leu Asp Ala Tyr Phe Trp Leu Lys
225                 230                 235                 240

Pro Pro Gly Glu Ala Asp Gly Ser Asp Thr Gly Ser Arg Ala Asp Pro
                245                 250                 255

Val Cys Gly Arg Glu Asp Ser Phe Pro Gly Ala Pro Asp Ala Gly Ser
            260                 265                 270

Trp Phe Ser Glu Tyr Phe Ala Ser Met Leu Glu Lys Ser Pro Phe Tyr
        275                 280                 285

Gly Glu Gly Ile Glu Glu Pro Glu Pro Glu Glu Pro Leu Cys
    290                 295                 300

Ser Gln Lys Phe Leu Asp Gln Tyr Gln Cys Cys Ser Gln Cys Gly
305                 310                 315                 320

Thr Ile Tyr Tyr Val Asp Asp Ala Gly Asn Trp Gly Val Glu Asn Asn
                325                 330                 335

Glu Trp Cys Gly Leu Pro Glu Asp Cys
```

```
                340                 345
```

<210> SEQ ID NO 98
<211> LENGTH: 457
<212> TYPE: PRT
<213> ORGANISM: Micromonospora cellulolyticum

<400> SEQUENCE: 98

Val Ala Ile Leu Ser Ala Arg Arg Ser Ala Ile Ser Val Thr
1               5                   10                  15

Ala Val Ala Gly Leu Ala Ala Ala Gly Val Leu Arg Val Gly Gly Val
                20                  25                  30

Ala Gly Thr Val Ser Gly Ser Leu Tyr Arg Asp Pro Ser Ser Ala Val
            35                  40                  45

Val Arg Trp Val Ala Ala Asn Pro Gly Asp Phe Arg Ala Ala Val Ile
    50                  55                  60

Arg Glu Lys Ile Ala Ser Gln Pro Gln Ala Arg Trp Tyr Ala Asn Phe
65                  70                  75                  80

Asn Pro Ser Thr Ile Gln Ser Glu Val Ser Ala Phe Ile Gly Ala Ala
                85                  90                  95

Asn Ser Ala Gln Gln Ile Pro Val Leu Ser Val Tyr Glu Ile Thr Asn
            100                 105                 110

Arg Asp Cys Gly Gly Ala His Ala Gly Gly Ala Pro Asp Leu Asn Gln
        115                 120                 125

Tyr Gln Thr Trp Val Ser Asn Phe Ala Arg Gly Leu Gly Asn Gln Thr
    130                 135                 140

Val Leu Ile Ile Leu Glu Thr Asp Ser Leu Ala Leu Gln Thr Cys Leu
145                 150                 155                 160

Ser Thr Ser Glu Leu Asn Ala Arg Asn Gln Ala Leu Ser Thr Ala Thr
                165                 170                 175

Gln Thr Ile Lys Ser Ala Asn Pro Asn Ala Lys Val Tyr Leu Asp Gly
            180                 185                 190

Gly His Ser Thr Trp Asn Ser Ala Asn Asp Thr Ala Asn Arg Leu Arg
        195                 200                 205

Ala Ala Gly Val Gln Tyr Ala Asp Gly Phe Phe Thr Asn Val Ser Asn
    210                 215                 220

Phe Asn Pro Thr Ser Ser Glu Ala Asn Phe Gly Arg Ala Val Ile Ser
225                 230                 235                 240

Ala Leu Asn Gly Met Gly Ile Ser Gly Lys Arg Gln Val Ile Asp Thr
                245                 250                 255

Ser Arg Asn Gly Gly Ala Ala Gly Asp Trp Cys Ala Asp Asn Thr
            260                 265                 270

Asp Arg Arg Ile Gly Gln Tyr Pro Thr Thr Asn Thr Gly Asp Ala Asn
        275                 280                 285

Ile Asp Ala Tyr Leu Trp Val Lys Pro Pro Gly Glu Ala Asp Gly Cys
    290                 295                 300

Ala Thr Arg Gly Ser Phe Gln Pro Asp Leu Ala Phe Ser Leu Ala Asn
305                 310                 315                 320

Gly Val Pro Asn Pro Thr Thr Ala Pro Thr Thr Asn Arg Ala
                325                 330                 335

Asp Asp Arg Pro Pro Thr Thr Ala Pro Thr Thr Asp Thr Pro Thr
            340                 345                 350

Thr Ala Pro Pro Thr Thr Pro Pro Ala Gly Asn Gly Leu Ser Ala
        355                 360                 365

```
Ser Val Ala Ile Thr Gln Trp Asn Gly Gly Phe Thr Ala Ser Val Asn
    370                 375                 380

Val Thr Ala Gly Ser Ala Ile Asn Gly Trp Thr Val Thr Val Ala Leu
385                 390                 395                 400

Pro Gly Gly Ala Ala Ile Thr Gly Thr Trp Asn Ala Gln Ala Ser Gly
                405                 410                 415

Thr Ser Gly Thr Val Arg Phe Thr Asn Val Gly Tyr Asn Gly Gln Val
            420                 425                 430

Gly Ala Gly Gln Thr Thr Asn Phe Gly Phe Gln Gly Thr Gly Thr Gly
        435                 440                 445

Gln Gly Ala Thr Ala Thr Cys Ala Ala
    450                 455
```

<210> SEQ ID NO 99
<211> LENGTH: 193
<212> TYPE: PRT
<213> ORGANISM: Orpinomyces sp. PC-2

<400> SEQUENCE: 99

```
Thr Leu His Lys Asn Ala Leu Ser Tyr Ala Val Asn Val Phe Gly Ser
1               5                   10                  15

Met Lys Asn Val Ser Val Tyr Leu Asp Ala Ala His Gly Met Trp Leu
            20                  25                  30

Ser Ala Val Ala Asp Lys Thr Ala Ala Val Ile Lys Glu Val Leu Asp
        35                  40                  45

Asn Ala Pro Asn Gly Lys Ile Arg Gly Leu Ser Thr Asn Ile Ser Asn
    50                  55                  60

Tyr Gln Pro Val Tyr Ser Glu Tyr Lys Tyr His Glu Lys Leu Ser Ala
65                  70                  75                  80

Glu Leu Glu Lys Leu Gly Val Ser Asp Ile His Phe Ile Val Asp Thr
                85                  90                  95

Gly Arg Asn Gly Val Asp Ile Thr Glu Thr Phe Ser Lys Thr Gln Thr
            100                 105                 110

Trp Cys Asn Phe Val Gly Thr Gly Phe Gly Glu Arg Pro Gln Gly Asn
        115                 120                 125

Pro Asp Pro Val Lys Met Pro Leu Leu Asp Ala Tyr Met Trp Leu Lys
    130                 135                 140

Thr Pro Gly Glu Ala Asp Gly Ser Asp Thr Gly Ser Arg Ala Asp Pro
145                 150                 155                 160

Val Cys Ala Arg Glu Asp Ser Leu Pro Gly Ser Pro Asp Ala Gly Gln
                165                 170                 175

Trp Phe His Asp Tyr Phe Val Gln Leu Leu Glu Asn Ala Asn Pro Ala
            180                 185                 190

Phe
```

<210> SEQ ID NO 100
<211> LENGTH: 458
<212> TYPE: PRT
<213> ORGANISM: Catenulispora acidiphila

<400> SEQUENCE: 100

```
Met Val Ala Thr Gln Leu Gly Gly Val Ala Met Ala Gly Thr Ile Ala
1               5                   10                  15

Ser Gly Thr Gln Phe Tyr Ala Asp Pro Asn Ser Gln Val Val Lys Trp
            20                  25                  30

Asp Ala Ala Asn Pro Gly Asp Ala Arg Glu Pro Ala Ile Ala Ser Gln
```

```
                35                  40                  45
Ile Ala Ser Val Ser Gln Gly Ile Trp Phe Ser Asn Tyr Arg Pro Ser
 50                  55                  60

Thr Val Gln Ser Asp Val Ser Ala Val Thr Thr Ala Ala Ala Ala
 65                  70                  75                  80

Gly Lys Thr Pro Val Leu Val Val Tyr Glu Ile Pro Asn Arg Asp Cys
                 85                  90                  95

Gly Gly Ala Ser Ala Gly Gly Ala Pro Asp Ile Ser Ser Tyr Glu Asn
                100                 105                 110

Tyr Ile Gln Ser Phe Ala Asn Gly Leu Gly Ser His Gln Val Ile Val
                115                 120                 125

Ile Leu Glu Pro Asp Ser Leu Ala Leu Gln Thr Cys Leu Ser Ser Gln
130                 135                 140

Gln Ala Thr Asp Arg Asp Asn Ala Ile Ala Phe Ala Gly Ala His Leu
145                 150                 155                 160

Lys Ser Ala Asp Pro Ala Ala Lys Val Tyr Leu Asp Ala Gly His Ser
                165                 170                 175

Ser Trp Asn Ser Pro Ser Ala Gln Ala Ala Leu Asn Ala Ala Gly
                180                 185                 190

Val Lys Thr Ser Ser Asp Gly Ile Phe Ser Asn Val Ser Asn Phe Gln
                195                 200                 205

Thr Thr Ala Ser Glu Val Ser Tyr Asp Lys Gln Val Leu Ala Ala Leu
210                 215                 220

Gly Ser Pro Ser Asn Leu His Ile Val Val Asp Thr Ser Arg Asn Gly
225                 230                 235                 240

Asn Gly Pro Ala Gly Ser Ala Trp Cys Asp Pro Ser Gly Arg Ala Leu
                245                 250                 255

Gly Gln Ala Pro Thr Ala Asn Thr Gly Asp Ala Ala Val Asp Ala Phe
                260                 265                 270

Leu Trp Ile Lys Pro Pro Gly Glu Ala Asp Gly Cys Ala Asp Ala Ala
                275                 280                 285

Gly Thr Phe Asp Pro Ala Leu Ala Tyr Ala Leu Ile Thr Asn Gly Gly
                290                 295                 300

Gly Pro Pro Pro Thr Ser Pro Ser Ser Thr Pro Ser Thr Thr Pro Ser
305                 310                 315                 320

Thr Thr Pro Ser Thr Thr Pro Ser Thr Thr Pro Ser Thr Thr Pro Ser
                325                 330                 335

Thr Thr Pro Ser Thr Pro Pro Ser Thr Thr Pro Ser Ser Pro Pro Ser
                340                 345                 350

Ser Ser Pro Ala Gly Cys Gln Val Thr Tyr Thr Arg Thr Asn Glu Trp
                355                 360                 365

Ala Gly Gly Phe Thr Ala Asn Val Ser Ile Thr Ser Ser Lys Ala Leu
                370                 375                 380

Ser Ser Trp Thr Val Gly Phe Thr Tyr Gly Gly Asp Gln Gln Ile Thr
385                 390                 395                 400

Asn Ser Trp Asn Gly Asn His Thr Gln Ser Gly Arg Asn Val Thr Leu
                405                 410                 415

Thr Ser Leu Ser Tyr Asn Gly Ser Ile Gly Ala Gly Gln Thr Leu Thr
                420                 425                 430

Gly Val Gly Val Gln Gly Thr Trp Thr Ser Ser Asp Ala Ala Pro Ser
                435                 440                 445

Ala Phe Thr Leu Asn Gly Val Ala Cys His
450                 455
```

<210> SEQ ID NO 101
<211> LENGTH: 422
<212> TYPE: PRT
<213> ORGANISM: Actinosynnema mirum

<400> SEQUENCE: 101

| | | | | | | | | | | | | | | |
|---|---|---|---|---|---|---|---|---|---|---|---|---|---|---|
| Met | Ala | Gly | Ala | Ala | Val | Leu | Val | Thr | Gly | Gly | Gln | Thr | Ala | Thr |
| 1 | | | | 5 | | | | | 10 | | | | | 15 |
| Ala | Ala | Asp | Ser | Ala | Phe | Tyr | Thr | Asp | Pro | Gly | Ser | Ser | Ala | Arg |
| | | | 20 | | | | | 25 | | | | | 30 | |
| Trp | Val | Ala | Ala | Asn | Pro | Asn | Asp | Ser | Arg | Ala | Val | Ile | Arg | Asp |
| | | | 35 | | | | 40 | | | | | 45 | | |
| Arg | Val | Ala | Ser | Val | Pro | Gln | Ala | Lys | Trp | Phe | Thr | Thr | Asn | Thr |
| | 50 | | | | | 55 | | | | | 60 | | | |
| Ser | Thr | Val | Arg | Ser | Glu | Val | Ser | Ala | Phe | Val | Gly | Ala | Ala | Ser |
| 65 | | | | | 70 | | | | | 75 | | | | 80 |
| Ala | Gly | Lys | Ile | Pro | Ile | Leu | Val | Val | Tyr | Asn | Ile | Pro | Asn | Arg | Asp |
| | | | | 85 | | | | | 90 | | | | | 95 | |
| Cys | Gly | Gly | Ala | Ser | Gly | Gly | Ala | Pro | Ser | His | Gln | Ala | Tyr | Arg |
| | | | 100 | | | | | 105 | | | | | 110 | |
| Ala | Trp | Val | Asp | Glu | Val | Ala | Ala | Gly | Leu | Gly | Gly | Arg | Pro | Ala | Ser |
| | | 115 | | | | | 120 | | | | | 125 | | | |
| Ile | Ile | Leu | Glu | Pro | Asp | Val | Leu | Pro | Ile | Met | Ser | Asn | Cys | Gln | Ser |
| 130 | | | | | 135 | | | | | 140 | | | | | |
| Ala | Asp | Gln | Gln | Asn | Gln | Thr | Lys | Ala | Ser | Met | Ser | Tyr | Ala | Gly | Arg |
| 145 | | | | | 150 | | | | | 155 | | | | | 160 |
| Lys | Leu | Lys | Ser | Gly | Ser | Gly | Gln | Ala | Lys | Val | Tyr | Phe | Asp | Ile | Gly |
| | | | | 165 | | | | | 170 | | | | | 175 | |
| Asn | Ser | Asp | Trp | Leu | Ala | Pro | Ala | Glu | Ala | Ala | Asn | Arg | Leu | Arg | Gly |
| | | | 180 | | | | | 185 | | | | | 190 | | |
| Ala | Asp | Val | Ser | Gly | Ser | Ser | Asp | Gly | Ile | Ala | Ser | Asn | Val | Ser | Asn |
| | | | 195 | | | | | 200 | | | | | 205 | | |
| Tyr | Arg | Ala | Thr | Gln | Ala | Glu | Val | Ser | Tyr | Thr | Lys | Ala | Ile | Leu | Asn |
| | 210 | | | | | 215 | | | | | 220 | | | | |
| Ala | Leu | Gly | Asp | Gly | Arg | Leu | Lys | Ala | Val | Ile | Asp | Thr | Ser | Arg | Asn |
| 225 | | | | | 230 | | | | | 235 | | | | | 240 |
| Gly | Asn | Gly | Pro | Leu | Gly | Ser | Glu | Trp | Cys | Asp | Pro | Gly | Arg | Ala |
| | | | | 245 | | | | | 250 | | | | | 255 |
| Ile | Gly | Thr | Pro | Ser | Thr | Lys | Asn | Thr | Gly | Asp | Ser | Gln | Ile | Asp | Ala |
| | | | 260 | | | | | 265 | | | | | 270 | | |
| Phe | Leu | Trp | Val | Lys | Ile | Val | Gly | Glu | Ala | Asp | Gly | Cys | Ile | Ala | Ser |
| | | 275 | | | | | 280 | | | | | 285 | | | |
| Ala | Gly | Gln | Phe | Val | Pro | Gln | Arg | Ala | Tyr | Asp | Leu | Ala | Val | Ala | Ala |
| | 290 | | | | | 295 | | | | | 300 | | | | |
| Gly | Pro | Val | Pro | Thr | Thr | Thr | Thr | Thr | Pro | Gly | Gly | Asn | Pro | Gly |
| 305 | | | | | 310 | | | | | 315 | | | | | 320 |
| Gly | Gly | Cys | Ala | Val | Thr | His | Arg | Val | Val | Ser | Gln | Trp | Asn | Gly | Gly |
| | | | | 325 | | | | | 330 | | | | | 335 | |
| Phe | Thr | Gly | Glu | Val | Val | Glu | Asn | Arg | Gly | Pro | Ala | Ile | Ser | Ser |
| | | | 340 | | | | | 345 | | | | | 350 | | |
| Trp | Thr | Leu | Glu | Phe | Ser | Ala | Pro | Gly | Val | Thr | Val | Thr | Gln | Gly | Trp |
| | | 355 | | | | | 360 | | | | | 365 | | | |
| Asn | Gly | Thr | Trp | Thr | Asp | Thr | Gly | Asp | Gly | Val | Arg | Val | Val | Asn | Thr |

```
                370               375               380
Ala Trp Asn Gly Ala Leu Ala Ser Gly Gly Arg Val Thr Ala Gly Tyr
385               390               395               400

Asn Ala Asn Tyr Gly Gly Ala Pro Pro Phe Ser Ser Pro Thr Leu
            405               410               415

Asn Gly Ala Ala Cys Ser
            420
```

<210> SEQ ID NO 102
<211> LENGTH: 444
<212> TYPE: PRT
<213> ORGANISM: Actinosynnema mirum

<400> SEQUENCE: 102

```
Met Ala Ala Gly Ala Leu Ser Ser Ala Leu Val Ala Ala Thr Ala
1               5                  10                  15

Ile Ala Thr Gly Thr Ala Ser Pro Ala Val Ala Ala Asp Ser Glu
                20                  25                  30

Phe Tyr Ser Asp Pro Ala Thr Ser Ala Ala Arg Trp Val Ala Ala Asn
            35                  40                  45

Pro Asn Asp Ser Arg Ala Ala Val Ile Arg Asp Arg Val Ala Ser Val
50                  55                  60

Pro Gln Ala Lys Trp Phe Thr Thr Thr Asn Thr Ser Thr Ile Arg Ala
65                  70                  75                  80

Glu Val Asp Ala His Thr Ser Ala Ala Ser Ala Gly Lys Thr Pro
                85                  90                  95

Ile Leu Val Val Tyr Asn Ile Pro Asn Arg Asp Cys Gly Gly Ala Ser
                100                 105                 110

Gly Gly Gly Ala Pro Ser His Gly Ala Tyr Arg Gln Trp Val Asp Gln
            115                 120                 125

Phe Ala Ala Gly Leu Ala Gly Arg Pro Ala Ala Ile Ile Leu Glu Pro
130                 135                 140

Asp Val Leu Pro Ile Met Ser Thr Cys Gln Ser Ala Ser Gln Gln Ala
145                 150                 155                 160

Glu Thr Arg Ala Ser Met Ala Tyr Ala Gly Lys Ala Leu Lys Ala Ala
                165                 170                 175

Ser Ser Gln Ala Lys Val Tyr Phe Asp Ile Gly His Ser Ala Trp Leu
            180                 185                 190

Thr Pro Ala Glu Ala Ala Asn Arg Leu Arg Ala Ala Glu Val Ser Thr
            195                 200                 205

Ser Ala Asp Gly Ile Ala Thr Asn Val Ser Asn Tyr Arg Arg Thr Ala
210                 215                 220

Asp Glu Val Ala Phe Ala Lys Ala Thr Leu Asn Ala Leu Gly Asp Gly
225                 230                 235                 240

Arg Leu Lys Ala Val Val Asp Thr Ser Arg Asn Gly Asn Gly Pro Leu
                245                 250                 255

Gly Ser Glu Trp Cys Asp Pro Pro Gly Arg Ala Ile Gly Thr Pro Ser
            260                 265                 270

Thr Arg Asn Thr Gly Asp Pro Gln Ile Asp Ala Phe Leu Trp Val Lys
            275                 280                 285

Ile Pro Gly Glu Ala Asp Gly Cys Ile Ala Gly Ala Gly Gln Phe Val
            290                 295                 300

Pro Gln Arg Ala Tyr Asp Met Ala Val Ala Ala Gly Pro Ala Pro Thr
305                 310                 315                 320
```

```
Thr Thr Thr Thr Thr Thr Thr Thr Arg Val Thr Thr Thr Thr
            325                 330                 335

Thr Pro Pro Pro Asn Gly Ala Ala Cys Val Val Arg His Arg Val Val
        340                 345                 350

Ser Ser Trp Ser Gly Gly His Thr Gly Glu Val Val Ile Glu Asn Arg
        355                 360                 365

Gly Pro Ala Leu Gln Asn Trp Thr Leu Glu Phe Ser Ala Pro Gly Val
        370                 375                 380

Ala Val Ser Gln Gly Trp Asn Gly Thr Trp Thr Asp Leu Gly Asp Thr
385                 390                 395                 400

Val Arg Val Thr Ser Ala Ser Trp Asn Gly Gly Ile Ala Thr Gly Gly
                405                 410                 415

Thr Ala Thr Thr Gly Tyr Ser Ala Ser Phe Ser Gly Gly Thr Pro Pro
                420                 425                 430

Phe Thr Ser Pro Val Leu Asn Gly Thr Ala Cys Ala
        435                 440

<210> SEQ ID NO 103
<211> LENGTH: 426
<212> TYPE: PRT
<213> ORGANISM: Nocardiopsis dassonvillei

<400> SEQUENCE: 103

Met Ser Ser Val Ser Ala Leu Ala Leu Gly Thr Ala Leu Leu Ala Thr
1               5                   10                  15

Ala Pro Ala Ser Ala Ala Asp Ser Glu Phe Tyr Val Asn Pro Asn Thr
            20                  25                  30

Ser Ala Ala Val Trp Val Glu Glu Asn Pro Asn Asp Pro Arg Ala Asp
        35                  40                  45

Val Ile Arg Asp Arg Ile Ala Ser Val Ala Gln Ala Thr Trp Phe Thr
50                  55                  60

Gln Tyr Asn Pro Ala Glu Val Arg Asp Asp Val Asp Ala Val Val Ser
65                  70                  75                  80

Ala Ala Asp Ala Gln Gly Gln Thr Pro Ile Leu Val Val Tyr Asn Ile
                85                  90                  95

Pro Gly Arg Asp Cys Gly Asn His Ser Gly Gly Gly Ala Pro Ser His
            100                 105                 110

Asp Ala Tyr Arg Ala Trp Val Asp Glu Val Ala Ala Gly Leu Glu Gly
            115                 120                 125

Arg Ser Ala Thr Ile Val Leu Glu Pro Asp Ala Leu Pro Leu Val Ser
130                 135                 140

Gly Cys Ser Asp Pro Ser Glu Leu Leu Asp Ser Met Ala Tyr Ala Gly
145                 150                 155                 160

Lys Ala Leu Met Glu Gly Ser Ser Glu Ala Arg Val Tyr Phe Asp Ile
                165                 170                 175

Gly Asn Ser Ala Trp Leu Asp Pro Gln Glu Ala Ala Gly Leu Leu Asn
            180                 185                 190

Gly Ala Asp Val Ala Asn Ser Ala His Gly Val Ala Thr Asn Thr Ser
            195                 200                 205

Asn Tyr Asn Trp Thr His Asp Glu Val Ala Phe Ala Glu Ala Val Ile
        210                 215                 220

Ala Ala Thr Gly Val Pro Gly Leu Gly Ala Val Ile Asp Thr Ser Arg
225                 230                 235                 240

Asn Gly Asn Gly Pro Ala Pro Gln Asn Glu Trp Cys Asp Pro Pro Gly
                245                 250                 255
```

```
Arg Met Ile Gly Arg Pro Ser Thr Thr Asp Thr Gly Asn Pro Leu Ile
            260                 265                 270

Asp Ala Phe Ile Trp Thr Lys Leu Pro Gly Glu Ala Asp Gly Cys Ile
            275                 280                 285

Ala Pro Ala Gly Gln Phe Val Pro Gln Ala Ala Tyr Asp Met Ala Val
            290                 295                 300

Asn Ala Pro Glu Tyr Pro Thr Asp Pro Gly Glu Pro Thr Asp Pro Glu
305                 310                 315                 320

Glu Pro Thr Asp Pro Pro Glu Gly Gly Cys Thr Ala Asp Tyr Arg
                325                 330                 335

Val Val Ser Glu Trp Gly Asn Gly Phe Gln Ala Ala Val Thr Val Thr
            340                 345                 350

Ala Glu Asp Ser Leu Ser Gly Trp Thr Val Thr Trp Thr Tyr Ala Asp
            355                 360                 365

Gly Gln Arg Phe Ser Gln Gly Trp Asn Ala Glu Phe Ser Ser Ser Gly
            370                 375                 380

Ser Arg Val Thr Ala Ser Asp Leu Gly Trp Asn Gly Thr Leu Ser Ala
385                 390                 395                 400

Gly Gly Ser Thr Glu Phe Gly Phe Thr Gly Thr His Gly Gly Ser Asn
            405                 410                 415

Gly Val Pro Glu Val Thr Cys Ser Ala Ala
            420                 425

<210> SEQ ID NO 104
<211> LENGTH: 286
<212> TYPE: PRT
<213> ORGANISM: Thermobifida fusca

<400> SEQUENCE: 104

Asn Asp Ser Pro Phe Tyr Val Asn Pro Asn Met Ser Ser Ala Glu Trp
1               5                   10                  15

Val Arg Asn Asn Pro Asn Asp Pro Arg Thr Pro Val Ile Arg Asp Arg
            20                  25                  30

Ile Ala Ser Val Pro Gln Gly Thr Trp Phe Ala His His Asn Pro Gly
        35                  40                  45

Gln Ile Thr Gly Gln Val Asp Ala Leu Met Ser Ala Gln Ala Ala
    50                  55                  60

Gly Lys Ile Pro Ile Leu Val Val Ser Asn Ala Pro Gly Arg Asp Cys
65              70                  75                  80

Gly Asn His Ser Ser Gly Gly Ala Pro Ser His Ser Ala Tyr Arg Ser
            85                  90                  95

Trp Ile Asp Glu Phe Ala Ala Gly Leu Lys Asn Arg Pro Ala Tyr Ile
            100                 105                 110

Ile Val Glu Pro Asp Leu Ile Ser Leu Met Ser Ser Cys Met Gln His
        115                 120                 125

Val Gln Gln Glu Val Leu Glu Thr Met Ala Tyr Ala Gly Lys Ala Leu
    130                 135                 140

Lys Ala Gly Ser Ser Gln Ala Arg Ile Tyr Phe Asp Ala Gly His Ser
145                 150                 155                 160

Ala Trp His Ser Pro Ala Gln Met Ala Ser Trp Leu Gln Gln Ala Asp
            165                 170                 175

Ile Ser Asn Ser Ala His Gly Ile Ala Thr Asn Thr Ser Asn Tyr Arg
        180                 185                 190

Trp Thr Ala Asp Glu Val Ala Tyr Ala Lys Ala Val Leu Ser Ala Ile
```

```
                195                 200                 205
Gly Asn Pro Ser Leu Arg Ala Val Ile Asp Thr Ser Arg Asn Gly Asn
            210                 215                 220

Gly Pro Ala Gly Asn Glu Trp Cys Asp Pro Ser Gly Arg Ala Ile Gly
225                 230                 235                 240

Thr Pro Ser Thr Thr Asn Thr Gly Asp Pro Met Ile Asp Ala Phe Leu
                245                 250                 255

Trp Ile Lys Leu Pro Gly Glu Ala Asp Gly Cys Ile Ala Gly Ala Gly
                260                 265                 270

Gln Phe Val Pro Gln Ala Ala Tyr Glu Met Ala Ile Ala Ala
                275                 280                 285

<210> SEQ ID NO 105
<211> LENGTH: 448
<212> TYPE: PRT
<213> ORGANISM: Micromonospora sp. ATCC 39149

<400> SEQUENCE: 105

Met Ala Ala Ser Ala Leu Thr Ala Val Ala Val Ser Ile Leu Gly
1               5                   10                  15

Gly Thr Pro Ala Ser Ala Ala Asp Ser Ala Phe Tyr Val Asp Pro Gln
            20                  25                  30

Ala Ser Ala Ala Arg Trp Val Ala Ala Asn Pro Gly Asp Trp Arg Ala
        35                  40                  45

Ala Val Ile Arg Asp Arg Ile Ala Ala Val Pro Gln Gly Arg Trp Phe
    50                  55                  60

Thr Thr Thr Asn Thr Ser Thr Val Arg Ser Glu Val Asp Gln Phe Val
65                  70                  75                  80

Gly Ala Ala Ala Ala Gly Lys Val Pro Ile Met Val Val Tyr Asn
                85                  90                  95

Ile Pro Asn Arg Asp Cys Ser Gly Ala Ser Gly Gly Ala Pro Ser
            100                 105                 110

His Thr Ala Tyr Arg Gln Trp Val Asp Gln Val Ala Ala Gly Leu Ala
        115                 120                 125

Gly Arg Pro Ala Thr Ile Val Leu Glu Pro Asp Val Leu Pro Ile Met
    130                 135                 140

Thr Asn Cys Gln Asn Ala Ser Gln Gln Ala Glu Thr Arg Ala Ser Met
145                 150                 155                 160

Ala Tyr Ala Gly Lys Lys Leu Lys Ser Gly Ser Ala Gln Ala Lys Val
                165                 170                 175

Tyr Phe Asp Ala Gly Asn Ser Ala Trp Leu Ala Pro Ala Glu Ile Ala
            180                 185                 190

Ser Arg Leu Asn Gly Ala Asp Ile Ala Asn Ser Ala Asp Gly Ile Ser
        195                 200                 205

Leu Asn Val Ser Asn Tyr Arg Thr Thr Ala Glu Ser Val Ser Tyr Ala
    210                 215                 220

Lys Gln Val Ile Ala Ala Thr Gly Val Ser Arg Leu Lys Ala Val Ile
225                 230                 235                 240

Asp Thr Ser Arg Asn Gly Asn Gly Pro Leu Gly Ser Glu Trp Cys Asp
                245                 250                 255

Pro Pro Gly Arg Ala Ile Gly Thr Pro Ser Thr Thr Ala Thr Gly Asp
            260                 265                 270

Ser Ala Ile Ala Ala Tyr Leu Trp Val Lys Leu Pro Gly Glu Ala Asp
        275                 280                 285
```

```
Gly Cys Ile Ala Pro Ala Gly Gln Phe Val Pro Gln Arg Ala Tyr Asp
        290                 295                 300

Leu Ala Ile Ala Ala Gly Pro Val Pro Thr Thr Ala Pro Pro Thr Thr
305                 310                 315                 320

Ala Pro Pro Thr Thr Ala Pro Pro Thr Thr Ala Pro Pro Thr Thr Ala
                325                 330                 335

Pro Pro Thr Thr Pro Pro Asn Gly Ala Cys Lys Val Thr Phe Thr Pro
                340                 345                 350

Asn Thr Trp Ser Gly Gly Phe Thr Ala Glu Leu Arg Val Thr Asn Gly
                355                 360                 365

Gly Ser Ala Leu Asn Gly Trp Ser Leu Ser Phe Gly Phe Gly Ser Gly
370                 375                 380

Ser Gly Val Arg Leu Thr Ser Gly Trp Asn Gly Glu Trp Ser Gln Asn
385                 390                 395                 400

Gly Asp Val Phe Leu Val Arg Asn Ala Ala Trp Asn Gly Asn Leu Pro
                405                 410                 415

Ala Gly Gly Thr Leu Ser Val Gly Phe Gln Gly Thr Phe Ser Gly Ala
                420                 425                 430

Ser Leu Pro Thr Ala Val Gly Phe Thr Leu Asn Gly Ser Arg Cys Asn
                435                 440                 445

<210> SEQ ID NO 106
<211> LENGTH: 456
<212> TYPE: PRT
<213> ORGANISM: Thermobispora bispora

<400> SEQUENCE: 106

Met Ser Arg Ile Arg Arg Phe Leu Ala Thr Ala Leu Ala Ala Ala Thr
1               5                   10                  15

Ala Gly Val Gly Ala Ile Val Thr Ala Ile Ala Ser Ala Gly Pro Ala
                20                  25                  30

His Ala Tyr Asp Ser Pro Phe Tyr Val Asp Pro Gln Ser Asn Ala Ala
            35                  40                  45

Lys Trp Val Ala Ala Asn Pro Asn Asp Pro Arg Thr Pro Val Ile Arg
50                  55                  60

Asp Arg Ile Ala Ala Val Pro Thr Gly Arg Trp Phe Ala Asn Tyr Asn
65                  70                  75                  80

Pro Ser Thr Val Arg Ala Glu Val Asp Ala Tyr Val Gly Ala Ala Ala
                85                  90                  95

Ala Ala Gly Lys Ile Pro Ile Met Val Val Tyr Ala Met Pro Asn Arg
                100                 105                 110

Asp Cys Gly Gly Pro Ser Ala Gly Gly Ala Pro Asn His Thr Ala Tyr
            115                 120                 125

Arg Ala Trp Ile Asp Glu Ile Ala Ala Gly Leu Arg Asn Arg Pro Ala
        130                 135                 140

Val Ile Ile Leu Glu Pro Asp Ala Leu Pro Ile Met Thr Asn Cys Met
145                 150                 155                 160

Ser Pro Ser Glu Gln Ala Glu Val Gln Ala Ser Ala Val Gly Ala Gly
                165                 170                 175

Lys Lys Phe Lys Ala Ala Ser Ser Gln Ala Lys Val Tyr Phe Asp Ala
                180                 185                 190

Gly His Asp Ala Trp Val Pro Ala Asp Glu Met Ala Ser Arg Leu Arg
        195                 200                 205

Gly Ala Asp Ile Ala Asn Ser Ala Asp Gly Ile Ala Leu Asn Val Ser
        210                 215                 220
```

```
Asn Tyr Arg Tyr Thr Ser Gly Leu Ile Ser Tyr Ala Lys Ser Val Leu
225                 230                 235                 240

Ser Ala Ile Gly Ala Ser His Leu Arg Ala Val Ile Asp Thr Ser Arg
            245                 250                 255

Asn Gly Asn Gly Pro Leu Gly Ser Glu Trp Cys Asp Pro Pro Gly Arg
        260                 265                 270

Ala Thr Gly Thr Trp Ser Thr Thr Asp Thr Gly Asp Pro Ala Ile Asp
        275                 280                 285

Ala Phe Leu Trp Ile Lys Pro Pro Gly Glu Ala Asp Gly Cys Ile Ala
    290                 295                 300

Thr Pro Gly Val Phe Val Pro Asp Arg Ala Tyr Glu Leu Ala Met Asn
305                 310                 315                 320

Ala Ala Pro Pro Thr Tyr Ser Pro Ser Pro Thr Pro Ser Thr Pro Ser
                325                 330                 335

Pro Ser Pro Ser Gln Ser Asp Pro Gly Ser Pro Ser Pro Ser Pro Ser
                340                 345                 350

Gln Pro Pro Ala Gly Arg Ala Cys Glu Ala Thr Tyr Ala Leu Val Asn
            355                 360                 365

Gln Trp Pro Gly Gly Phe Gln Ala Glu Val Thr Val Lys Asn Thr Gly
    370                 375                 380

Ser Ser Pro Ile Asn Gly Trp Thr Val Gln Trp Thr Leu Pro Ser Gly
385                 390                 395                 400

Gln Ser Ile Thr Gln Leu Trp Asn Gly Asp Leu Ser Thr Ser Gly Ser
                405                 410                 415

Asn Val Thr Val Arg Asn Val Ser Trp Asn Gly Asn Val Pro Ala Gly
            420                 425                 430

Gly Ser Thr Ser Phe Gly Phe Leu Gly Ser Gly Thr Gly Gln Leu Ser
            435                 440                 445

Ser Ser Ile Thr Cys Ser Ala Ser
    450                 455

<210> SEQ ID NO 107
<211> LENGTH: 5
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (3)..(3)
<223> OTHER INFORMATION: Xaa is A, G or C

<400> SEQUENCE: 107

Gly Glu Xaa Asp Gly
1               5
```

POLYPEPTIDES HAVING CELLULASE ACTIVITY

CROSS REFERENCE TO RELATED APPLICATIONS

The application claims priority under 35 U.S.C. §119 to U.S. Provisional Application Ser. Nos. 61/166,993, filed, Apr. 6, 2009, and 61/177,882, filed May 13, 2009, the disclosures of which are incorporated herein by reference.

STATEMENT REGARDING FEDERALLY SPONSORED RESEARCH

The U.S. Government has certain rights in this invention pursuant to Grant No. GM068664 awarded by the National Institutes of Health and Grant No. DAAD19-03-0D-0004 awarded by ARO—US Army Robert Morris Acquisition Center.

TECHNICAL FIELD

The disclosure relates to biomolecular engineering and design, and engineered proteins and nucleic acids.

BACKGROUND

The performance of cellulase mixtures in biomass conversion processes depends on many enzyme properties including stability, product inhibition, synergy among different cellulase components, productive binding versus nonproductive adsorption and pH dependence, in addition to the cellulose substrate physical state and composition. Given the multivariate nature of cellulose hydrolysis, it is desirable to have diverse cellulases to choose from in order to optimize enzyme formulations for different applications and feedstocks.

SUMMARY

The disclosure provides recombinant polypeptides having cellulase activity and increased thermostability and activity compared to a wild-type protein. The disclosure provides and demonstrates that CBHII chimeras and the native enzymes having a Cys to Ser mutation at the C-terminal end (e.g., at about amino acid 310-315 depending upon the native protein sequence, see, e.g., SEQ ID NO:2 and 4) hydrolyze more solid cellulose than the native enzyme in long time hydrolysis assays.

The disclosure provides a recombinant polypeptide comprising a C→S substitution in the C-terminal region in a motif comprising the sequence GECDG (SEQ ID NO:2 from 312-316), wherein the variant comprises increased thermostability and cellulase activity compared to a wild-type cellobiohydrolase. For example, the disclosure provide polypeptides having increased thermostability and cellulase activity comprising a sequence that is at least 85%, 90%, 95%, 98%, 99% identical SEQ ID NO:2 comprising a C314S; is at least 85%, 90%, 95%, 98%, 99% identical SEQ ID NO:4 comprising a C311S; is at least 85%, 90%, 95%, 98%, 99% identical SEQ ID NO:12 comprising a C310S; is at least 85%, 90%, 95%, 98%, 99% identical SEQ ID NO:13 comprising a C312S; is at least 85%, 90%, 95%, 98%, 99% identical SEQ ID NO:14 comprising a C314S; is at least 85%, 90%, 95%, 98%, 99% identical SEQ ID NO:15 comprising a C315S; is at least 85%, 90%, 95%, 98%, 99% identical SEQ ID NO:16 comprising a C313S; is at least 85%, 90%, 95%, 98%, 99% identical SEQ ID NO:17 comprising a C311S; is at least 85%, 90%, 95%, 98%, 99% identical SEQ ID NO:19 comprising a C313S; is at least 85%, 90%, 95%, 98%, 99% identical SEQ ID NO:21 comprising a C312S; is at least 85%, 90%, 95%, 98%, 99% identical SEQ ID NO:22 comprising a C311S; is at least 85%, 90%, 95%, 98%, 99% identical SEQ ID NO:64 comprising a C400S; is at least 85%, 90%, 95%, 98%, 99% identical SEQ ID NO:65 comprising a C407S; is at least 85%, 90%, 95%, 98%, 99% identical SEQ ID NO:66 comprising a C394S; is at least 85%, 90%, 95%, 98%, 99% identical SEQ ID NO:67 comprising a C400S; is at least 85%, 90%, 95%, 98%, 99% identical SEQ ID NO:68 comprising a C400S; is at least 85%, 90%, 95%, 98%, 99% identical SEQ ID NO:69 comprising a C400S; is at least 85%, 90%, 95%, 98%, 99% identical SEQ ID NO:70 comprising a C400S; is at least 85%, 90%, 95%, 98%, 99% identical SEQ ID NO:71 comprising a C400S; is at least 85%, 90%, 95%, 98%, 99% identical SEQ ID NO:72 comprising a C400S; is at least 85%, 90%, 95%, 98%, 99% identical SEQ ID NO:73 comprising a C400S; is at least 85%, 90%, 95%, 98%, 99% identical SEQ ID NO:74 comprising a C400S; is at least 85%, 90%, 95%, 98%, 99% identical SEQ ID NO:75 comprising a C400S; is at least 85%, 90%, 95%, 98%, 99% identical SEQ ID NO:76 comprising a C407S; is at least 85%, 90%, 95%, 98%, 99% identical SEQ ID NO:77 comprising a C394S; or is at least 85%, 90%, 95%, 98%, 99% identical SEQ ID NO:78 comprising a C412S, wherein the foregoing polypeptides have cellulase activity and improved thermostability compared to their corresponding parental (wild-type) protein lacking a Cys→Ser mutation.

The disclosure also provides substantially purified polypeptides that are either recombinantly produced, synthetic made, or otherwise non-naturally generated wherein the polypeptide comprises a sequence as set forth below having from 1-10, 10-20 or 20-30 conservative amino acid substitutions except at the position identified below wherein a C→S substitution is present: SEQ ID NO:2 comprising a C314S; SEQ ID NO:4 comprising a C311S; SEQ ID NO:12 comprising a C310S; SEQ ID NO:13 comprising a C312S; SEQ ID NO:14 comprising a C314S; SEQ ID NO:15 comprising a C315S; SEQ ID NO:16 comprising a C313S; SEQ ID NO:17 comprising a C311S; SEQ ID NO:19 comprising a C313S; SEQ ID NO:21 comprising a C312S; SEQ ID NO:22 comprising a C311S; SEQ ID NO:64 comprising a C400S; SEQ ID NO:65 comprising a C407S; SEQ ID NO:66 comprising a C394S; SEQ ID NO:67 comprising a C400S; SEQ ID NO:68 comprising a C400S; SEQ ID NO:69 comprising a C400S; SEQ ID NO:70 comprising a C400S; SEQ ID NO:71 comprising a C400S; SEQ ID NO:72 comprising a C400S; SEQ ID NO:73 comprising a C400S; SEQ ID NO:74 comprising a C400S; SEQ ID NO:75 comprising a C400S; SEQ ID NO:76 comprising a C407S; SEQ ID NO:77 comprising a C394S; or SEQ ID NO:78 comprising a C412S.

The disclosure provides a recombinant polypeptide comprising a sequence selected from the group consisting of: (a) a polypeptide having at least 85% or greater identity to SEQ ID NO:2, having a Ser at position 314, and wherein the polypeptide has cellulase activity; (b) a polypeptide having at least 70% or greater identity to SEQ ID NO:4, having a Ser at position 311, and wherein the polypeptide has cellulase activity; (c) a polypeptide having 70% or greater identity to a sequence selected from the group consisting of: (i) SEQ ID NO:12 and having a Ser at position 310, (ii) SEQ ID NO:13 and having a Ser at position 312, (iii) SEQ ID NO:14 and having a Ser at position 314, (iv) SEQ ID NO:15 and having a Ser at position 315, (v) SEQ ID NO:16 and having a Ser at position 313, (vi) SEQ ID NO:17 and having a Ser at position 311, (vii) SEQ ID NO:19 and having a Ser at position 313, (viii) SEQ ID NO:21 and having a Ser at position 312, and (ix)

SEQ ID NO:22 and having a Ser at position 311, and wherein each of the foregoing polypeptides has cellulase activity; and (d) a chimeric polypeptide comprising at least two domains from two different parental cellobiohydrolase polypeptides, wherein the domains comprise from N- to C-terminus: (segment 1)-(segment 2)-(segment 3)-(segment 4)-(segment 5)-(segment 6)-(segment 7)-(segment 8); wherein: segment 1 comprises a sequence that is at least 50-100% identity to amino acid residue from about 1 to about $x_1$ of SEQ ID NO:2 ("1"), SEQ ID NO:4 ("2") or SEQ ID NO:6 ("3"); segment 2 comprises a sequence that is at least 50-100% identity to amino acid residue $x_1$ to about $x_2$ of SEQ ID NO:2 ("1"), SEQ ID NO:4 ("2") or SEQ ID NO:6 ("3"); segment 3 comprises a sequence that is at least 50-100% identity to amino acid residue $x_2$ to about $x_3$ of SEQ ID NO:2 ("1"), SEQ ID NO:4 ("2") or SEQ ID NO:6 ("3"); segment 4 comprises a sequence that is at least 50-100% identity to amino acid residue $x_3$ to about $x_4$ of SEQ ID NO:2 ("1"), SEQ ID NO:4 ("2") or SEQ ID NO:6 ("3"); segment 5 comprises a sequence that is at least 50-100% identity to about amino acid residue $x_4$ to about $x_5$ of SEQ ID NO:2 ("1"), SEQ ID NO:4 ("2") or SEQ ID NO:6 ("3"); segment 6 comprises a sequence that is at least 50-100% identity to amino acid residue $x_5$ to about $x_6$ of SEQ ID NO:2 ("1"), SEQ ID NO:4 ("2") or SEQ ID NO:6 ("3"); segment 7 comprises a sequence that is at least 50-100% identity to amino acid residue $x_6$ to about $x_7$ of SEQ ID NO:2 ("1") or SEQ ID NO:4 ("2"); and segment 8 comprises a sequence that is at least 50-100% identity to amino acid residue $x_7$ to about $x_8$ of SEQ ID NO:2 ("1") or SEQ ID NO:4 ("2"); wherein $x_1$ is residue 43, 44, 45, 46, or 47 of SEQ ID NO:2, or residue 42, 43, 44, 45, or 46 of SEQ ID NO:4 or SEQ ID NO:6; $x_2$ is residue 70, 71, 72, 73, or 74 of SEQ ID NO:2, or residue 68, 69, 70, 71, 72, 73, or 74 of SEQ ID NO:4 or SEQ ID NO:6; $x_3$ is residue 113, 114, 115, 116, 117 or 118 of SEQ ID NO:2, or residue 110, 111, 112, 113, 114, 115, or 116 of SEQ ID NO:4 or SEQ ID NO:6; $x_4$ is residue 153, 154, 155, 156, or 157 of SEQ ID NO:2, or residue 149, 150, 151, 152, 153, 154, 155 or 156 of SEQ ID NO:4 or SEQ ID NO:6; $x_5$ is residue 220, 221, 222, 223, or 224 of SEQ ID NO:2, or residue 216, 217, 218, 219, 220, 221, 222 or 223 of SEQ ID NO:4 or SEQ ID NO:6; $x_6$ is residue 256, 257, 258, 259, 260 or 261 of SEQ ID NO:2, or residue 253, 254, 255, 256, 257, 258, 259 or 260 of SEQ ID NO:4 or SEQ ID NO:6; $x_7$ is residue 312, 313, 314, 315 or 316 of SEQ ID NO:2, or residue 309, 310, 311, 312, 313, 314, 315 or 318 of SEQ ID NO:4; and $x_8$ is an amino acid residue corresponding to the C-terminus of the polypeptide have the sequence of SEQ ID NO:2, SEQ ID NO:4 or SEQ ID NO:6, wherein the chimeric polypeptide comprises a Ser at position 314 of SEQ ID NO:2 or position 311 of SEQ ID NO:4 and wherein the chimeric polypeptide has cellulase activity and improved thermostability and/or pH stability compared to a CBH II polypeptide comprising SEQ ID NO:2, 4, or 6. In one embodiment of the recombinant polypeptide segment 1 comprises amino acid residue from about 1 to about $x_1$ of SEQ ID NO:2 ("1"), SEQ ID NO:4 ("2") or SEQ ID NO:6 ("3") and having 1-10 conservative amino acid substitutions; segment 2 is from about amino acid residue $x_1$ to about $x_2$ of SEQ ID NO:2 ("1"), SEQ ID NO:4 ("2") or SEQ ID NO:6 ("3") and having about 1-10 conservative amino acid substitutions; segment 3 is from about amino acid residue $x_2$ to about $x_3$ of SEQ ID NO:2 ("1"), SEQ ID NO:4 ("2") or SEQ ID NO:6 ("3") and having about 1-10 conservative amino acid substitutions; segment 4 is from about amino acid residue $x_3$ to about $x_4$ of SEQ ID NO:2 ("1"), SEQ ID NO:4 ("2") or SEQ ID NO:6 ("3") and having about 1-10 conservative amino acid substitutions; segment 5 is from about amino acid residue $x_4$ to about $x_5$ of SEQ ID NO:2 ("1"), SEQ ID NO:4 ("2") or SEQ ID NO:6 ("3") and having about 1-10 conservative amino acid substitutions; segment 6 is from about amino acid residue $x_5$ to about $x_6$ of SEQ ID NO:2 ("1"), SEQ ID NO:4 ("2") or SEQ ID NO:6 ("3") and having about 1-10 conservative amino acid substitutions; segment 7 is from about amino acid residue $x_6$ to about $x_7$ of SEQ ID NO:2 ("1"), SEQ ID NO:4 ("2") or SEQ ID NO:6 ("3") and having about 1-10 conservative amino acid substitutions; and segment 8 is from about amino acid residue $x_7$ to about $x_8$ of SEQ ID NO:2 ("1"), SEQ ID NO:4 ("2") or SEQ ID NO:6 ("3") and having about 1-10 conservative amino acid substitutions except at position 314 of SEQ ID NO:2, position 311 or SEQ ID NO:4 or 313 of SEQ ID NO:6. In yet another embodiment, the chimeric polypeptide comprises a sequence that is at least 80%, 90%, 95%, 98% or 99% identical to a sequence selected from the group consisting of SEQ ID NO:12-62 and 63.

The disclosure also provides a recombinant polypeptide consisting of a sequence as set forth in SEQ ID NO:12-62 or 63.

The disclosure also provides a polynucleotide encoding any of the polypeptides as described above, vectors containing the polynucleotide and host cells containing the polynucleotide or vector.

The disclosure also provides an enzymatic preparation comprising a polypeptide of the disclosure in substantially purified form or as part of a cell lysate.

The disclosure also provides a method of treating a biomass comprising cellulose, the method comprising contacting the biomass with a polypeptide or enzymatic preparation of the disclosure.

(SEQ ID NO: 8)
ASCSSVWGQCGGQNWSGPTCCASGSTCVYSNDYYSQCLPGAASSSSSTRA

ASTTSRVSPTTSRSSSATPPPGSTTTRVPPVGSGTATYS.

Figure 8:
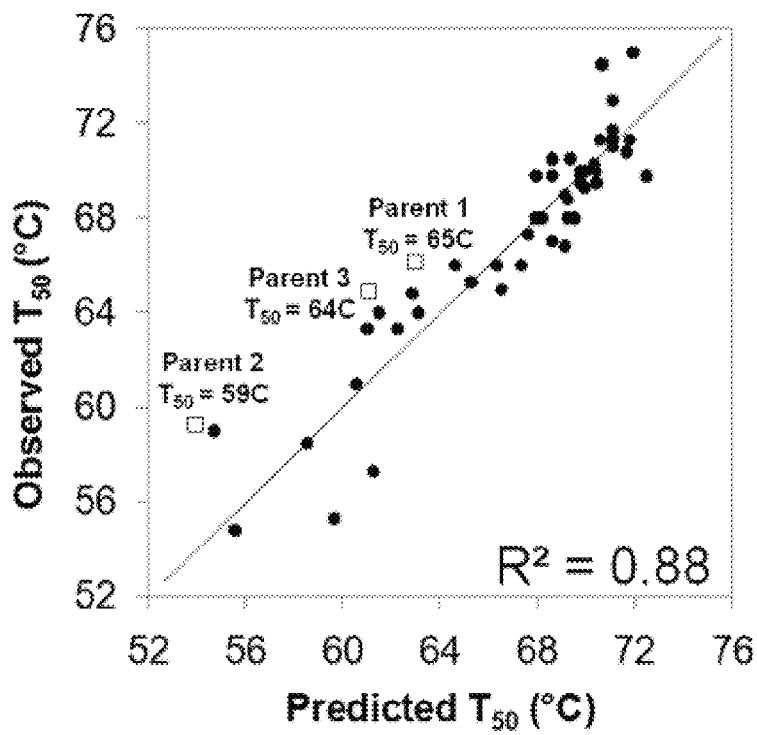

FIG. 8 shows Observed and predicted $T_{50}$ values for CBH II parents and 51 CBH II chimeras. Line denotes linear regression model equation (parameters in Table 7). Parent CBH II $T_{50}$ values are denoted as squares.

Figure 9A:
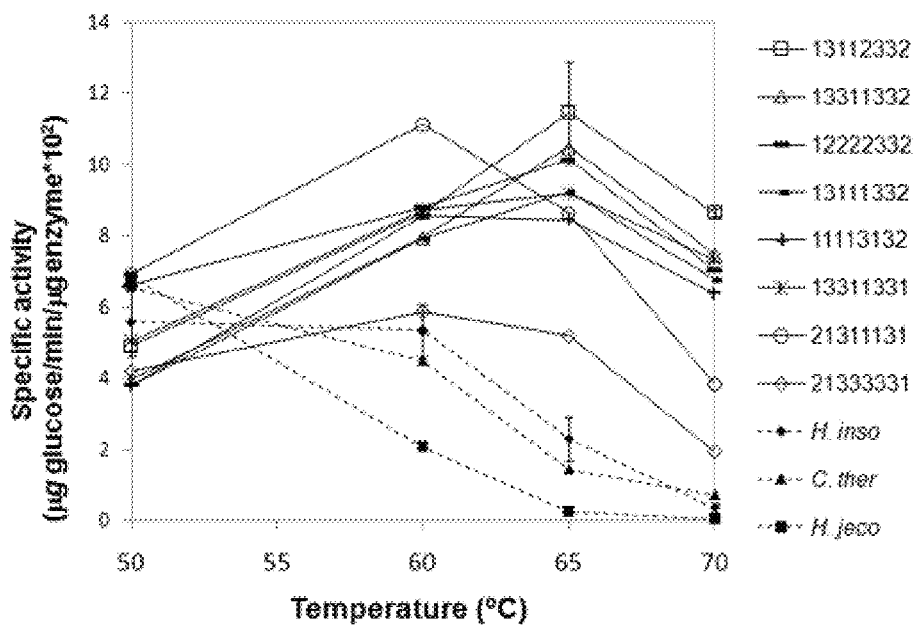
Figure 9B:
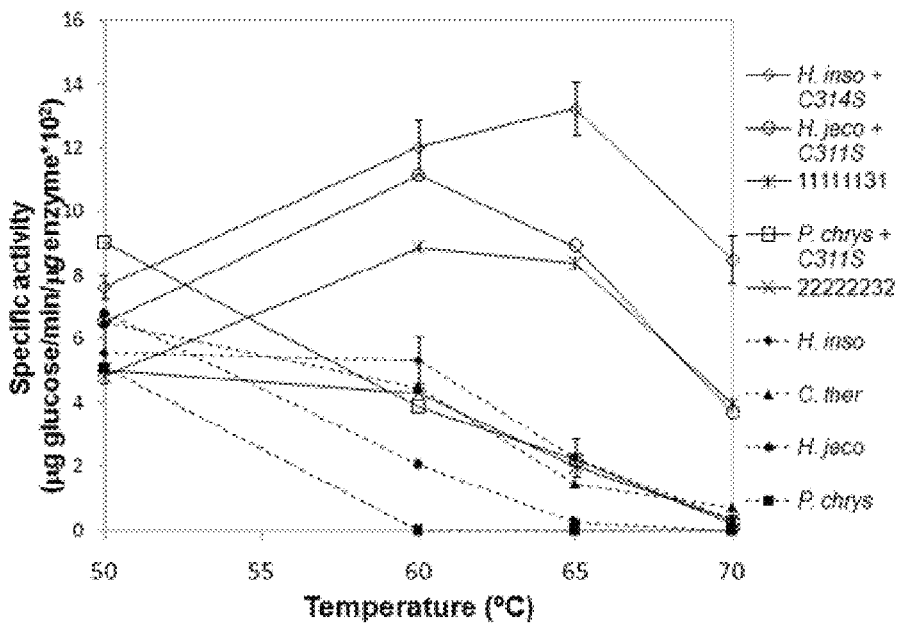
Figure 9C:
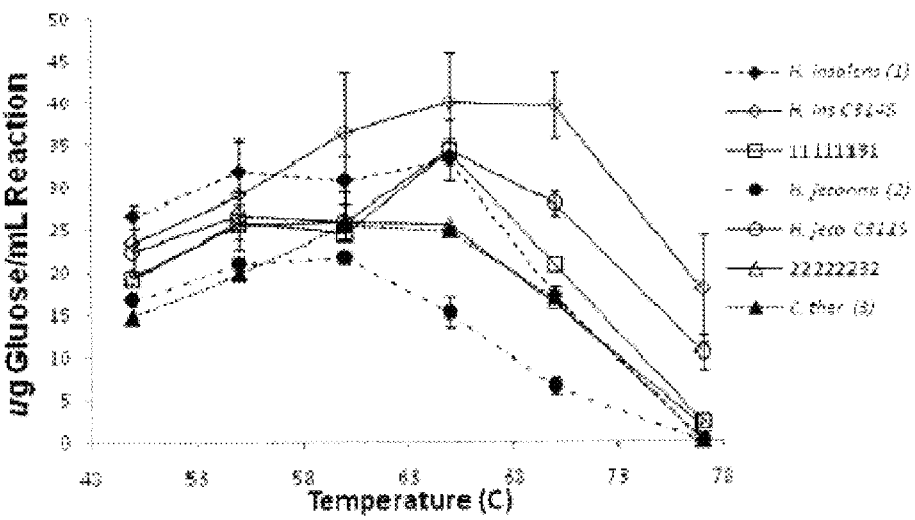

FIG. 9A-C shows CBH II specific activities toward Avicel as a function of temperature. (a) CBH II parent and chimera specific activities. (b) CBH II parent, C311S mutant and B7P3 single block substitution chimera specific activities. Reactions were run for 16 hours in 50 mM sodium acetate, pH 4.8 with an Avicel concentration of 15 mg/mL. (c) CBH II parent, single point mutant and single block substitution chimera activities (μg/glucose/mL reaction) toward avicel as a function of temperature. Reactions were run for 150 minutes in 50 mM sodium acetate, pH 4.8 with an avicel concentration of 15 mg/mL. CBH II yeast culture supernatants were dosed to achieve roughly equivalent reducing sugar product concentrations at 55° C. Data presented are averages of two independent replicates with error bars indicating the duplicate activity values for each temperature point.

Figure 10:

FIG. 10 shows ClustalW multiple sequence alignment for block 7 from parent 1, *H. insolens* and parent 3, *C. thermophilum*. Arrows denote residues changed in reversion mutants.

Figure 11:
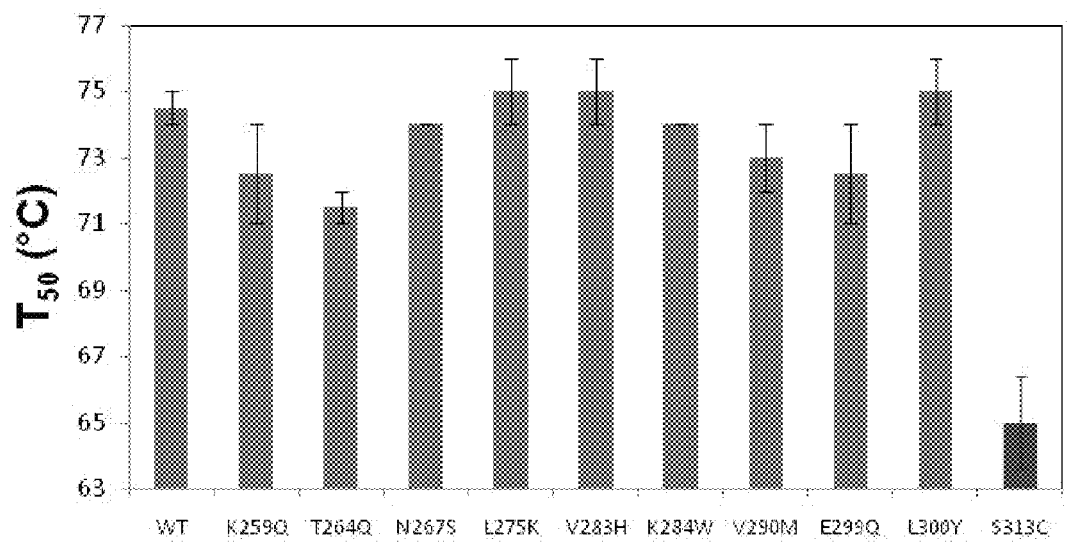

FIG. 11 shows $T_{50}$ values for 21111331 chimera point mutants. Values shown as average of two independent duplicates, error bars indicate duplicate $T_{50}$ values for each point mutant. Inactivation was carried out for 10 minutes at the temperature being tested in 50 mM sodium acetate buffer, pH 4.8. Residual activity was determined by incubation with 1 g/L phosphoric acid swollen cellulose (PASC) in above buffer for 100 minutes at 50° C.

Figure 12:
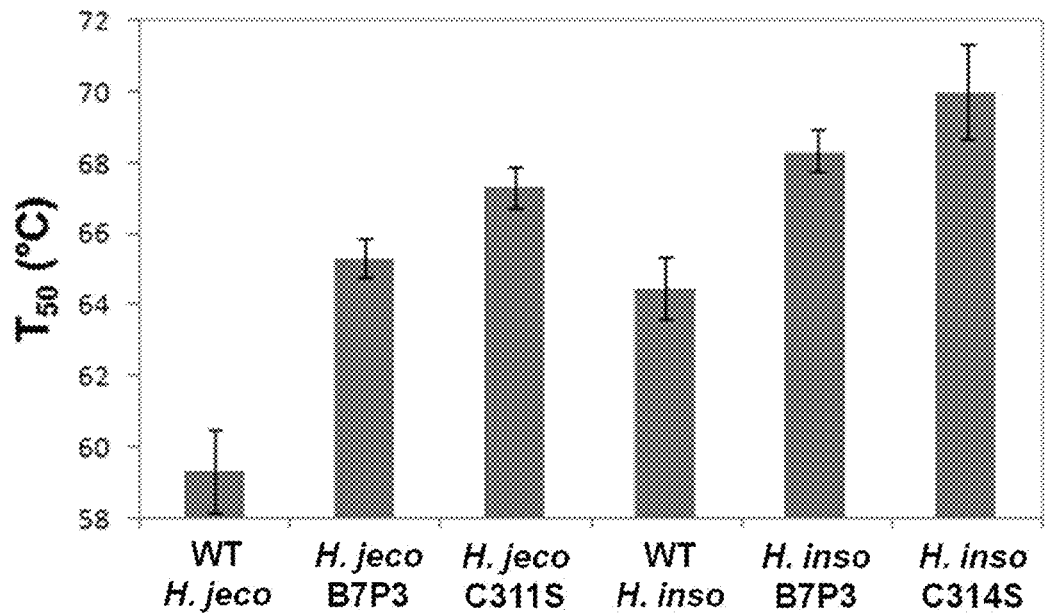

FIG. 12 shows $T_{50}$ values for *H. insolens* and *H. jecorina* parent CBH IIs, Ser single point mutants and B7P3 block substitution chimeras. Values shown as average of three independent replicates, error bars indicate one standard deviation for each CBH II. Inactivation was carried out for 10 minutes at the temperature being tested in 50 mM sodium acetate buffer, pH 4.8. Residual activity was determined by incubation with 1 g/L phosphoric acid swollen cellulose (PASC) in above buffer for 100 minutes at 50° C.

Figure 13:
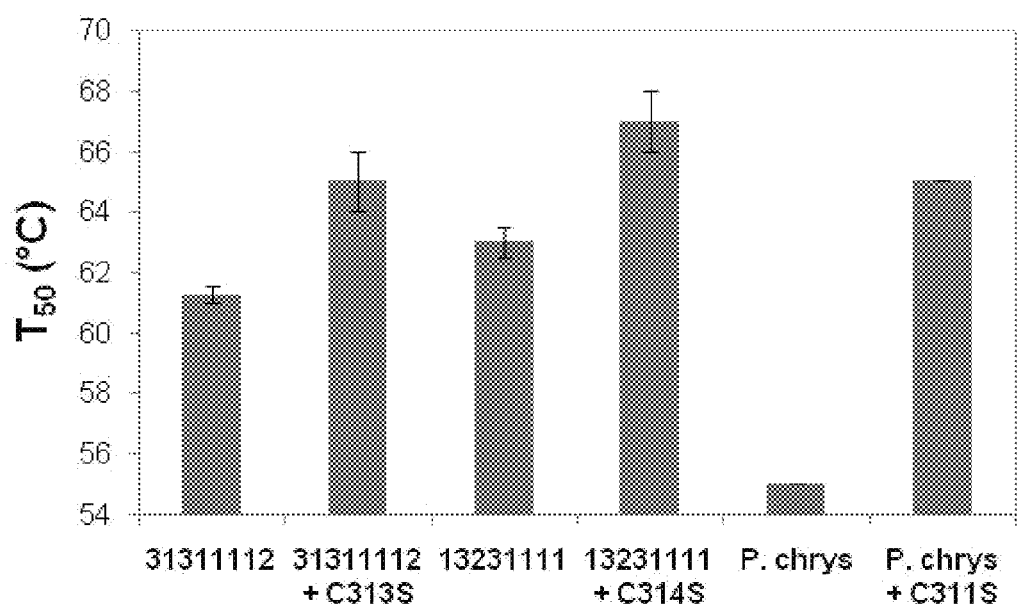

FIG. 13 shows $T_{50}$ values for CBH II chimeras 31311112, 13231111 and the wild type CBH II catalytic domain from *P. chrysosporium* (fused to the *H. jecorina* CBM) and heterologously secreted from *S. cerevisiae*. Values shown as two independent replicates with error bars indicating values for each trial. Inactivation was carried out for 10 minutes at the temperature tested, in 50 mM sodium acetate buffer, pH 4.8. Residual activity was determined by incubation with 1 g/L phosphoric acid swollen cellulose (PASC) in above buffer for 100 minutes at 50° C.

FIG. 14A-D shows CBH II recombination block interfaces. (a) Inter-block sites where novel non-parental residue pairs are possible (connected spheres) are usually surface-exposed, potentially allowing solvent to screen the interactions. (b) An example interface (B5-B6) illustrates conservation of the backbone (cartoons for aligned *H. jecorina* and *H. insolens*), variable residues on the surface, and the comparatively rare possibility of a novel buried hydrophobic pair at residues 173 and 253 (arrow). (c) Blocks 1-4 from *H. jecorina* (black cartoon) match cognate *H. insolens* blocks (color-coded cartoon) without large deviations, though movement associated with substrate binding is observed (arrow) in part of B3 (yellow). (d) Cognate blocks 5-8 are also similar, though the indel at the B6,B7 junction (arrow) will require conformational change.

Figure 15:
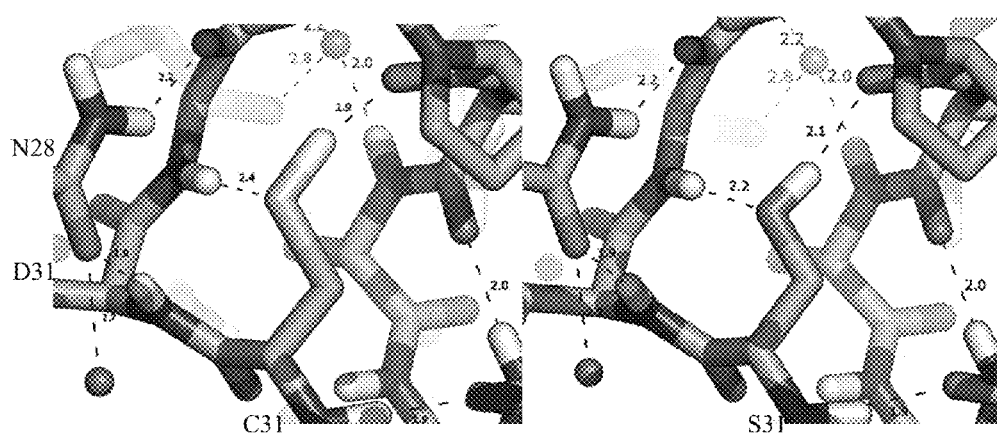

FIG. 15 shows a structural analysis of C314S mutation and its stabilizing effect. (a) Hydrogen positions for high-resolution *H. insolens* structure (1ocn) were added with REDUCE.1 (b) The reconfigured geometry of the analogous serine structure was modeled in PyMOL (http://(//)www.pymol.org). Sidechain optimization in the SHARPEN2 modeling platform (with an all-atom Rosetta energy function) also suggested that both the Cys314 and Ser314 would donate hydrogen bonds to the carbonyl of Pro339, and accept hydrogen bonds from the amide of Gly316. The superior hydrogen bonding capacity of serine may play a role in the greater stability of the serine containing variants. Another possible explanation is geometric complementarity. Specifically, the Cys position from 1ocn shows evidence of conformational strain in that the sidechain is noticeably bent (i.e. the improper dihedral angle from N—C—Cα-Cβ is 6° from the standard position), increasing the distance from the Pro carbonyl. Numbers in figure not preceded by letters denote hydrogen bond distances (Å).

DETAILED DESCRIPTION

As used herein and in the appended claims, the singular forms "a," "and," and "the" include plural referents unless the context clearly dictates otherwise. Thus, for example, reference to "a domain" includes a plurality of such domains and reference to "the protein" includes reference to one or more proteins, and so forth.

Also, the use of "or" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

Although methods and materials similar or equivalent to those described herein can be used in the practice of the disclosed methods and compositions, the exemplary methods, devices and materials are described herein.

Unless defined otherwise, all technical and scientific terms used herein have the same meaning as commonly understood to one of ordinary skill in the art to which this disclosure belongs. Thus, as used throughout the instant application, the following terms shall have the following meanings.

Recent studies have documented the superior performance of cellulases from thermophilic fungi relative to their mesophilic counterparts in laboratory scale biomass conversion processes, where enhanced stability leads to retention of activity over longer periods of time at both moderate and elevated temperatures. Fungal cellulases are attractive because they are highly active and can be expressed in fungal hosts such as Hypocrea jecorina (anamorph Trichoderma reesei) at levels up to 40 g/L in the supernatant. Unfortunately, the set of documented thermostable fungal cellulases is small. In the case of the processive cellobiohydrolase class II (CBH II) enzymes, fewer than 10 natural thermostable gene sequences are annotated in the CAZy database.

As described more fully herein, using recursive chimeric polypeptide generation and analysis particular stabilizing domains and ultimately specific amino acid were identified the imparted thermostability and improved activity.

As will be described in more detail below, the invention is based, at least in part, on the generation and expression of novel enzymes that catalyze the hydrolysis of cellulose. In one embodiment, novel polypeptides that have been engineered to hydrolyze cellose at increased temperatures are provided. Such polypeptides include cellobiohydrolase variants that have been altered to include amino acid substitutions at specified residues. While these variants will be described in more detail below, it is understood that polypeptides of the disclosure may contain one or more modified amino acids. The presence of modified amino acids may be advantageous in, for example, (a) increasing a polypeptide's half-life, (b) thermostability, and (c) increased substrate turnover. Amino acid(s) are modified, for example, co-translationally or post-translationally during recombinant production (e.g., N-linked glycosylation at N—X—S/T motifs during expression in mammalian cells) or modified by synthetic means. Accordingly, a "mutant", "variant" or "modified" protein, enzyme, polynucleotide, gene, or cell, means a protein, enzyme, polynucleotide, gene, or cell, that has been altered or derived, or is in some way different or changed, from a parent protein, enzyme, polynucleotide, gene, or cell. A mutant or modified protein or enzyme is usually, although not necessarily, expressed from a mutant polynucleotide or gene.

A "mutation" means any process or mechanism resulting in a mutant protein, enzyme, polynucleotide, gene, or cell. This includes any mutation in which a protein, enzyme, polynucleotide, or gene sequence is altered, and any detectable change in a cell arising from such a mutation. Typically, a mutation occurs in a polynucleotide or gene sequence, by point mutations, deletions, or insertions of single or multiple nucleotide residues. A mutation includes polynucleotide alterations arising within a protein-encoding region of a gene as well as alterations in regions outside of a protein-encoding sequence, such as, but not limited to, regulatory or promoter sequences. A mutation in a gene can be "silent", i.e., not reflected in an amino acid alteration upon expression, leading to a "sequence-conservative" variant of the gene. This generally arises when one amino acid corresponds to more than one codon.

Non-limiting examples of a modified amino acid include a glycosylated amino acid, a sulfated amino acid, a prenlyated (e.g., farnesylated, geranylgeranylated) amino acid, an acetylated amino acid, an acylated amino acid, a pegylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM (Humana Press, Towata, N.J.).

Recombinant methods for producing and isolating modified cellobiohydrolase polypeptides of the disclosure are described herein. In addition to recombinant production, the polypeptides may be produced by direct peptide synthesis using solid-phase techniques (e.g., Stewart et al. (1969) Solid-Phase Peptide Synthesis (WH Freeman Co, San Francisco); and Merrifield (1963) J. Am. Chem. Soc. 85: 2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer.

"Cellobiohydrolase II" or "CBH II enzyme" means an enzyme in the cellulase family 6 proteins, which are widely distributed in bacteria and fungi. The enzymes are involved in hydrolysis of cellulose.

By "cellulase activity" means an enzyme that is capable of hydrolyzing cellulose. Cellulase refers to a class of enzymes produced by fungi, bacteria, and protozoans that catalyze the hydrolysis of cellulose. However, there are also cellulases produced by other types of organisms such as plants and animals. The EC number for this group of enzymes is EC 3.2.1.4. There are five generatl types of cellulases based on the type of reaction catalyzed: endo-cellulase; exo-cellulase, within this category there are two main types of exo-cellulases (or cellobiohydrolases, abbreviate CBH)—one type working processively from the reducing end, and one type working processively from the non-reducing end of cellulose; cellobiase or beta-glucosidase hydrolyses; oxidative cellulases; and cellulose phosphorylases that depolymerize cellulose using phosphates instead of water. Most fungal cellulases have two-domains: a catalytic domain and a cellulose binding domain, that are connected by a flexible linker. In specific embodiments of the disclosure the cellulase activity is a CBH activity. The sequences described herein include, in some instances, both the cellulose binding domain and the catalytic domain or just the catalytic domain. In such instances where only the catalytic domain sequence is provided it will be recognized that a cellulose binding domain (CBD) such as that provided in SEQ ID NO:8, may be functional linked (either as part of the coding sequence or fused later) to the catalytic domain either directly or through a linker.

A "protein" or "polypeptide", which terms are used interchangeably herein, comprises one or more chains of chemical building blocks called amino acids that are linked together by chemical bonds called peptide bonds. An "enzyme" means any substance, preferably composed wholly or largely of protein, that catalyzes or promotes, more or less specifically, one or more chemical or biochemical reactions. A "native" or "wild-type" protein, enzyme, polynucleotide, gene, or cell, means a protein, enzyme, polynucleotide, gene, or cell that occurs in nature.

An "amino acid sequence" is a polymer of amino acids (a protein, polypeptide, etc.) or a character string representing an amino acid polymer, depending on context. The terms "protein," "polypeptide," and "peptide" are used interchangeably herein. "Amino acid" is a molecule having the structure wherein a central carbon atom is linked to a hydrogen atom, a carboxylic acid group (the carbon atom of which is referred to herein as a "carboxyl carbon atom"), an amino group (the nitrogen atom of which is referred to herein as an "amino nitrogen atom"), and a side chain group, R. When incorporated into a peptide, polypeptide, or protein, an amino acid loses one or more atoms of its amino acid carboxylic groups in the dehydration reaction that links one amino acid to another. As a result, when incorporated into a protein, an amino acid is referred to as an "amino acid residue."

A particular amino acid sequence of a given protein (i.e., the polypeptide's "primary structure," when written from the amino-terminus to carboxy-terminus) is determined by the nucleotide sequence of the coding portion of a mRNA, which is in turn specified by genetic information, typically genomic DNA (including organelle DNA, e.g., mitochondrial or chloroplast DNA). Thus, determining the sequence of a gene assists in predicting the primary sequence of a corresponding polypeptide and more particular the role or activity of the polypeptide or proteins encoded by that gene or polynucleotide sequence.

"Conservative amino acid substitution" or, simply, "conservative variations" of a particular sequence refers to the replacement of one amino acid, or series of amino acids, with essentially identical amino acid sequences. One of skill will recognize that individual substitutions, deletions or additions which alter, add or delete a single amino acid or a percentage of amino acids in an encoded sequence result in "conservative variations" where the alterations result in the deletion of an amino acid, addition of an amino acid, or substitution of an amino acid with a chemically similar amino acid.

Conservative substitution tables providing functionally similar amino acids are well known in the art. For example, one conservative substitution group includes Alanine (A), Serine (S), and Threonine (T). Another conservative substitution group includes Aspartic acid (D) and Glutamic acid (E). Another conservative substitution group includes Asparagine (N) and Glutamine (Q). Yet another conservative substitution group includes Arginine (R) and Lysine (K). Another conservative substitution group includes Isoleucine, (I) Leucine (L), Methionine (M), and Valine (V). Another conservative substitution group includes Phenylalanine (F), Tyrosine (Y), and Tryptophan (W).

Thus, "conservative amino acid substitutions" of a listed polypeptide sequence (e.g., SEQ ID NOs: 2, 4, 6, and 12-78) include substitutions of a percentage, typically less than 10%, of the amino acids of the polypeptide sequence, with a conservatively selected amino acid of the same conservative substitution group. Accordingly, a conservatively substituted variation of a polypeptide of the disclosure can contain 100, 75, 50, 25, or 10 substitutions with a conservatively substituted variation of the same conservative substitution group.

It is understood that the addition of sequences which do not alter the encoded activity of a nucleic acid molecule, such as the addition of a non-functional or non-coding sequence, is a conservative variation of the basic nucleic acid. The "activity" of an enzyme is a measure of its ability to catalyze a reaction, i.e., to "function", and may be expressed as the rate at which the product of the reaction is produced. For example, enzyme activity can be represented as the amount of product produced per unit of time or per unit of enzyme (e.g., concentration or weight), or in terms of affinity or dissociation constants. As used interchangeably herein a "cellobiohydrolase activity or cellulase activity", "biological activity of cellobiohydrolase or cellulase" or "functional activity of cellobiohydrolase or cellulase", refers to an activity exerted by a protein, polypeptide having cellulase activity and in specific embodiments cellobiohydrolase activity on a cellulose substrate, as determined in vivo, or in vitro, according to standard techniques.

One of skill in the art will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the polypeptides provided herein.

"Conservative variants" are proteins or enzymes in which a given amino acid residue has been changed without altering overall conformation and function of the protein or enzyme, including, but not limited to, replacement of an amino acid with one having similar properties, including polar or nonpolar character, size, shape and charge. Amino acids other than those indicated as conserved may differ in a protein or enzyme so that the percent protein or amino acid sequence similarity between any two proteins of similar function may vary and can be, for example, at least 30%, at least 50%, at least 70%, at least 80%, or at least 90%, as determined according to an alignment scheme. As referred to herein, "sequence similarity" means the extent to which nucleotide or protein sequences are related. The extent of similarity between two sequences can be based on percent sequence identity and/or conservation. "Sequence identity" herein means the extent to which two nucleotide or amino acid sequences are invariant. "Sequence alignment" means the process of lining up two or more sequences to achieve maximal levels of identity (and, in the case of amino acid sequences, conservation) for the purpose of assessing the degree of similarity. Numerous methods for aligning sequences and assessing similarity/identity are known in the art such as, for example, the Cluster Method, wherein similarity is based on the MEGALIGN algorithm, as well as BLASTN, BLASTP, and FASTA (Lipman and Pearson, 1985; Pearson and Lipman, 1988). When using all of these programs, the preferred settings are those that results in the highest sequence similarity.

Non-conservative modifications of a particular polypeptide are those which substitute any amino acid not characterized as a conservative substitution. For example, any substitution which crosses the bounds of the six groups set forth above. These include substitutions of basic or acidic amino acids for neutral amino acids, (e.g., Asp, Glu, Asn, or Gln for Val, Ile, Leu or Met), aromatic amino acid for basic or acidic amino acids (e.g., Phe, Tyr or Trp for Asp, Asn, Glu or Gln) or any other substitution not replacing an amino acid with a like amino acid. Basic side chains include lysine (K), arginine (R), histidine (H); acidic side chains include aspartic acid (D), glutamic acid (E); uncharged polar side chains include glycine (G), asparagine (N), glutamine (Q), serine (S), threonine (T), tyrosine (Y), cysteine (C); nonpolar side chains include alanine (A), valine (V), leucine (L), isoleucine (I), proline (P), phenylalanine (F), methionine (M), tryptophan (W); beta-branched side chains include threonine (T), valine (V), isoleucine (I); aromatic side chains include tyrosine (Y), phenylalanine (F), tryptophan (W), histidine (H).

A "parent" protein, enzyme, polynucleotide, gene, or cell, is any protein, enzyme, polynucleotide, gene, or cell, from which any other protein, enzyme, polynucleotide, gene, or cell, is derived or made, using any methods, tools or techniques, and whether or not the parent is itself native or mutant. A parent polynucleotide or gene encodes for a parent protein or enzyme.

In addition to providing variants of CBH II polypeptides, chimeric polypeptides that comprise: 1) a variant domain isolated from a first parental strand and modified to include an amino acid substitution; and 2) a domain isolated from a second parental strand either unmodified or modified to include a new activity or an activity that a complements the domain, are provided. Methods for engineering a chimeric polypeptide of the disclosure are disclosed herein.

The disclosure provides cellulase and cellobiohydrolase (CBH) II variants, mutants and chimeras having increased thermostability compared to a wild-type or parental protein, wherein the wild-type protein consisting of SEQ ID NO:2, 4 or 6. The variant comprises a Serine in the C-terminal region in a motif comprising the sequence GEXDG, wherein X is C, A or G (SEQ ID NO:107), wherein X is substituted with Serine, the variant comprising cellulase activity and wherein the polypeptide has increased thermostability compared to a wild-type cellulase lacking a serine in the sequence GEXDG (SEQ ID NO:107). In one embodiment, the variants comprise at least a mutation of a Cys→Ser in the motif GECDG (see, e.g., SEQ ID NO:2 from amino acid 312-316) found in most cellulase and cellobiohydrolase II proteins (as described more fully below) and may comprise additional mutations that improve thermostability or activity. The identity between cellulases can be quite low. The serine substitution as described above is applicable to any cellulase having the motif of SEQ ID NO:107 (e.g., wherein the polypeptide has at least 60% or greater identity to SEQ ID NO:2 or 4).

For example, the disclosure provide polypeptides having increased thermostability and cellulase activity comprising a sequence that is at least 85%, 90%, 95%, 98%, 99% identical SEQ ID NO:2 comprising a C314S; is at least 85%, 90%, 95%, 98%, 99% identical SEQ ID NO:4 comprising a C311S; is at least 85%, 90%, 95%, 98%, 99% identical SEQ ID NO:12 comprising a C310S; is at least 85%, 90%, 95%, 98%, 99% identical SEQ ID NO:13 comprising a C312S; is at least 85%, 90%, 95%, 98%, 99% identical SEQ ID NO:14 comprising a C314S; is at least 85%, 90%, 95%, 98%, 99% identical SEQ ID NO:15 comprising a C315S; is at least 85%, 90%, 95%, 98%, 99% identical SEQ ID NO:16 comprising a C313S; is at least 85%, 90%, 95%, 98%, 99% identical SEQ ID NO:17 comprising a C311S; is at least 85%, 90%, 95%, 98%, 99% identical SEQ ID NO:19 comprising a C313S; is at least 85%, 90%, 95%, 98%, 99% identical SEQ ID NO:21 comprising a C312S; is at least 85%, 90%, 95%, 98%, 99% identical SEQ ID NO:22 comprising a C311S; is at least 85%, 90%, 95%, 98%, 99% identical SEQ ID NO:64 comprising a C400S; is at least 85%, 90%, 95%, 98%, 99% identical SEQ ID NO:65 comprising a C407S; is at least 85%, 90%, 95%, 98%, 99% identical SEQ ID NO:66 comprising a C394S; is at least 85%, 90%, 95%, 98%, 99% identical SEQ ID NO:67 comprising a C400S; is at least 85%, 90%, 95%, 98%, 99% identical SEQ ID NO:68 comprising a C400S; is at least 85%, 90%, 95%, 98%, 99% identical SEQ ID NO:69 comprising a C400S; is at least 85%, 90%, 95%, 98%, 99% identical SEQ ID NO:70 comprising a C400S; is at least 85%, 90%, 95%, 98%, 99% identical SEQ ID NO:71 comprising a C400S; is at least 85%, 90%, 95%, 98%, 99% identical SEQ ID NO:72 comprising a C400S; is at least 85%, 90%, 95%, 98%, 99% identical SEQ ID NO:73 comprising a C400S; is at least 85%, 90%, 95%, 98%, 99% identical SEQ ID NO:74 comprising a C400S; is at least 85%, 90%, 95%, 98%, 99% identical SEQ ID NO:75 comprising a C400S; is at least 85%, 90%, 95%, 98%, 99% identical SEQ ID NO:76 comprising a C407S; is at least 85%, 90%, 95%, 98%, 99% identical SEQ ID NO:77 comprising a C394S; or is at least 85%, 90%, 95%, 98%, 99% identical SEQ ID NO:78 comprising a C412S, wherein the foregoing polypeptides have cellulase activity and improved thermostability compared to their corresponding parental (wild-type) protein lacking a Cys→Ser mutation.

In yet another embodiment, the disclosure provides polypeptide as described above, however, they further comprise at least one addition mutation that can be determined by alignment to SEQ ID NO:64, wherein SEQ ID NO:64 comprises a Pro at position 413, or a Ser or Thr at position 231, or a Ser or Thr at position 305, or a Gln or Asn at position 410, or a Glu at position 82, or any combination of the foregoing. Similar substitutions can be identified by sequence alignment of the amino acid sequence of SEQ ID NO:64 with those of SEQ ID NOs:2, 4, 6, 12-63, and 65-78.

The disclosure also provides substantially purified polypeptides that are either recombinantly produced, synthetic made, or otherwise non-naturally generated wherein the polypeptide comprise a sequence as set forth below having from 1-10, 10-20 or 20-30 conservative amino acid substitutions except at the position identified below wherein a C→S substitution is present:

SEQ ID NO:2 comprising a C314S;
SEQ ID NO:4 comprising a C311S;
SEQ ID NO:12 comprising a C310S;
SEQ ID NO:13 comprising a C312S;
SEQ ID NO:14 comprising a C314S;
SEQ ID NO:15 comprising a C315S;
SEQ ID NO:16 comprising a C313S;
SEQ ID NO:17 comprising a C311S;
SEQ ID NO:19 comprising a C313S;
SEQ ID NO:21 comprising a C312S;
SEQ ID NO:22 comprising a C311S;
SEQ ID NO:64 comprising a C400S;
SEQ ID NO:65 comprising a C407S;
SEQ ID NO:66 comprising a C394S;
SEQ ID NO:67 comprising a C400S;
SEQ ID NO:68 comprising a C400S;
SEQ ID NO:69 comprising a C400S;
SEQ ID NO:70 comprising a C400S;
SEQ ID NO:71 comprising a C400S;
SEQ ID NO:72 comprising a C400S;
SEQ ID NO:73 comprising a C400S;
SEQ ID NO:74 comprising a C400S;
SEQ ID NO:75 comprising a C400S;
SEQ ID NO:76 comprising a C407S;
SEQ ID NO:77 comprising a C394S; or
SEQ ID NO:78 comprising a C412S.

"Isolated polypeptide" refers to a polypeptide which is separated from other contaminants that naturally accompany it, e.g., protein, lipids, and polynucleotides. The term embraces polypeptides which have been removed or purified from their naturally-occurring environment or expression system (e.g., host cell or in vitro synthesis).

"Substantially pure polypeptide" refers to a composition in which the polypeptide species is the predominant species present (i.e., on a molar or weight basis it is more abundant than any other individual macromolecular species in the composition), and is generally a substantially purified composition when the object species comprises at least about 50 percent of the macromolecular species present by mole or % weight. Generally, a substantially pure polypeptide composition will comprise about 60% or more, about 70% or more, about 80% or more, about 90% or more, about 95% or more, and about 98% or more of all macromolecular species by mole or % weight present in the composition. In some embodiments, the object species is purified to essential homogeneity (i.e., contaminant species cannot be detected in the composition by conventional detection methods) wherein the composition consists essentially of a single macromolecular species. Solvent species, small molecules (<500 Daltons), and elemental ion species are not considered macromolecular species.

"Reference sequence" refers to a defined sequence used as a basis for a sequence comparison. A reference sequence may be a subset of a larger sequence, for example, a segment of a full-length gene or polypeptide sequence. Generally, a reference sequence can be at least 20 nucleotide or amino acid residues in length, at least 25 nucleotide or residues in length, at least 50 nucleotides or residues in length, or the full length of the nucleic acid or polypeptide. Since two polynucleotides or polypeptides may each (1) comprise a sequence (i.e., a portion of the complete sequence) that is similar between the two sequences, and (2) may further comprise a sequence that is divergent between the two sequences, sequence comparisons between two (or more) polynucleotides or polypeptides are typically performed by comparing sequences of the two polynucleotides or polypeptides over a "comparison window" to identify and compare local regions of sequence similarity.

"Sequence identity" means that two amino acid sequences are substantially identical (i.e., on an amino acid-by-amino acid basis) over a window of comparison. The term "sequence similarity" refers to similar amino acids that share the same biophysical characteristics. The term "percentage of sequence identity" or "percentage of sequence similarity" is calculated by comparing two optimally aligned sequences over the window of comparison, determining the number of positions at which the identical residues (or similar residues) occur in both polypeptide sequences to yield the number of matched positions, dividing the number of matched positions by the total number of positions in the window of comparison (i.e., the window size), and multiplying the result by 100 to yield the percentage of sequence identity (or percentage of sequence similarity). With regard to polynucleotide sequences, the terms sequence identity and sequence similarity have comparable meaning as described for protein sequences, with the term "percentage of sequence identity" indicating that two polynucleotide sequences are identical (on a nucleotide-by-nucleotide basis) over a window of comparison. As such, a percentage of polynucleotide sequence identity (or percentage of polynucleotide sequence similarity, e.g., for silent substitutions or other substitutions, based upon the analysis algorithm) also can be calculated. Maximum correspondence can be determined by using one of the sequence algorithms described herein (or other algorithms available to those of ordinary skill in the art) or by visual inspection.

As applied to polypeptides, the term substantial identity or substantial similarity means that two peptide sequences, when optimally aligned, such as by the programs BLAST, GAP or BESTFIT using default gap weights or by visual inspection, share sequence identity or sequence similarity. Similarly, as applied in the context of two nucleic acids, the term substantial identity or substantial similarity means that the two nucleic acid sequences, when optimally aligned, such as by the programs BLAST, GAP or BESTFIT using default gap weights (described elsewhere herein) or by visual inspection, share sequence identity or sequence similarity.

One example of an algorithm that is suitable for determining percent sequence identity or sequence similarity is the FASTA algorithm, which is described in Pearson, W. R. & Lipman, D. J., (1988) Proc. Natl. Acad. Sci. USA 85:2444. See also, W. R. Pearson, (1996) Methods Enzymology 266: 227-258. Preferred parameters used in a FASTA alignment of DNA sequences to calculate percent identity or percent similarity are optimized, BL50 Matrix 15: −5, k-tuple=2; joining penalty=40, optimization=28; gap penalty −12, gap length penalty=−2; and width=16.

Another example of a useful algorithm is PILEUP. PILEUP creates a multiple sequence alignment from a group of related sequences using progressive, pairwise alignments to show relationship and percent sequence identity or percent sequence similarity. It also plots a tree or dendogram showing the clustering relationships used to create the alignment. PILEUP uses a simplification of the progressive alignment method of Feng & Doolittle, (1987) J. Mol. Evol. 35:351-360. The method used is similar to the method described by Higgins & Sharp, CABIOS 5:151-153, 1989. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using the following parameters: default gap weight (3.00), default gap length weight (0.10), and weighted end gaps. PILEUP can be obtained from the GCG sequence analysis software package, e.g., version 7.0 (Devereaux et al., (1984) Nuc. Acids Res. 12:387-395).

Another example of an algorithm that is suitable for multiple DNA and amino acid sequence alignments is the CLUSTALW program (Thompson, J. D. et al., (1994) Nuc. Acids Res. 22:4673-4680). CLUSTALW performs multiple pairwise comparisons between groups of sequences and assembles them into a multiple alignment based on sequence identity. Gap open and Gap extension penalties were 10 and 0.05 respectively. For amino acid alignments, the BLOSUM algorithm can be used as a protein weight matrix (Henikoff and Henikoff, (1992) Proc. Natl. Acad. Sci. USA 89:10915-10919).

As mentioned above, cellobiohydrolase and cellulase family members can be identified by sequence alignment and a substitution in the motif GECDG (see, e.g., SEQ ID NO:2 from amino acid 312-316) made. The modified polypeptide may then be assayed for activity as described below at various temperatures and conditions to identify those modifications that introduce a favorable activity. Exemplary sequences can be found in the following GenBank accession numbers, the sequences of which are incorporated herein by reference.

| P07987 | Q6E581 |
|---|---|
| GUX2_TRIRE | Q6E581_9AGAR |

| | |
|---|---|
| Q9HEY8 | B7X9Z0 |
| Q9HEY8_TRIRE | B7X9Z0_COPC1 |
| Q7LSP2 | A8NEJ3 |
| Q7LSP2_TRIKO | A8NEJ3_COPC7 |
| Q6UJX9 | Q96V98 |
| Q6UJX9_TRIVI | Q96V98_ORPSP |
| A3QVU7 | Q7Z7X6 |
| A3QVU7_TRIVI | Q7Z7X5_PIREQ |
| 1HCL5 | Q870B2 |
| Q1HCL5_TRIKO | Q87082_9FUNG |
| Q66PN1 | Q874E1 |
| Q66PN1_9HYPO | Q874E1_ORPSP |
| B5TWC7 | A9FHT2 |
| B5TWC7_9HYPO | A9FHT2_SORC5 |
| Q9C1S9 | B0FEV9 |
| GUX6_HUMIN | B0FEV9_9FUNG |
| Q2GMP2 | Q6EY63 |
| Q2GMP2_CHAGB | Q6EY63_9FUNG |
| A7E6G7 | Q6EH22 |
| A7E6G7_SCLS1 | Q6EH22_NEOFR |
| Q0UPA5 | B6EA50 |
| Q0UPA5_PHANO | B6EA50_NEOPA |
| A6S7A6 | B0FEV4 |
| A6S7A6_BOTFB | B0FEV4_NEOPA |
| P49075 | 6EIY8 |
| GUX3_AGABI | Q6EIY8_NEOFR |
| Q02321 | Q9UW10 |
| Q02321_PHACH | Q9UW10_9FUNG |
| Q9C1R4 | Q12646 |
| Q9C1R4_LENED | Q12646_NEOPA |
| Q96VU2 | Q6A4K7 |
| Q96VU2_LENED | Q6A4K7_9FUNG |
| B2ABX7 | Q9UW11 |
| B2ABX7_PODAN | Q9UW11_9FUNG |
| A4RPH6 | Q9P8Q8 |
| A4RPH6_MAGGR | Q9P8Q8_9FUNG |
| | B0FEV8 |
| | B0FEV8_9FUNG |

In yet other embodiments, the family of variant cellulase polypeptide having improved thermostability include those set forth in the following table having a C→S, G→S or A→S substitution. In addition, polypeptides having 85%, 90%, 95%, 98%, or 99% sequence identity to any of the following sequences having the identified substitutions in the following table, having cellulase activity and thermostability are also encompassed by the disclosure.

Alignment of amino acid frame bracketing *H. jecorina* CBH II Cys311 for protein sequences having highest identity to *H. jecorina* CBH II. Residues at 311 equivalent position denoted by bold, underline are shown. Sequences for recombinant *H. insolens* and *P. chrys* CBH IIs studied in this work are denoted as *H. inso* and *P. chrys*. Fifty-four of the 250 most identical sequences were excluded due to redundancy (i.e. point mutants for structural studies or >95% identical isoforms). The accession number for the cellulase is identified and the corresponding sequence is incorporated herein by reference as if copied directly from the accession number. The sequences associated with the accession numbers are referred to as SEQ ID NO:79-106. A replacement of the bold-underlined residue (e.g., C, A or G) with S. The number in parenthesis following the sequence identified the SEQ ID NO:)

```
H.jeco        ----T---G---D----S---L--LDSFVWVKPGGECDG--T----S------------   (4)

XP_001903170  ----T---G---L----D---I--EDAFVWIKPGGECDG--T----S------------  (79)

XP_001226029  ----T---G---H----D---L--LDAFVWIKPGGECDG--T----S------------  (80)

XP_360146     ----T---G---S----E---L--ADAFVWIKPGGECDG--V----S------------  (81)

H.inso        ----T---G---H----Q---Y--VDAFVWVKPGGECDG--T----S------------   (2)

XP_001598803  ----T---G---D----A---L--EDAFVWVKPGGEADG--T----S------------  (82)

XP_001796781  ----T---D---D----P---L--LDAYVWVKPGGEGDG--T----S------------  (83)

AAA50608      ----T---G---S----S---L--IDAIVWVKPGGECDG--T----S------------  (84)

AAK28357      ----T---G---S----S---L--IDSIVWVKPGGECDG--T----S------------  (85)

BAH59082      ----T---G---S----P---L--IDSIVWVKPGGECDG--T----S------------  (86)

AAT64008      ----T---G---S----S---L--IDAIVWIKPGGECDG--T----T------------  (87)

P.crys        ----T---G---S----Q---F--IDSIVWVKPGGECDG--T----S------------  (12)

BAH59083      ----T---P---S----S---L--IDSIVWVKPGGEADG--T----S------------  (88)

XP_001833045  ----T---P---S----S---A--IDAIVWIKPGGEADG--T----S------------  (89)

XP_002391276  ----T---G---S----S---L--IDSIVWVKPGGE---------------------   (90)

AAD51055      ----P---D---S----SKP-L--LDAYMWIKTPGEADG--S----S------------  (91)

ABY52798      ----S---G---Y----PL-----LDAFMWLKTPGEADG--S----A------------  (92)

AAF34679      ----P---D---A----SMP-L--LDAYMWLKTPGEADG--S----A------------  (93)

ABY52797      ----P---S---K----P---L--LDAYMWIKTPGEADG--S----S------------  (94)

AAR08200      ----PNP-G---M----P---L--LDAYMWLKTPGEADG--S----S------------  (95)

AAB92678      ----P---N---P----GSMPL--LDAYMWIKTPGEADG--S----S------------  (96)
```

```
ABY52799      ----S---P---DPEKFP---L--LDAYFWLKPPGEADG--S----D-------------     (97)

AAC60491      ----T---G---D----A---N--IDAYLWVKPPGEADG--------------------     (98)

AAC09068      ----V---K---M----P---L--LDAYMWLKTPGEADG--S----D-------------     (99)

ZP_04371095   ----T---G---D----A---A--VDAFLWIKPPGEADG--C----A-------------     (100)

ZP_03818362   ----T---G---D----S---Q--IDAFLWVKIVGEADG--------------------     (101)

ZP_03817628   ----T---G---D----P---Q--IDAFLWVKIPGEADG--------------------     (102)

ZP_04331392   ----T---G---N----P---L--IDAFIWTKLPGEADG--------------------     (103)

2BOE-X        ----T---G---D----P---M--IDAFLWIKLPGEADG--------------------     (104)

ZP_04608509   ----T---G---D----S---A--IAAYLWVKLPGEADG--------------------     (105)

P26414        ----T---G---D----P---A--IDAFLWIKPPGEADG--------------------     (106)
```

For the purposes of the disclosure, a polypeptide of the disclosure exhibits improved thermostability with respect to a corresponding parent polypeptide if it has a $T_{50}$ which is at least about 4° C., or at least about 9° C. higher than that of the parent cellulase, or for example a cellobiohydrolase having a $T_{50}$ from about 4° C. to about 30° C. higher, or any amount therebetween, or a $T_{50}$ from about 9° C. to about 30° C. higher, or any amount therebetween, when compared to that of the parent cellobiohydrolase. The $T_{50}$ is the temperature at which the modified or the natural enzyme retains 50% of its residual activity after a pre-incubation for 15 minutes and is determined by the assay detailed in Examples below or as known in the art.

The modified cellobiohydrolases or cellulases of the disclosure may have $T_{50}$ which is about 4° C. to about 30° C. higher than that of a corresponding parent cellobiohydrolase (e.g., SEQ ID NO:2, 4 or 6), or any range therebetween, about 5° C. to about 20° C. higher, or any range therebetween, about 8° C. to about 15° C. higher, or any range therebetween, or from about 9° C. to about 15° C. higher, or any range therebetween. For example, the modified cellulase may have a $T_{50}$ that is at least about 4, 5, 6, 7, 8, 9, 10, 12, 14, 16, 18, 20, 22, 24, 26, 28, or 30° C. higher than that of the corresponding parent cellobiohydrolase.

The variants identified herein can also be used to generate chimeric cellobiohydrolases. For example, SCHEMA has been used previously to create families of hundreds of active β-lactamase and cytochrome P450 enzyme chimeras. SCHEMA uses protein structure data to define boundaries of contiguous amino acid "blocks" which minimize <E>, the library average number of amino acid sidechain contacts that are broken when the blocks are swapped among different parents. It has been shown that the probability that a β-lactamase chimera was folded and active was inversely related to the value of E for that sequence. The RASPP (Recombination as Shortest Path Problem) algorithm was used to identify the block boundaries that minimized <E> relative to the library average number of mutations, <m>. More than 20% of the ~500 unique chimeras characterized from a β-lactamase collection comprised of 8 blocks from 3 parents ($3^8$=6,561 possible sequences) were catalytically active. A similar approach produced a 3-parent, 8-block cytochrome P450 chimera family containing more than 2,300 novel, catalytically active enzymes. Chimeras from these two collections were characterized by high numbers of mutations, 66 and 72 amino acids on average from the closest parent, respectively. SCHEMA/RASPP thus enabled design of chimera families having significant sequence diversity and an appreciable fraction of functional members.

It has also been shown that the thermostabilities of SCHEMA chimeras can be predicted based on sequence-stability data from a small sample of the sequences. Linear regression modeling of thermal inactivation data for 184 cytochrome P450 chimeras showed that SCHEMA blocks made additive contributions to thermostability. More than 300 chimeras were predicted to be thermostable by this model, and all 44 that were tested were more stable than the most stable parent. It was estimated that as few as 35 thermostability measurements could be used to predict the most thermostable chimeras. Furthermore, the thermostable P450 chimeras displayed unique activity and specificity profiles, demonstrating that chimeragenesis can lead to additional useful enzyme properties. Here SCHEMA recombination of CBH II enzymes can generate chimeric cellulases that are active on phosphoric acid swollen cellulose (PASC) at high temperatures, over extended periods of time, and broad ranges of pH.

Using the methods described herein a number of chimeric polypeptides having cellobiohydrolases activity were generated having improved characteristics compared to the wild-type parental CBH II proteins.

A diverse family of novel CBH II enzymes was constructed by swapping blocks of sequence from three fungal CBH II enzymes. Twenty-three of 48 chimeric sequences sampled from this set were secreted in active form by *S. cerevisiae*, and five have half-lives at 63° C. that were greater than the most stable parent. Given that this 48-member sample set represents less than 1% of the total possible 6,561 sequences, we predict that this one collection of chimeras already contains hundreds of active, thermostable CBH II enzymes, a number that dwarfs the approximately twenty fungal CBH II enzymes in the CAZy database.

The approach of using the sample set sequence-stability data to identify blocks that contribute positively to chimera thermostability was validated by finding that all 10 catalytically active chimeras in the second CBH II validation set were more thermostable than the most stable parent, a naturally-thermostable CBH II from the thermophilic fungus, *H. insolens*. This disclosure has thus far generated a total of 33 new CBH II enzymes that are expressed in catalytically active form in *S. cerevisiae,* 15 of which are more thermostable than the most stable parent from which they were constructed. These 15 thermostable enzymes are diverse in sequence, differing from each other and their closest natural homologs at as many as 94 and 58 amino acid positions, respectively.

Analysis of the thermostabilities of CBH II chimeras in the combined sample and validation sets indicates that the four thermostabilizing blocks identified, B1P1, B6P3, B7P3 and B8P2, make cumulative contributions to thermal stability when present in the same chimera. Four of the five sample set chimeras that are more thermostable than the *H. insolens* CBH II contain either two or three of these stabilizing blocks (Table 1). The ten active members of the validation set, all of which are more stable than the *H. insolens* enzyme, contain at least two stabilizing blocks, with five of the six most thermostable chimeras in this group containing either three or four stabilizing blocks.

The disclosure demonstrates that stabilizing blocks can be recombined to create novel highly stable, active cellulases. The stability regression model predicts that the CBH II SCHEMA library contains 2,026 chimeras that are more stable than the most stable parent enzyme. These chimeras are diverse and distinct from the native cellulases: they differ from the parents by between 8 and 72 mutations (an average of 50) and from each other by an average of 63 mutations. A total of 33 genes from this set were synthesized and expressed in *S. cerevisiae*: every one of these chimeric CBH IIs was found to be more stable than the most stable parent cellulase, from the thermophilic fungus *H. insolens*, as measured either by its half-life of inactivation at 63° C. or $T_{50}$. Reducing the sequence complexity by making chimeras of only eight blocks allowed the generation of a sequence-stability model and identification of a single highly stabilizing sequence block. By testing only ten amino acid substitutions in this block a single, highly stabilizing substitution was identified. The very large stabilizing effect of the C313S (with reference to SEQ ID NO:6; C314S, SEQ ID NO:2 and C311S, SEQ ID NO:4) substitution observed across the chimeras and in the native *P. chrysosporium*, *H. insolens* and *H. jecorina* CBH II enzymes suggests that mutation of any residue at this position to Ser may stabilize any family 6 cellulase into which it is introduced.

Minimizing the number of broken contacts upon recombination (FIG. 2C) allows the blocks to be approximated as decoupled units that make independent contributions to the stability of the entire protein, thus leading to cumulative or even additive contributions to chimera thermostability. For this CBH II enzyme recombination, SCHEMA was effective in minimizing such broken contacts: whereas there are 303 total interblock contacts defined in the *H. insolens* parent CBH II crystal structure, the CBH II SCHEMA library design results in only 33 potential broken contacts. Given that the CBH II enzyme parents do not feature obvious structural subdomains, and only four of the eight blocks (1, 5, 7 and 8) resemble compact structural units, or modules, the low number of broken contacts demonstrates that the SCHEMA/RASPP algorithm is effective for cases in which the number of blocks appears greater than the number of structural subdivisions. As previously observed for β-lactamase and cytochrome P450 chimeras, low E values were predictive of chimera folding and activity. Although not used here, this relationship should be valuable for designing chimera sample sets that contain a high fraction of active members.

Figure 4:
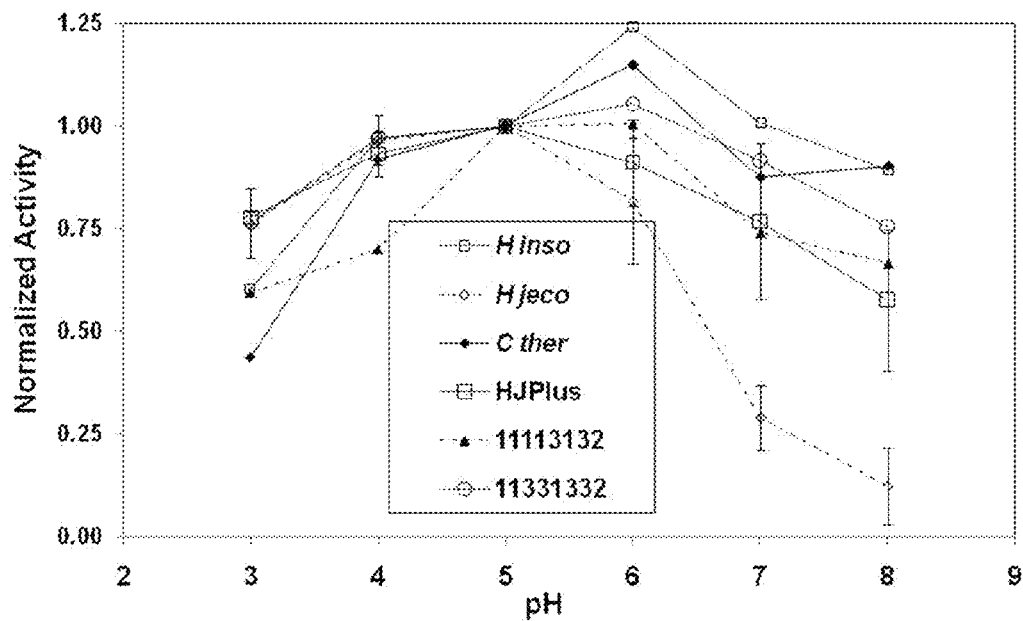
FIG. 4 shows specific activity, normalized to pH 5.0, as a function of pH for parent CBH II enzymes and three thermostable chimeras. Data presented are averages for two replicates, where error bars for HJPlus and *H. jeco* denote values for two independent trials. 16-hr reaction, 300 ug enzyme/g PASC, 50° C., 12.5 mM sodium citrate/12.5 mM sodium phosphate buffer at pH as shown.

The disclosure also used chimera to determine if the pH stability could be improved in CBH II enzymes. Whereas the specific activity of *H. jecorina* CBH II declines sharply as pH increases above the optimum value of 5, HJPlus, created by substituting stabilizing blocks onto the most industrially relevant *H. jecorina* CBH II enzyme, retains significantly more activity at these higher pHs (FIG. 4). The thermostable 11113132 and 13311332 chimeras, and also the *H. insolens* and *C. thermophilum* CBH II cellulase parents, have even broader pH/activity profiles than HJPlus. The narrow pH/activity profile of *H. jecorina* CBH II has been attributed to the deprotonation of several carboxyl-carboxylate pairs, which destabilizes the protein above pH ~6. The substitution of parent 3 in block 7 in HJPlus changes aspartate 277 to histidine, eliminating the carboxyl-carboxylate pair between D277 and D316 (of block 8). Replacing D277 with the positively charged histidine may prevent destabilizing charge repulsion at nonacidic pH, allowing HJPlus to retain activity at higher pH than *H. jecorina* CBH II. The even broader pH/activity profiles of the remaining two thermostable chimeras and the *H. insolens* and *C. thermophilum* parent CBH II enzymes may be due to the absence of acidic residues at positions corresponding to the E57-E119 carboxyl-carboxylate pair of HJPlus and *H. jecorina* CBH II.

Figure 5:
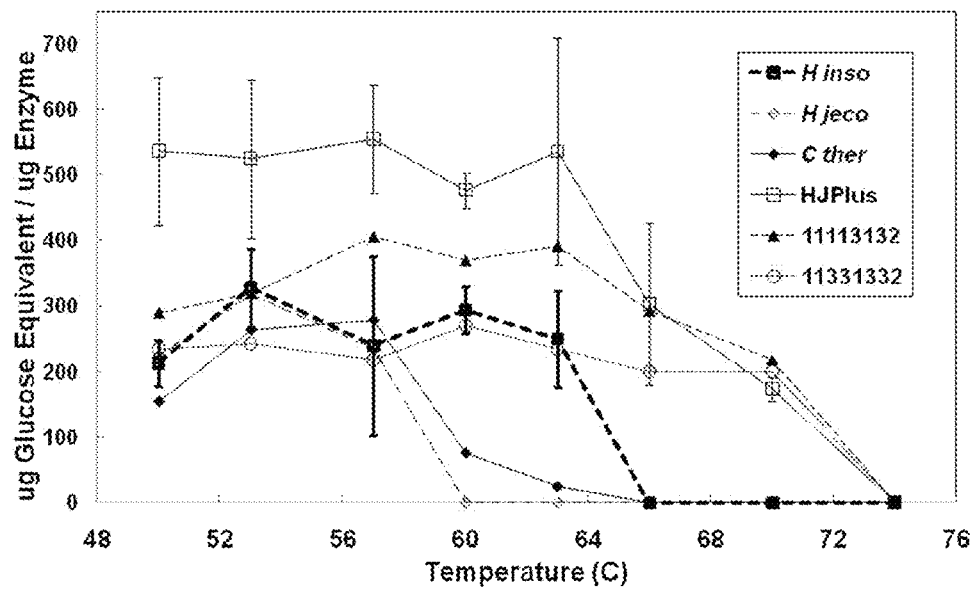
FIG. 5 shows long-time cellulose hydrolysis assay results (ug glucose reducing sugar equivalent/ug CBH II enzyme) for parents and thermostable chimeras across a range of temperatures. Error bars indicate standard errors for three replicates of HJPlus and *H. insolens* CBH II enzymes. 40-hr reaction, 100 ug enzyme/g PASC, 50 mM sodium acetate, pH 4.8.

HJPlus exhibits both relatively high specific activity and high thermostability. FIG. 5 shows that these properties lead to good performance in long-time hydrolysis experiments: HJPlus hydrolyzed cellulose at temperatures 7-15° C. higher than the parent CBH II enzymes and also had a significantly increased long-time activity relative to all the parents at their temperature optima, bettering *H. jecorina* CBH II by a factor of 1.7. Given that the specific activity of the HJPlus chimera is less than that of the *H. jecorina* CBH II parent, this increased long-time activity can be attributed to the ability of the thermostable HJPlus to retain activity at optimal hydrolysis temperatures over longer reaction timer.

The other two thermostable chimeras shared HJPlus's broad temperature range. This observation supports a positive correlation between $t_{1/2}$ at elevated temperature and maximum operating temperature, and suggests that many of the thermostable chimeras among the 6,561 CBH II chimera sequences will also be capable of degrading cellulose at elevated temperatures. While this ability to hydrolyze the amorphous PASC substrate at elevated temperatures bodes well for the potential utility of thermostable fungal CBH II chimeras, studies with more challenging crystalline substrates and substrates containing lignin will provide a more complete assessment of this novel CBH II enzyme family's relevance to biomass degradation applications.

The majority of biomass conversion processes use mixtures of fungal cellulases (primarily CBH II, cellobiohydrolase class I (CBH I), endoglucanases and β-glucosidase) to achieve high levels of cellulose hydrolysis. Generating a diverse group of thermostable CBH II enzyme chimeras is the first step in building an inventory of stable, highly active cellulases from which enzyme mixtures can be formulated and optimized for specific applications and feedstocks.

"Peptide segment" refers to a portion or fragment of a larger polypeptide or protein. A peptide segment need not on its own have functional activity, although in some instances, a peptide segment may correspond to a domain of a polypeptide wherein the domain has its own biological activity. A stability-associated peptide segment is a peptide segment found in a polypeptide that promotes stability, function, or folding compared to a related polypeptide lacking the peptide segment. A destabilizing-associated peptide segment is a peptide segment that is identified as causing a loss of stability, function or folding when present in a polypeptide.

"Fused," "operably linked," and "operably associated" are used interchangeably herein to broadly refer to a chemical or physical coupling of two otherwise distinct domains or peptide segments, wherein each domain or peptide segment when operably linked can provide a functional polypeptide having a desired activity. Domains or peptide segments can be connected through peptide linkers such that they are functional or can be fused through other intermediates or chemical bonds. For example, two domains can be part of the same coding sequence, wherein the polynucleotides are in frame such that the polynucleotide when transcribed encodes a single mRNA that when translated comprises both domains as a single polypeptide. Alternatively, both domains can be separately expressed as individual polypeptides and fused to one another using chemical methods. Typically, the coding domains will be linked "in-frame" either directly of separated by a peptide linker and encoded by a single polynucleotide. Various coding sequences for peptide linkers and peptide are known in the art.

"Polynucleotide" or "nucleic acid sequence" refers to a polymeric form of nucleotides. In some instances a polynucleotide refers to a sequence that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the disclosure can be ribonucleotides, deoxyribonucleotides, or modified forms of either nucleotide. A polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The term polynucleotide encompasses genomic DNA or RNA (depending upon the organism, i.e., RNA genome of viruses), as well as mRNA encoded by the genomic DNA, and cDNA.

"Nucleic acid segment," "oligonucleotide segment" or "polynucleotide segment" refers to a portion of a larger polynucleotide molecule. The polynucleotide segment need not correspond to an encoded functional domain of a protein; however, in some instances the segment will encode a functional domain of a protein. A polynucleotide segment can be about 6 nucleotides or more in length (e.g., 6-20, 20-50, 50-100, 100-200, 200-300, 300-400 or more nucleotides in length). A stability-associated peptide segment can be encoded by a stability-associated polynucleotide segment, wherein the peptide segment promotes stability, function, or folding compared to a polypeptide lacking the peptide segment.

"Chimera" refers to a combination of at least two segments of at least two different parent proteins. As appreciated by one of skill in the art, the segments need not actually come from each of the parents, as it is the particular sequence that is relevant, and not the physical nucleic acids themselves. For example, a chimeric fungal class II cellobiohydrolases (CBH II cellulases) will have at least two segments from two different parent CBH II polypeptides. The two segments are connected so as to result in a new polypeptide having cellulase activity. In other words, a protein will not be a chimera if it has the identical sequence of either one of the full length parents. A chimeric polypeptide can comprise more than two segments from two different parent proteins. For example, there may be 2, 3, 4, 5-10, 10-20, or more parents for each final chimera or library of chimeras. The segment of each parent polypeptide can be very short or very long, the segments can range in length of contiguous amino acids from 1 to 90%, 95%, 98%, or 99% of the entire length of the protein. In one embodiment, the minimum length is 10 amino acids. In one embodiment, a single crossover point is defined for two parents. The crossover location defines where one parent's amino acid segment will stop and where the next parent's amino acid segment will start. Thus, a simple chimera would only have one crossover location where the segment before that crossover location would belong to one parent and the segment after that crossover location would belong to the second parent. In one embodiment, the chimera has more than one crossover location. For example, 2, 3, 4, 5, 6, 7, 8, 9, 10, 11-30, or more crossover locations. How these crossover locations are named and defined are both discussed below. In an embodiment where there are two crossover locations and two parents, there will be a first contiguous segment from a first parent, followed by a second contiguous segment from a second parent, followed by a third contiguous segment from the first parent. Contiguous is meant to denote that there is nothing of significance interrupting the segments. These contiguous segments are connected to form a contiguous amino acid sequence. For example, a CBH II chimera from Humicola insolens (hereinafter "1") and H. jecori (hereinafter "2"), with two crossovers at 100 and 150, could have the first 100 amino acids from 1, followed by the next 50 from 2, followed by the remainder of the amino acids from 1, all connected in one contiguous amino acid chain. Alternatively, the CBH II chimera could have the first 100 amino acids from 2, the next 50 from 1 and the remainder followed by 2. As appreciated by one of skill in the art, variants of chimeras exist as well as the exact sequences. Thus, not 100% of each segment need be present in the final chimera if it is a variant chimera. The amount that may be altered, either through additional residues or removal or alteration of residues will be defined as the term variant is defined. Of course, as understood by one of skill in the art, the above discussion applies not only to amino acids but also nucleic acids which encode for the amino acids.

The disclosure describes in addition to specific variants, variants that can be used to generate CBH II chimeras. A directed SCHEMA recombination library was used to generate cellobiohydrolase enzymes based on a particularly well-studied member of this diverse enzyme family, and more particularly cellobiohydrolase II enzymes: H. insolens is parent "1" (SEQ ID NO:2), H. jecorina is parent "2" (SEQ ID NO:4) and C. thermophilum is parent "3" (SEQ ID NO:6). SCHEMA is a computational based method for predicting which fragments of homologous proteins can be recombined without affecting the structural integrity of the protein (see, e.g., Meyer et al., (2003) Protein Sci., 12:1686-1693). This computational approached identified seven recombination points in the CBH II parental proteins, thereby allowing the formation of a library of CBH II chimera polypeptides, where each polypeptide comprise eight segments. Chimeras with higher stability are identifiable by determining the additive contribution of each segment to the overall stability, either by use of linear regression of sequence-stability data, or by reliance on consensus analysis of the MSAs of folded versus unfolded proteins. SCHEMA recombination ensures that the chimeras retain biological function and exhibit high sequence diversity by conserving important functional residues while exchanging tolerant ones.

Thus, as illustrated by various embodiments herein, the disclosure provides CBH II polypeptides comprising a chimera of parental domains of which a parental strand or the resulting chimeic coding sequence may be modified to comprise a C→S substitution as described above. In some embodiments, the polypeptide comprises a chimera having a plurality of domains from N- to C-terminus from different parental CBH II proteins: (segment 1)-(segment 2)-(segment 3)-(segment 4)-(segment 5)-(segment 6)-(segment 7)-(segment 8);

wherein segment 1 comprises amino acid residue from about 1 to about $x_1$ of SEQ ID NO:2 ("1"), SEQ ID NO:4 ("2") or SEQ ID NO:6 ("3"); segment 2 is from about amino acid residue $x_1$ to about $x_2$ of SEQ ID NO:2 ("1"), SEQ ID NO:4 ("2") or SEQ ID NO:6 ("3"); segment 3 is from about amino acid residue $x_2$ to about $x_3$ of SEQ ID NO:2 ("1"), SEQ ID NO:4 ("2") or SEQ ID NO:6 ("3"); segment 4 is from about amino acid residue $x_3$ to about $x_4$ of SEQ ID NO:2 ("1"), SEQ ID NO:4 ("2") or SEQ ID NO:6 ("3"); segment 5 is from about amino acid residue $x_4$ to about $x_5$ of SEQ ID NO:2 ("1"), SEQ ID NO:4 ("2") or SEQ ID NO:6 ("3"); segment 6 is from about amino acid residue $x_5$ to about $x_6$ of SEQ ID NO:2 ("1"), SEQ ID NO:4 ("2") or SEQ ID NO:6 ("3"); segment 7 is from about amino acid residue x6 to about $x_7$ of SEQ ID NO:2 ("1"), SEQ ID NO:4 ("2") or SEQ ID NO:6 ("3"); and segment 8 is from about amino acid residue $x_7$ to about $x_8$ of SEQ ID NO:2 ("1"), SEQ ID NO:4 ("2") or SEQ ID NO:6 ("3");

wherein: $x_1$ is residue 43, 44, 45, 46, or 47 of SEQ ID NO:2, or residue 42, 43, 44, 45, or 46 of SEQ ID NO:4 or SEQ ID NO:6; $x_2$ is residue 70, 71, 72, 73, or 74 of SEQ ID NO:2, or residue 68, 69, 70, 71, 72, 73, or 74 of SEQ ID NO:4 or SEQ ID NO:6; $x_3$ is residue 113, 114, 115, 116, 117 or 118 of SEQ ID NO:2, or residue 110, 111, 112, 113, 114, 115, or 116 of SEQ ID NO:4 or SEQ ID NO:6; $x_4$ is residue 153, 154, 155, 156, or 157 of SEQ ID NO:2, or residue 149, 150, 151, 152, 153, 154, 155 or 156 of SEQ ID NO:4 or SEQ ID NO:6; $x_5$ is residue 220, 221, 222, 223, or 224 of SEQ ID NO:2, or residue 216, 217, 218, 219, 220, 221, 222 or 223 of SEQ ID NO:4 or SEQ ID NO:6; $x_6$ is residue 256, 257, 258, 259, 260 or 261 of SEQ ID NO:2, or residue 253, 254, 255, 256, 257, 258, 259 or 260 of SEQ ID NO:4 or SEQ ID NO:6; $x_7$ is residue 312, 313, 314, 315 or 316 of SEQ ID NO:2, or residue 309, 310, 311, 312, 313, 314, 315 or 318 of SEQ ID NO:4 or SEQ ID NO:6; and $x_8$ is an amino acid residue corresponding to the C-terminus of the polypeptide have the sequence of SEQ ID NO:2, SEQ ID NO:4 or SEQ ID NO:6.

Using the foregoing domain references a number of chimeric structure were generated as set forth in Table 1. 1,588 CBH II chimera sequences with $T_{50}$ values predicted to be greater than the measured $T_{50}$ value of 64.8 C for the *H. insolens* parent CBH II.

| | | | | | | | |
|---|---|---|---|---|---|---|---|
| 31313232 | 13132231 | 13212231 | 21113231 | 22112331 | 33211132 | 22223232 | 32123131 |
| 31323333 | 11221233 | 13331133 | 21133232 | 21222133 | 33211131 | 31213132 | 11221333 |
| 11212133 | 33123232 | 13232232 | 22221133 | 32333132 | 12311232 | 22223231 | 11211231 |
| 31313231 | 33123231 | 13232231 | 21133231 | 32333131 | 12321333 | 22322232 | 11231232 |
| 31333232 | 21311333 | 22121133 | 23211232 | 22132332 | 33231132 | 31213131 | 11231231 |
| 11232133 | 21331333 | 33223232 | 23221333 | 22132331 | 12311231 | 31312132 | 33123332 |
| 31333231 | 32213332 | 23111232 | 23211231 | 33313332 | 33231131 | 22322231 | 33123331 |
| 21323112 | 32213331 | 23121333 | 23231232 | 33313331 | 12331232 | 31312131 | 31321232 |
| 21323111 | 32312332 | 33223231 | 11311333 | 33333332 | 12331231 | 31233132 | 31321231 |
| 32113332 | 21211133 | 33322232 | 23231231 | 33333331 | 23122232 | 31233131 | 33122132 |
| 32113331 | 32312331 | 23111231 | 21122133 | 33213132 | 23122231 | 31332132 | 33122131 |
| 31223133 | 13321112 | 33322231 | 11331333 | 33213131 | 11113232 | 31332131 | 12123232 |
| 21111133 | 32233332 | 23131232 | 11211133 | 33312132 | 11123333 | 23321133 | 12123231 |
| 31322133 | 13321111 | 23131231 | 11231133 | 33312131 | 11113231 | 23222232 | 32121332 |
| 32133332 | 32233331 | 11323112 | 33113132 | 12313232 | 11133232 | 23222231 | 32121331 |
| 32133331 | 32332332 | 11323111 | 33113131 | 12323333 | 12221133 | 11213232 | 21323133 |
| 21131133 | 21231133 | 11111133 | 33133132 | 33233132 | 11133231 | 11223333 | 13122232 |
| 32112132 | 32332331 | 11131133 | 33133131 | 12313231 | 31111332 | 11213231 | 13122231 |
| 32112131 | 32121232 | 32221232 | 31321133 | 33233131 | 31111331 | 11312232 | 22113132 |
| 32132132 | 32121231 | 32221231 | 31222232 | 33332132 | 31131332 | 11322333 | 22113131 |
| 32132131 | 13313133 | 22313232 | 31222231 | 33332131 | 13211232 | 11312231 | 22133132 |
| 21321312 | 32212132 | 22323333 | 12123133 | 12333232 | 31131331 | 11233232 | 22133131 |
| 33112332 | 32212131 | 22313231 | 32111132 | 12333231 | 13221333 | 11233231 | 23113332 |
| 21321311 | 13333133 | 22333232 | 13113232 | 32311332 | 13211231 | 11332232 | 23113331 |
| 33112331 | 32232132 | 22333231 | 13123333 | 32311331 | 13231232 | 11332231 | 23133332 |
| 11223233 | 32232131 | 31122232 | 32111131 | 32331332 | 22212332 | 31211332 | 23133331 |
| 33132332 | 33212332 | 31122231 | 13113231 | 32331331 | 13231231 | 31211331 | 12212332 |
| 11322233 | 33212331 | 11321312 | 32131132 | 12223133 | 22212331 | 31231332 | 21311232 |
| 33132331 | 22123133 | 11321311 | 13133232 | 12322133 | 11122133 | 31231331 | 12212331 |
| 31211232 | 33232332 | 22223133 | 32131131 | 31113332 | 22232332 | 12112332 | 21321333 |
| 31221333 | 33232331 | 22322133 | 13133231 | 31113331 | 22232331 | 31323232 | 21311231 |
| 31211231 | 23113232 | 23213232 | 33111332 | 31133332 | 33321232 | 12112331 | 12232332 |
| 21313333 | 23123333 | 23223333 | 33111331 | 32211132 | 33321231 | 11222133 | 21331232 |
| 31231232 | 23113231 | 23213231 | 33131332 | 13213232 | 23323133 | 31323231 | 12232331 |
| 31231231 | 23133232 | 23312232 | 11321233 | 31133331 | 31213332 | 12132332 | 21331231 |
| 21221112 | 23133231 | 23322333 | 33131331 | 13223333 | 31213331 | 12132331 | 23112132 |
| 21333333 | 11121112 | 23312231 | 13122133 | 32211131 | 31312332 | 32123332 | 23112131 |
| 21221111 | 12311133 | 23233232 | 12111232 | 13213231 | 31312331 | 32123331 | 23132132 |
| 12112232 | 11121111 | 11313333 | 12121333 | 13312232 | 31233332 | 21121133 | 23132131 |
| 12122333 | 12212232 | 23233231 | 12111231 | 13322333 | 31233331 | 32122132 | 32223332 |
| 12112231 | 12222333 | 23332232 | 12131232 | 13312231 | 31332332 | 32122131 | 22111332 |
| 12132232 | 12212231 | 23332231 | 12131231 | 32231132 | 31332331 | 33122332 | 32223331 |
| 12132231 | 21321233 | 11221112 | 32313332 | 13233232 | 31121232 | 33122331 | 32322332 |
| 21213133 | 12331133 | 11333333 | 32313331 | 32231131 | 31121231 | 31221232 | 22111331 |
| 21312133 | 12232232 | 11221111 | 21311133 | 13233231 | 22321133 | 31221231 | 21221133 |
| 13323112 | 12232231 | 23222133 | 21212232 | 13332232 | 22222232 | 21313232 | 32322331 |
| 13323111 | 13311333 | 11213133 | 21222333 | 13332231 | 31212132 | 21323333 | 22131332 |
| 21233133 | 23122133 | 11312133 | 32333332 | 33211332 | 22222231 | 21313231 | 22131331 |
| 21332133 | 13331333 | 11233133 | 21212231 | 33211331 | 31212131 | 21333232 | 13323133 |
| 32123232 | 11113133 | 11332133 | 32333331 | 33231332 | 31232132 | 21333231 | 32222132 |
| 32123231 | 11133133 | 22211232 | 21331133 | 33231331 | 31232131 | 12122232 | 32222131 |
| 13111133 | 32223232 | 22221333 | 21232232 | 22122232 | 23311232 | 12122231 | 33311132 |
| 13131133 | 22111232 | 22211231 | 21232231 | 31112132 | 23321333 | 22113332 | 33311131 |
| 12321112 | 22121333 | 22231232 | 32213132 | 22122231 | 23311231 | 22113331 | 33222332 |
| 12321111 | 32223231 | 22231231 | 32213131 | 31112131 | 23331232 | 21223133 | 33222331 |

-continued

| | | | | | | | |
|---|---|---|---|---|---|---|---|
| 33122232 | 32322232 | 31323133 | 32312132 | 31132132 | 23331231 | 21322133 | 33331132 |
| 33122231 | 22111231 | 21112232 | 32312131 | 33323232 | 21123133 | 22133332 | 33331131 |
| 21211333 | 32322231 | 21122333 | 32233132 | 31132131 | 23221133 | 22133331 | 23123232 |
| 13321312 | 22131232 | 21112231 | 32233131 | 13222133 | 11311133 | 13121133 | 23123231 |
| 13321311 | 22131231 | 21132232 | 32332132 | 33323231 | 11212232 | 22112132 | 12321133 |
| 21231333 | 13211133 | 21132231 | 32332131 | 12211232 | 11222333 | 22112131 | 12222232 |
| 11123112 | 13231133 | 32113132 | 33213332 | 12221333 | 11212231 | 22132132 | 12222231 |
| 12313133 | 11323312 | 32113131 | 33213331 | 12211231 | 11331133 | 22132131 | 13311232 |
| 11123111 | 11323311 | 11211333 | 33312232 | 12231232 | 11232232 | 33313132 | 13321133 |
| 21323233 | 33321133 | 12133132 | 33312231 | 12231231 | 11232231 | 33313131 | 13311231 |
| 12333133 | 33222232 | 32133131 | 33233332 | 23121133 | 31223232 | 23112332 | 22213332 |
| 13313333 | 33222231 | 11231333 | 33233331 | 11112232 | 21111232 | 23112331 | 13331232 |
| 32212332 | 11111333 | 33113332 | 33332332 | 11122333 | 21121333 | 33333132 | 22213331 |
| 32212331 | 11131333 | 33113331 | 33332331 | 11112231 | 31223231 | 33333131 | 22312332 |
| 13221112 | 11223112 | 33133332 | 33121232 | 11132232 | 31322232 | 23132332 | 13331231 |
| 13333333 | 11223111 | 11323233 | 33121231 | 32321232 | 21111231 | 23132331 | 22312331 |
| 13221111 | 11322112 | 33133331 | 33212132 | 11132231 | 31322231 | 21211232 | 11123133 |
| 32232332 | 11322111 | 31311232 | 33212131 | 32321231 | 21131232 | 21221333 | 22233332 |
| 32232331 | 13321233 | 31321333 | 12213232 | 31123232 | 21131231 | 21211231 | 22233331 |
| 22113232 | 22213232 | 31311231 | 12223333 | 31123231 | 32122332 | 21231232 | 22332332 |
| 22123333 | 22223333 | 31331232 | 12213231 | 22323133 | 32122331 | 21231231 | 22332331 |
| 22113231 | 22213231 | 31331231 | 12312232 | 33221232 | 13123133 | 12323133 | 22121232 |
| 22133232 | 22312232 | 21321112 | 12322333 | 33221231 | 33111132 | 32311132 | 31111132 |
| 22133231 | 22322333 | 33112132 | 33232132 | 23313232 | 33111131 | 13313232 | 22121231 |
| 13213133 | 22312231 | 21321111 | 12312231 | 23323333 | 33131132 | 13323333 | 31111131 |
| 13312133 | 22233232 | 33112131 | 33232131 | 23313231 | 33131131 | 32311131 | 31131132 |
| 13233133 | 22233231 | 12113232 | 12233232 | 23333232 | 21213232 | 13313231 | 31131131 |
| 13332133 | 22332232 | 12123333 | 12233231 | 23333231 | 21223333 | 32222332 | 13221133 |
| 11121312 | 22332231 | 12113231 | 12332232 | 11321112 | 21213231 | 32222331 | 22212132 |
| 12311333 | 31121133 | 33132132 | 12332231 | 11321111 | 21312232 | 32331132 | 22212131 |
| 11121311 | 11221312 | 33132131 | 32211332 | 23223133 | 21322333 | 13333232 | 22232132 |
| 22122133 | 11221311 | 12133232 | 32211331 | 23322133 | 21312231 | 32331131 | 22232131 |
| 12331333 | 22222133 | 12133231 | 23123133 | 11313133 | 21233232 | 13333231 | 23212332 |
| 33323133 | 23311133 | 32111332 | 32231332 | 11333133 | 21233231 | 33311332 | 23232331 |
| 23112232 | 23212232 | 32111331 | 32231331 | 22311232 | 21332232 | 33311331 | 23232332 |
| 23122333 | 23222333 | 31221133 | 32323232 | 22321333 | 21332231 | 33331332 | 23232331 |
| 23112231 | 23212231 | 32131332 | 12222133 | 22311231 | 12121133 | 22123232 | 11111232 |
| 11113333 | 23331133 | 21313133 | 32323231 | 31212332 | 13111232 | 33331331 | 11121333 |
| 23132232 | 11213333 | 32131331 | 31112332 | 31212331 | 13121333 | 31113132 | 11111231 |
| 23132231 | 23232232 | 21333133 | 31112331 | 22331232 | 13111231 | 22123231 | 11131232 |
| 11133333 | 11312333 | 12122133 | 13311133 | 22331231 | 32313132 | 31113131 | 11131231 |
| 12211133 | 23232231 | 13112232 | 31132332 | 31232332 | 32313131 | 31133132 | 31313332 |
| 21221233 | 11233333 | 13122333 | 13212232 | 31232331 | 13131232 | 31133131 | 31313331 |
| 12231133 | 11332333 | 13112231 | 31132331 | 21113232 | 22112332 | 13223133 | 31333332 |
| 13211333 | 11121233 | 13132232 | 13222333 | 21123333 | 13131231 | 13322133 | 31333331 |
| 22131131 | 22331331 | 13111331 | 33323132 | 33321132 | 22121132 | 11311132 | 11321132 |
| 33223332 | 21113332 | 13131332 | 33323131 | 33321131 | 11311131 | 11311131 | 11321131 |
| 23111332 | 21113331 | 13131331 | 23122332 | 11111332 | 23121332 | 11222332 | 11323132 |
| 33223331 | 21133332 | 21212132 | 23122331 | 11111331 | 23121331 | 11222331 | 11323131 |
| 33322332 | 22211132 | 21212131 | 11113332 | 11131332 | 11111132 | 11331132 | 11321332 |
| 23111331 | 21133331 | 21232132 | 11113331 | 11131331 | 11111131 | 11331131 | 11321331 |
| 33322331 | 22211131 | 21232131 | 11133332 | 13321232 | 11131132 | 21121332 | 11221132 |
| 23131332 | 22231132 | 12313332 | 12211132 | 13321231 | 11131131 | 21121331 | 11221131 |
| 23131331 | 22231131 | 12313331 | 11133331 | 22223332 | 22323332 | 13123132 | 21321132 |
| 33222132 | 23211132 | 12333332 | 12211131 | 22223331 | 22323331 | 13123131 | 21321131 |
| 33222131 | 23211331 | 12333331 | 21221232 | 22322332 | 22223132 | 21223332 | 13321132 |
| 12223232 | 23231332 | 33121132 | 21221231 | 22322331 | 22223131 | 21223331 | 13321131 |
| 12223231 | 23231331 | 33121131 | 12231132 | 31121132 | 22322132 | 21322332 | 11121132 |
| 12322232 | 21112132 | 12213132 | 12231131 | 31121131 | 22322331 | 21322331 | 11121131 |
| 12322231 | 21112131 | 12213131 | 13211332 | 22222132 | 22323332 | 12121132 | 11323332 |
| 32221332 | 21132132 | 12312132 | 13211331 | 22222131 | 23323331 | 12121131 | 11323331 |
| 32221331 | 23323232 | 12312131 | 13231332 | 23311132 | 23322332 | 13121332 | 11223132 |
| 22313332 | 21132131 | 21223232 | 13231331 | 23311131 | 23322331 | 13121331 | 11223131 |
| 22313331 | 23323231 | 21223231 | 11112132 | 23222332 | 11313332 | 21222132 | 11322132 |
| 22333332 | 11323133 | 21322232 | 11112131 | 23222331 | 11313331 | 21222131 | 11322131 |
| 22333331 | 22321232 | 12233132 | 11132132 | 23331132 | 11333332 | 12323332 | 11221332 |
| 31122332 | 31311132 | 21322231 | 32321132 | 11213332 | 11333331 | 12323331 | 11221331 |
| 31122331 | 22321231 | 12233131 | 33323232 | 23331131 | 23222131 | 12223131 | 21323132 |
| 13321133 | 31311131 | 12332132 | 11132131 | 11213331 | 23222131 | 12223131 | 21323131 |
| 13222232 | 31222332 | 12332131 | 32321131 | 11312332 | 11213132 | 12322132 | 21321332 |
| 13222231 | 31222331 | 13213332 | 13323231 | 11312331 | 11213131 | 12322131 | 21321331 |
| 22213132 | 31331132 | 13213331 | 33321332 | 11233332 | 11312132 | 13223332 | 21221132 |
| 22213131 | 31331131 | 13312332 | 33321331 | 11233331 | 11312131 | 13223331 | 21221131 |
| 22312132 | 12113132 | 13312331 | 31123132 | 11332332 | 11233132 | 13322332 | 13323132 |
| 22312131 | 12113131 | 13233332 | 31123131 | 11332331 | 11233131 | 13322331 | 13323131 |
| 22233132 | 21123232 | 13233331 | 33221132 | 11121232 | 11332132 | 13222132 | 12321132 |
| 22233131 | 21123231 | 13332332 | 33221131 | 11121231 | 11332131 | 13222131 | 12321131 |
| 22332132 | 12133132 | 13332331 | 23313132 | 31323332 | 22221332 | 12221332 | 13321332 |
| 22332131 | 12133131 | 13121232 | 12321232 | 11212132 | 22221331 | 12221331 | 13321331 |

```
23213332  13113332  13121231  23313131  31323331  31323132  23121132  11123132
23213331  13113331  32323132  12321231  11212131  31323131  23121131  11123131
23312332  13133332  32323131  23333132  11232132  21122332  11122332  13221132
23312331  13133331  22122332  23333131  11232131  21122331  11122331  13221131
23233332  23221232  22122331  11123232  31223132  11211332  22323132  11121332
23233331  23221231  33323332  11123231  21111132  11211331  22323131  11121331
23332332  11311232  13212132  31121332  31223131  11231332  23323332  23321132
23332331  11321333  33323331  31121331  31322132  11231331  23323331  23321131
23121232  11311231  13212131  13221232  21111131  11323232  23223132  11223332
23121231  11331232  13232132  13221231  31322131  11323231  23223131  11223331
23212132  11331231  13232131  22311132  21131132  31321332  23322132  11322332
23212131  13112132  12211332  22311131  21131131  31321331  23322131  11322331
23232132  13112131  12211331  22222332  11223232  12123332  11313132  11222132
23232131  13132132  12231332  22222331  11223231  12123331  11313131  11222131
22211332  13132131  12231331  22331132  11322232  31221132  11333132  21121132
22211331  12111332  33223132  22331131  11322231  31221131  11333131  21121131
11121133  12111331  23111132  23311132  31221332  21313132  22321332  21323132
22231332  11221133  33223131  23311131  31221131  21313131  22321331  21323331
22231331  12131332  33322132  23331332  21313332  21333132  21123332  21223132
22323232  12131331  23111131  23331331  21313331  21333131  21123331  21223131
31313132  33123132  33322131  21113132  21333332  12122132  22221132  21322132
22323231  33123131  12323232  21113131  21333331  12122131  22221131  21322131
31313131  21212332  12323231  21133132  12122332  13122332  23221332  13121132
21112332  21212331  23131132  21133131  12122331  13122331  23221331  13121131
21112331  21232332  23131131  23211132  21213132  11221232  11311332  21221332
31333132  21232331  11112332  23211131  21213131  11221231  11311331  21221331
31333131  32121132  11112331  23231132  21312132  21311332  21122132  12323132
21132332  13123232  11132332  23231131  21312131  21311331  21122131  12323131
21132331  32121131  32321332  11212332  21233132  21331332  11331332  13323332
23223232  13123231  11132331  11212331  21233131  21331331  11331331  13323331
23223231  33121332  32321331  11232332  21332132  21211132  11211132  13223132
23322232  33121331  31123332  11232331  21332131  21211131  11211131  13223131
23322231  12213332  31123331  31223332  13111132  21231132  11231132  13322132
11313232  12213331  32221132  21111332  13111131  21231131  11231131  13322131
11323333  12312332  13223232  31223331  13131132  13313132  31321132  12321332
11313231  12312331  32221131  31322332  13131131  13313131  31321131  12321331
11333232  12233332  13223231  21111331  21211332  13333132  12123132  11123332
11333231  12233331  13322232  31223331  21211331  13333131  12123131  11123331
31311332  12332332  13322231  21131332  21231332  22123132  13123332  12221132
31311331  12332331  22313132  21131331  21231331  22123131  13123331  12221131
31331332  23113132  22313131  31222132  12313132  23123332  11321232  13221332
31331331  12121232  22333132  31222131  12313131  23123331  11321231  13221331
12113332  23113131  33221332  23321232  21323232  12311132  13122132  11122132
12113331  12121231  22333131  23321231  21323231  12311131  13122131  11122131
11223133  23133132  33221331  13113132  12333132  12222332  12121332  23323132
11322133  23133131  23313332  13113131  12333131  21321232  12121331  23323131
12133332  32323332  23313331  13133132  13313132  12222231  21311132  22321132
12133331  12212132  31122132  13133131  13313331  21321231  21311131  22321131
22221232  32323331  23333332  11321133  13333332  12331132  21222332  23321332
31211132  12212131  31122131  11222232  13333331  12331131  21222331  23321331
22221231  21321133  23333331  11222231  22123332  13311332  21331132  21123132
31211131  21222232  23213132  21213332  22123331  13311331  21331131  21123131
31231132  21222231  12221232  21213331  13213132  23122132  12223332  23221132
31231131  12232132  23213131  21312332  13213131  23122131  12223331  23221131
12112132  12232131  23312132  21312131  13312132  13331332  12322332
12112131  13212332  23312131  21233332  13312131  13331331  12322331
21122232  13212331  23312131  21233331  13233132  11113132  23123132
21122231  13232332  23233132  21332332  13233131  11113131  23123131
12132132  13232331  23233132  12111132  13332132  11133132  12222132
12132131  32223132  23332132  21332331  13332131  11133131  12222131
13112332  22111132  23332131  12111131  12311332  22121332  13311132
13112331  32223131  22311332  21121232  12311331  22121331  13311131
13132332  32322132  22311331  21121231  22122132  13211132  13222332
13132331  22111131  11122232  12131132  22122131  13211131  13222331
32123132  32322131  22331332  12131131  12331332  13231132  13331132
11211232  22131132  11122231  13111332  12331331  13231131  13331131
```

Referring to the table above, each digit refers to a domain of a chimeric CBH II polypeptide. The number denotes the parental strand the domain was derived from. For example, a chimeric CBH II chimeric polypeptide having the sequence 12111131, indicates that the polypeptide comprises a sequence from the N-terminus to the C-terminus of: amino acids from about 1 to $x_1$ of SEQ ID NO:2 ("1") linked to amino acids from about $x_1$ to $x_2$ of SEQ ID NO:4 ("2") linked to amino acids from about $x_2$ to about $x_3$ of SEQ ID NO:2 linked to amino acids from about $x_3$ to about $x_4$ of SEQ ID NO:2 linked to amino acids from about $x_4$ to about $x_5$ of SEQ ID NO:2 linked to amino acids from about $x_5$ to about $x_6$ of SEQ ID NO:2 linked to amino acids from about $x_6$ to $x_7$ of SEQ ID NO:6 ("3") linked to amino acids from about $x_7$ to $x_8$ (e.g., the C-terminus) of SEQ ID NO:2.

In some embodiments, the CBH II polypeptide has a chimeric segment structure selected from the group consisting of:

11113132, 21333331, 21311131, 22232132, 33133132, 33213332, 13333232, 12133333, 13231111, 11313121, 11332333, 12213111, 23311333, 13111313, 31311112, 23231222, 33123313, 22212231, 21223122, 21131311, 23233133, 31212111 and 32333113.

In some embodiments, the polypeptide has improved thermostability compared to a wild-type polypeptide of SEQ ID NO:2, 4, or 6. The activity of the polypeptide can be measured with any one or combination of substrates as described in the examples. As will be apparent to the skilled artisan, other compounds within the class of compounds exemplified by those discussed in the examples can be tested and used.

In some embodiments, the polypeptide can have various changes to the amino acid sequence with respect to a reference sequence. The changes can be a substitution, deletion, or insertion of one or more amino acids. Where the change is a substitution, the change can be a conservative, a non-conservative substitution, or a combination of conservative and non-conservative substitutions. For example, the chimera can comprises a C→S substitution at C314 of SEQ ID NO:2 or C311 of SEQ ID NO:4.

Thus, in some embodiments, the polypeptides can comprise a general structure from N-terminus to C-terminus: (segment 1)-(segment 2)-(segment 3)-(segment 4)-(segment 5)-(segment 6)-(segment 7)-(segment 8), wherein segment 1 comprises amino acid residue from about 1 to about $x_1$ of SEQ ID NO:2 ("1"), SEQ ID NO:4 ("2") or SEQ ID NO:6 ("3") and having 1-10 conservative amino acid substitutions; segment 2 is from about amino acid residue $x_1$ to about $x_2$ of SEQ ID NO:2 ("1"), SEQ ID NO:4 ("2") or SEQ ID NO:6 ("3") and having about 1-10 conservative amino acid substitutions; segment 3 is from about amino acid residue $x_2$ to about $x_3$ of SEQ ID NO:2 ("1"), SEQ ID NO:4 ("2") or SEQ ID NO:6 ("3") and having about 1-10 conservative amino acid substitutions; segment 4 is from about amino acid residue $x_3$ to about $x_4$ of SEQ ID NO:2 ("1"), SEQ ID NO:4 ("2") or SEQ ID NO:6 ("3") and having about 1-10 conservative amino acid substitutions; segment 5 is from about amino acid residue $x_4$ to about $x_5$ of SEQ ID NO:2 ("1"), SEQ ID NO:4 ("2") or SEQ ID NO:6 ("3") and having about 1-10 conservative amino acid substitutions; segment 6 is from about amino acid residue $x_5$ to about $x_6$ of SEQ ID NO:2 ("1"), SEQ ID NO:4 ("2") or SEQ ID NO:6 ("3") and having about 1-10 conservative amino acid substitutions; segment 7 is from about amino acid residue $x_6$ to about $x_7$ of SEQ ID NO:2 ("1"), SEQ ID NO:4 ("2") or SEQ ID NO:6 ("3") and having about 1-10 conservative amino acid substitutions; and segment 8 is from about amino acid residue $x_7$ to about $x_8$ of SEQ ID NO:2 ("1"), SEQ ID NO:4 ("2") or SEQ ID NO:6 ("3") and having about 1-10 conservative amino acid substitutions;

wherein $x_1$ is residue 43, 44, 45, 46, or 47 of SEQ ID NO:2, or residue 42, 43, 44, 45, or 46 of SEQ ID NO:4 or SEQ ID NO:6; $x_2$ is residue 70, 71, 72, 73, or 74 of SEQ ID NO:2, or residue 68, 69, 70, 71, 72, 73, or 74 of SEQ ID NO:4 or SEQ ID NO:6; $x_3$ is residue 113, 114, 115, 116, 117 or 118 of SEQ ID NO:2, or residue 110, 111, 112, 113, 114, 115, or 116 of SEQ ID NO:4 or SEQ ID NO:6; $x_4$ is residue 153, 154, 155, 156, or 157 of SEQ ID NO:2, or residue 149, 150, 151, 152, 153, 154, 155 or 156 of SEQ ID NO:4 or SEQ ID NO:6; $x_5$ is residue 220, 221, 222, 223, or 224 of SEQ ID NO:2, or residue 216, 217, 218, 219, 220, 221, 222 or 223 of SEQ ID NO:4 or SEQ ID NO:6; $x_6$ is residue 256, 257, 258, 259, 260 or 261 of SEQ ID NO:2, or residue 253, 254, 255, 256, 257, 258, 259 or 260 of SEQ ID NO:4 or SEQ ID NO:6; $x_7$ is residue 312, 313, 314, 315 or 316 of SEQ ID NO:2, or residue 309, 310, 311, 312, 313, 314, 315 or 318 of SEQ ID NO:4 or SEQ ID NO:6; and $x_8$ is an amino acid residue corresponding to the C-terminus of the polypeptide have the sequence of SEQ ID NO:2, SEQ ID NO:4 or SEQ ID NO:6 and wherein the chimera has an algorithm as set forth in Table 1 and wherein the chimera comprises a C→S substitution corresponding to C314 of SEQ ID NO:2 or C311 of SEQ ID NO:4.

In some embodiments, the number of substitutions can be 2, 3, 4, 5, 6, 8, 9, or 10, or more amino acid substitutions (e.g., 10-20, 21-30, 31-40 and the like amino acid substitutions).

In some embodiments, the functional CBH II polypeptides can have cellulase activity along with increased thermostability, such as for a defined substrate discussed in the Examples, and also have a level of amino acid sequence identity to a reference cellobiohydrolase, or segments thereof. The reference enzyme or segment, can be that of a wild-type (e.g., naturally occurring) or an engineered enzyme. Thus, in some embodiments, the polypeptides of the disclosure can comprise a general structure from N-terminus to C-terminus:

wherein segment 1 comprises a sequence that is at least 50-100% identity to amino acid residue from about 1 to about $x_1$ of SEQ ID NO:2 ("1"), SEQ ID NO:4 ("2") or SEQ ID NO:6 ("3"); segment 2 comprises a sequence that is at least 50-100% identity to amino acid residue $x_1$ to about $x_2$ of SEQ ID NO:2 ("1"), SEQ ID NO:4 ("2") or SEQ ID NO:6 ("3"); segment 3 comprises a sequence that is at least 50-100% identity to amino acid residue $x_2$ to about $x_3$ of SEQ ID NO:2 ("1"), SEQ ID NO:4 ("2") or SEQ ID NO:6 ("3"); segment 4 comprises a sequence that is at least 50-100% identity to amino acid residue $x_3$ to about $x_4$ of SEQ ID NO:2 ("1"), SEQ ID NO:4 ("2") or SEQ ID NO:6 ("3"); segment 5 comprises a sequence that is at least 50-100% identity to about amino acid residue $x_4$ to about $x_5$ of SEQ ID NO:2 ("1"), SEQ ID NO:4 ("2") or SEQ ID NO:6 ("3"); segment 6 comprises a sequence that is at least 50-100% identity to amino acid residue $x_5$ to about $x_6$ of SEQ ID NO:2 ("1"), SEQ ID NO:4 ("2") or SEQ ID NO:6 ("3"); segment 7 comprises a sequence that is at least 50-100% identity to amino acid residue $x_6$ to about $x_7$ of SEQ ID NO:2 ("1"), SEQ ID NO:4 ("2") or SEQ ID NO:6 ("3"); and segment 8 comprises a sequence that is at least 50-100% identity to amino acid residue $x_7$ to about $x_8$ of SEQ ID NO:2 ("1"), SEQ ID NO:4 ("2") or SEQ ID NO:6 ("3");

wherein $x_1$ is residue 43, 44, 45, 46, or 47 of SEQ ID NO:2, or residue 42, 43, 44, 45, or 46 of SEQ ID NO:4 or SEQ ID NO:6; $x_2$ is residue 70, 71, 72, 73, or 74 of SEQ ID NO:2, or residue 68, 69, 70, 71, 72, 73, or 74 of SEQ ID NO:4 or SEQ ID NO:6; $x_3$ is residue 113, 114, 115, 116, 117 or 118 of SEQ ID NO:2, or residue 110, 111, 112, 113, 114, 115, or 116 of SEQ ID NO:4 or SEQ ID NO:6; $x_4$ is residue 153, 154, 155, 156, or 157 of SEQ ID NO:2, or residue 149, 150, 151, 152, 153, 154, 155 or 156 of SEQ ID NO:4 or SEQ ID NO:6; $x_5$ is residue 220, 221, 222, 223, or 224 of SEQ ID NO:2, or residue 216, 217, 218, 219, 220, 221, 222 or 223 of SEQ ID NO:4 or SEQ ID NO:6; $x_6$ is residue 256, 257, 258, 259, 260 or 261 of SEQ ID NO:2, or residue 253, 254, 255, 256, 257, 258, 259 or 260 of SEQ ID NO:4 or SEQ ID NO:6; $x_7$ is residue 312, 313, 314, 315 or 316 of SEQ ID NO:2, or residue 309, 310, 311, 312, 313, 314, 315 or 318 of SEQ ID NO:4 or SEQ ID NO:6; and $x_8$ is an amino acid residue corresponding to the C-terminus of the polypeptide have the sequence of SEQ ID NO:2, SEQ ID NO:4 or SEQ ID NO:6 and wherein the chimera has an algorithm as set forth in Table 1 and wherein the chimera comprises a C→S substitution corresponding to C314 of SEQ ID NO:2 or C311 of SEQ ID NO:4.

In some embodiments, each segment of the chimeric polypeptide can have at least 60%, 70%, 80%, 90%, 95%, 96%, 97%, 98%, or 99% or more sequence identity as compared to the reference segment indicated for each of the (segment 1), (segment 2), (segment 3), (segment 4)-(segment 5), (segment 6), (segment 7), and (segment 8) of SEQ ID NO:2, SEQ ID NO:4, or SEQ ID NO:6.

In some embodiments, the polypeptide variants can have improved thermostability compared to the enzyme activity of the wild-type polypeptide of SEQ ID NO:2, 4, or 6 and wherein the chimera comprises a C→S substitution corresponding to C314 of SEQ ID NO:2 or C311 of SEQ ID NO:4.

The chimeric enzymes described herein may be prepared in various forms, such as lysates, crude extracts, or isolated preparations. The polypeptides can be dissolved in suitable solutions; formulated as powders, such as an acetone powder (with or without stabilizers); or be prepared as lyophilizates. In some embodiments, the polypeptide can be an isolated polypeptide.

In some embodiments, the polypeptides can be in the form of arrays. The enzymes may be in a soluble form, for example, as solutions in the wells of mircotitre plates, or immobilized onto a substrate. The substrate can be a solid substrate or a porous substrate (e.g, membrane), which can be composed of organic polymers such as polystyrene, polyethylene, polypropylene, polyfluoroethylene, polyethyleneoxy, and polyacrylamide, as well as co-polymers and grafts thereof. A solid support can also be inorganic, such as glass, silica, controlled pore glass (CPG), reverse phase silica or metal, such as gold or platinum. The configuration of a substrate can be in the form of beads, spheres, particles, granules, a gel, a membrane or a surface. Surfaces can be planar, substantially planar, or non-planar. Solid supports can be porous or non-porous, and can have swelling or non-swelling characteristics. A solid support can be configured in the form of a well, depression, or other container, vessel, feature, or location. A plurality of supports can be configured on an array at various locations, addressable for robotic delivery of reagents, or by detection methods and/or instruments.

The disclosure also provides polynucleotides encoding the engineered CBH II polypeptides disclosed herein. The polynucleotides may be operatively linked to one or more heterologous regulatory or control sequences that control gene expression to create a recombinant polynucleotide capable of expressing the polypeptide. Expression constructs containing a heterologous polynucleotide encoding the CBH II chimera can be introduced into appropriate host cells to express the polypeptide.

Given the knowledge of specific sequences of the CBH II chimera enzymes (e.g., the segment structure of the chimeric CBH II), the polynucleotide sequences will be apparent form the amino acid sequence of the engineered CBH II chimera enzymes to one of skill in the art. The knowledge of the codons corresponding to various amino acids coupled with the knowledge of the amino acid sequence of the polypeptides allows those skilled in the art to make different polynucleotides encoding the polypeptides of the disclosure. Thus, the disclosure contemplates each and every possible variation of the polynucleotides that could be made by selecting combinations based on possible codon choices, and all such variations are to be considered specifically disclosed for any of the polypeptides described herein.

In some embodiments, the polynucleotides encode the polypeptides described herein but have about 80% or more sequence identity, about 85% or more sequence identity, about 90% or more sequence identity, about 91% or more sequence identity, about 92% or more sequence identity, about 93% or more sequence identity, about 94% or more sequence identity, about 95% or more sequence identity, about 96% or more sequence identity, about 97% or more sequence identity, about 98% or more sequence identity, or about 99% or more sequence identity at the nucleotide level to a reference polynucleotide encoding the CBH II variant of chimera polypeptides and having a C→S substitution as described above (e.g., wherein the polypeptide or chimera comprises a C→S substitution corresponding to C314 of SEQ ID NO:2 or C311 of SEQ ID NO:4).

In some embodiments, the isolated polynucleotides encoding the polypeptides may be manipulated in a variety of ways to provide for expression of the polypeptide. Manipulation of the isolated polynucleotide prior to its insertion into a vector may be desirable or necessary depending on the expression vector. The techniques for modifying polynucleotides and nucleic acid sequences utilizing recombinant DNA methods are well known in the art. Guidance is provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007.

In some embodiments, the polynucleotides are operatively linked to control sequences for the expression of the polynucleotides and/or polypeptides. In some embodiments, the control sequence may be an appropriate promoter sequence, which can be obtained from genes encoding extracellular or intracellular polypeptides, either homologous or heterologous to the host cell. For bacterial host cells, suitable promoters for directing transcription of the nucleic acid constructs of the present disclosure, include the promoters obtained from the *E. coli* lac operon, *Bacillus subtilis* xylA and xylB genes, *Bacillus megatarium* xylose utilization genes (e.g., Rygus et al., (1991) Appl. Microbiol. Biotechnol. 35:594-599; Meinhardt et al., (1989) Appl. Microbiol. Biotechnol. 30:343-350), prokaryotic beta-lactamase gene (VIIIa-Kamaroff et al., (1978) Proc. Natl. Acad. Sci. USA 75: 3727-3731), as well as the tac promoter (DeBoer et al., (1983) Proc. Natl. Acad. Sci. USA 80: 21-25). Various suitable promoters are described in "Useful proteins from recombinant bacteria" in Scientific American, 1980, 242:74-94; and in Sambrook et al., supra.

In some embodiments, the control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used.

In some embodiments, the control sequence may also be a suitable leader sequence, a nontranslated region of an mRNA that is important for translation by the host cell. The leader sequence is operably linked to the 5' terminus of the nucleic acid sequence encoding the polypeptide. Any leader sequence that is functional in the host cell of choice may be used.

In some embodiments, the control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region that encodes the secreted polypeptide. Alternatively, the 5' end of the coding sequence may contain a signal peptide coding region that is foreign to the coding sequence. The foreign signal peptide coding region may be required where the coding sequence does not naturally contain a signal peptide coding region. Effective signal peptide coding regions for bacterial host cells can be the signal peptide coding regions obtained from the genes for *Bacillus* NClB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, (1993) Microbiol Rev 57: 109-137.

The disclosure is further directed to a recombinant expression vector comprising a polynucleotide encoding the engineered CBH II variant or chimera polypeptide, and one or more expression regulating regions such as a promoter and a terminator, a replication origin, etc., depending on the type of hosts into which they are to be introduced. In creating the expression vector, the coding sequence is located in the vector so that the coding sequence is operably linked with the appropriate control sequences for expression.

The recombinant expression vector may be any vector (e.g., a plasmid or virus), which can be conveniently subjected to recombinant DNA procedures and can bring about the expression of the polynucleotide sequence. The choice of the vector will typically depend on the compatibility of the vector with the host cell into which the vector is to be introduced. The vectors may be linear or closed circular plasmids.

The expression vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon, may be used.

In some embodiments, the expression vector of the disclosure contains one or more selectable markers, which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers, which confer antibiotic resistance such as ampicillin, kanamycin, chloramphenicol (Example 1) or tetracycline resistance. Other useful markers will be apparent to the skilled artisan.

In another embodiment, the disclosure provides a host cell comprising a polynucleotide encoding the CBH II variant or chimera polypeptide, the polynucleotide being operatively linked to one or more control sequences for expression of the polypeptide in the host cell. Host cells for use in expressing the polypeptides encoded by the expression vectors of the disclosure are well known in the art and include, but are not limited to, bacterial cells, such as *E. coli* and *Bacillus megaterium*; eukaryotic cells, such as yeast cells, CHO cells and the like, insect cells such as *Drosophila* S2 and *Spodoptera* Sf9 cells; animal cells such as CHO, COS, BHK, 293, and Bowes melanoma cells; and plant cells. Other suitable host cells will be apparent to the skilled artisan. Appropriate culture mediums and growth conditions for the above-described host cells are well known in the art.

The CBH II variant or chimera polypeptides of the disclosure can be made by using methods well known in the art. Polynucleotides can be synthesized by recombinant techniques, such as that provided in Sambrook et al., 2001, Molecular Cloning: A Laboratory Manual, 3rd Ed., Cold Spring Harbor Laboratory Press; and Current Protocols in Molecular Biology, Ausubel. F. ed., Greene Pub. Associates, 1998, updates to 2007. Polynucleotides encoding the enzymes, or the primers for amplification can also be prepared by standard solid-phase methods, according to known synthetic methods, for example using phosphoramidite method described by Beaucage et al., (1981) Tet Lett 22:1859-69, or the method described by Matthes et al., (1984) EMBO J. 3:801-05, e.g., as it is typically practiced in automated synthetic methods. In addition, essentially any nucleic acid can be obtained from any of a variety of commercial sources, such as The Midland Certified Reagent Company, Midland, Tex., The Great American Gene Company, Ramona, Calif., ExpressGen Inc. Chicago, Ill., Operon Technologies Inc., Alameda, Calif., and many others.

Engineered enzymes expressed in a host cell can be recovered from the cells and or the culture medium using any one or more of the well known techniques for protein purification, including, among others, lysozyme treatment, sonication, filtration, salting-out, ultra-centrifugation, chromatography, and affinity separation (e.g., substrate bound antibodies). Suitable solutions for lysing and the high efficiency extraction of proteins from bacteria, such as *E. coli*, are commercially available under the trade name CelLytic BTM from Sigma-Aldrich of St. Louis Mo.

Chromatographic techniques for isolation of the polypeptides include, among others, reverse phase chromatography high performance liquid chromatography, ion exchange chromatography, gel electrophoresis, and affinity chromatography. Conditions for purifying a particular enzyme will depend, in part, on factors such as net charge, hydrophobicity, hydrophilicity, molecular weight, molecular shape, etc., and will be apparent to those having skill in the art.

Descriptions of SCHEMA directed recombination and synthesis of chimeric polypeptides are described in the examples herein, as well as in Otey et al., (2006), PLoS Biol. 4 (5):e112; Meyer et al., (2003) Protein Sci., 12:1686-1693; U.S. patent application Ser. No. 12/024,515, filed Feb. 1, 2008; and U.S. patent application Ser. No. 12/027,885, filed Feb. 7, 2008; such references incorporated herein by reference in their entirety.

As discussed above, the polypeptide can be used in a variety of applications, such as, among others, biofuel generation, cellulose breakdown and the like.

The following examples are meant to further explain, but not limited the foregoing disclosure or the appended claims.

EXAMPLES

Figure 6:
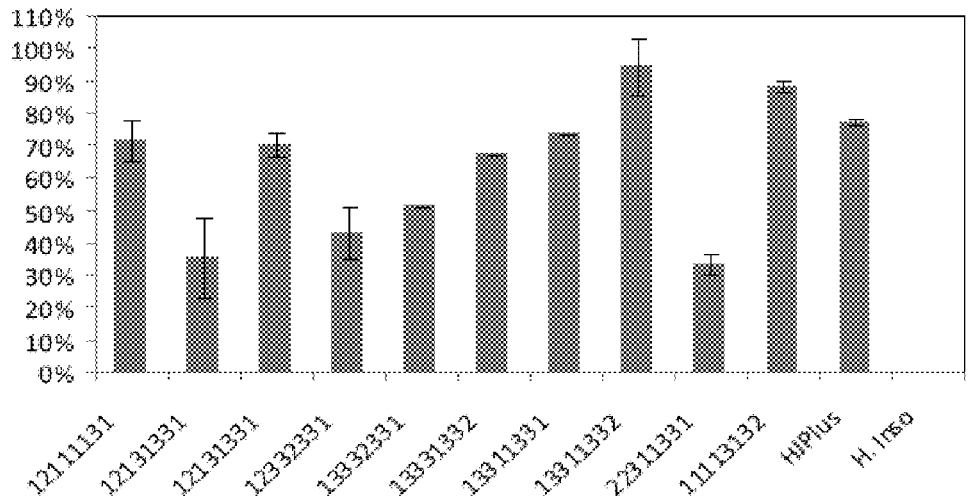
FIG. 6 shows normalized residual activities for validation set chimeras after a 12-h incubation at 63° C. Residual activities for CBH II enzymes in concentrated culture supernatants determined in 2-hr assay with PASC as substrate, 50° C., 25 mM sodium acetate buffer, pH 4.8.
Figure 7:
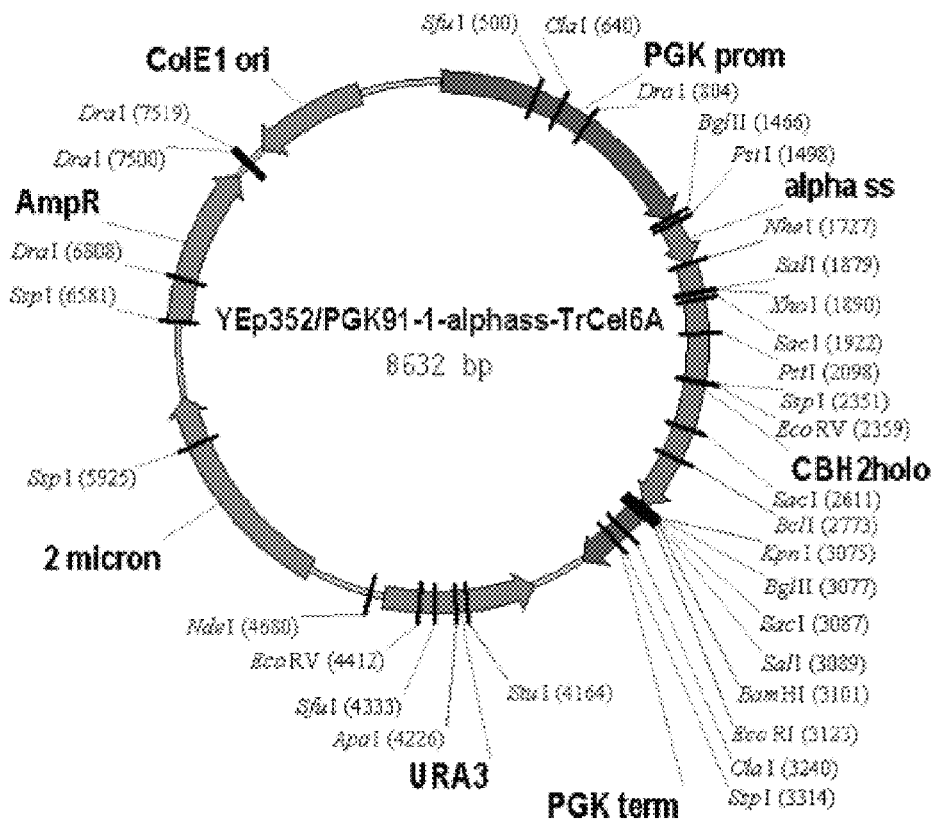
FIG. 7 Map for parent and chimera CBH II enzyme expression vector Yep352/PGK91-1-ss. Vector pictured contains wild type *H. jecorina* cel6a (CBH II enzyme) gene. For both chimeric and parent CBH II enzymes, the CBD/linker amino acid sequence following the ss Lys-Arg Kex2 site is.

CBH II expression plasmid construction. Parent and chimeric genes encoding CBH II enzymes were cloned into yeast expression vector YEp352/PGK91-1-αss (FIG. 6). DNA sequences encoding parent and chimeric CBH II catalytic domains were designed with *S. cerevisiae* codon bias using GeneDesigner software (DNA2.0) and synthesized by DNA2.0. The CBH II catalytic domain genes were digested with XhoI and KpnI, ligated into the vector between the XhoI and KpnI sites and transformed into *E. coli* XL-1 Blue (Stratagene). CBH II genes were sequenced using primers: CBH2L (5'-GCTGAACGTGTCATCGGTTAC-3' (SEQ ID NO:9) and RSQ3080 (5'-GCAACACCTGGCAATTCCTTACC-3' (SEQ ID NO:10)). C-terminal $His_6$ parent and chimera CBH II constructs were made by amplifying the CBH II gene with forward primer CBH2LPCR (5'-GCTGAACGTGTCATCGTTACTTAG-3' (SEQ ID NO:11)) and reverse primers complementary to the appropriate CBH II gene with $His_6$ overhangs and stop codons. PCR products were ligated, transformed and sequenced as above.

CBH II enzyme expression in *S. cerevisiae*. *S. cerevisiae* strain YDR483W BY4742 (Matα his3Δ1 leu2Δ0 lys2Δ0 ura3Δ0 ΔKRE2, ATCC No. 401-4317) was made competent using the EZ Yeast II Transformation Kit (Zymo Research), transformed with plasmid DNA and plated on synthetic dropout-uracil agar. Colonies were picked into 5 mL overnight cultures of synthetic dextrose casamino acids (SDCAA) media (20 g/L dextrose, 6.7 g/L Difco yeast nitrogen base, 5 g/L Bacto casamino acids, 5.4 g/L $Na_2HPO_4$, 8.56 g/L $NaH_2PO_4.H_2O$) supplemented with 20 ug/mL tryptophan and grown overnight at 30° C., 250 rpm. 5 mL cultures were expanded into 40 mL SDCAA in 250 mL Tunair flasks (Shelton Scientific) and shaken at 30° C., 250 rpm for 48 hours. Cultures were centrifuged, and supernatants were concentrated to 500 uL, using an Amicon ultrafiltration cell fitted with 30-kDa PES membrane, for use in $t_{1/2}$ assays. Concentrated supernatants were brought to 1 mM phenylmethylsulfonylfluoride and 0.02% $NaN_3$. $His_6$-tagged CBH II proteins were purified using Ni-NTA spin columns (Qiagen) per the manufacturer's protocol and the proteins exchanged into 50 mM sodium acetate, pH 4.8, using Zeba-Spin desalting columns (Pierce). Purified protein concentration was determined using Pierce Coomassie Plus protein reagent with BSA as standard. SDS-PAGE analysis was performed by loading either 20 uL of concentrated culture supernatant or approximately 5 ug of purified CBH II enzyme onto a 7.5% Tris-HCl gel (Biorad) and staining with SimplyBlue safe stain (Invitrogen). CBH II supernatants or purified proteins were treated with EndoH (New England Biolabs) for 1 hr at 37° C. per the manufacturer's instructions. CBH II enzyme activity in concentrated yeast culture supernatants was measured by adding 37.5 uL concentrated culture supernatant to 37.5 uL PASC and incubating for 2 hr at 50° C. Reducing sugar equivalents formed were determined via Nelson-Somogyi assay as described below.

Half-life, specific activity, pH-activity and long-time cellulose hydrolysis measurements. Phosphoric acid swollen cellulose (PASC) was prepared. To enhance CBH II enzyme activity on the substrate, PASC was pre-incubated at a concentration of 10 g/L with 10 mg/mL *A. niger* endoglucanase (Sigma) in 50 mM sodium acetate, pH 4.8 for 1 hr at 37° C. Endoglucanase was inactivated by heating to 95° C. for 15 minutes, PASC was washed twice with 50 mM acetate buffer and resuspended at 10 g/L in deionized water.

CBH II enzyme $t_{1/2}$s were measured by adding concentrated CBH II expression culture supernatant to 50 mM sodium acetate, pH 4.8 at a concentration giving $A_{520}$ of 0.5 as measured in the Nelson-Somogyi reducing sugar assay after incubation with treated PASC as described below. 37.5 uL CBH II enzyme/buffer mixtures were inactivated in a water bath at 63° C. After inactivation, 37.5 uL endoglucanase-treated PASC was added and hydrolysis was carried out for 2 hr at 50° C. Reaction supernatants were filtered through Multiscreen HTS plates (Millipore). Nelson-Somogyi assay log ($A_{520}$) values, obtained using a SpectraMax microplate reader (Molecular Devices) corrected for background absorbance, were plotted versus time and CBH II enzyme half-lives obtained from linear regression using Microsoft Excel.

For specific activity measurements, purified CBH II enzyme was added to PASC to give a final reaction volume of 75 uL 25 mM sodium acetate, pH 4.8, with 5 g/L PASC and CBH II enzyme concentration of 3 mg enzyme/g PASC. Incubation proceeded for 2 hr in a 50° C. water bath and the reducing sugar concentration determined. For pH/activity profile measurements, purified CBH II enzyme was added at a concentration of 300 ug/g PASC in a 75 uL reaction volume. Reactions were buffered with 12.5 mM sodium citrate/12.5 mM sodium phosphate, run for 16 hr at 50° C. and reducing sugar determined. Long-time cellulose hydrolysis measurements were performed with 300 uL volumes of 1 g/L treated PASC in 100 mM sodium acetate, pH 4.8, 20 mM NaCl. Purified CBH II enzyme was added at 100 ug/g PASC and reactions carried out in water baths for 40 hr prior to reducing sugar determination.

Figure 1A:
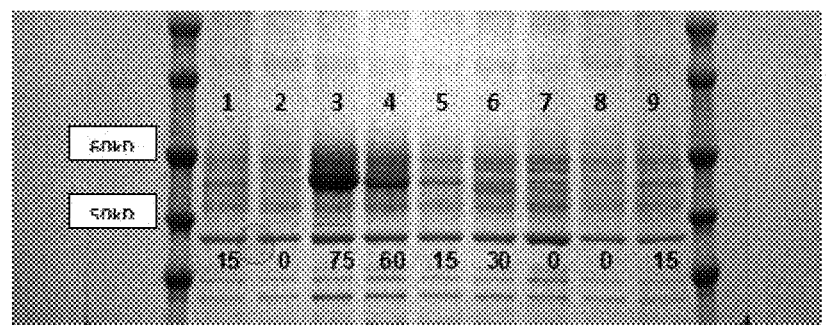
FIG. 1A-B SDS-PAGE gel of candidate CBH II parent gene yeast expression culture supernatants. (A) Gel Lanes (Left-to-Right): 1-*H. jecorina*, 2-Empty vector, 3-*H. insolens*, 4-*C. thermophilum*, 5-*H. jecorina* (duplicate), 6-*P. chrysosporium*, 7-*T. emersonii*, 8-Empty vector (duplicate), 9-*H. jecorina* (triplicate). Numbers at bottom of gel represent concentration of reducing sugar (ug/mL) present in reaction after 2-hr, 50° C. PASC hydrolysis assay. Subsequent SDS-PAGE comparison with BSA standard allowed estimation of *H. insolens* expression level of 5-10 mg/L. (B) Shows SDS-PAGE gel analysis of *S. cerevisiae* CBH II expression culture supernatants. CBH II bands appear just below 60 kDa molecular weight standard. Lanes, left-to-right, 1-wild type *H. jeco*, 2-*H. jeco* B7P3, 3-*H. jeco* C311S, 4-wild type *C. ther*, 5-wild type *H. inso*, 6-*H. inso* B7P3, 7-*H. inso* C314S. Numbers denote μg glucose equivalent/mL reaction volume per mL SDCAA expression culture supernatant equivalent produced during 100-minute incubation with PASC (1 mg/mL) at 50° C. in 50 mM sodium acetate, pH 4.8. Values for lanes 1-4 have been divided by 2 to corret for twice the volume of concentrated culture supernatant being loaded where omitting this correctin would make the specific activity values for the *H. insolens* enzymes appear artificially low.
Figure 1B:
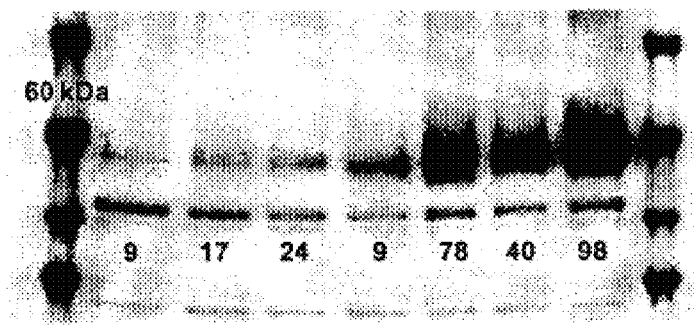

Five candidate parent genes encoding CBH II enzymes were synthesized with *S. cerevisiae* codon bias. All five contained identical N-terminal coding sequences, where residues 1-89 correspond to the cellulose binding module (CBM), flexible linker region and the five N-terminal residues of the *H. jecorina* catalytic domain. Two of the candidate CBH II enzymes, from *Humicola insolens* and *Chaetomium thermophilum*, were secreted from *S. cerevisiae* at much higher levels than the other three, from *Hypocrea jecorina*, *Phanerochaete chrysosporium* and *Talaromyces emersonii* (FIG. 1). Because bands in the SDS-PAGE gel for the three weakly expressed candidate parents were difficult to discern, activity assays in which concentrated culture supernatants were incubated with phosphoric acid swollen cellulose (PASC) were performed to confirm the presence of active cellulase. The values for the reducing sugar formed, presented in FIG. 1, confirmed the presence of active CBH II in concentrated *S. cerevisiae* culture supernatants for all enzymes except *T. emersonii* CBH II. *H. insolens* and *C. thermophilum* sequences were chose to recombine with the most industrially relevant fungal CBH II enzyme, from *H. jecorina*. The respective sequence identities of the catalytic domains are 64% (1:2), 66% (2:3) and 82% (1:3), where *H. insolens* is parent 1, *H. jecorina* is parent 2 and *C. thermophilum* is parent 3. These respective catalytic domains contain 360, 358 and 359 amino acid residues.

Heterologous protein expression in the filamentous fungus *H. jecorina*, the organism most frequently used to produce cellulases for industrial applications, is much more arduous than in *Saccharomyces cerevisiae*. The observed secretion of *H. jecorina* CBH II from *S. cerevisiae* motivated the choice of this heterologous host. To minimize hyperglycosylation, which has been reported to reduce the activity of recombinant cellulases, the recombinant CBH II genes were expressed in a glycosylation-deficient dKRE2 *S. cerevisiae* strain. This strain is expected to attach smaller mannose oligomers to both N-linked and O-linked glycosylation sites than wild type strains, which more closely resembles the glycosylation of natively produced *H. jecorina* CBH II enzyme. SDS-PAGE gel analysis of the CBH II proteins, both with and without EndoH treatment to remove high-mannose structures, showed that EndoH treatment did not increase the electrophoretic mobility of the enzymes secreted from this strain, confirming the absence of the branched mannose moieties that wild type *S. cerevisiae* strains attach to glycosylation sites in the recombinant proteins.

Figure 2:
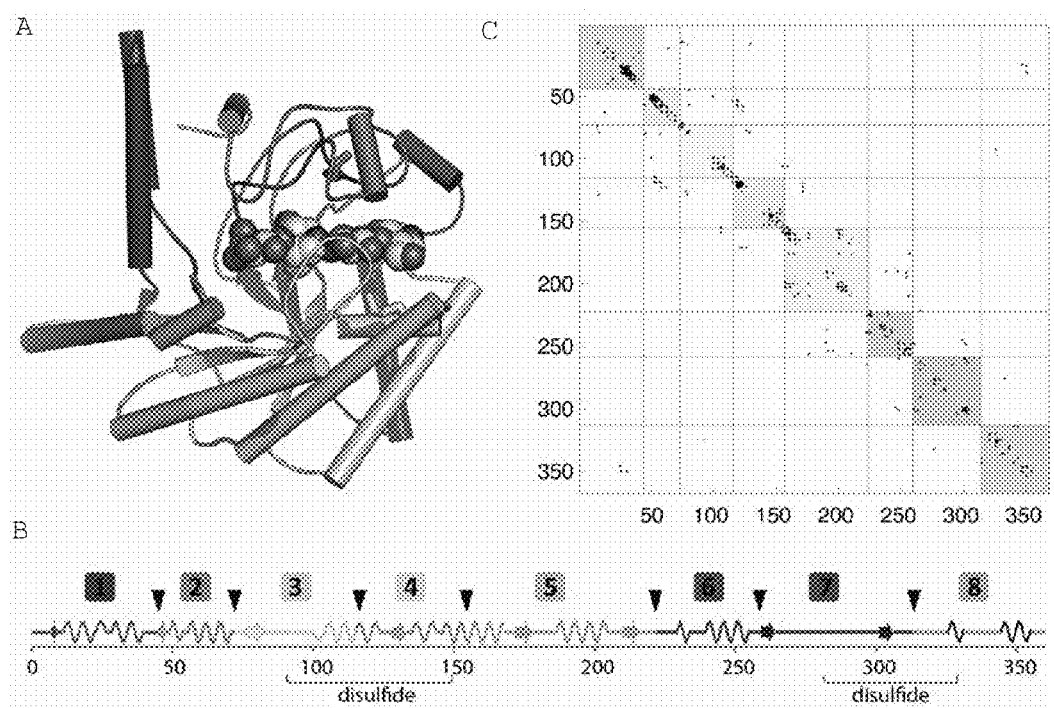
FIG. 2A-C shows illustrations of CBH II chimera library block boundaries. (A) *H. insolens* CBH II catalytic domain ribbon diagram with blocks distinguished by color. CBH II enzyme is complexed with cellobio-derived isofagomine glycosidase inhibitor. (B) Linear representation of *H. insolens* catalytic domain showing secondary structure elements, disulfide bonds and block divisions denoted by black arrows. (C) Sidechain contact map denoting contacts (side chain heavy atoms within 4.5 Å) that can be broken upon recombination. The majority of broken contacts occur between consecutive blocks.

The high resolution structure of *H. insolens* (pdb entry 1ocn) was used as a template for SCHEMA to identify contacts that could be broken upon recombination. RASPP returned four candidate libraries, each with <E> below 15. The candidate libraries all have lower <E> than previously constructed chimera libraries, suggesting that an acceptable fraction of folded, active chimeras could be obtained for a relatively high <m>. Chimera sequence diversity was maximized by selecting the block boundaries leading to the greatest <m>=50. The blocks for this design are illustrated in FIG. 2B and detailed in Table 2.

TABLE 2

ClustalW multiple sequence alignment for parent CBH II enzyme catalytic domains.
Blocks 2, 4, 6 and 8 are denoted by boxes and grey shading. Blocks 1, 3, 5 and 7 are not
shaded. (*H. inso*: SEQ ID NO: 2; *H. Jeco*: SEQ ID NO: 4 and *C. Ther*: SEQ ID NO: 6).

```
H. inso  GNPFEGVQLWANNYYRSEVHTLAIPQITDPALRAAASAVAEVPSFQWLDRNVTVDTLLVQ  60
C. ther  GNPFSGVQLWANTYYSSEVHTLAIPSLS-PELAAKAAKVAEVPSFQWLDRNVTVDTLFSG  59
H. jeco  GNPFVGVTPWANAYYASEVSSLAIPSLT-GAMATAAAAVAKVPSFMWLDT-LDKTPLMEQ  58
         ****  **   *** **  ***  :****.::      :   *: **:****  ***      :    .*:

H. inso  TLSEIREANQAGANPQYAAQIVVYDLPDRDCAAAASNGEWAIANNGVNNYKAYINRIREI  120
C. ther  TLAEIRAANQRGANPPYAGIFVVYDLPDRDCAAAASNGEWSIANNGANNYKRYIDRIREL  119
H. jeco  TLADIRTANKNGGN--YAGQFVVYDLPDRDCAALASNGEYSIADGGVAKYKNYIDTIRQI  116
         **::**  **:  *  *     **  .:************ *****.:**::.*.  :** **:  **::

H. inso  LISFSDVRTILVIEPDSLANMVTNMNVPKCSGAASTYRELTIYALKQLDLPHVAMYMDAG  180
C. ther  LIQYSDIRTILVIEPDSLANMVTNMNVQKCSNAATYKELTVYALKQLNLPHVAMYMDAG  179
H. jeco  VVEYSDIRTLLVIEPDSLANLVTNLGTPKCANAQSAYLECINYAVTQLNLPNVAMYLDAG  176
         :::.**:**.************:***: .. *** ::*:*    **::**:****:.***

H. inso  HAGWLGWPANIQPAAELFAKIYEDAGKPRAVRGLATNVANYNAWSVSSPPPYTSPNPNYD  240
C. ther  HAGWLGWPANIQPAAELFAQIYRDAGRPAAVRGLATNVANYNAWSIASPPSYTSPNPNYD  239
H. jeco  HAGWLGWPANQDPAAQLFANVYKNASSPRALRGLATNVANYNGWNITSPPSYTQGNAVYN  236
         **********  :***:***:::*.:*. *  *.************.*.:::***.**.  *.  *:

H. inso  EKHYIEAFRPLLEARGFP-AQFIVDQGRSGKQPTGQKEWGHWCNAIGTGFGMRPTANTGH  299
C. ther  EKHYIEAFAPLLRNQGFD-AKFIVDTGRNGKQPTGQLEWGHWCNVKGTGFGVRPTANTGH  298
H. jeco  EKLYIHAIGPLLANHGWSNAFFITDQGRSGKQPTGQQQWGDWCNVIGTGFGIRPSANTGD  296
         ** **.*:  ***    :*:     * **.* **.*******  :**.***  *****:**:****.

H. inso  QYVDAFVWVKPGGECDGTSDTTAARYDYHCGLEDALKPAPEAGQWFNEYFIQLLRNANPP  359
C. ther  ELVDAFVWVKPGGESDGTSDTSAARYDYHCGLSDALTPAPEAGQWFQAYFEQLLINANPP  358
H. jeco  SLLDSFVWVKPGGECDGTSDSSAPRFDSHCALPDALQPAPQAGAWFQAYFVQLLTNANPS  356
         . :*:*********.******:*:*  :*.*  ***.***:**.**:.**  ***  ***.

H. inso  F  360
C. ther  F  359
H. jeco  FL 358
         *
```

The *H. insolens* CBH II catalytic domain has an α/β barrel structure in which the eight helices define the barrel perimeter and seven parallel β-sheets form the active site (FIG. 2A). Two extended loops form a roof over the active site, creating a tunnel through which the substrate cellulose chains pass during hydrolysis. Five of the seven block boundaries fall between elements of secondary structure, while block 4 begins and ends in the middle of consecutive α-helices (FIGS. 2A, 2B). The majority of interblock sidechain contacts occur between blocks that are adjacent in the primary structure (FIG. 2C).

A sample set of 48 chimera genes was designed as three sets of 16 chimeras having five blocks from one parent and three blocks from either one or both of the remaining two parents (Table 3); the sequences were selected to equalize the representation of each parent at each block position. The corresponding genes were synthesized and expressed.

TABLE 3

Sequences of sample set CBH II enzyme chimeras.

| Inactive | Active |
|---|---|
| 13121211 | 11332333 |
| 12122221 | 21131311 |
| 33332321 | 31212111 |
| 33321331 | 22232132 |
| 21322232 | 33213332 |
| 21112113 | 23233133 |
| 31121121 | 13231111 |
| 32312223 | 12213111 |
| 23223223 | 31311112 |
| 31313323 | 11113132 |
| 32121222 | 13111313 |
| 12121113 | 21311131 |
| 22133222 | 11313121 |

TABLE 3-continued

Sequences of sample set CBH II enzyme chimeras.

| Inactive | Active |
|---|---|
| 33222333 | 21223122 |
| 11131231 | 22212231 |
| 11112321 | 23231222 |
| 12111212 | 32333113 |
| 31222212 | 12133333 |
| 22322312 | 13333232 |
| 12222213 | 33123313 |
| 12221122 | 21333331 |
| 22212323 | 23311333 |
| 23222321 | 33133132 |
| 32333223 | |
| 33331213 | |

Twenty-three of the 48 sample set *S. cerevisiae* concentrated culture supernatants exhibited hydrolytic activity toward PASC. These results suggest that thousands of the 6,561 possible CBH II chimera sequences (see e.g., Table 1) encode active enzymes. The 23 active CBH II sample set chimeras show considerable sequence diversity, differing from the closest parental sequence and each other by at least 23 and 36 amino acid substitutions and as many as 54 and 123, respectively. Their average mutation level <m> is 36.

Figure 3:
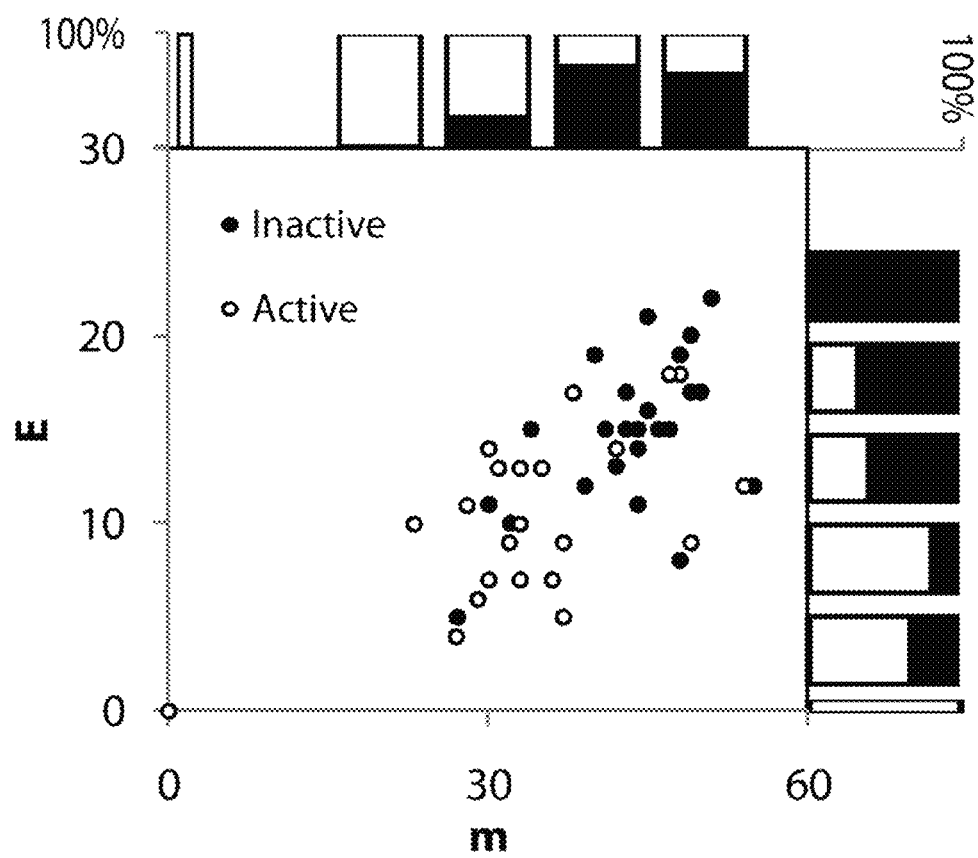
FIG. 3 shows a number of broken contacts (E) and number of mutations from closest parent (m) for 23 secreted/active and 15 not secreted/not active sample set chimeras.

As Meyer et al. found correlations between E, m and the probability that a chimera is folded and active, analysis of whether similar correlations existed for the sample set CBH II chimeras was analyzed. The amount of CBH II enzyme activity in concentrated expression culture supernatants, as measured by assaying for activity on PASC, was correlated to the intensity of CBH II bands in SDS-PAGE gels (FIG. 1). As with the *H. jecorina* CBH II parent, activity could be detected for some CBH II chimeras with undetectable gel bands. There were no observations of CBH II chimeras presenting gel bands but lacking activity. The probability of a CBH II chimera being secreted in active form was inversely related to both E and m (FIG. 3).

Half-lives of thermal inactivation ($t_{1/2}$) were measured at 63° C. for concentrated culture supernatants of the parent and active chimeric CBH II enzymes. The *H. insolens*, *H. jecorina* and *C. thermophilum* CBH II parent half-lives were 95, 2 and 25 minutes, respectively (Table 1). The active sample set chimeras exhibited a broad range of half-lives, from less than 1 minute to greater than 3,000. Five of the 23 active chimeras had half-lives greater than that of the most thermostable parent, *H. insolens* CBH II.

In attempting to construct a predictive quantitative model for CBH II chimera half-life, five different linear regression data modeling algorithms were used (Table 4). Each algorithm was used to construct a model relating the block compositions of each sample set CBH II chimera and the parents to the $\log(t_{1/2})$. These models produced thermostability weight values that quantified a block's contribution to $\log(t_{1/2})$. For all five modeling algorithms, this process was repeated 1,000 times, with two randomly selected sequences omitted from each calculation, so that each algorithm produced 1,000 weight values for each of the 24 blocks. The mean and standard deviation (SD) were calculated for each block's thermostability weight. The predictive accuracy of each model algorithm was assessed by measuring how well each model predicted the $t_{1/2}$s of the two omitted sequences. The correlation between measured and predicted values for the 1,000 algorithm iterations is the model algorithm's cross-validation score. For all five models, the cross-validation scores (X-val) were less than or equal to 0.57 (Table 4), indicating that linear regression modeling could not be applied to this small, 23 chimera $t_{1/2}$ data set for quantitative CBH II chimera half-life prediction.

TABLE 4

Cross validation values for application of 5 linear regression algorithms to CBH II enzyme chimera block stability scores.

| Method | Ridge | PLS | SVMR | LSVM | LPBoost |
|---|---|---|---|---|---|
| X-val | 0.56 | 0.55 | 0.50 | 0.42 | 0.43 |

Algorithm abbreviations: ridge regression (RR), partial least square regression (PLSR), support vector machine regression (SVMR), linear programming support vector machine regression (LPSVMR) and linear programming boosting regression (LPBoostR).

Linear regression modeling was used to qualitatively classify blocks as stabilizing, destabilizing or neutral. Each block's impact on chimera thermostability was characterized using a scoring system that accounts for the thermostability contribution determined by each of the regression algorithms. For each algorithm, blocks with a thermostability weight value more than 1 SD above neutral were scored "+1", blocks within 1 SD of neutral were assigned zero and blocks 1 or more SD below neutral were scored "−1". A "stability score" for each block was obtained by summing the 1, 0, −1 stability scores from each of the five models. Table 5 summarizes the scores for each block. Block 1/parent 1 (B1P1), B6P3, B7P3 and B8P2 were identified as having the greatest stabilizing effects, while B1P3, B2P1, B3P2, B6P2, B7P1, B7P2 and B8P3 were found to be the most strongly destabilizing blocks.

TABLE 5

Qualitative block classification results generated by five linear regression algorithms[1] for sample set CBH II enzyme chimeras.

| Block | Ridge | PLS | SVMR | LSVM | LPBoost | Sum |
|---|---|---|---|---|---|---|
| B1P1 | 1 | 0 | 1 | 1 | 0 | 3 |
| B1P2 | 0 | 0 | 0 | −1 | 0 | −1 |
| B1P3 | −1 | 0 | −1 | −1 | −1 | −4 |
| B2P1 | −1 | 0 | 0 | −1 | −1 | −3 |
| B2P2 | 1 | 0 | 0 | 0 | 0 | 1 |
| B2P3 | 1 | 0 | 0 | 0 | 0 | 1 |
| B3P1 | 1 | 0 | 1 | 0 | 0 | 2 |
| B3P2 | −1 | 0 | −1 | −1 | −1 | −4 |
| B3P3 | 1 | 0 | 1 | 0 | 0 | 2 |
| B4P1 | 0 | 0 | 0 | 0 | 0 | 0 |
| B4P2 | 0 | 0 | 0 | 0 | 0 | 0 |
| B4P3 | 0 | 0 | 0 | −1 | 0 | −1 |
| B5P1 | 0 | 0 | 0 | 0 | 0 | 0 |
| B5P2 | 0 | 0 | 0 | 0 | −1 | −1 |
| B5P3 | −1 | 0 | 0 | −1 | 0 | −2 |
| B6P1 | 1 | 0 | 0 | −1 | −1 | −1 |
| B6P2 | −1 | 0 | −1 | −1 | −1 | −4 |
| B6P3 | 1 | 1 | 1 | 1 | 1 | 5 |
| B7P1 | −1 | 0 | −1 | −1 | −1 | −4 |
| B7P2 | −1 | 0 | −1 | −1 | −1 | −4 |
| B7P3 | 1 | 0 | 1 | 1 | 1 | 4 |
| B8P1 | 1 | 0 | 1 | −1 | 0 | 1 |
| B8P2 | 1 | 0 | 1 | 1 | 0 | 3 |
| B8P3 | −1 | 0 | −1 | −1 | −1 | −4 |

Score of +1 denotes a block with thermostability weight (dimensionless metric for contribution of a block to chimera thermostability) greater than one standard deviation above neutral (stabilizing), score of 0 denotes block with weight within one standard deviation of neutral and −1 denotes block with weight more than one standard deviation below neutral (destabilizing).

A second set of genes encoding CBH II enzyme chimeras was synthesized in order to validate the predicted stabilizing blocks and identify cellulases more thermostable than the most stable parent. The 24 chimeras included in this validation set (Table 6) were devoid of the seven blocks predicted to be most destabilizing and enriched in the four most stabilizing blocks, where representation was biased toward higher stability scores. Additionally, the "HJPlus" 12222332 chimera was constructed by substituting the predicted most stabilizing blocks into the *H. jecorina* CBH II enzyme (parent 2).

TABLE 6

Sequences of 24 validation set CBH II enzyme chimeras, nine of which were expressed in active form.

| Inactive | Active |
|---|---|
| 12122132 | 12111131 |
| 12132332 | 12132331 |
| 12122331 | 12131331 |
| 12112132 | 12332331 |
| 13122332 | 13332331 |
| 13111132 | 13331332 |
| 13111332 | 13311331 |
| 13322332 | 13311332 |
| 22122132 | 22311331 |
| 22322132 | |
| 22311332 | |
| 23111332 | |
| 23321131 | |
| 23321332 | |
| 23321331 | |

Concentrated supernatants of *S. cerevisiae* expression cultures for nine of the 24 validation set chimeras, as well as the HJPlus chimera, showed activity toward PASC (Table 6). Of the 15 chimeras for which activity was not detected, nine contained block B4P2. Of the 16 chimeras containing B4P2 in the initial sample set, only one showed activity toward PASC. Summed over both chimera sets and HJPlus, just two of 26 chimeras featuring B4P2 were active, indicating that this particular block is highly detrimental to expression of active cellulase in *S. cerevisiae*.

The stabilities of the 10 functional chimeric CBH II enzymes from the validation set were evaluated. Because the stable enzymes already had half-lives of more than 50 hours, residual hydrolytic activity toward PASC after a 12-hour thermal inactivation at 63° C. was used as the metric for preliminary evaluation. This 12-hour incubation produced a measurable decrease in the activity of the sample set's most thermostable chimera, 11113132, and completely inactivated the thermostable *H. insolens* parent CBH II. All ten of the functional validation set chimeras retained a greater fraction of their activities than the most stable parent, *H. insolens* CBH II.

The activities of selected thermostable chimeras using purified enzymes was analyzed. The parent CBH II enzymes and three thermostable chimeras, the most thermostable sample set chimera 11113132, the most thermostable validation set chimera 13311332 and the HJPlus chimera 12222332, were expressed with C-terminal $His_6$ purification tags and purified. To minimize thermal inactivation of CBH II enzymes during the activity test, we used a shorter, two-hour incubation with the PASC substrate at 50° C., pH 4.8. As shown in Table 3, the parent and chimera CBH II specific activities were within a factor of four of the most active parent CBH II enzyme, from *H. jecorina*. The specific activity of HJPlus was greater than all other CBH II enzymes tested, except for *H. jecorina* CBH II.

The pH dependence of cellulase activity is also important, as a broad pH/activity profile would allow the use of a CBH II chimera under a wider range of potential cellulose hydrolysis conditions. *H. jecorina* CBH II has been observed to have optimal activity in the pH range 4 to 6, with activity markedly reduced outside these values.[16] FIG. 4 shows that the *H. insolens* and *C. thermophilum* CBH II enzymes and all three purified thermostable CBH II chimeras have pH/activity profiles that are considerably broader than that of *H. jecorina* CBH II. Although Liu et al. report an optimal pH of 4 for *C. thermophilum* CBH II, the optimal pH of the recombinant enzyme here was near 7. Native *H. insolens* CBH II has a broad pH/activity profile, with maximum activity around pH 9 and approximately 60% of this maximal activity at pH 4. A similarly broad profile was observed for the recombinant enzyme. The HJPlus chimera has a much broader pH/activity profile than *H. jecorina* CBH II, showing a pH dependence similar to the other two parent CBH II enzymes.

Achieving activity at elevated temperature and retention of activity over extended time intervals are two primary motivations for engineering highly stable CBH II enzymes. The performance of thermostable CBH II chimeras in cellulose hydrolysis was tested across a range of temperatures over a 40-hour time interval. As shown in FIG. 5, all three thermostable chimeras were active on PASC at higher temperatures than the parent CBH II enzymes. The chimeras retained activity at 70° C., whereas the *H. jecorina* CBH II did not hydrolyze PASC above 57° C. and the stable *H. insolens* enzyme showed no hydrolysis above 63° C. The activity of HJPlus in long-time cellulose hydrolysis assays exceeded that of all the parents at their respective optimal temperatures.

The CBH II library has fewer potential disruptions for several reasons. In addition to the higher identity of the CBH II parent sequences, the barrel topology of the CBH II fold limits the number of long-range contacts that can be broken by recombination. Between-block contacts (heavy atoms within 4.5 Å) comprise only 27% (503/1831) of the total in a contact map derived from *H. insolens* structure 1ocn. When only counting contacts for which novel residue pairs are possible in chimeras, the inter-block total is reduced to 23% (68/294). Furthermore, most of these interactions are between residues on the protein surface, and the possibility of solvent screening further decreases the chances of dramatic disruptive residue-residue interactions (FIG. 14*a*). One exception, a buried interaction between positions 176 and 256, is illustrated in FIG. 14*b*. At this site, chimeras with B6P2 and either B5P1 or B5P3 pair Met173:Trp253 (larger amino acid than parental pairs Met176:Phe256 or Leu173:Trp253). Nevertheless, upon inspection of the parental crystallographic models, a steric clash at this position was deemed unlikely due to movement in the portion of the protein backbone which positions Trp253 and the intrinsic flexibility of Met side chains. Notably, one characterized chimera fits this pattern (13333232) and is more stable than the parents (67° C.), in accord with the regression model fit (68° C.).

Another mechanism by which coupling could arise, block structural divergence, does not depend on the presence of novel residue pairs at block interfaces. Instead, as parental sequences diverge, intrinsic block structures may diverge, hindering modular block transplants. In the case of the CBH II library, the high parent pair sequence identity values (82%, 66%, and 64%) suggest that only minor structure deviations are likely (<1 Å RMSD). This possibility can be evaluated by comparing crystallographic structures for *H. insolens* and *H. jecorina* CBH II (*C. thermophilum* CBH II lacks a crystal structure but is 82% identical to *H. insolens*). Aligning blocks from structures for each parent (1ocn and 1cb2), generates low alpha carbon RMSD values (0.5, 0.5, 0.6, 0.5, 0.3, 0.7, 0.3, and 0.4 Å RMSD). *H. jecorina* blocks superimposed onto *H. insolens* are illustrated in Supplemental FIG. 5*c*. To check for context-dependent effects an in silico structural recombination was performed, splicing each aligned block onto the opposing host structure. It is possible to construct non-clashing structural models (alpha carbons >3 Å apart) for all single-block substitution chimeras (e.g., 11112111 or 22122222), with the exception of a minor clash (2.65 Å) when using B7P2 (11111121) due to the Asn insertion between blocks 6 and 7 (FIG. 14D).

Further experiments were performed to determine the contributions of various blocks/segments to the chimera's stability and improved thermostability and/or pH stability. Parent and chimeric genes encoding CBH II enzymes were cloned into yeast expression vector YEp352/PGK91-1-αss and expression in synthetic dextrose casamino acids (SDCAA) media. For Avicel activity assays, yeast peptone dextrose (YPD) culture supernatants were brought to 1 mM phenylmethylsulfonylfluoride and 0.02% $NaN_3$ and used without concentration. CBH II enzyme activity in concentrated SDCAA yeast culture supernatants was measured by adding dilutions of concentrated culture supernatant to 37.5 μL PASC and 225 μL 50 mM sodium acetate, pH 4.8 and incubating for 2 hr at 50° C. Reducing sugar equivalents formed were determined via Nelson-Somogyi assay.

CBH II enzyme $T_{50}$ values were measured by adding concentrated CBH II SDCAA expression culture supernatant to 50 mM sodium acetate, pH 4.8 at a concentration giving $A_{520}$ of 0.5 as measured in the Nelson-Somogyi reducing sugar assay after incubation with endoglucanase-treated PASC. 200 μL CBH II enzyme/buffer mixtures were incubated in a water bath at the temperature of interest for 10 minutes. After incubation, 37.5 μL endoglucanase-treated PASC and 62.5 μL of 50 mM sodium acetate were added, and hydrolysis was carried out for 2 hr at 50° C. The incubation temperature at which the enzyme lost one-half of its activity was determined by linear interpolation of the Nelson-Somogyi assay $A_{520}$ values plotted versus temperature.

For long-time Avicel PH101 (Fluka) hydrolysis measurements, 0.3 µg of purified CBH II was incubated with 3 mg of Avicel in 270 µL of 50 mM sodium acetate, pH 4.8, in PCR tubes placed in a water bath for 16 hours. Tubes were cooled in a room temperature water bath for 10 minutes, centrifuged at 1000 g for 10 minutes and supernatants withdrawn for reducing sugar analysis.

For estimation of CBH II activity in YPD expression culture supernatants, supernatant volumes ranging from 2 mL to 40 mL were added to 800 µL of 33 mg/mL Avicel suspended in 50 mM sodium acetate, pH 4.8 in conical tubes. CBH IIs were allowed to bind Avicel at 4° C. for one hour, centrifuged at 2000 g for 2 minutes and washed twice with 50 mM sodium acetate, pH 4.8. After the second wash, CBH II-bound Avicel was resuspended in 2.75 mL of sodium acetate buffer, split into 270 µL aliquots and incubated at 50° C. for 2.5 hours. Centrifugation and supernatant reducing sugar analysis were carried out as above.

The Linear Regression package in Mathematica was used to fit CBH II chimera $T_{50}$ data to a 17-parameter, block additive model and was also used for cross validation analysis. Block effects are reported relative to a parent 1 (*H. insolens* CBH II) reference state with 16 parameters representing substitution of each of the 8 blocks from parents 2 and 3.

Values of $T_{50}$, defined here as the temperature at which an enzyme loses 50% of its activity during a ten-minute incubation, were determined for the three parent cellobiohydrolases, 33 active CBH II chimeras from prior experiments and 18 additional chimeras that qualitative stability modeling predicted to be among the most thermostable, i.e. containing none of the 7 predicted destabilizing blocks and either 3 or 4 of the 4 predicted stabilizing blocks. All 51 chimera sequences are listed in Table 8. Re-culturing and re-concentrating all of the predicted thermostable chimeras previously classified as not secreted allowed for the obtaining of sufficient amounts of 12112132, 13111132 and 13322332 CBH IIs for $T_{50}$ determination. The complete set of $T_{50}$ values for the chimeras and parent CBH IIs is provided in Table 8. The amino acid sequences for all these CBH IIs appear in Table 7. All 31 predicted thermostable chimeras tested have $T_{50}$ values more than two degrees higher than that of the most thermostable parent enzyme (64.8° C.). The table also identifies the Cys residue in block/domain 7 that can be mutated to a Ser to provide increased thermostability. Accordingly, the disclosure provides polypeptide of any of the following sequences wherein the underlined/italicized/bold Cys is substituted with a Ser residue and wherein the resulting polypeptide has improved thermostability compared to a wild-type enzyme.

TABLE 7

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, (SEQ ID NO: 8)
CSSVWGQCGGQNWSGPTCCASGSTCVYSNDYYSQCLPGAASSSSSTRAASTTSRVSPTTSRSSSATPP
PGSTTTRVPPVGSGTATYS.

Parent 1 (*H. insolens*)

(SEQ ID NO: 2)
GNPFEGVQLWANNYYRSEVHTLAIPQITDPALRAAASAVAEVPSFQWLDRNVTVDTLLVQTLSEIREA
NQAGANPQYAAQIVVYDLPDRDCAAAASNGEWAIANNGVNNYKAYINRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSVSSPPPYTSPNPNYDEKHYIEAFRPLLEARGFPAQFIVDQGRSGKQP
TGQKEWGHWCNAIGTGFGMRPTANTGHQYVDAFVWVKPGGE*C*DGTSDTTAARYDYHCGLEDALKPAPE
AGQWFNEYFIQLLRNANPPF

Parent 2 (*H. jecorina*)

(SEQ ID NO: 4)
GNPFVGVTPWANAYYASEVSSLAIPSLTGAMATAAAAVAKVPSFMWLDTLDKTPLMEQTLADIRTANK
NGGNYAGQFVVYDLPDRDCAALASNGEYSIADGGVAKYKNYIDTIRQIVVEYSDIRTLLVIEPDSLAN
LVTNLGTPKCANAQSAYLECINYAVTQLNLPNVAMYLDAGHAGWLGWPANQDPAAQLFANVYKNASSP
RALRGLATNVANYNGWNITSPPSYTQGNAVYNEKLYIHAIGPLLANHGWSNAFFITDQGRSGKQPTGQ
QQWGDWCNVIGTGFGIRPSANTGDSLLDSFVWVKPGGE*C*DGTSDSSAPRFDSHCALPDALQPAPQAGA
WFQAYFVQLLTNANPSFL

Parent 3 (*C. thermophilum*)

(SEQ ID NO: 6)
GNPFSGVQLWANTYYSSEVHTLAIPSLSPELAAKAAKVAEVPSFQWLDRNVTVDTLFSGTLAEIRAAN
QRGANPPYAGIFVVYDLPDRDCAAAASNGEWSIANNGANNYKRYIDRIRELLIQYSDIRTILVIEPDS
LANMVTNMNVQKCSNAASTYKELTVYALKQLNLPHVAMYMDAGHAGWLGWPANIQPAAELFAQIYRDA
GRPAAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTSAARYDYHCGLSDALTPAPEA
GQWFQAYFEQLLINANPPF

*P. chrysosporium* CBH II (SEQ ID NO: 12)
NNPWTGFQIFLSPYYANEVAAAAKQITDPTLSSKAASVANIPTFTWLDSVAKIPDLGTYLASASALGK
STGTKQLVQIVIYDLPDRDCAAKASNGEFSIANNGQANYENYIDQIVAQIQQFPDVRVVAVIEPDSLA
NLVTNLNVQKCANAKTTYLACVNYALTNLAKVGVYMYMDAGHAGWLGWPANLSPAAQLFTQVWQNAGK
SPFIKGLATNVANYNALQAASPDPITQGNPNYDEIHYINALAPLLQQAGWDATFIVDQGRSGVQNIRQ
QWGDWCNIKGAGFGTRPTTNTGSQFIDSIVWVKPGGE*C*DGTSNSSSPRYDSTCSLPDAAQPAPEAGTW
FQAYFQTLVSAANPPL

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, 32333113
(SEQ ID NO: 13)
GNPFSGVQLWANTYYSSEVHTLAIPSLSPELAAKAAKVAEVPSFMWLDTLDKTPLMEQTLADIRTANK
NGANPPYAGIFVVYDLPDRDCAAAASNGEWSIANNGANNYKRYIDRIRELLIQYSDIRTILVIEPDSL
ANMVTNMNVQKCSNAASTYKELTVYALKQLNLPHVAMYMDAGHAGWLGWPANIQPAAELFAQIYRDAG
RPAAVRGLATNVANYNAWSVSSPPPYTSPNPNYDEKHYIEAFRPLLEARGFPAQFIVDQGRSGKQPTG
QKEWGHWCNAIGTGFGMRPTANTGHQYVDAFVWVKPGGE*c*DGTSDTSAARYDYHCGLSDALTPAPEAG
QWFQAYFEQLLINANPPF 13111313
(SEQ ID NO: 14)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFDAQFIVDQGRSGKQP
TGQKEWGHWCNAIGTGFGMRPTANTGHQYVDAFVWVKPGGE*c*DGTSDTSAARYDYHCGLSDALTPAPE
AGQWFQAYFEQLLINANPPF 11313121
(SEQ ID NO: 15)
GNPFEGVQLWANNYYRSEVHTLAIPQITDPALRAAASAVAEVPSFQWLDRNVTVDTLLVQTLSEIREA
NQAGANPPYAGIFVVYDLPDRDCAAAASNGEWSIANNGANNYKRYIDRIREILISFSDVRTILVIEPD
SLANMVTNMNVPKCSGAASTYKELTVYALKQLNLPHVAMYMDAGHAGWLGWPANIQPAAELFAQIYRD
AGRPAAVRGLATNVANYNAWSVSSPPPYTSPNPNYDEKHYIEAFRPLLEARGFPNAFFITDQGRSGKQ
PTGQQQWGDWCNVIGTGFGIRPSANTGDSLLDSFVWVKPGGE*c*DGTSDTTAARYDYHCGLEDALKPAP
EAGQWFNEYFIQLLRNANPPF 21131311
(SEQ ID NO: 16)
GNPFVGVTPWANAYYASEVSSLAIPSLTGAMATAAAAVAKVPSFQWLDRNVTVDTLLVQTLSEIREAN
QAGANPQYAAQIVVYDLPDRDCAAAASNGEWAIANNGVNNYKAYINRIRELLIQYSDIRTILVIEPDS
LANMVTNMNVQKCSNAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAQFIVDQGRSGKQPT
GQKEWGHWCNAIGTGFGMRPTANTGHQYVDAFVWVKPGGE*c*DGTSDTTAARYDYHCGLEDALKPAPEA
GQWFNEYFIQLLRNANPPF 31212111
(SEQ ID NO: 17)
GNPFSGVQLWANTYYSSEVHTLAIPSLSPELAAKAAKVAEVPSFQWLDRNVTVDTLLVQTLSEIREAN
QAGGNYAGQFVVYDLPDRDCAALASNGEYSIADGGVAKYKNYIDRIREILISFSDVRTILVIEPDSLA
NMVTNMNVPKCSGAASAYLECINYAVTQLNLPNVAMYLDAGHAGWLGWPANQDPAAQLFANVYKNASS
PRALRGLATNVANYNAWSVSSPPPYTSPNPNYDEKHYIEAFRPLLEARGFPAQFIVDQGRSGKQPTGQ
KEWGHWCNAIGTGFGMRPTANTGHQYVDAFVWVKPGGE*c*DGTSDTTAARYDYHCGLEDALKPAPEAGQ
WFNEYFIQLLRNANPPF 23233133
(SEQ ID NO: 18)
GNPFVGVTPWANAYYASEVSSLAIPSLTGAMATAAAAVAKVPSFQWLDRNVTVDTLFSGTLAEIRAAN
QRGGNYAGQFVVYDLPDRDCAALASNGEYSIADGGVAKYKNYIDRIRELLIQYSDIRTILVIEPDSLA
NMVTNMNVQKCSNAASTYKELTVYALKQLNLPHVAMYMDAGHAGWLGWPANIQPAAELFAQIYRDAGR
PAAVRGLATNVANYNAWSVSSPPPYTSPNPNYDEKHYIEAFRPLLEARGFPAKFIVDTGRNGKQPTGQ
LEWGHWCNVKGTGFGVRPTANTGHELVDAFVWVKPGGESDGTSDTSAARYDYHCGLSDALTPAPEAGQ
WFQAYFEQLLINANPPF 31311112
(SEQ ID NO: 19)
GNPFSGVQLWANTYYSSEVHTLAIPSLS_PELAAKAAKVAEVPSFQWLDRNVTVDTLLVQTLSEIREA
NQAGANPPYAGIFVVYDLPDRDCAAAASNGEWSIANNGANNYKRYIDRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSVSSPPPYTSPNPNYDEKHYIEAFRPLLEARGFP_AQFIVDQGRSGKQ
PTGQKEWGHWCNAIGTGFGMRPTANTGHQYVDAFVWVKPGGE*c*DGTSDSSAPRFDSHCALPDALQPAP
QAGAWFQAYFVQLLTNANPSFL 22212231
(SEQ ID NO: 20)
GNPFVGVTPWANAYYASEVSSLAIPSLTGAMATAAAAVAKVPSFMWLDTLDKTPLMEQTLADIRTANK
NGGNYAGQFVVYDLPDRDCAALASNGEYSIADGGVAKYKNYIDRIREILISFSDVRTILVIEPDSLAN
MVTNMNVPKCSGAASAYLECINYAVTQLNLPNVAMYLDAGHAGWLGWPANQDPAAQLFANVYKNASSP
RALRGLATNVANYNGWNITSPPSYTQGNAVYNEKLYIHAIGPLLANHGWS_AKFIVDTGRNGKQPTGQ
LEWGHWCNVKGTGFGVRPTANTGHELVDAFVWVKPGGESDGTSDTTAARYDYHCGLEDALKPAPEAGQ
WFNEYFIQLLRNANPPF

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, 13231111
(SEQ ID NO: 21)
GNPFEGVQLWANNYYRSEVHTLAIPQITDPALRAAASAVAEVPSFQWLDRNVTVDTLFSGTLAEIRAA
NQRGGNYAGQFVVYDLPDRDCAALASNGEYSIADGGVAKYKNYIDRIRELLIQYSDIRTILVIEPDSL
ANMVTNMNVQKCSNAASTYRELTIYALKQLDLPHVAMYMDAGHAGWLGWPANIQPAAELFAKIYEDAG
KPRAVRGLATNVANYNAWSVSSPPPYTSPNPNYDEKHYIEAFRPLLEARGFPAQFIVDQGRSGKQPTG
QKEWGHWCNAIGTGFGMRPTANTGHQYVDAFVWVKPGGEcDGTSDTTAARYDYHCGLEDALKPAPEAG
QWFNEYFIQLLRNANPPF 12213111
(SEQ ID NO: 22)
GNPFEGVQLWANNYYRSEVHTLAIPQITDPALRAAASAVAEVPSFMWLDTLDKTPLMEQTLADIRTAN
KNGGNYAGQFVVYDLPDRDCAALASNGEYSIADGGVAKYKNYIDRIREILISFSDVRTILVIEPDSLA
NMVTNMNVPKCSGAASTYKELTVYALKQLNLPHVAMYMDAGHAGWLGWPANIQPAAELFAQIYRDAGR
PAAVRGLATNVANYNAWSVSSPPPYTSPNPNYDEKHYIEAFRPLLEARGFPAQFIVDQGRSGKQPTGQ
KEWGHWCNAIGTGFGMRPTANTGHQYVDAFVWVKPGGEcDGTSDTTAARYDYHCGLEDALKPAPEAGQ
WFNEYFIQLLRNANPPF 12133333
(SEQ ID NO: 23)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIRELLIQYSDIRTILVIEPDS
LANMVTNMNVQKCSNAASTYKELTVYALKQLNLPHVAMYMDAGHAGWLGWPANIQPAAELFAQIYRDA
GRPAAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTSAARYDYHCGLSDALTPAPEA
GQWFQAYFEQLLINANPPF 33133132
(SEQ ID NO: 24)
GNPFSGVQLWANTYYSSEVHTLAIPSLSPELAAKAAKVAEVPSFQWLDRNVTVDTLFSGTLAEIRAAN
QRGANPQYAAQIVVYDLPDRDCAAAASNGEWAIANNGVNNYKAYINRIRELLIQYSDIRTILVIEPDS
LANMVTNMNVQKCSNAASTYKELTVYALKQLNLPHVAMYMDAGHAGWLGWPANIQPAAELFAQIYRDA
GRPAAVRGLATNVANYNAWSVSSPPPYTSPNPNYDEKHYIEAFRPLLEARGFPAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL 11332333
(SEQ ID NO: 25)
GNPFEGVQLWANNYYRSEVHTLAIPQITDPALRAAASAVAEVPSFQWLDRNVTVDTLLVQTLSEIREA
NQAGANPPYAGIFVVYDLPDRDCAAAASNGEWSIANNGANNYKRYIDRIRELLIQYSDIRTILVIEPD
SLANMVTNMNVQKCSNAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDTSAARYDYHCGLSDALTPAPE
AGQWFQAYFEQLLINANPPF 23311333
(SEQ ID NO: 26)
GNPFVGVTPWANAYYASEVSSLAIPSLTGAMATAAAAVAKVPSFQWLDRNVTVDTLFSGTLAEIRAAN
QRGANPPYAGIFVVYDLPDRDCAAAASNGEWSIANNGANNYKRYIDRIREILISFSDVRTILVIEPDS
LANMVTNMNVPKCSGAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTSAARYDYHCGLSDALTPAPEA
GQWFQAYFEQLLINANPPF 33213332
(SEQ ID NO: 27)
GNPFSGVQLWANTYYSSEVHTLAIPSLSPELAAKAAKVAEVPSFQWLDRNVTVDTLFSGTLAEIRAAN
QRGGNYAGQFVVYDLPDRDCAALASNGEYSIADGGVAKYKNYIDRIREILISFSDVRTILVIEPDSLA
NMVTNMNVPKCSGAASTYKELTVYALKQLNLPHVAMYMDAGHAGWLGWPANIQPAAELFAQIYRDAGR
PAAVRGLATNVANYNAWSIASPPSYTSPNPNYDEKHYIEAFAPLLRNQGFDAKFIVDTGRNGKQPTGQ
LEWGHWCNVKGTGFGVRPTANTGHELVDAFVWVKPGGESDGTSDSSAPRFDSHCALPDALQPAPQAGA
WFQAYFVQLLTNANPSFL 13333232
(SEQ ID NO: 28)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIRELLIQYSDIRTILVIEPD
SLANMVTNMNVQKCSNAASTYKELTVYALKQLNLPHVAMYMDAGHAGWLGWPANIQPAAELFAQIYRD
AGRPAAVRGLATNVANYNGWNITSPPSYTQGNAVYNEKLYIHAIGPLLANHGWS_AKFIVDTGRNGKQ
PTGQLEWGHWCNVKGTGFGVRPTANTGHELVDAFVWVKPGGESDGTSDSSAPRFDSHCALPDALQPAP
QAGAWFQAYFVQLLTNANPSFL

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II,

22232132

(SEQ ID NO: 29)
GNPFVGVTPWANAYYASEVSSLAIPSLTGAMATAAAAVAKVPSFMWLDTLDKTPLMEQTLADIRTANK
NGGNYAGQFVVYDLPDRDCAALASNGEYSIADGGVAKYKNYIDRIRELLIQYSDIRTILVIEPDSLAN
MVTNMNVQKCSNAASAYLECINYAVTQLNLPNVAMYLDAGHAGWLGWPANQDPAAQLFANVYKNASSP
RALRGLATNVANYNAWSVSSPPPYTSPNPNYDEKHYIEAFRPLLEARGFPAKFIVDTGRNGKQPTGQL
EWGHWCNVKGTGFGVRPTANTGHELVDAFVWVKPGGESDGTSDSSAPRFDSHCALPDALQPAPQAGAW
FQAYFVQLLTNANPSFL

11113132

(SEQ ID NO: 30)
GNPFEGVQLWANNYYRSEVHTLAIPQITDPALRAAASAVAEVPSFQWLDRNVTVDTLLVQTLSEIREA
NQAGANPQYAAQIVVYDLPDRDCAAAASNGEWAIANNGVNNYKAYINRIREILISFSDVRTILVIEPD
SLANMVTNMNVPKCSGAASTYKELTVYALKQLNLPHVAMYMDAGHAGWLGWPANIQPAAELFAQIYRD
AGRPAAVRGLATNVANYNAWSVSSPPPYTSPNPNYDEKHYIEAFRPLLEARGFPAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

21333331

(SEQ ID NO: 31)
GNPFVGVTPWANAYYASEVSSLAIPSLTGAMATAAAAVAKVPSFQWLDRNVTVDTLLVQTLSEIREAN
QAGANPPYAGIFVVYDLPDRDCAAAASNGEWSIANNGANNYKRYIDRIRELLIQYSDIRTILVIEPDS
LANMVTNMNVQKCSNAASTYKELTVYALKQLNLPHVAMYMDAGHAGWLGWPANIQPAAELFAQIYRDA
GRPAAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF

21311131

(SEQ ID NO: 32)
GNPFVGVTPWANAYYASEVSSLAIPSLTGAMATAAAAVAKVPSFQWLDRNVTVDTLLVQTLSEIREAN
QAGANPPYAGIFVVYDLPDRDCAAAASNGEWSIANNGANNYKRYIDRIREILISFSDVRTILVIEPDS
LANMVTNMNVPKCSGAASTYRELTIYALKQLDLPHVAMYMDAGHAGWLGWPANIQPAAELFAKIYEDA
GKPRAVRGLATNVANYNAWSVSSPPPYTSPNPNYDEKHYIEAFRPLLEARGFPAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF

12332331

(SEQ ID NO: 33)
GNPFEGVQLWANNYYRSEVHTLAIPQITDPALRAAASAVAEVPSFMWLDTLDKTPLMEQTLADIRTAN
KNGANPPYAGIFVVYDLPDRDCAAAASNGEWSIANNGANNYKRYIDRIRELLIQYSDIRTILVIEPDS
LANMVTNMNVQKCSNAASAYLECINYAVTQLNLPNVAMYLDAGHAGWLGWPANQDPAAQLFANVYKNA
SSPRALRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF

13112332

(SEQ ID NO: 34)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIREILISFSDVRTILVIEPD
SLANMVTNMNVPKCSGAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

22311331

(SEQ ID NO: 35)
GNPFVGVTPWANAYYASEVSSLAIPSLTGAMATAAAAVAKVPSFMWLDTLDKTPLMEQTLADIRTANK
NGANPPYAGIFVVYDLPDRDCAAAASNGEWSIANNGANNYKRYIDRIREILISFSDVRTILVIEPDSL
ANMVTNMNVPKCSGAASTYRELTIYALKQLDLPHVAMYMDAGHAGWLGWPANIQPAAELFAKIYEDAG
KPRAVRGLATNVANYNAWSIASPPSYTSPNPNYDEKHYIEAFAPLLRNQGFDAKFIVDTGRNGKQPTG
QLEWGHWCNVKGTGFGVRPTANTGHELVDAFVWVKPGGESDGTSDTTAARYDYHCGLEDALKPAPEAG
QWFNEYFIQLLRNANPPF

12111332

(SEQ ID NO: 36)
GNPFEGVQLWANNYYRSEVHTLAIPQITDPALRAAASAVAEVPSFMWLDT_LDKTPLMEQTLADIRTA
NKNGANPQYAAQIVVYDLPDRDCAAAASNGEWAIANNGVNNYKAYINRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFD_AKFIVDTGRNGKQ
PTGQLEWGHWCNVKGTGFGVRPTANTGHELVDAFVWVKPGGESDGTSDSSAPRFDSHCALPDALQPAP
QAGAWFQAYFVQLLTNANPSFL

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, 12112332 (SEQ ID NO: 37)
GNPFEGVQLWANNYYRSEVHTLAIPQITDPALRAAASAVAEVPSFMWLDT_LDKTPLMEQTLADIRTA
NKNGANPQYAAQIVVYDLPDRDCAAAASNGEWAIANNGVNNYKAYINRIREILISFSDVRTILVIEPD
SLANMVTNMNVPKCSGAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFD_AKFIVDTGRNGKQ
PTGQLEWGHWCNVKGTGFGVRPTANTGHELVDAFVWVKPGGESDGTSDSSAPRFDSHCALPDALQPAP
QAGAWFQAYFVQLLTNANPSFL 12131331 (SEQ ID NO: 38)
GNPFEGVQLWANNYYRSEVHTLAIPQITDPALRAAASAVAEVPSFMWLDTLDKTPLMEQTLADIRTA
KNGANPQYAAQIVVYDLPDRDCAAAASNGEWAIANNGVNNYKAYINRIRELLIQYSDIRTILVIEPDS
LANMVTNMNVQKCSNAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF 12131332 (SEQ ID NO: 39)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIRELLIQYSDIRTILVIEPDS
LANMVTNMNVQKCSNAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL 12332332 (SEQ ID NO: 40)
GNPFEGVQLWANNYYRSEVHTLAIPQITDPALRAAASAVAEVPSFMWLDTLDKTPLMEQTLADIRTAN
KNGANPPYAGIFVVYDLPDRDCAAAASNGEWSIANNGANNYKRYIDRIRELLIQYSDIRTILVIEPDS
LANMVTNMNVQKCSNAASAYLECINYAVTQLNLPNVAMYLDAGHAGWLGWPANQDPAAQLFANVYKNA
SSPRALRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL 12111131 (SEQ ID NO: 41)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIREILISFSDVRTILVIEPDS
LANMVTNMNVPKCSGAASTYRELTIYALKQLDLPHVAMYMDAGHAGWLGWPANIQPAAELFAKIYEDA
GKPRAVRGLATNVANYNAWSVSSPPPYTSPNPNYDEKHYIEAFRPLLEARGFPAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF 12311332 (SEQ ID NO: 42)
GNPFEGVQLWANNYYRSEVHTLAIPQITDPALRAAASAVAEVPSFMWLDTLDKTPLMEQTLADIRTAN
KNGANPPYAGIFVVYDLPDRDCAAAASNGEWSIANNGANNYKRYIDRIREILISFSDVRTILVIEPDS
LANMVTNMNVPKCSGAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL 13332331 (SEQ ID NO: 43)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIRELLIQYSDIRTILVIEPD
SLANMVTNMNVQKCSNAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDTTAARYDYHCGLEDALKPAPE
AGQWFNEYFIQLLRNANPPF 12132331 (SEQ ID NO: 44)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIRELLIQYSDIRTILVIEPDS
LANMVTNMNVQKCSNAASAYLECINYAVTQLNLPNVAMYLDAGHAGWLGWPANQDPAAQLFANVYKNA
SSPRALRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDTTAARYDYHCGLEDALKPAPEA
GQWFNEYFIQLLRNANPPF

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II,

12132332

(SEQ ID NO: 45)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIRELLIQYSDIRTILVIEPDS
LANMVTNMNVQKCSNAASAYLECINYAVTQLNLPNVAMYLDAGHAGWLGWPANQDPAAQLFANVYKNA
SSPRALRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL

13332332

(SEQ ID NO: 46)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIRELLIQYSDIRTILVIEPD
SLANMVTNMNVQKCSNAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

12112132

(SEQ ID NO: 47)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIREILISFSDVRTILVIEPDS
LANMVTNMNVPKCSGAASAYLECINYAVTQLNLPNVAMYLDAGHAGWLGWPANQDPAAQLFANVYKNA
SSPRALRGLATNVANYNAWSVSSPPPYTSPNPNYDEKHYIEAFRPLLEARGFPAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL

13322332

(SEQ ID NO: 48)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDTIRQIVVEYSDIRTLLVIEPD
SLANLVTNLGTPKCANAQSAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

13131332

(SEQ ID NO: 49)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIRELLIQYSDIRTILVIEPD
SLANMVTNMNVQKCSNAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

12331332

(SEQ ID NO: 50)
GNPFEGVQLWANNYYRSEVHTLAIPQITDPALRAAASAVAEVPSFMWLDTLDKTPLMEQTLADIRTAN
KNGANPPYAGIFVVYDLPDRDCAAAASNGEWSIANNGANNYKRYIDRIRELLIQYSDIRTILVIEPDS
LANMVTNMNVQKCSNAASTYRELTIYALKQLDLPHVAMYMDAGHAGWLGWPANIQPAAELFAKIYEDA
GKPRAVRGLATNVANYNAWSIASPPSYTSPNPNYDEKHYIEAFAPLLRNQGFDAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL

13312332

(SEQ ID NO: 51)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIREILISFSDVRTILVIEPD
SLANMVTNMNVPKCSGAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

11113332

(SEQ ID NO: 52)
GNPFEGVQLWANNYYRSEVHTLAIPQITDPALRAAASAVAEVPSFQWLDRNVTVDTLLVQTLSEIREA
NQAGANPQYAAQIVVYDLPDRDCAAAASNGEWAIANNGVNNYKAYINRIREILISFSDVRTILVIEPD
SLANMVTNMNVPKCSGAASTYKELTVYALKQLNLPHVAMYMDAGHAGWLGWPANIQPAAELFAQIYRD
AGRPAAVRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL

TABLE 7-continued

Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, 13113132
(SEQ ID NO: 53)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIREILISFSDVRTILVIEPD
SLANMVTNMNVPKCSGAASTYKELTVYALKQLNLPHVAMYMDAGHAGWLGWPANIQPAAELFAQIYRD
AGRPAAVRGLATNVANYNAWSVSSPPPYTSPNPNYDEKHYIEAFRPLLEARGFPAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL 11112132
(SEQ ID NO: 54)
GNPFEGVQLWANNYYRSEVHTLAIPQITDPALRAAASAVAEVPSFQWLDRNVTVDTLLVQTLSEIREA
NQAGANPQYAAQIVVYDLPDRDCAAAASNGEWAIANNGVNNYKAYINRIREILISFSDVRTILVIEPD
SLANMVTNMNVPKCSGAASAYLECINYAVTQLNLPNVAMYLDAGHAGWLGWPANQDPAAQLFANVYKN
ASSPRALRGLATNVANYNAWSVSSPPPYTSPNPNYDEKHYIEAFRPLLEARGFP_AKFIVDTGRNGKQ
PTGQLEWGHWCNVKGTGFGVRPTANTGHELVDAFVWVKPGGESDGTSDSSAPRFDSHCALPDALQPAP
QAGAWFQAYFVQLLTNANPSFL 12113132
(SEQ ID NO: 55)
GNPFEGVQLWANNYYRSEVHTLAIPQITDPALRAAASAVAEVPSFMWLDTLDKTPLMEQTLADIRTAN
KNGANPQYAAQIVVYDLPDRDCAAAASNGEWAIANNGVNNYKAYINRIREILISFSDVRTILVIEPDS
LANMVTNMNVPKCSGAASTYKELTVYALKQLNLPHVAMYMDAGHAGWLGWPANIQPAAELFAQIYRDA
GRPAAVRGLATNVANYNAWSVSSPPPYTSPNPNYDEKHYIEAFRPLLEARGFPAKFIVDTGRNGKQPT
GQLEWGHWCNVKGTGFGVRPTANTGHELVDAFVWVKPGGESDGTSDSSAPRFDSHCALPDALQPAPQA
GAWFQAYFVQLLTNANPSFL 13132332
(SEQ ID NO: 56)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIRELLIQYSDIRTILVIEPD
SLANMVTNMNVQKCSNAASAYLECINYAVTQLNLPNVAMYLDAGHAGWLGWPANQDPAAQLFANVYKN
ASSPRALRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL 11111132
(SEQ ID NO: 57)
GNPFEGVQLWANNYYRSEVHTLAIPQITDPALRAAASAVAEVPSFQWLDRNVTVDTLLVQTLSEIREA
NQAGANPQYAAQIVVYDLPDRDCAAAASNGEWAIANNGVNNYKAYINRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSVSSPPPYTSPNPNYDEKHYIEAFRPLLEARGFPAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL 13331332
(SEQ ID NO: 58)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIRELLIQYSDIRTILVIEPD
SLANMVTNMNVQKCSNAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL 13111132
(SEQ ID NO: 59)
GNPFEGVQLWANNYYRSEVHTLAIPQITDPALRAAASAVAEVPSFQWLDRNVTVDTLFSGTLAEIRAA
NQRGANPQYAAQIVVYDLPDRDCAAAASNGEWAIANNGVNNYKAYINRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSVSSPPPYTSPNPNYDEKHYIEAFRPLLEARGFP_AKFIVDTGRNGKQ
PTGQLEWGHWCNVKGTGFGVRPTANTGHELVDAFVWVKPGGESDGTSDSSAPRFDSHCALPDALQPAP
QAGAWFQAYFVQLLTNANPSFL 12222132
(SEQ ID NO: 60)
GNPFEGVQLWANNYYRSEVHTLAIPQITDPALRAAASAVAEVPSFMWLDTLDKTPLMEQTLADIRTAN
KNGGNYAGQFVVYDLPDRDCAALASNGEYSIADGGVAKYKNYIDTIRQIVVEYSDIRTLLVIEPDSLA
NLVTNLGTPKCANAQSAYLECINYAVTQLNLPNVAMYLDAGHAGWLGWPANQDPAAQLFANVYKNASS
PRALRGLATNVANYNAWSVSSPPPYTSPNPNYDEKHYIEAFRPLLEARGFPAKFIVDTGRNGKQPTGQ
LEWGHWCNVKGTGFGVRPTANTGHELVDAFVWVKPGGESDGTSDSSAPRFDSHCALPDALQPAPQAGA
WFQAYFVQLLTNANPSFL TABLE 7-continued Amino acid sequences for CBH II parent and chimera catalytic domains shown in Table 8. Table also includes catalytic domain for *P. chrysosporium* CBH II. All recombinant CBH IIs share the N-terminal CBM and linker from the native *H. jecorina* CBH II, 12222332
(SEQ ID NO: 61)
GNPFEGVQLWANNYYRSEVHTLAIPQITDPALRAAASAVAEVPSFMWLDTLDKTPLMEQTLADIRTAN
KNGGNYAGQFVVYDLPDRDCAALASNGEYSIADGGVAKYKNYIDTIRQIVVEYSDIRTLLVIEPDSLA
NLVTNLGTPKCANAQSAYLECINYAVTQLNLPNVAMYLDAGHAGWLGWPANQDPAAQLFANVYKNASS
PRALRGLATNVANYNAWSIASPPSYTSPNPNYDEKHYIEAFAPLLRNQGFDAKFIVDTGRNGKQPTGQ
LEWGHWCNVKGTGFGVRPTANTGHELVDAFVWVKPGGESDGTSDSSAPRFDSHCALPDALQPAPQAGA
WFQAYFVQLLTNANPSFL 13311332
(SEQ ID NO: 62)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFDAKFIVDTGRNGKQP
TGQLEWGHWCNVKGTGFGVRPTANTGHELVDAFVWVKPGGESDGTSDSSAPRFDSHCALPDALQPAPQ
AGAWFQAYFVQLLTNANPSFL 13311331
(SEQ ID NO: 63)
GNPFEGVQLWANNYYRSEVHTLAIPQITDPALRAAASAVAEVPSFQWLDRNVTVDTLFSGTLAEIRAA
NQRGANPPYAGIFVVYDLPDRDCAAAASNGEWSIANNGANNYKRYIDRIREILISFSDVRTILVIEPD
SLANMVTNMNVPKCSGAASTYRELTIYALKQLDLPHVAMYMDAGHAGWLGWPANIQPAAELFAKIYED
AGKPRAVRGLATNVANYNAWSIASPPSYTSPNPNYDEKHYIEAFAPLLRNQGFD_AKFIVDTGRNGKQ
PTGQLEWGHWCNVKGTGFGVRPTANTGHELVDAFVWVKPGGESDGTSDTTAARYDYHCGLEDALKPAP
EAGQWFNEYFIQLLRNANPPF

TABLE 8

Two independent duplicate $T_{50}$ values (° C.) for parent CBH IIs, 23 original sample set CBH II chimeras and predicted thermostable CBH II chimeras.

| Sample Set Chimeras & Parents | | | | Predicted Thermostable Chimeras | | | |
| --- | --- | --- | --- | --- | --- | --- | --- |
| Sequence | $T_{50}(1)$ | $T_{50}(2)$ | Mean$T_{50}$ | Sequence | $T_{50}(1)$ | $T_{50}(2)$ | Mean$T_{50}$ |
| 32333113 | 52 | 51 | 51.5 | 12332331 | 66.5 | 67 | 66.8 |
| 13111313 | 56 | 53.5 | 54.8 | *13112332 | 67 | 67 | 67 |
| 11313121 | 55 | 55.5 | 55.3 | 22311331 | 68 | 68 | 68 |
| 21131311 | 57.5 | 57 | 57.3 | *12111332 | 68 | 68 | 68 |
| 31212111 | 59 | 58 | 58.5 | *12112332 | 68.5 | 67.5 | 68 |
| Parent 2 | 60 | 58 | 59 | 12131331 | 68.5 | 69 | 68.8 |
| 23233133 | 61 | 61 | 61 | *12131332 | 70 | 67.5 | 68.8 |
| 31311112 | 60 | 62 | 61 | *12332332 | 69 | 69 | 69 |
| 22212231 | 63 | 61 | 62 | 12111131 | 70 | 68.5 | 69.3 |
| 13231111 | 63 | 6.5 | 63.3 | 12311332 | 70 | 69 | 69.5 |
| 12213111 | 63 | 63.5 | 63.3 | 13332331 | 70 | 69 | 69.5 |
| Parent 3 | 63.5 | 64.5 | 64 | 12132331 | 70.5 | 69 | 69.8 |
| 12133333 | 64 | 64 | 64 | *12132332 | 70.5 | 69 | 69.8 |
| Parent 1 | 64 | 65.5 | 64.8 | *13332332 | 69.5 | 70 | 69.8 |
| 33133132 | 65 | 66 | 65 | 12112132 | 71 | 68.5 | 69.8 |
| 11332333 | 64.5 | 66 | 65.3 | 13322332 | 71 | 68.5 | 69.8 |
| 23311333 | 65 | 66 | 65.5 | *13131332 | 70 | 70 | 70 |
| 33213332 | 66 | 66 | 66 | *12331332 | 71 | 69 | 70 |
| 13333232 | 67.5 | 67 | 67.3 | *13312332 | 70 | 70 | 70 |
| 22232132 | 68 | 68 | 68 | *11113332 | 69.5 | 70.5 | 70 |
| 11113132 | 71.5 | 71 | 71.3 | *13113132 | 70.5 | 69.5 | 70 |
| 21333331 | 73.5 | 75.5 | 74.5 | *11112132 | 70.5 | 70 | 70.3 |
| 21311131 | 75.5 | 75.5 | 75 | *12113132 | 70.5 | 70.5 | 70.5 |
| | | | | *13132332 | 69.5 | 71.5 | 70.5 |
| | | | | *11111132 | 71 | 70.5 | 70.8 |
| | | | | 13331332 | 72 | 70 | 71 |
| | | | | *13111132 | 72 | 69.5 | 71.3 |
| | | | | *12222132 | 72.5 | 70 | 71.3 |
| | | | | 12222332 | 72 | 69.5 | 71.3 |
| | | | | 13311332 | 71 | 71.5 | 71.7 |
| | | | | 13311331 | 73.5 | 72.5 | 73 |

The 18 chimeras synthesized for this work are preceded by an asterisk.

Applying linear regression to the sequence-stability data resulted in a ten-parameter model that fit the observed $T_{50}$ values with $R^2=0.88$ (FIG. 8). To better estimate the predictive capacity of the regression model outside the training set, an eleven-fold cross-validation was performed resulting in a $R^2$ of 0.57, where removal of two outliers, (11313121 and 22222222) increases the cross validation $R^2$ to 0.76. The regression model model uses the most stable parent 1 (*H. insolens*) as the reference state $T_{50}$ and includes nine additional terms having p values ≤0.1. The model parameters (Table 9) show that a single block, block 7 from parent 3 (B7P3), is by far the strongest contributor to chimera thermostability relative to *H. insolens* CBH II. This block from *C. thermophilum* CBH II contributes approximately 8.5° C. to the stability of chimeras that contain it. Two of the 8 remaining blocks with p values ≤0.1 were found to make smaller stability contributions, of 1.2° C. and 2.7° C., whereas the other six decrease stability.

TABLE 9

$T_{50}$ linear regression model parameters and p-values. Parameter values with p ≤ 0.1, used to calculate the regression fit line of FIG. 1, appear in bold. Block effects are reported relative to a parent 1 (*H. insolens* CBH II) reference state with 16 parameters representing substitution of each of the 8 blocks from parents 2 and 3.

| Block | Parameter Value | p-value |
|---|---|---|
| Parent1 | 62.8 | 0.00 |
| B12 | −0.9 | 0.35 |
| B13 | −3.5 | 0.00 |
| B22 | −1.7 | 0.06 |
| B23 | −1.1 | 0.25 |
| B32 | 0.5 | 0.68 |
| B33 | 1.2 | 0.10 |
| B42 | 2.7 | 0.05 |
| B43 | 0.0 | 0.99 |
| B52 | −1.3 | 0.10 |
| B53 | −0.6 | 0.50 |
| B62 | −3.5 | 0.02 |
| B63 | −0.7 | 0.37 |
| B72 | −3.8 | 0.05 |
| B73 | 8.5 | 0.00 |
| B82 | 0.0 | 1.00 |
| B83 | −5.6 | 0.00 |

Alignment of the B7P1 and B7P3 sequences (FIG. 10) shows that block 7 differs at 10 out of 56 amino acid positions in the *H. insolens* and *C. thermophilum* enzymes. In the background of the chimera with the highest $T_{50}$ value, 21311131, each residue in B7P3 (segment 7 of parent 3 (SEQ ID NO:6)) was individually mutated to the corresponding residue in B7P1 (segment 7 of parent 1 (SEQ ID NO:2)) and determined $T_{50}$ values for each of the point mutants was obtained. A mutation, S313C, markedly altered the chimera's thermostability: this single mutation reduced the $T_{50}$ of 21311131 by approximately 10° C. (FIG. 11).

To study the effect of the reverse mutation in different backgrounds, genes for the *H. insolens* and *H. jecorina* parent CBH IIs encoding the C313S substitution (C314S in *H. insolens* and C311S in *H. jecorina*) were constructed, expressed, and the enzymes' $T_{50}$ values were determined. The stabilities of chimeras 11111131 and 22222232, in which the stabilizing B7P3 is substituted into the wildtype *H. insolens* and *H. jecorina* enzymes were also quantified. Both the B7P3 block substitution and the Cys-Ser point mutation markedly stabilized the parent CBH IIs; the largest effect was a ~8° C. increase in $T_{50}$ for *H. jecorina* CBH II containing the C311S substitution (FIG. 12). The Cys-Ser mutation was also tested in two chimeras, 31311112 and 13231111, that did not contain B7P3 as well as in a homologous CBH II (from *Phanerochaete chrysosporium*) which was not in the recombination parent set. The *P. chrysosporium* CBH II catalytic domain is only 55-56% identical to the parent CBH II catalytic domains. All of these enzymes were stabilized by the Cys-Ser substitution; the *P. chrysosporium* CBH II was stabilized by a remarkable 10° C. (FIG. 13).

Eight of the thermostable CBH II chimeras and the parent enzymes containing the equivalent C313S mutation were His6-tagged and purified so that their specific activities could be determined. As shown in Table 10A, the specific activities, as measured on amorphous cellulose (PASC) at 50° C., for these chimeras and native enzymes containing the Cys-Ser mutation are similar to those of the wildtype parents. Thus the increased thermostability does not come at the expense of specific activity.

TABLE 10A

Specific activity values (μg glucose reducing sugar equivalent/(μg CBH II enzyme × min × $10^2$)) for native, point mutant and selected thermostable chimeric CBH IIs. Error bars show standard errors, where standard error is defined as standard dev/sqrt (n), for three replicates. 2-hr reaction, 3 mg enzyme/g PASC, 50° C., 25 mM sodium acetate, pH 4.8.

| CBH II Enzyme | Specific Activity μg Reducing Sugar/ (μg Enzyme × min) × $10^2$ |
|---|---|
| *Humicola insolens* (Parent 1) | 5.3 +/− 0.5 |
| *Hypocrea jecorina* (Parent 2) | 8.4 +/− 0.4 |
| *Chaetomium thermophilum* (Parent 3) | 4.8 +/− 0.3 |
| *Phanerochaete chyrsosporium* | 7.7 +/− 0.3 |
| *Humicola insolens* C314S | 5.3 +/− 0.9 |
| *Hypocrea jecorina* C311S | 7.8 +/− 0.5 |
| *Phanerochaete chyrsosporium* C311S | 8.5 +/− 0.1 |
| HJPlus (Chimera 12222332) | 9.6 +/− 0.8 |
| Chimera 13111132 | 8.5 +/− 0.3 |
| Chimera 22222232 | 7.7 +/− 0.3 |
| Chimera 13311332 | 6.8 +/− 0.6 |
| Chimera 13311331 | 6.2 +/− 0.3 |
| Chimera 11111131 | 6.1 +/− 0.9 |
| Chimera 13112332 | 5.6 +/− 0.4 |
| Chimera 21311131 | 5.5 +/− 0.3 |
| Chimera 11113132 | 5.3 +/− 0.5 |
| Chimera 21333331 | 3.8 +/− 0.4 |

TABLE 10B total activity in both synthetic (SDCAA) and rich (YPD) expression culture media supernatants for *H. jecorina* and *H. insolens* wild type, C313S point mutant and B7P3 block susbstitution CBH IIs.

| CBH II | SDCAA (1) | SDCAA (2) | SDCAA Mean | YPD (1) | YPD (2) | YPD Mean |
|---|---|---|---|---|---|---|
| *H. jecorina* | 19 | 17 | 18 | 0.4 | 0.4 | 0.4 |
| *H. jeco* C311S | 50 | 43 | 47 | 6.1 | 5.5 | 5.9 |
| *H. jeco* B7P3 | 35 | 33 | 34 | 3.9 | 3.6 | 3.8 |
| *H. insolens* | 73 | 83 | 78 | 6.2 | 6.0 | 6.1 |
| *H. inso* C314S | 100 | 97 | 98 | 8.8 | 8.0 | 8.4 |
| *H. inso* B7P3 | 39 | 42 | 40 | 4.4 | 4.1 | 4.2 |

Values presented are μg glucose/mL cellulase activity assay per mL of expression culture supernatant CBH II equivalent added to cellulase activity assay. For SDCAA cultures, concentrated SDCAA culture supernatants were used and activity toward phosphoric acid swollen cellulose (1 mg/mL) at 50° C. for 100 minutes in 50 mM sodium acetate, pH 4.8, was measured. YPD supernatant CBH II was concentrated by binding to avicel and activity toward avicel (15 mg/mL) at 55° C. for 150 minutes in 50 mM sodium acetate, pH 4.8, was measured.

These same eight thermostable chimeras ($T_{50}$ 2-10° C. higher than the most stable parent) were then tested for activity on crystalline cellulose during a 16-hour incubation over a range of temperatures, including temperatures where the parent enzymes exhibit little or no activity. FIG. 9a shows that 7 of 8 tested thermostable chimeras were maximally active toward Avicel at 60-65° C., with all 8 chimeras retaining activity at 70° C., the highest temperature tested. In contrast, the three parent CBH IIs show maximum activity at 50° C. and are either completely or almost completely inactive at 70° C. Additionally, the seven chimeras with increased optimum activity temperatures hydrolyze significantly more Avicel than any of the parent CBH II enzymes. As shown in FIG. 9b, similar behaviors are observed for the *H. insolens* and *H. jecorina* parents containing the Cys-Ser point mutation. The Cys-Ser point mutation also increased the Avicel hydrolysis and maximum operating temperature for the *P. chrysosporium* CBH II. The P3B7 block substitution, which was made in the *H. insolens* and *H. jecorina* parents, increased both the operating temperature and hydrolysis of the *H. insolens* CBH II but, despite increasing maximum operating temperature, did not improve overall cellulose hydrolysis by the *H. jecorina* enzyme.

Low (<1 mg/L) secretion of wildtype *H. jecorina* CBH II was observed from the heterologous *S. cerevisiae* expression host. The C311S mutation in the wildtype *H. jecorina* CBH II enzyme markedly increases total secreted CBH II activity (Table 11). In synthetic (SDCAA) medium, the C311S and B7P3 substitutions increase *H. jecorina* CBH II total secreted activity by a factor of two, while in rich (YPD) medium the activity increase is tenfold. For the *H. insolens* CBH II parent, which is expressed at much higher levels than the other two parent CBH IIs, the C314S mutation increased secreted activity by a factor of ~1.5 whereas the B7P3 block substitution decreased it. Because the *H. insolens* and *H. jecorina* wildtype and Cys-Ser mutants all have similar specific activities (Table 10), the increase in total secreted cellulase activity is the result of improved secretion of the functional enzyme. A correlation between *S. cerevisiae* heterologous protein secretion and protein stability has been observed, suggesting that the increased secretion of the Cys-Ser mutant CBH IIs might reflect their higher stabilities.

TABLE 11

Specific activity values (μg glucose reducing sugar equivalent/(μg CBH II enzyme × min × $10^2$)) for native, point mutant and selected thermostable chimeric CBH IIs. Error bars show standard errors, where standard error is defined as standard dev/sqrt (n), for three replicates. 2-hr reaction, 3 mg enzyme/g PASC, 50° C., 25 mM sodium acetate, pH 4.8.

| CBH II Enzyme | Specific Activity μg Reducing Sugar/ (μg Enzyme × min) × $10^2$ |
|---|---|
| *Humicola insolens* (Parent 1) | 5.3 +/− 0.5 |
| *Hypocrea jecorina* (Parent 2) | 8.4 +/− 0.4 |
| *Chaetomium thermophilum* (Parent 3) | 4.8 +/− 0.3 |
| *Phanerochaete chyrsosporium* | 7.7 +/− 0.3 |
| *Humicola insolens* C314S | 5.3 +/− 0.9 |
| *Hypocrea jecorina* C311S | 7.8 +/− 0.5 |
| *Phanerochaete chyrsosporium* C311S | 8.5 +/− 0.1 |
| HJPlus (Chimera 12222332) | 9.6 +/− 0.8 |
| Chimera 13111132 | 8.5 +/− 0.3 |
| Chimera 22222232 | 7.7 +/− 0.3 |
| Chimera 13311332 | 6.8 +/− 0.6 |
| Chimera 13311331 | 6.2 +/− 0.3 |
| Chimera 11111131 | 6.1 +/− 0.9 |
| Chimera 13112332 | 5.6 +/− 0.4 |
| Chimera 21311131 | 5.5 +/− 0.3 |
| Chimera 11113132 | 5.3 +/− 0.5 |
| Chimera 21333331 | 3.8 +/− 0.4 |

Figure 14:
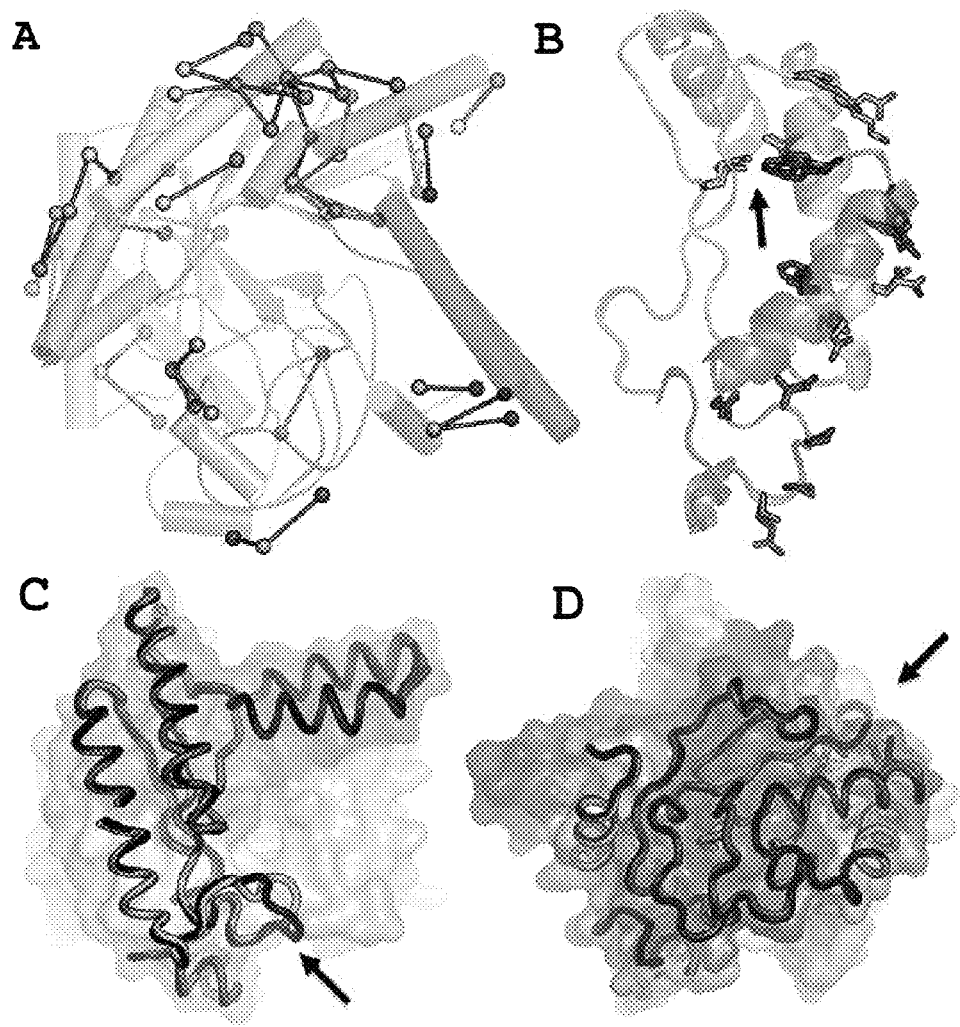

To model the Cys-Ser mutation, the high-resolution *H. insolens* CBH II 1ocn crystal structure was used. First, the hydrogen bond network was optimized with REDUCE. Cys314 was predicted to form a hydrogen bond to the carbonyl of Pro 339. To confirm this prediction, sidechain packing was optimized using the modeling platform SHARPEN. Ser314 is predicted to make the similar interactions to Cys314, resulting in stronger hydrogen bonding and a more favorable geometry (FIG. 14).

A number of effects might explain why the Cys-Ser mutation stabilizes a broad range of CBH IIs, including native CBH IIs and chimeras. Cys and Ser are similar (though not isosteric), and these two amino acids dominate sequence alignments at this position compared to other alternatives. The hydrogen bonding partners for this residue are backbone elements (the amide of Gly316 and the carbonyl of Pro339 and are therefore less likely to be dependent on third-party amino acid variations. Furthermore, the immediate neighboring side chains for this pocket (Asn283, Pro339, Phe345) are conserved among all four native CBH II cellulases studied.

The high-resolution (1.3 Å) *H. insolens* crystal structure (pdb entry 1ocn6) shows that Cys314 is part of a hydrogen bonding network (FIG. 15). The increased hydrogen bonding capacity of Ser relative to Cys may suggest a role for stronger hydrogen bonding interactions in the stabilization. The crystal structure also suggests that Ser may be preferred for steric reasons. Specifically, when the Cys side chain is rebuilt with canonical bond angles, a 6° bend is removed and Cys is pushed closer to the carbonyl of Pro339, creating an unfavorable steric interaction.

An alignment of the 196 protein sequences sharing the greatest identity to the *H. jecorina* CBH II. Fifty-four of the 250 most identical sequences were excluded from the alignment due to redundancy (i.e. point mutants for structural studies or >95% identical isoforms). There is a bias in favor of Ser311: 158 sequences have Ser, 20 have Ala, 10 have Cys, 5 have a deletion, and 3 have Gly. However, there are 42 other positions where the most frequent choice occurs with greater than twice the frequency of the *H. jecorina* amino acid.

The large stabilizing effect of the Cys-Ser mutation raises the possibility that Ser at this position is a global indicator of native cellulase thermostability. However, the $T_{50}$ of 64.8° C. for *H. insolens* CBH II, which features Cys at this position, is greater than that of the *C. thermophilum* CBH II (64.0° C.), indicating that Ser is not the only stability determinant.

Thermostability is not the only property of interest for industrial cellulases. Specific activity, changes to cellulose binding, and effects on expression and product inhibition are all important as well. The chimeras and data herein demonstrate that recombination yields CBH II chimeras whose improved thermostability comes without cost to specific activity measured in short-time (e.g., 2-hour) cellulose hydrolysis assays. Similar observations were made for CBH IIs containing the thermostabilizing Cys-Ser mutation. In long-time hydrolysis assays, several of the CBH II chimeras and all three tested Cys-Ser mutant CBH IIs hydrolyzed more cellulose than the native CBH IIs. This superior performance is likely the result of having specific activity comparable to that of the parent CBH IIs along with greater thermostability that allows the enzyme to continue to function for longer time at the elevated temperatures. Because these assays were carried out with equal amounts of purified parent, chimera and Cys-Ser mutant enzymes, the observed high temperature hydrolysis improvements are not the result of increased secretion from the *S. cerevisiae* expression host. The thermostable chimeras and the Cys-Ser mutants may therefore prove to be useful components of enzyme formulations for cellulose degradation.

While various specific embodiments have been illustrated and described, it will be appreciated that various changes can be made without departing from the spirit and scope of the invention(s).

What is claimed is:

1. A recombinant variant of a parent cellulase comprising the sequence of SEQ ID NO:2, 4, 12, or 64-66 wherein the residue corresponding to position 311 of SEQ ID NO:4 is substituted with serine in said variant, wherein the variant has cellulase activity and increased thermostability compared to the parent cellulase lacking a serine at the same position.

2. A recombinant polypeptide comprising a sequence that (i) is between 95% to 99% identical to SEQ ID NO:13 comprising a C312S; (ii) is between 95% to 100% identical to SEQ ID NO:14 comprising a C314S; (iii) is between 95% to 100% identical to SEQ ID NO:15 comprising a C315S; (vi) is between 95% to 100% identical to SEQ ID NO:16 comprising a C313S; (v) is between 95% to 100% identical to SEQ ID NO:17 comprising a C311S; (vi) is between 95% to 100% identical to SEQ ID NO:19 comprising a C313S; (vii) is between 95% to 100% identical to SEQ ID NO:21 comprising a C312S; or (viii) is between 95% to 100% identical to SEQ ID NO:22 comprising a C31 S wherein the foregoing polypeptides have cellulase activity and improved thermostability compared to their corresponding parental (wild-type) protein lacking a Cys→Ser mutation.

3. A recombinant polypeptide, comprising a sequence selected from the group consisting of:
   (a) a polypeptide having greater than 97% identity to a sequence selected from the group consisting of: (i) SEQ ID NO:13 and having a Ser at position 312, (ii) SEQ ID NO:14 and having a Ser at position 314, (iii) SEQ ID NO:15 and having a Ser at position 315, (iv) SEQ ID NO:16 and having a Ser at position 313 (v) SEQ ID NO:17 and having a Ser at position 311, (vi) SEQ ID NO:19 and having a Ser at position 313, (vii) SEQ ID NO:21 and having a Ser at position 312, and (viii) SEQ ID NO:22 and having a Ser at position 311, and wherein each of the foregoing polypeptides have cellulase activity; and (b) a chimeric polypeptide comprising at least two domains from two different parental cellobiohydrolase polypeptides, wherein the domains comprise from N- to C-terminus: (segment 1)-(segment 2)-(segment 3)-(segment 4)-(segment 5)-(segment 6)-(segment 7)-(segment 8); wherein:

segment 1 comprises a sequence that is at least 95-100% identical to amino acid residue from about 1 to about $x_1$ of SEQ ID NO:2 ("1"), SEQ ID NO:4 ("2") or SEQ ID NO:6 ("3"); segment 2 comprises a sequence that is at least 95-100% identical to amino acid residue $x_1$ to about $x_2$ of SEQ ID NO:2 ("1"), SEQ ID NO:4 ("2") or SEQ ID NO:6 ("3"); segment 3 comprises a sequence that is at least 95-100% identical to amino acid residue $x_2$ to about $x_3$ of SEQ ID NO:2 ("1"), SEQ ID NO:4 ("2") or SEQ ID NO:6 ("3"); segment 4 comprises a sequence that is at least 95-100% identical to amino acid residue $x_3$ to about $x_4$ of SEQ ID NO:2 ("1"), SEQ ID NO:4 ("2") or SEQ ID NO:6 ("3"); segment 5 comprises a sequence that is at least 95-100% identical to about amino acid residue $x_4$ to about $x_5$ of SEQ ID NO:2 ("1"), SEQ ID NO:4 ("2") or SEQ ID NO:6 ("3"); segment 6 comprises a sequence that is at least 95-100% identical to amino acid residue $x_5$ to about $x_6$ of SEQ ID NO:2 ("1"), SEQ ID NO:4 ("2") or SEQ ID NO:6 ("3"); segment 7 comprises a sequence that is at least 95-100% identical to amino acid residue $x_6$ to about $x_7$ of SEQ ID NO:2 ("1"), SEQ ID NO:4 ("2") or SEQ ID NO:6 ("3"); and segment 8 comprises a sequence that is at least 95-100% identical to amino acid residue $x_7$ to about $x_8$ of SEQ ID NO:2 ("1"), SEQ ID NO:4 ("2") or SEQ ID NO:6 ("3");

wherein $x_1$ is residue 43, 44, 45, 46, or 47 of SEQ ID NO:2, or residue 42, 43, 44, 45, or 46 of SEQ ID NO:4 or SEQ ID NO:6; $x_2$ is residue 70, 71, 72, 73, or 74 of SEQ ID NO:2, or residue 68, 69, 70, 71, 72, 73, or 74 of SEQ ID NO:4 or SEQ ID NO:6; $x_3$ is residue 113, 114, 115, 116, 117 or 118 of SEQ ID NO:2, or residue 110, 111, 112, 113, 114, 115, or 116 of SEQ ID NO:4 or SEQ ID NO:6; $x_4$ is residue 153, 154, 155, 156, or 157 of SEQ ID NO:2, or residue 149, 150, 151, 152, 153, 154, 155 or 156 of SEQ ID NO:4 or SEQ ID NO:6; $x_5$ is residue 220, 221, 222, 223, or 224 of SEQ ID NO:2, or residue 216, 217, 218, 219, 220, 221, 222 or 223 of SEQ ID NO:4 or SEQ ID NO:6; $x_6$ is residue 256, 257, 258, 259, 260 or 261 of SEQ ID NO:2, or residue 253, 254, 255, 256, 257, 258, 259 or 260 of SEQ ID NO:4 or SEQ ID NO:6; $X_7$ is residue 312, 313, 314, 315 or 316 of SEQ ID NO:2, or residue 309, 310, 311, 312, 313, 314, 315 or 318 of SEQ ID NO:4 or SEQ ID NO:6; and $x_8$ is an amino acid residue corresponding to the C-terminus of the polypeptide have the sequence of SEQ ID NO:2, SEQ ID NO:4 or SEQ ID NO:6, wherein the chimeric polypeptide comprises a Ser at position corresponding to position 314 of SEQ ID NO:2 or position 311 of SEQ ID NO:4 and wherein the chimeric polypeptide has cellulase activity and improved thermostability and/or pH stability compared to a CBH II polypeptide comprising SEQ ID NO:2, 4, or 6.

4. The recombinant polypeptide of claim 3, wherein segment 1 comprises amino acid residue from about 1 to about $x_1$ of SEQ ID NO:2 ("1"), SEQ ID NO:4 ("2") or SEQ ID NO:6 ("3"); segment 2 is from about amino acid residue $x_1$ to about $x_2$ of SEQ ID NO:2 ("1"), SEQ ID NO:4 ("2") or SEQ ID NO:6 ("3"); segment 3 is from about amino acid residue $x_2$ to about $x_3$ of SEQ ID NO:2 ("1"), SEQ ID NO:4 ("2") or SEQ ID NO:6 ("3"); segment 4 is from about amino acid residue $x_3$ to about $x_4$ of SEQ ID NO:2 ("1"), SEQ ID NO:4 ("2") or SEQ ID NO:6 ("3"); segment 5 is from about amino acid residue $x_4$ to about $x_5$ of SEQ ID NO:2 ("1"), SEQ ID NO:4 ("2") or SEQ ID NO:6 ("3"); segment 6 is from about amino acid residue $x_5$ to about $x_6$ of SEQ ID NO:2 ("1"), SEQ ID NO:4 ("2") or SEQ ID NO:6 ("3"); segment 7 is from about amino acid residue $x_6$ to about $x_7$ of SEQ ID NO:2 ("1"), SEQ ID NO:4 ("2") or SEQ ID NO:6 ("3"); and segment 8 is from about amino acid residue $x_7$ to about $x_8$ of SEQ ID NO:2 ("1"), SEQ ID NO:4 ("2") or SEQ ID NO:6 ("3").

5. An enzymatic preparation comprising a polypeptide of claim 1, 2 or 3.

6. A method of treating a biomass comprising cellulose, the method comprising contacting the biomass with a polypeptide of claim 1, 2 or 3.

7. A method of treating a biomass comprising cellulose, the method comprising contacting the biomass with an enzymatic preparation of claim 5.

* * * * *

UNITED STATES PATENT AND TRADEMARK OFFICE
CERTIFICATE OF CORRECTION

| | | |
|---|---|---|
| PATENT NO. | : 9,249,401 B2 | |
| APPLICATION NO. | : 12/755328 | |
| DATED | : February 2, 2016 | |
| INVENTOR(S) | : Frances H. Arnold and Pete Heinzelman | |

It is certified that error appears in the above-identified patent and that said Letters Patent is hereby corrected as shown below:

In column 1, line 15, after CROSS REFERENCE TO RELATED APPLICATIONS, please replace the paragraph "STATEMENT REGARDING FEDERALLY SPONSORED RESEARCH
This invention was made with government support under pursuant to Grant No. GM068664 awarded by the National Institutes of Health and under Grant No. DAAD19-03-0D-0004 awarded by the US Army. The government has certain rights in the invention." with:

--STATEMENT REGARDING FEDERALLY SPONSORED RESEARCH

This invention was made with government support under Grant No. GM068664 awarded by the National Institutes of Health and under Grant No. DAAD19-03-D-0004 awarded by the US Army. The government has certain rights in the invention.--

Signed and Sealed this
Sixteenth Day of August, 2016

Michelle K. Lee
*Director of the United States Patent and Trademark Office*